(12) United States Patent
Marban

(10) Patent No.: US 11,660,317 B2
(45) Date of Patent: *May 30, 2023

(54) COMPOSITIONS COMPRISING CARDIOSPHERE-DERIVED CELLS FOR USE IN CELL THERAPY

(75) Inventor: Eduardo Marban, Beverly Hills, CA (US)

(73) Assignee: The Johns Hopkins University, Baltimore, MD (US)

( * ) Notice: Subject to any disclaimer, the term of this patent is extended or adjusted under 35 U.S.C. 154(b) by 410 days.

This patent is subject to a terminal disclaimer.

(21) Appl. No.: 13/412,051

(22) Filed: Mar. 5, 2012

(65) Prior Publication Data

US 2012/0315252 A1    Dec. 13, 2012

Related U.S. Application Data

(63) Continuation-in-part of application No. 11/666,685, filed as application No. PCT/US2005/040359 on Nov. 8, 2005, now abandoned.

(60) Provisional application No. 60/625,695, filed on Nov. 8, 2004.

(51) Int. Cl.
| | | |
|---|---|---|
| A61K 35/12 | (2015.01) | |
| A61P 35/00 | (2006.01) | |
| A61K 35/28 | (2015.01) | |
| C12N 5/077 | (2010.01) | |
| C12N 5/0775 | (2010.01) | |

(52) U.S. Cl.
CPC ............ *A61K 35/28* (2013.01); *C12N 5/0657* (2013.01); *C12N 5/0668* (2013.01)

(58) Field of Classification Search
CPC ..... A61K 35/28; C12N 5/0657; C12N 5/0668
See application file for complete search history.

(56) References Cited

U.S. PATENT DOCUMENTS

| | | |
|---|---|---|
| 3,470,876 A | 10/1969 | Barchilon |
| 3,964,468 A | 6/1976 | Schulz |
| 4,106,488 A | 8/1978 | Gordon |
| 4,659,839 A | 4/1987 | Nicolotti |
| 4,921,482 A | 5/1990 | Hammerslag et al. |
| 4,960,134 A | 10/1990 | Webster, Jr. |
| 5,028,588 A | 7/1991 | Hoffman et al. |
| 5,052,402 A | 10/1991 | Bencini et al. |
| 5,104,787 A | 4/1992 | Lindstrom et al. |
| 5,175,004 A | 12/1992 | Matsumura |
| 5,199,950 A | 4/1993 | Schmitt |
| 5,228,441 A | 7/1993 | Lundquist |
| 5,243,167 A | 9/1993 | Lundquist |
| 5,287,857 A | 2/1994 | Mann |
| 5,315,996 A | 5/1994 | Lundquist |
| 5,322,064 A | 6/1994 | Lundquist |
| 5,329,923 A | 7/1994 | Lundquist |
| 5,334,145 A | 8/1994 | Lundquist et al. |
| 5,383,852 A | 1/1995 | Stevens-Wright |
| 5,436,128 A | 7/1995 | Harpold et al. |
| 5,454,787 A | 10/1995 | Lundquist |
| 5,477,856 A | 12/1995 | Lundquist |
| 5,492,825 A | 2/1996 | Jan et al. |
| 5,507,725 A | 4/1996 | Savage et al. |
| 5,616,568 A | 4/1997 | Prestwick et al. |
| 5,618,294 A | 4/1997 | Aust et al. |
| 5,670,335 A | 9/1997 | Jan et al. |
| 5,685,868 A | 11/1997 | Lundquist |
| 5,702,433 A | 12/1997 | Taylor et al. |
| 5,702,905 A | 12/1997 | Takahashi et al. |
| 5,762,069 A | 6/1998 | Kelleher et al. |
| 5,782,748 A | 7/1998 | Palmer et al. |
| 5,824,031 A | 10/1998 | Cookston et al. |
| 5,840,502 A | 11/1998 | Van Vlasselaer |
| 5,851,212 A | 12/1998 | Zirps et al. |
| 5,856,155 A | 1/1999 | Li |
| 5,872,109 A | 2/1999 | Akima et al. |
| 5,874,417 A | 2/1999 | Prestwick et al. |
| 5,938,603 A | 8/1999 | Ponzi |
| 5,955,275 A | 9/1999 | Kamb |
| 5,957,863 A | 9/1999 | Koblish et al. |
| 5,981,165 A | 11/1999 | Weiss et al. |
| 6,004,295 A | 12/1999 | Langer et al. |
| 6,074,408 A | 6/2000 | Freeman |
| 6,077,287 A | 6/2000 | Taylor et al. |
| 6,086,582 A | 7/2000 | Altman et al. |
| 6,099,832 A | 8/2000 | Mickle et al. |

(Continued)

FOREIGN PATENT DOCUMENTS

| | | |
|---|---|---|
| CA | 2488346 | 12/2003 |
| CN | 1537646 | 10/2004 |

(Continued)

OTHER PUBLICATIONS

Cho et al., "Secondary Sphere Formation Enhances the Functionality of cardiac Progenitor Cells", Molecular Therapy, 2012, vol. 20, No. 9, pp. 1750-1766.*

Burstein et al., "Systemic and Coronary Delivery of Marrow Stromal Cells for Cellular Cardiomyoplasty: Advantages and Precautions", Basic Appl Myol 2003, 13(1), pp. 7-10.*

Piper et al., "Determinants of cardiomyocyte development in long term primary culture", Journal of cardiomyocyte and cellular cardiology, 1988, vol. 20, Issue 9, pp. 825-835, abstract only.*

Piper et al., "Determinants of cardiomyocyte development in long term primary culture", Journal of cardiomyocyte and cellular cardiology, 1988, vol. 20, Issue 9, pp. 825-835.*

(Continued)

*Primary Examiner* — Laura Schuberg
(74) *Attorney, Agent, or Firm* — DLA Piper LLP (US)

(57) ABSTRACT

The present application relates to methods and compositions for treating diseased or damaged cardiac tissue comprising regenerative cells harvested from donor cardiac tissue. In one embodiment, regenerative cells are harvested from an allogeneic source and after administration result in increased viability and/or functional improvement of damaged or diseased cardiac tissue.

13 Claims, 66 Drawing Sheets

(56) References Cited

U.S. PATENT DOCUMENTS

| | | |
|---|---|---|
| 6,102,887 A | 8/2000 | Altman |
| 6,132,390 A | 10/2000 | Cookston et al. |
| 6,153,582 A | 11/2000 | Skelnik |
| 6,165,164 A | 12/2000 | Hill et al. |
| 6,193,763 B1 | 2/2001 | Mackin |
| 6,203,487 B1 | 3/2001 | Consigny |
| 6,224,587 B1 | 5/2001 | Gibson |
| 6,296,630 B1 | 10/2001 | Altman et al. |
| RE37,463 E | 12/2001 | Altman |
| 6,326,198 B1 | 12/2001 | Emerson et al. |
| 6,337,387 B1 | 1/2002 | Sakano et al. |
| 6,338,942 B2 | 1/2002 | Kraus et al. |
| 6,346,099 B1 | 2/2002 | Altman |
| 6,358,247 B1 | 3/2002 | Altman et al. |
| 6,361,997 B1 | 3/2002 | Huss |
| 6,387,369 B1 | 5/2002 | Pittenger |
| 6,408,203 B2 | 6/2002 | Mackin |
| 6,416,510 B1 | 7/2002 | Altman et al. |
| 6,443,949 B2 | 9/2002 | Altman |
| 6,478,776 B1 | 11/2002 | Rosenman et al. |
| 6,488,659 B1 | 12/2002 | Rosenman |
| 6,500,167 B1 | 12/2002 | Webster., Jr. |
| 6,511,471 B2 | 1/2003 | Rosenman et al. |
| 6,511,477 B2 | 1/2003 | Altman et al. |
| 6,514,481 B1 | 2/2003 | Prasad et al. |
| 6,530,944 B2 | 3/2003 | West et al. |
| 6,540,725 B1 | 4/2003 | Ponzi |
| 6,547,787 B1 | 4/2003 | Altman et al. |
| 6,569,144 B2 | 5/2003 | Altman |
| 6,572,611 B1 | 6/2003 | Falwell |
| 6,577,895 B1 | 6/2003 | Altman |
| 6,585,716 B2 | 7/2003 | Altman |
| 6,716,242 B1 | 4/2004 | Altman |
| 6,726,654 B2 | 4/2004 | Rosenman |
| 6,726,662 B2 | 4/2004 | Altman |
| 6,739,342 B1 | 5/2004 | Fredriksson et al. |
| 6,783,510 B1 | 8/2004 | Gibson et al. |
| 6,796,963 B2 | 9/2004 | Carpenter et al. |
| 6,805,860 B1 | 10/2004 | Alt |
| 6,818,757 B2 | 11/2004 | Lee et al. |
| 6,866,117 B2 | 3/2005 | Moss et al. |
| 6,866,843 B2 | 3/2005 | Habener et al. |
| 6,905,827 B2 | 6/2005 | Wohlgemuth et al. |
| 6,925,327 B2 | 8/2005 | Altman |
| 6,971,998 B2 | 12/2005 | Rosenman et al. |
| 6,997,863 B2 | 2/2006 | Handy et al. |
| 7,026,121 B1 | 4/2006 | Wohlgemuth et al. |
| 7,029,466 B2 | 4/2006 | Altman |
| 7,034,008 B2 | 4/2006 | Donahue et al. |
| 7,037,648 B1 | 5/2006 | Marban |
| 7,048,711 B2 | 5/2006 | Rosenman et al. |
| 7,074,175 B2 | 7/2006 | Handy et al. |
| 7,104,988 B2 | 9/2006 | Altman et al. |
| 7,138,275 B2 | 11/2006 | Kremer et al. |
| 7,156,824 B2 | 1/2007 | Rosenman et al. |
| 7,220,582 B2 | 5/2007 | Eptsein et al. |
| 7,259,011 B2 | 8/2007 | Lucas et al. |
| 7,280,863 B2 | 10/2007 | Shachar |
| 7,329,638 B2 | 2/2008 | Yang et al. |
| 7,351,237 B2 | 4/2008 | Altman |
| 7,402,151 B2 | 7/2008 | Rosenman et al. |
| 7,452,532 B2 | 11/2008 | Eckhard |
| 7,468,276 B2 | 12/2008 | Hariri |
| 7,470,425 B2 | 12/2008 | Vacanti et al. |
| 7,500,970 B2 | 3/2009 | Altman |
| 7,514,074 B2 | 4/2009 | Pittenger et al. |
| 7,517,686 B2 | 4/2009 | Kremer et al. |
| 7,531,354 B2 | 5/2009 | Stice et al. |
| 7,547,301 B2 | 6/2009 | Altman et al. |
| 7,547,674 B2 | 6/2009 | Anversa et al. |
| 7,553,663 B2 | 6/2009 | Kremer et al. |
| 7,592,177 B2 | 9/2009 | Chen |
| 7,625,581 B2 | 12/2009 | Laredo et al. |
| 7,659,118 B2 | 2/2010 | Furcht et al. |
| 7,686,799 B2 | 3/2010 | Leonhardt et al. |
| 7,731,648 B2 | 6/2010 | Ivkov |
| 7,745,113 B2 | 6/2010 | Evans et al. |
| 7,794,702 B2 | 9/2010 | Rosen et al. |
| 7,837,631 B2 | 11/2010 | Diamond et al. |
| 7,862,810 B2 | 1/2011 | Anversa |
| 7,875,451 B2 | 1/2011 | Murray et al. |
| 7,971,592 B2 | 7/2011 | Ochi |
| 7,999,025 B2 | 8/2011 | Shumaker-Pam et al. |
| 8,008,254 B2 | 8/2011 | Anversa |
| 8,017,389 B2 | 9/2011 | Phillips et al. |
| 8,119,123 B2 | 2/2012 | Anversa et al. |
| 8,193,161 B2 | 6/2012 | Hosoda |
| 8,232,102 B2 | 7/2012 | Dobson et al. |
| 8,258,113 B2 | 9/2012 | Dimmeler et al. |
| 8,268,619 B2 | 9/2012 | Giacomello et al. |
| 8,562,972 B2 | 10/2013 | Edinger et al. |
| 8,772,030 B2 | 7/2014 | Giacomello et al. |
| 8,846,396 B2 | 9/2014 | Giacomello et al. |
| 8,945,558 B2 | 2/2015 | Kobara |
| 9,249,392 B2 | 2/2016 | Marbán et al. |
| 9,828,603 B2 | 11/2017 | Marbán et al. |
| 9,845,457 B2 | 12/2017 | Marbán et al. |
| 9,884,076 B2 | 2/2018 | Kreke et al. |
| 10,457,942 B2 | 10/2019 | Marbán et al. |
| 2001/0024824 A1 | 9/2001 | Moss et al. |
| 2002/0022259 A1 | 2/2002 | Lee et al. |
| 2002/0061587 A1 | 5/2002 | Anversa |
| 2002/0098167 A1 | 7/2002 | Anversa et al. |
| 2002/0155101 A1 | 10/2002 | Donahue et al. |
| 2002/0156383 A1 | 10/2002 | Altman et al. |
| 2002/0177772 A1 | 11/2002 | Altman et al. |
| 2003/0054973 A1 | 3/2003 | Anversa |
| 2003/0129221 A1 | 7/2003 | Semple et al. |
| 2003/0135113 A1 | 7/2003 | Altman et al. |
| 2003/0161817 A1 | 8/2003 | Young et al. |
| 2003/0195432 A1 | 10/2003 | Kortenbach et al. |
| 2003/0229386 A1 | 12/2003 | Rosenman et al. |
| 2004/0014209 A1 | 1/2004 | Lassar et al. |
| 2004/0018174 A1 | 1/2004 | Palasis |
| 2004/0030286 A1 | 2/2004 | Altman |
| 2004/0033214 A1 | 2/2004 | Young et al. |
| 2004/0076619 A1 | 4/2004 | Anversa et al. |
| 2004/0087016 A1 | 5/2004 | Keating et al. |
| 2004/0102759 A1 | 5/2004 | Altman et al. |
| 2004/0110287 A1 | 6/2004 | Clarke et al. |
| 2004/0137621 A1 | 6/2004 | Rosen et al. |
| 2004/0126879 A1 | 7/2004 | Schneider et al. |
| 2004/0136966 A1 | 7/2004 | Anversa |
| 2004/0153139 A1 | 8/2004 | Altman |
| 2004/0158313 A1 | 8/2004 | Altman |
| 2004/0168341 A1 | 9/2004 | Petersen et al. |
| 2004/0214182 A1 | 10/2004 | Sharma et al. |
| 2004/0254134 A1 | 12/2004 | Marbán et al. |
| 2005/0031854 A1 | 2/2005 | Lorenz et al. |
| 2005/0058630 A1 | 3/2005 | Harris et al. |
| 2005/0074880 A1 | 4/2005 | Sang et al. |
| 2005/0090732 A1 | 4/2005 | Ivkov |
| 2005/0176620 A1 | 8/2005 | Prestwich et al. |
| 2005/0214938 A1* | 9/2005 | Gold ................... C12N 5/0657 435/366 |
| 2005/0215991 A1 | 9/2005 | Altman et al. |
| 2005/0255588 A1 | 11/2005 | Young et al. |
| 2005/0260748 A1 | 11/2005 | Chang et al. |
| 2005/0260750 A1 | 11/2005 | Kerr-Conte et al. |
| 2005/0271745 A1 | 12/2005 | Gruettner et al. |
| 2006/0018897 A1 | 1/2006 | Lee et al. |
| 2006/0020158 A1 | 1/2006 | Altman |
| 2006/0025713 A1 | 2/2006 | Rosengart et al. |
| 2006/0041182 A1 | 2/2006 | Forbes et al. |
| 2006/0078496 A1 | 4/2006 | Altman et al. |
| 2006/0083712 A1 | 4/2006 | Anversa |
| 2006/0084089 A1 | 4/2006 | Fort et al. |
| 2006/0084943 A1 | 4/2006 | Rosenman et al. |
| 2006/0142749 A1 | 6/2006 | Ivkov |
| 2006/0165805 A1 | 7/2006 | Steinhoff |
| 2006/0198829 A1 | 9/2006 | Rosen et al. |
| 2006/0205071 A1 | 9/2006 | Hasson et al. |
| 2006/0224111 A1 | 10/2006 | Rosenman et al. |
| 2006/0233712 A1 | 10/2006 | Penades et al. |

(56) References Cited

U.S. PATENT DOCUMENTS

| | | |
|---|---|---|
| 2006/0234375 A1 | 10/2006 | Doronin et al. |
| 2006/0239980 A1 | 10/2006 | Miana et al. |
| 2006/0239983 A1 | 10/2006 | Anversa |
| 2006/0281791 A1 | 12/2006 | Keating et al. |
| 2007/0003528 A1 | 1/2007 | Consigny et al. |
| 2007/0014869 A1 | 1/2007 | Matheny |
| 2007/0020758 A1 | 1/2007 | Giacomello et al. |
| 2007/0048383 A1 | 3/2007 | Helmus |
| 2007/0053839 A1 | 3/2007 | Zhang |
| 2007/0054397 A1 | 3/2007 | Ott et al. |
| 2007/0072291 A1 | 3/2007 | Kremer et al. |
| 2007/0088244 A1 | 4/2007 | Miller et al. |
| 2007/0099268 A1 | 5/2007 | Cohen et al. |
| 2007/0129296 A1 | 6/2007 | Zhou |
| 2007/0134210 A1 | 6/2007 | Heidaran |
| 2007/0142774 A1 | 6/2007 | Rosenman |
| 2007/0166288 A1 | 7/2007 | Murray et al. |
| 2007/0196281 A1 | 8/2007 | Jm et al. |
| 2007/0196918 A1 | 8/2007 | Sayre et al. |
| 2007/0197891 A1 | 8/2007 | Shachar et al. |
| 2007/0231393 A1 | 10/2007 | Ritter et al. |
| 2007/0248580 A1 | 10/2007 | Garcia et al. |
| 2007/0286848 A1 | 12/2007 | Louis-Georges et al. |
| 2007/0292353 A1 | 12/2007 | Levy et al. |
| 2008/0006281 A1 | 1/2008 | Ou et al. |
| 2008/0027313 A1 | 1/2008 | Shachar |
| 2008/0031854 A1 | 2/2008 | Prestwick et al. |
| 2008/0076176 A1 | 3/2008 | Dominko et al. |
| 2008/0089874 A1 | 4/2008 | Li et al. |
| 2008/0103536 A1 | 5/2008 | Xiao |
| 2008/0138416 A1 | 6/2008 | Rauh et al. |
| 2008/0187514 A1 | 8/2008 | Anversa |
| 2008/0213230 A1 | 9/2008 | Phillips et al. |
| 2008/0213812 A1 | 9/2008 | Andrews et al. |
| 2008/0260704 A1 | 10/2008 | Riordan et al. |
| 2008/0267921 A1 | 10/2008 | Marban et al. |
| 2008/0268061 A1 | 10/2008 | Jordan et al. |
| 2008/0274998 A1 | 11/2008 | Cohen et al. |
| 2008/0287918 A1 | 11/2008 | Rosenman et al. |
| 2008/0297287 A1 | 12/2008 | Shachar et al. |
| 2008/0319420 A1 | 12/2008 | Rosenman et al. |
| 2009/0011004 A1 | 1/2009 | Lutz et al. |
| 2009/0074728 A1 | 3/2009 | Gronthos et al. |
| 2009/0081170 A1 | 3/2009 | Riley |
| 2009/0081276 A1 | 3/2009 | Alsberg et al. |
| 2009/0099611 A1 | 4/2009 | Sigg et al. |
| 2009/0123366 A1 | 5/2009 | Dobson et al. |
| 2009/0136582 A1 | 5/2009 | Albrecht et al. |
| 2009/0143296 A1 | 6/2009 | Anversa et al. |
| 2009/0143748 A1 | 6/2009 | Mickley et al. |
| 2009/0148415 A1 | 6/2009 | de la Fuente et al. |
| 2009/0148421 A1 | 6/2009 | Anversa et al. |
| 2009/0157046 A1 | 6/2009 | Anversa |
| 2009/0162329 A1 | 6/2009 | Anversa et al. |
| 2009/0169525 A1 | 7/2009 | Anversa et al. |
| 2009/0177152 A1 | 7/2009 | Altman |
| 2009/0180998 A1 | 7/2009 | Anversa et al. |
| 2009/0226521 A1 | 9/2009 | Smyth et al. |
| 2009/0317369 A1 | 12/2009 | Hosoda et al. |
| 2010/0010073 A1 | 1/2010 | Thum et al. |
| 2010/0012880 A1 | 1/2010 | Rampersaud et al. |
| 2010/0040587 A1 | 2/2010 | Haag |
| 2010/0068811 A1 | 3/2010 | Marbán et al. |
| 2010/0081200 A1 | 4/2010 | Raj et al. |
| 2010/0233216 A1 | 9/2010 | Cantaluppi et al. |
| 2010/0239538 A9 | 9/2010 | Anversa et al. |
| 2010/0255034 A1 | 10/2010 | Meinke et al. |
| 2010/0303716 A1 | 12/2010 | Jin et al. |
| 2010/0303722 A1 | 12/2010 | Jin et al. |
| 2010/0303909 A1 | 12/2010 | Oh et al. |
| 2010/0310534 A1 | 12/2010 | Oved et al. |
| 2011/0003003 A1 | 1/2011 | Goldberg et al. |
| 2011/0003008 A1 | 1/2011 | Lim |
| 2011/0034753 A1 | 2/2011 | Dobson et al. |
| 2011/0064675 A1 | 3/2011 | Hadjipanayis et al. |
| 2011/0070153 A1 | 3/2011 | Hyde et al. |
| 2011/0070154 A1 | 3/2011 | Hyde et al. |
| 2011/0091428 A1 | 4/2011 | Anversa |
| 2011/0091448 A1 | 4/2011 | Moon et al. |
| 2011/0092961 A1 | 4/2011 | Hyde et al. |
| 2011/0110897 A1 | 5/2011 | Schwarz et al. |
| 2011/0111412 A1 | 5/2011 | Tai et al. |
| 2011/0123500 A1 | 5/2011 | Anversa et al. |
| 2011/0135577 A1 | 6/2011 | Wu et al. |
| 2011/0152835 A1 | 6/2011 | Anversa |
| 2011/0165068 A1 | 7/2011 | Liu et al. |
| 2011/0177054 A1 | 7/2011 | Gibbings et al. |
| 2011/0256105 A1 | 10/2011 | Marbán et al. |
| 2011/0256621 A1 | 10/2011 | Albrecht et al. |
| 2011/0258716 A1 | 10/2011 | Baltimore et al. |
| 2011/0280834 A1 | 11/2011 | Forrester et al. |
| 2011/0300111 A1 | 12/2011 | White et al. |
| 2011/0300112 A1 | 12/2011 | Marbán et al. |
| 2012/0021019 A1 | 1/2012 | Giacomello et al. |
| 2012/0034156 A1 | 2/2012 | Hyde et al. |
| 2012/0034157 A1 | 2/2012 | Hyde et al. |
| 2012/0039857 A1 | 2/2012 | Smith et al. |
| 2012/0093879 A1 | 4/2012 | Giacomello et al. |
| 2012/0093885 A1 | 4/2012 | Sahoo et al. |
| 2012/0165392 A1 | 6/2012 | Olson |
| 2012/0171291 A1 | 7/2012 | Rademacher et al. |
| 2012/0177574 A1 | 7/2012 | Gho et al. |
| 2012/0183528 A1 | 7/2012 | Ebert et al. |
| 2012/0201795 A1 | 8/2012 | Ware et al. |
| 2012/0238619 A1 | 9/2012 | Dimmeler et al. |
| 2012/0253102 A1 | 10/2012 | Marbaán et al. |
| 2012/0258093 A1 | 10/2012 | Butler-Browne et al. |
| 2012/0315252 A1 | 12/2012 | Marbán et al. |
| 2013/0059006 A1 | 3/2013 | Schmuck et al. |
| 2013/0177593 A1 | 7/2013 | Gunn et al. |
| 2013/0189780 A1 | 7/2013 | Shoemaker et al. |
| 2013/0266543 A1 | 10/2013 | Nadal-Ginard |
| 2013/0280205 A1 | 10/2013 | Mozaffari et al. |
| 2013/0288962 A1 | 10/2013 | Anversa et al. |
| 2013/0295060 A1 | 11/2013 | Yang et al. |
| 2013/0309304 A1 | 11/2013 | Nadal-Ginard |
| 2014/0031256 A1 | 1/2014 | Lim |
| 2014/0120066 A1 | 5/2014 | Yeghiazarians et al. |
| 2014/0121171 A1 | 5/2014 | Muñoz-Cánoves et al. |
| 2014/0156200 A1 | 6/2014 | Verhsegh et al. |
| 2014/0235526 A1 | 8/2014 | Srivastava et al. |
| 2014/0275976 A1 | 9/2014 | Moro |
| 2015/0010640 A1 | 1/2015 | Marbán et al. |
| 2015/0140658 A1 | 5/2015 | Kamp et al. |
| 2015/0246030 A1 | 9/2015 | Armer et al. |
| 2015/0273113 A1 | 10/2015 | Marbán et al. |
| 2015/0328263 A1 | 11/2015 | Kaushal |
| 2016/0158291 A1 | 6/2016 | Kreke et al. |
| 2016/0244723 A1 | 8/2016 | Giacomello et al. |
| 2017/0037375 A1 | 2/2017 | Palecek et al. |
| 2017/0049793 A1 | 2/2017 | Moon et al. |
| 2017/0087087 A1 | 3/2017 | Leonard et al. |
| 2017/0290860 A1 | 10/2017 | Marbaán et al. |
| 2017/0304368 A1 | 10/2017 | Marbán et al. |
| 2019/0000888 A1 | 1/2019 | Marbán et al. |
| 2019/0062740 A1 | 2/2019 | Zhu |
| 2019/0160111 A1 | 5/2019 | Marbaán et al. |
| 2019/0255119 A1 | 8/2019 | Marbán et al. |
| 2020/0024604 A1 | 1/2020 | Marban et al. |
| 2020/0121727 A1 | 4/2020 | Marbaán et al. |
| 2020/0316226 A1 | 10/2020 | Marbán et al. |
| 2021/0032598 A1 | 2/2021 | Ibrahim et al. |
| 2021/0085724 A1 | 3/2021 | Grigorian et al. |

FOREIGN PATENT DOCUMENTS

| | | |
|---|---|---|
| CN | 1772300 | 5/2006 |
| CN | 1785430 | 6/2006 |
| EP | 1857544 | 11/2007 |
| EP | 1970446 | 9/2008 |
| EP | 2182053 | 5/2010 |
| EP | 2228444 | 9/2010 |
| EP | 1631318 | 11/2010 |
| EP | 1650293 | 12/2010 |

(56) References Cited

FOREIGN PATENT DOCUMENTS

| | | |
|---|---|---|
| EP | 2371370 | 10/2011 |
| EP | 2385120 | 11/2011 |
| EP | 2446929 | 5/2012 |
| EP | 1945256 | 7/2012 |
| EP | 2094869 | 7/2012 |
| EP | 2486944 | 8/2012 |
| EP | 2277548 | 1/2013 |
| EP | 2687219 | 1/2014 |
| JP | 2005506845 | 3/2005 |
| JP | 2005110565 | 4/2005 |
| JP | 2006006125 | 1/2006 |
| JP | 2008504816 | 2/2008 |
| KR | 100830889 | 5/2008 |
| KR | 101818560 | 11/2016 |
| WO | WO 1997005265 | 2/1997 |
| WO | WO 1997012912 | 4/1997 |
| WO | WO 1998004708 | 2/1998 |
| WO | WO 1998032866 | 7/1998 |
| WO | WO 1999011809 | 3/1999 |
| WO | WO 1999039624 | 8/1999 |
| WO | 199949015 | 9/1999 |
| WO | WO 1999051297 | 10/1999 |
| WO | WO 2000009185 | 2/2000 |
| WO | WO 2000024452 | 5/2000 |
| WO | WO 2001010482 | 2/2001 |
| WO | WO 2001026585 | 4/2001 |
| WO | WO 2001026706 | 4/2001 |
| WO | WO 2001026727 | 4/2001 |
| WO | 01/48151 A1 | 7/2001 |
| WO | WO 2001076679 | 10/2001 |
| WO | WO 2001076682 | 10/2001 |
| WO | 200209650 | 2/2002 |
| WO | 200213760 | 2/2002 |
| WO | WO 2002051489 | 7/2002 |
| WO | 200308535 | 1/2003 |
| WO | 2003006950 | 1/2003 |
| WO | WO 2003004626 | 1/2003 |
| WO | WO 2003049626 | 6/2003 |
| WO | WO 2003064463 | 8/2003 |
| WO | 2003103611 | 12/2003 |
| WO | WO 2003103764 | 12/2003 |
| WO | 2004/044142 A2 | 5/2004 |
| WO | 2005012510 | 2/2005 |
| WO | WO 2006007529 | 1/2006 |
| WO | WO 2006/014156 | 2/2006 |
| WO | 2006052925 | 5/2006 |
| WO | WO 2006065949 | 6/2006 |
| WO | WO 2006081190 | 8/2006 |
| WO | WO 2007019398 | 2/2007 |
| WO | WO 2007069666 | 6/2007 |
| WO | 2007100530 | 9/2007 |
| WO | WO 2007106175 | 9/2007 |
| WO | WO 2008036776 | 3/2008 |
| WO | WO 2008043521 | 4/2008 |
| WO | 2008058273 | 5/2008 |
| WO | WO 2008058216 | 5/2008 |
| WO | WO 2008118820 | 10/2008 |
| WO | WO 2008124133 | 10/2008 |
| WO | WO 2009032456 | 3/2009 |
| WO | WO 2009056116 | 5/2009 |
| WO | WO 2009058818 | 5/2009 |
| WO | WO 2009062143 | 5/2009 |
| WO | WO 2009062169 | 5/2009 |
| WO | WO 2009067644 | 5/2009 |
| WO | WO 2009073518 | 6/2009 |
| WO | WO 2009073594 | 6/2009 |
| WO | WO 2009073616 | 6/2009 |
| WO | WO 2009073618 | 6/2009 |
| WO | WO 2009/013818 | 8/2009 |
| WO | WO 2009/103818 | 8/2009 |
| WO | WO 2009100137 | 8/2009 |
| WO | WO 2009149956 | 12/2009 |
| WO | WO 2009152111 | 12/2009 |
| WO | WO 2010015665 | 2/2010 |
| WO | WO 2010028090 | 3/2010 |
| WO | WO 2010033285 | 3/2010 |
| WO | WO 2010059806 | 5/2010 |
| WO | WO 2010083466 | 7/2010 |
| WO | WO 2010118059 | 10/2010 |
| WO | WO 2010135570 | 11/2010 |
| WO | WO 2011029092 | 3/2011 |
| WO | WO 2011029903 | 3/2011 |
| WO | WO 2011053901 | 5/2011 |
| WO | WO 2011056685 | 5/2011 |
| WO | WO 2011057249 | 5/2011 |
| WO | WO 2011057251 | 5/2011 |
| WO | WO 2011062244 | 5/2011 |
| WO | WO 2011064354 | 6/2011 |
| WO | WO 2011084460 | 7/2011 |
| WO | WO 2011121120 | 10/2011 |
| WO | WO 2011127625 | 10/2011 |
| WO | WO 2011138328 | 11/2011 |
| WO | WO 2011143499 | 11/2011 |
| WO | WO 2012019103 | 2/2012 |
| WO | WO 2012020307 | 2/2012 |
| WO | WO 2012020308 | 2/2012 |
| WO | WO 2012055971 | 5/2012 |
| WO | WO 2012065027 | 5/2012 |
| WO | WO 2012125471 | 9/2012 |
| WO | WO 2012135253 | 10/2012 |
| WO | WO 2012149557 | 11/2012 |
| WO | WO 2012162741 | 12/2012 |
| WO | WO 2013048734 | 4/2013 |
| WO | WO 2013170170 | 11/2013 |
| WO | WO 2013184527 | 12/2013 |
| WO | WO 2014013258 | 1/2014 |
| WO | WO 2014028493 | 2/2014 |
| WO | WO 2014/114465 | 7/2014 |
| WO | WO 2014160153 | 10/2014 |
| WO | WO 2015/055857 | 4/2015 |
| WO | WO 2015/092020 | 6/2015 |
| WO | WO 2015085096 | 6/2015 |
| WO | WO 2015120150 | 8/2015 |
| WO | WO 2016054591 | 4/2016 |
| WO | WO 2016057560 | 4/2016 |
| WO | WO 2017/160884 | 9/2017 |
| WO | WO 2017/173034 | 10/2017 |
| WO | WO 2019/015702 | 1/2019 |
| WO | WO 2019028223 | 2/2019 |
| WO | WO 2019/050071 | 3/2019 |
| WO | WO 2019126068 | 6/2019 |
| WO | WO 2019152549 | 8/2019 |
| WO | WO 2020/0227489 | 11/2020 |
| WO | WO 2021/178514 | 9/2021 |
| WO | WO 2021/188899 | 9/2021 |

OTHER PUBLICATIONS

Heng et al., "Strategies for directing the differentiation of stem cells into the cardiomyogenic lineage in vitro", Cardiovascular Research, 2004, vol. 62, pp. 34-42.*

Smith et al., "Regenerative Potential of Cardiosphere-Derived Cells Expanded From Percutaneous Endomyocardial Biopsy Specimens", Circulation, 2007, vol. 115, pp. 896-908. (Year: 2007).*

Smith et al., "Regenerative Potential of Cardiosphere-Derived Cells Expanded From Percutaneous Endomyocardial Biopsy Specimens", Circulation, 2007, vol. 115, pp. 896-908 Supplement, at http://circ.ahajournals.org/cgi/content/full/CIRCULATIONAHA.106.655209/DC1. (Year: 2007).*

Non-Final Office Action issued in related U.S. Appl. No. 12/622,143, dated Feb. 19, 2013.

Non-Final Office Action issued in related U.S. Appl. No. 12/622,106, dated Feb. 19, 2013.

Vanwinkle et al, "Cardiogel: A Biosynthetic Extracellular Matrix for Cardiomyocyte Culture," In Vitro Dev. Biol.—Animal, vol. 21, 1996, pp. 478-485.

P. Anversa et al., "Primitive Cells and Tissue Regeneration," Circ. Res., (2003), 92:579-92.

Balser, et al., Biophys. J., 57:433 (1990).

Balser, et al., J. Clin. Invest., 98:12, 2874 (1996).

Barile L. et al., Endogenous Cardiac Stem Cells. Prog. Cardiovas. Dis. 50(1):31-48 (2007).

(56) References Cited

OTHER PUBLICATIONS

Barile,L. et al., Cardiac stem cells: isolation, expansion and experimental use for myocardial regeneration. Nat. Clin. Pract. Cardiovasc. Med. 4 Suppl 1: S9-S14 (2007).
Barry et al., Circ Res., 77:361 (1995) or p. 561.
Barth AS et al., Lentiviral vectors bearing the cardiac promoter of the Na+-Ca2+ exchanger report cardiogenic differentiation in stem cells. Mol. Ther. 16(5):957-964 (2008).
Beltrami, AP et al., Evidence that human cardiac myocytes divide after myocardial infarction. N. Engl. J. Med. 344: 1750-1757 (2001).
Benardeau, A. et al., Primary culture of human atrial myocytes is associated with the appearance of structural and functional characteristics of immature myocardium. J. Mol. Cell Cardiol. 29: 1307-1320 (1997).
De Pomerai et al., Influence of serum factors on the prevalence of "normal" and "foreign" differentiation pathways in cultures of chick embryo neuroretinal cells, J. Embryol Exp Morphol., 1981, p. 291-308, vol. 62.
Deal, K.D. et al., Phys. Rev., 76:49 (1996).
Dispersyn, GD et al., Adult rabbit cardiomyocytes undergo hibernation-like dedifferentiation when co-cultured with cardiac fibroblasts. Cardiovasc. Res. 57: 230-240 (2001).
Dispersyn, GD et al., Dissociation of cardiomyocyte apoptosis and dedifferentiation in infarct border zones. Eur. Heart J. 23:849-857 (2002).
Dixon, et al., Circ. Res., 75:252 (1994).
Dixon, et al., Circ. Res., 79:659 (1996).
Donahue, et al., Proc. Natl. Acad. Sci. USA 94:4664 (1997).
Driesen, RB et al., Structural adaptation in adult rabbit ventricular myocytes: influence of dynamic physical interaction with fibroblasts. Cell. Biochem. Biophys. 44: 119-128 (2006).
Driesen, RB et al., Structural remodeling of cardiomyocytes in the border zone of infarcted rabbit heart. Mol. Cell. Biochem (2007).
Engle, FB et al. "p38 MAP kinase inhibition enables proliferation of adult mammalian cardiomyocytes", Genes & Dev., May 2005, vol. 19, No. 10, pp. 1175-1187.
Gidh-Jian, et al., Circulation Research, vol. 79, No. 4, 660 (1996).
Good et al., Biophys. J., 70:296 (1996).
Jackson et al., Regeneration of ischemic cardiac muscle and vascular endothelium by adult stem cells. J. Clin Invest. 107(11):1395-402, 2001.
Kaab, et al., Circulation Research, vol. 78, No. 2, 262 (1996).
Lee, et al., J. Thorac, and Cardio. Surg., 111:246 (1996).
Lyngbaek, S et al., Cardiac regeneration by resident stem and progenitor cells in the adult heart. Basic Res. Cardiol. 102: 101-114 (2007).
Maletic-Savatic, et al., J. Neurosci., 15: 3840 (1995).
Marban, E, Big cells, little cells, stem cells: agents of cardiac plasticity. Circ Res. 100(4):445-6 (2007).
Marshall, et al., Neuron, 14:211 (1995).
McGann, CJ et al., Mammalian myotube dedifferentiation induced by newt regeneration extract. Proc. Natl. Acad. Sci. USA 98, 13699-704 (2001).
Nadal-Ginard et al, Myocyte death, growth, and regeneration in cardiac hypertrophy and failure. Circ. Res. 92(2):139-50 (2003).
Nadal-Ginard et al., A matter of life and death: cardiac myocyte apoptosis and regeneration. J. Clin. Invest. 111: 1457-9 (2003).
Odelberg, SJ, Inducing cellular dedifferentiation: a potential method for enhancing endogenous regeneration in mammals., Semin Cell Dev. Biol., 13(5):335-43 (2002).
Odelberg, SJ et al., Dedifferentiation of mammalian myotubes induced by msx1. Cell 103(7):1099-1109 (2000).
Oh Hidemasa et al.: "Cardiac muscle plasticity in adult and embryo by heart-derived progenitor cells." Annals of The New York Academy of Sciences. vol. 1015, May 2004 (May 2004), pp. 182-189.
Passier, R et al., Origin and use of embryonic and adult stem cells in differentiation and tissue repair. Cardiovasc. Res. 58(2):324-35 (2003).

Plotinikov, AN, "Biological Pacemaker Implanted in Canine Left Bundle Branch Provides Ventricular Escape Rhythms that Have Physiologically Acceptable Rates" Circulation, 109, pp. 506-512 (2004).
Ribera, J. of Neurosci, 16:1123 (1996).
Rucker-Martin, C et al., Dedifferentiation of atrial myocytes during atrial fibrillation: role of fibroblast proliferation in vitro. Cardiovasc. Res. 55: 38-52 (2002).
Rudy, Neuroscience, 25:729 (1998).
Serodio, J. Neurophys., 75:2174 (1996).
Smith et al., Stem Cells in the heart: what's the buzz all about? Part 1: Preclinical considerations. Heart Rhythm 5(5):749-757(2008).
Smith et al., Stem Cells in the heart: what's the buzz all about? Part 2: Arrhythmic risks and clinical studies. Heart Rhythm 5(6):880-887 (2008).
Smith, RR et al., Regenerative potential of cardiosphere-derived cells expanded from percutaneous endomyocardial biopsy specimens. Circulation 115: 896-908 (2007).
Sussman et al., Myocardial aging and senescence: where have the stem cells gone? Annu Rev. Physiol. 66:29-48 (2004).
Torella, D et al., Cardiac stem cell and myocyte aging, heart failure, and insulin-like growth factor-I overexpression. Circ. Res 94:514-24 (2004).
Torella, D et al., Resident human cardiac stem cells: role in cardiac cellular homeostasis and potential for myocardial regeneration. Nat. Clin. Pract. Cardiovasc. Med. 3 Suppl 1:S8-13 (2006).
Urbanek, K et al., Cardiac Stem Cells Possess Growth Factor Receptor Systems That After Activation Regenerate the Infarcted Myocardium, Improving Ventricular Function and Long-term Survival. Circ. Res. 97:663-673 (2005).
Urbanek, K et al., Intense myocyte formation from cardiac stem cells in human cardiac hypertrophy. Proc. Natl. Acad. Sci. USA 100(18):10440-5 (2003).
Urbanek, K et al., Myocardial regeneration by activation of multipotent cardiac stem cells in ischemic heart failure. Proc. Natl. Acad. Sci. USA 102(24):8692-7 (2005).
Von Harsdorf, R, Can cardiomyocytes divide? Heart 86: 481-482 (2001).
Wagner, Nature Medicine, 1:1116 (1995).
Walder, S et al., Up-regulation of neural stem cell markers suggests the occurrence of dedifferentiation in regenerating spinal cord. Dev. Genes Evol. 213: 625-630 (2003).
Web Page titled; bioptome.com—Scholten Surgical Instructions; downloaded from <http://www.bioptome.com/pages.php?page=Products>, first date of publication unknown, printed on Nov. 1, 2005.
Wu et al., Cellular Therapy and Myocardial tissue engineering: the role of adult stem and progenitor cells. Eur. J. of Cardio-Thoracic Surg. 30:770-781 (2006).
Zammit, PS et. al, The skeletal muscle satellite cell: stem cell or son of stem cell? Differentiation 68: 193-204 (2001).
Duff, Sarah E. et al; "CD105 is important for angiogenesis: evidence and potential applications"; FASEB J.; Jun. 2003; vol. 17; No. 9; pp. 984-992.
D. C. Andersen et al., "Murine "Cardiospheres" Are not a Source of Stem Cells With Cardiomyogenic Potential," Stem Cells, 2009, vol. 27, No. 7, pp. 1571-1581.
Extended European Search Report dated Dec. 28, 2009, in European Application No. 05817349.3.
Web Page titled: bioioptome.com—Scholten Surgical Instructions; downloaded from <http://www.bioptome.com/pages.php?page=Products>, 2001.
Abela et al. "A New Method for Isolation of Cardiac Myocytes by Percutaneous Endomyocardial Biopsy" Catheterization and Cardiovascular Diagnosis 37:227-230 (1996).
Harvey 2002. Chapter 16. Molecular determinants of cardiac development and congenital disease. Mouse Development, Patterning, Morphogenesis, and Organogensis, pp. 331-370.
Messina E, et al. "Isolation and Expansion of Adult Cardiac Stem Cells From Human and Murine Heart." Circulation Research. 2004;95;911-921.

(56) References Cited

OTHER PUBLICATIONS

Beltrami AP. et al. "Adult cardiac stem cells are multi potent and support myocardial regeneration." Cell. Sep. 19, 2003; 114(6):763-76. Abstract.
Y. Tomita et al., "Cardiac Nural Crest Cells Contribute to the Dorman Multipotent Stem Cell in the Mammalian Heart," Journal of Cell Biology, Sep. 26, 2005, vol. 170, No. 7, pp. 1135-1148.
Fiset, et al., "Shal-type channels contribute to the Ca2+-independent transient outward K+ current in rat ventricle," Journal of Physiology, 500.1, pp. 51-64, 1997.
Barr et al., "Efficient catheter-mediated gene transfer into the heart using replication-defective adenovirus," Gene Therapy, 1, pp. 51-58, 1994.
Oh et al., "Cardiac progenitor cells from adult myocardium: Homeing, differentiation, and fusion after infarction," PNAS, Oct. 14, 2003, vol. 100, No. 21, pp. 12313-12318.
Edelberg JM, Lee SH, Kaur M, et al. Platelet-derived growth factor-AB limits the extent of myocardial infarction in a rat model: feasibility of restoring impaired angiogenic capacity in the aging heart. Circulation 2002;105(5):608-13.
European Search Report dated Nov. 13, 2012, in related European Application No. EP 12177594.
Fernandez-Aviles F, San Roman JA, Garcia-Frade J, et al. Experimental and clinical regenerative capability of human bone malTOW cells after myocardial infarction. Circ Res 2004;95(7):742-8.
Hoppe UC, Marban E, Johns D: Distinct gene-specific mechanisms of arrhythmia revealed by cardiac gene transfer of two long QT disease genes, HERG and KCNE 1. Proc Natl Acad Sci US A 2001;98(9):5335-40.
International Search Report and Written Opinion Issued in related International Application No. PCT/US2005/040359, dated May 9, 2008.
International Preliminary Report on Patentability Issued in related International Application No. PCT/US2005/040359 dated Mar. 17, 2009.
Japanese Office Action issued in related Japanese Application No. 2012-229481, dated Dec. 3, 2014.
Japanese Office Action issued in related Japanese Application. No. 2012-229481, dated Dec. 9, 2013.
Kobashigawa J, Miller L, Renlund D, et al. A randomized active-controlled trial of mycophenolate mofetil in heart transplant recipients. Mycophenolate Mofetil Investigators. Transplantation 1998;66(4):507-15.
Limana F, Germani, A, Zacheo A, et al. Exogenous High-Mobility Group Box 1 Protein Induces Myocardial Regeneration After Infarction via Enhanced Cardiac C-Kit+ Cell Proliferation and Differentiation. Cicr Res 2005.
Menasche P, Hagege AA, Vilquin JT, et al. Autologous skeletal myoblast transplantation for severe postinfarction left ventricular dysfunction. J Am Coll Cardiol 2003 ;41(7):1078-83.
Pfeffer MA, Pfeffer JM, Fishbein MC, et al. Myocardial infarct size and ventricular function in rats. Circ Res 1979;44(4):503-12.
Quaini F, Urbanek K, Beltrami AP, et al. Chimelism of the transplanted heart. N Engl J Med 2002;346(1):5-15.
Rubio D, Garcia-Castro J, Martin MC, et al. Spontaneous human adult stem cell transformation. Cancer Res 2005;65(8):3035-9.
Schachinger V, Assmus B, Britten MB, et al. Transplantation of progenitor cells and regeneration enhancement in acute myocardial infarction: final one-year results of the TOPCARE-AMI Trial. J Am Coll Cardiol 2004;44(8):1690-9.
Siminiak T, Kalawski R, Fiszer D, et al. Autologous skeletal myoblast transplantation for the treatment ofpostinfarction myocardial injury: phase I clinical study with 12 mouths of follow-up. Am Heart J 2004;148(3):531-7.
Smits PC, van Geuns RJ, Poldermans D, et al. Catheter-based intramyocardial injection of autologous skeletal myoblasts as a primary treatment of ischemic heart failure: clinical experience with six-month follow-up. J Am Coll Cardiol 2003;42(12):2063-9.
Strauer BE, Brehm M, Zeus T, et al. Repair of infarcted myocardium by autologous intracoronary mononuclear bone marrow cell transplantation in humans. Circulation 2002;106(15):1913-8.
Stull et al., "Chronic Treatment With Allopurinol Boosts Survival and Cardiac Contractility in Murine Postischemic Cardiomyopathy" Circ Res 2004;95(10):1005-11.
Taylor DO, Barr ML, Radovancevic B, et al. A randomized, multicenter comparison of tacrolimus and cyclosporine immunosuppressive regimens in cardiac transplantation: decreased hyperlipidemia and hypertension with tacrolimus. J Heart Lung Transplant 1999; 18( 4):336-45.
Urbanek K, Rota M, Cascapera S, et al. Cardiac Stem Cells Possess Growth Factor—Receptor Systems That After Activation Regenerate the Infarcted Myocardium Improving Ventricular Function and Long-Term Survival. Circ Res 2005.
Zeger SL, Liang KY. Longitudinal data analysis for discrete and continuous outcomes. Biometrics 1986;42(1):121-30.
Aminzadeh et al., "Mitigation of Skeletal Myopathy After Intramyocardial Injection of Cardiosphere-derived Cells in the Mdx Mouse Model of Duchenne Muscular Dystrophy", Circulation Research, Dec. 4, 2015, No. 22919, pp. e122-e127.
Gallet et al. "Exosomes Secreted by Cardiosphere-Derived Cells Reduce Scarring, Attenuate Adverse Remodeling, and Improve Function in Acute and Chronic Porcine Myocardial Infarction", European Heart Journal. Jan. 14, 201,7, vol. 38, pp. 201-211.
Rogers et al., "Intravenous Delivery of Cardiosphere-Derived Cells Improves Striated Muscle Function and Structure in a Murine Model of Duchenne Muscular Dystrophy", The FASEB Journal, Apr. 22-26, 2017, vol. 31, No. S1, pp. 3.
"ATS/ACCP Statement on Cardiopulmonary Exercise Testing", American Thoracic Societvi'American College of Chest Physicians, American Journal of Respiratory and Critical Care Medicine, 167: 211-277 2003.
"CArdiosphere-Derived aUtologous Stem CEIs to Reverse ventricular dysfunction (CADUCEUS)", ainicalTnals.gov, Identifier NCT00893360, 6, 2009.
"Culture Media Database", EGM-2 (Endothelial Growth Medium 2) - ID 63, downloaded from <http://biolonza.com/3018.html#ext-comp-1003:tab 63 change, printed on Jan. 14, 2 013, p. 1.
Abdel-Latif et al., "Adult Bone Marrow-Derived Cells for Cardiac Repair: A Systematic Review and Meta-Analysis", Archives of Internal Medicine, 167: 989-997, 2007.
Agrahari et al.. "How Are We Improving the Deliverv to Back of the Eye? Advances and Challenges of Novel Therapeutic Approaches", Expert Opinion on Drug Delivery, 14(10): 1145-1162, 2017.
Ajijola et al., "Ventricular Tachycardia in Ischemic Heart Disease Substrates", Indian Heart Journal, 66: S24-S34, 2014.
Albini et al., "A Rapid in Vitro Assay for Quantitating the Invasive Potential of Tumor Cells", Cancer Research, 47: 3239-3245, 1987.
Ames et al. , "Oxidants, Antioxidants, and the Degenerative Diseases of Aging", Proceedings of the National Academy of Sciences of the United States of America, 90: 7915-7922. 1993.
Aminzadeh et al., "Exosome-Mediated Benefits of Cell Therapy in Mouse and Human Models of Duchenne Muscular Dystrophy". Stem Cell Reports, 10(3): 942-955, 2018.
Aminzadeh et al., "Heart-Derived Cell Therapy for Duchenne Cardiomyopathy: Cardiosphere-Derived Cells and their Exosomes Improve Function, Restore Mitochondrial Integrity and Reverse Degenerative Changes in the Hearts ofMdx Mice", Circulation Research, 115(12): 24248, E90-E91. 20 14.
Assmus et al., "Transplantation of Progenitor Cells and Regeneration Enhancement in Acute Myocardial Infarction (TOPCARE-AMI)", Circulation, 106: 3009-3017. 2002.
Ausma et al., "Dedifferentiation of Atrial Cardiomyocytes: From in Vivo to In Vitro", Cardiovascular Research, 55(1): 9-12, 2002.
Baker et al. "Adaptation to Culture of Human Embryonic Stem Cells and Oncogenesis in Vivo" Nature Biotechnology, 25(2): 207-215,2007.
Barbash et al., "Systemic Delivery of Bone-Marrow-Derived Mesenchymal Stem Cells to the Infarcted Myocardium Feasibility, Cell Migration, and Bodv Distribution," Circulation, 108: 863-868,2003.

(56) References Cited

OTHER PUBLICATIONS

Barile et al., "Human Cardiospheres as a Source of Multipotent Stem and Progenitor Cells", Hindawi Publishing Corporation, Stem Cells International, 2013: 10, 2013.
Bearzi et al., "Human Cardiac Stem Cells", Proceedings of the National Academy of Sciences of the United States of America (PNAS), 104(35): 14068-14073, 2007.
Beltrami et al., "Multipotent Cells Can be Generated In Vitro from Several Adult Human Organs (Heart, Liver and Bone Marrow)". Stem Cells in Hematology, Blood, 110(9): 3438-3446, 2007.
Bergmann et al., "Evidence for Cardiomyocyte Renewal in Humans", Science, 324: 98-102, 2009.
Bernanke et al., "Effects of Hyaluronic Acid on Cardiac Cushion Tissue Cells in Collagen Matrix Cultures", Texas Reports on Biology and Medicine, 39: 271-285, 1979.
Bird et al., "The Human Adult Cardiomyocyte Phenotype", Cardiovascular Research, 58(2): 423-434, 2003.
Birks et al., "Left Ventricular Assist Device and Drug Therapy for the Reversal of Heart Failure", The New England Journal of Medicine, 355(18): 1873-1884, 2006.
Bjelakovic et al., "Mortality in Randomized Trials of Antioxidant Supplements for Primary and Secondary Prevention: Systematic Review and Meta-Analysis", JAMA, 297: 842-857, 2007.
Bosnali et al., "Generation of Transducible Versions of Transcription Factors Oct. 4 and Sox2". Biological Chemistry, 389: 851-861. 2008.
Bredemeyer et al., "ATM Stabilizes DNA Doubie-Strand-Break Complexes During V(D)J Recombination", Nature, 442: 466-470, 2006.
Cai et al., "Injectable Glycosaminoglycan Hydrogels for Controlled Release of Human Basic Fibroblast Growth Factor," Biomaterials, 26: 6054-6067, 2005.
Cambier et al., "Y RNA Fragment in Extracellular Vesicles Confers Cardioprotection via Modulation of IL-10 Expression and Secretion", EMBO Molecular Medicine, 9(3): 337-352, 2017.
Chambers et al., "Functional Expression Cloning of Nanog, a Pluripotency Sustaining Factor in Embryonic Stem Cells", Cell, May 30, 2003, 113(5): 643-655, 2003.
Chen et al., "Enhanced Tumorigenesis in p53 Knockout Mice Exposed in Utero to High-Dose Vitamin E", Carcinogenesis, 27(7): 1358-1368. 2006.
Chen et al., "Mesenchymal Stem Cell Secretes Microparticles Enriched in Pre-MicroRNAs", Nucleic Acids Research, 38(1): 215-224, 2010.
Chen et al., "Reduced Tumorigenesis in p53 Knockout Mice Exposed in Utero to Low-Dose Vitamin E", Cancer, 115: 1563-1575, 2009.
Chen et al., "The Role of Notch 1 Activation in Cardiosphere Derived Cell Differentiation", Stem Cells and Development, 21(12): 2122-2129, 2012.
Chen et al., "Vascular Endothelial Growth Factor Promotes Cardiomyocyte Differentiation of Embryonic Stem Cells". American Journal of Physiologv-Heart and Circulatory Physiology. 291(4): H1653-H165, 2006.
Cheng et al., "Functional Performance of Human Cardiosphere-Derived Cells Delivered in an in situ Polymerizable Hyaluronan-Gelatin Hydrogel", Biomaterials, 8 pages, 2012.
Cheng et al., "Magnetic Targeting Enhances Engraftment and Functional Benefit of Iron-Labeled Cardiosphere-Derived Cells in Myocardial Infarction", Circulation Research, 160: 1570-1581, 2010.
Cheng et al., "Relative Roles of CD90 and c-Kit to the Regenerative Efficacy of Cardiosphere-Derived Cells in Humans and in a Mouse Mode of Myocardial Infarction", Journal of the American Heart Association, 3(5): 1-10, 2014.
Cheng et al., "Transplantation of Platelet Gel Spike with Cardiosphere-Derived Cells Boosts Structural and Functional Benefits Relative to Gel Transplantation Alone in Rats with Myocardial Infarction", Biomaterials, 33: 2872-2879, 2012.
Chimenti et al., "Abstract 3182: Paracrine Contribution versus Direct Regeneration in Cardiosphere-Derived Cell Therapy for Acute Myocardial Infarction", Circulation, 120: S756, 2009.
Chimenti et al., "Relative Roles of Direct Regeneration Versus Paracrine Effects of Human Cardiosphere-Derived Cells Transplanted Into Infarcted Mice", Circulation Research, 160: 971-980, 2010.
Chlopcikova et al., "Neonatal Rat Cardiomyocytes—A Model for the Study of Morphological Biochemical and Electrophysiological Characteristics of the Heart", Biomedical Papers. 145(2): 49-55, 2001.
Christman et al., "Biomaterials lor the Treatment of Myocardial Infarction", Journal of the American College Of Cardiology, 48(5): 907-913, 2006.
Conkright et al., "A Gene Encoding an Intestinal-Enriched Member of the Krüppel-Like Factor Family Expressed in Intestinal Epithelia Cells", Nucleic Acids Research, 27(5): 1263-1270, 1999.
Cooper et al., "Immunobiological Barriers to Xenotransplantation", International Journal of Surgery, 23:211-216, 2015.
Crisostomo et al., "Embryonic Stem Cells Attenuate Myocardial Dysfunction and Inflammation After Surgical Global Ischemia Via Paracrine Actions", American Journal of Physiology-Heart and Circulatory Physiology, 295: H1726-H1735, 2008.
Csete, "Oxygen in the Cultivation of Stem Cells", Annals New York Academy of Sciences. 1049: 1-8, 2005.
Davis et al., "Human Cardiospheres are a Source of Stem Cells with Cardiomyogenic Potential", Stem Cells, 28(5): 903-904, 2010.
Davis et al., "Isolation and Expansion of Functionally-Competent Cardiac Progenitor Cells Directly from Heart Biopsies", Journal of Molecular and Cellular Cardiology, 49(2): 312-321, 2010.
Davis et al., "Validation of die Cardiosphere Method to Culture Cardiac Progenitor Cells from Myocardial Tissue", PLoS One, 4(9): e7195, pp. 1-8, 2009.
De Bakker et al. "Slow Conduction in the Infarcted Human Heart 'Zigzag' Course of Activation" . Circulation, 88(3): 915-926, 1993.
De Couto et al., "Macrophages Mediate Cardioprotective Cellular Postconditioning in Acute Myocardial Infarction", The Journal of Clinical Investigation. 125(8): 3147-3162, 2015.
Del Monte et al., "Abrogation of Ventricular Arrhythmias in a Model of Ischemia and Reperfusion by Targeting Myocardial Calcium Cycling", Proceedings of the National Academy of Sciences of the United States of America (PNAS), 101(15): 5622-5627, 2004.
Deregibus et al., "Endothelial Progenitor Cell-Derived Microvesicles Activate an Angiogenic Program in Endothelial Cells by a Horizontal Transfer of mRNA", Blood, 110(7): 2440-2448, 2007.
Derossi et al., "The Third Helix of the Antennapedia Homeodomain Translocates through Biological Membranes". The Journal of Biological Chemistry, 269(14): 10444-10450, 1994.
Di Meglio et al., "In Vitro Cultured Progenitors and Precursors of Cardiac Cell Lineages from Human Nornal and Post-Ischemic Hearts", European Journal of Histochemistry, October-Dec ember 51(4): 275-285, 2007.
Dib et al.. "Cell Therapy for Cardiovascular Disease: A Comparison of Methods of Delivery", Journal of Cardiovascular Translational Research, 4: 177-181,2011.
Djokic et al., "Post-Transplant Lymphoproliferative Disorder Subtypes Correlate with Different Recurring Chromosomal Abnormalities", Genes, Chromosomes & Cancer, 45: 313-318, 2006.
Dong et al., "Islet Cell and Extrapancreatic Expression of the LIM Domain Homeobox Gene isl-1", Molecular Endocrinology, 5(11): 1633-1641. 1991.
Drakos et al., "Impact of Mechanical Unloading on Microvasculature and Associated Central Remodeling Features of the Failing Human Heart", Journal of the American College of Cardiology, 56(5): 382-391, 2010.
Eguchi, "Recent Advances in Selective Opioid Receptor Agonists and Antagonists", Medicinal Research Reviews, 24(2): 182-212. 2004.
Elliott et al., "Intercellular Trafficking and Protein Delivery by a Herpesvirus Structural Protein", Cell, 88: 223-233, 1997.
Elliott et al... "Intercellular Trafficking of VP22-GFP Fusion Proteins". Gene Therapy, 6: 149-151. 1999.

(56) References Cited

OTHER PUBLICATIONS

Engel et al., FGF1/p38 MAP Kinase Inhibitor Therapy Induces Cardiomvocyte Mitosis, Reduces Scarring, and Rescues Function after Myocardial Infarction, Proceedings of the National Academy of Sciences of the United States of America (PNAS), 103(42): 15546-1555 i, 2006.
Eppenberger-Eberhardt et al., "Reexpression of a-Smooth Muscle Acting Isoform in Cultured Adult Rat Cardiomyocytes", Developmental Biology, 139(2): 269-278, 1990.
Eschenhagen et al., "Engineering Myocardial Tissue", Circulation Research, 97: 1220-1231,2005.
Falck et al., "Conserved Modes of Recruitment of Atm, Atr and DNA-PKcs to Sites of DNA Damage", Nature, 434: 605-611, 2005.
Fehrer et al. "Reduced Oxygen Tension Attenuates Differentiation Capacity of Human Mesenchymal Stem Cells and Prolongs their Lifespan", Aging Cell, 6: 745-757. 2007.
Foreman et al., "Reactive Oxygen Species Produced by NADPH Oxidase Regulate Plant Cell Growth", Nature, 422: 442-446, 2003.
Frankel et al., "Cellular Uptake of the Tat Protein from Human Immunodeficiency Virus", Cell, 55: 1189-1193,1988.
Freyman et al.. "A Quantitative, Randomized Studv Evaluating Three Methods of Mesenchymal Stem Cell Delivery Following Myocardial Infarction", European Heart Journal, 27: 1114-1122, 2006.
Furlani et al., "A Transformed Cell Population Derived From Cultured Mesenchymal Stem Cells Has No. Functional Effect After Transplantation Into the Injured Heart", Cell Transplantation. 18: 319-331.2009.
Gallet et al., "Cardiosphere-Derived Cells Reverse Heart Failure With Preserved Ejection Fraction in Rats by Decreasing Fibrosis and Inflammation". JACC: Basie to Translational Science. 1(1-2): 14-28,2016.
Gallet et al, "Intracoronary Delivery of Self-Assembling Heart-Derived Microtissues (Cardiospheres) For Prevention of Adverse Remodeling In a Pig Model of Convalescent Myocardial Infarction", <http://circinterventions.ahajournals.org, 21, 2015.
Galli et al., "Neural Stem Cells: An Overview", Circulation Research, 92(6): 598-608, 2003.
Gatti et al., Microvesicles Derived from Human Adult Mesenchymal Stem Cells Protect. Against Ischaemia-Reperfusion-Induced Acute and Chronic Kidney Injury, Nephrology Dialysis Transplantation. 26(5): 1474-1483, 2011.
George et al., "Echocardiographic Assessment of Flow Across Continuous-Flow Ventricular Assist Devices at Low Speeds", The Journal of Heart and Lung Transplantation, 29(11): 1245-1252, 2010.
Gibco, "Insulin-Transferrin-Seleniinn", Product Sheet, 2014.
Gibco, "Insulin-Transferrin-Selenium: 100X (For General Tissue Culture Applications)", Product Sheet, Form No. 2672: 1, 2001.
Glover et al., "Reduction of Infarct Size and Postischemic Inflammation from ATL-146e, a Highly Selective Adenosine A2A Receptor Agonist in Reperfused Canine Myocardium", American Journal of Physiology-Heart and Circulatory Physiology, 288(4): H1 851-H1858, 2005.
Gomez-Marquez et al., "Thymosin- Gene: Preliminary Characterization and Expression in Tissues, Thymic Cells, and Lymphocytes", The Journal of Immunology, 143(8): 2740-2744, 1989.
Goumans et al., "TGF-β1 Induces Efficient Differentiation of Human Cardiomyocyte Progenitor Cells into Functional Cardiomyocytes In Vitro", Stem Cell Research, 1: 13 8-149, 2008.
Grayson et al. "Hypoxia Enhances Proliferation and Tissue Formation of Human Mesenchymal Stem Cells", Biochemical and Biophysical Research Communications, 358: 948-953, 2007.
Green et al, "Autonomous Functional Domains of Chemically Synthesized Human Immunodeficiency Virus Tat Trans-Activator Protein", 55: 1179-1188, 1988.
Grigorian-Shamagian et al., "Cardiac and Systemic Rejuvenation After Cardiospliere-Derived Cell Therapy in Senescent Rats", European Heart Journal, 38(39): 2957-2967, 2017.
Grigorian-Shamagian et al., "Harnessing the Heart's Resistance to Malignant Tumors: Cardiac-Derived Extracellular Vesicles Decrease Fibrosarcoma Growth and Leukemia-Related Mortality in Rodents", Oncotarget, 8(59): 99624-99636, 2017.
Grossman et al., "Contractile State of the Left Ventricle in Man as Evaluated from End-Systolic Pressure-Volume Relations", Circulation, 56(5): 845-852, 1977.
Gu, "Bispecific Antibody Targeted Stem Cell Therapy for Myocardial Repair", Dissertation, University of California San Francisco and University of California Berkeley, p. 94, 2008.
Gubhay et al., "A Gene Mapping to the Sex-Determining Region of the Mouse Y Chromosome is a Member of a Novel Family of Embryonically Expressed Genes", Nature, 346: 245-250, 1990.
Hacein-Bey-Abina et al., "LMO2-Associated Clonal T Cell Proliferation in Two Patients after Gene Therapy for SCID-X1", Science, 302: 415-419 with Erratumin 1 p. 2003.
Haderk et al., "Tumor-Derived Exosomes Modulate PD-L1 Expression in Monocytes", Science Immunology. 2(13): 1-11, 2017.
Hagege et al., "Skeletal Myoblast Transplantation in Ischemic Heart Failure: Long-Term Follow-Up of the First Phase I Cohort of Patients", Circulation, 114(1): 1108-1113, 2006.
Haider et al., "Bone Marrow Stem Cell Transplantation for Cardiac Repair", American Journal of Physiology-Heart and Circulatory Physiology, 288: H2557-H2567, 2005.
Hainsworth et al., "The Nitrone Disodium 2,4-Sulphophenyl-N-Tert-Butylnitrone is Without Cytoprotective Effect on Sodium Nitroprusside-Induced Cell Death in NIE-115 Neuroblastoma Cells in vitro", Journal of Cerebral Blood Flow & Metabolism, 28: 24-28, 2008.
Haj-Yahia et al., "Limited Surgical Approach for Explanting the HeartMate II Left Ventricular Assist Device after Myocardial Recovery", The Journal of Thoracic and Cardiovascular Surgery, 135(2): 453-454, 2008.
Hens et al., "Incorporating Protein Transduction Domains (PTD) Within Recombinant 'Fusion' Transcription Factors. A Novel Strategy for Directing Stem Cell Differentiation?" Biomedicine and Pharmacotherapy, 59(3): 132-134, 2005.
Hergenreider et al., "Atheroprotective Communication Between Endothelial Cells and Smooth Muscle Cells Through miRNAs", Nature Cell Biology, 14(3): 249-256, 2012.
Herrera et al., "Human Liver Stem Cell-Derived Microvesicles Accelerate Hepatic Regeneration in Hepatectomized Rats", Journal of Cellular and Molecular Medicine, 14(6B):. 1605-1618, 2010.
Hierlihy et al., "The Post-Natal Heart Contains a Myocardial Stem Cell Population", FEBS Letters, 530(1-3): 239-243, 2002.
Hine et al., "NRF2 and the Phase II Response in Acute Stress Resistance Induced by Dietary Restriction", Journal of Clinical & Experimental Pathology, S4(4): 1-33, 2012.
Hochedlinger et al., "Nuclear Reprogramming and Pluripotency". Nature, 441: 1061-1067, 2006.
Hu et al., "MicroRNA-210 as a Novel Therapy for Treatment of Ischemic Heart Disease", Circulation, 122: Supplement 11, S124-S131, pp. 17, 2010.
Hullinger et al., Inhibition of miR-15 Protects Against Cardiac Ischemic Injury, Circulation Research, 110(1): 71-81, 2012.
Ibrahim et al., "Exosomes as Critical Agents of Cardiac Regeneration Triggered by Cell Therapy", Stem Cell Reports, 2: 606-619, 2014.
Ibrahim et al., "Exosomes: Fundamental Biology and Roles in Cardiovascular Physiologv", Annual Review of Physiology, 78: 67-83, 2016.
Ibrahim et al., "Microma-Containing Exosomes from Cardiospliere-Derived Cells Stimulate Cardiomyocyte Proliferation and Angiogenesis in Vitro, and Improve Functional Recovery after Myocardial Infarction in Mice", 126: Abs. 14697,4, 2012.
Ibrahim et al., "Role of Exosomes and Their MicroRNA Constituents in Mediating the Therapeutic Benefits of Human Cardiosphere-Derived Cells in Vitro and in Mice with Myocardial Infarction", Circulation, 128(22): Abs. 19186, 2, 2013.
Ikehara, et al., "Grand Challenges in Stem Cell Treatments", Frontiers in Cell and Developmental Biology. 1(2): 2, 2013.
Ivanovic, "Hypoxia or In Situ Normoxia: The Stem Cell Paradigm", Journal of Cellular Physiology, 219:271-275, 2009.

(56) References Cited

OTHER PUBLICATIONS

Javawardena et al., MicroRNA-Mediated In Vitro and In Vivo Direct Reprogramming of Cardiac Fibroblasts to Cardiomyocytes, Circulation Research, 110(11): 1465-1473, 2012.
Jolnston et al., "Engraftment, Differentiation, and Functional Benefits of Autologous Cardiosphere-Derived Cells in Porcine Ischemic Cardiomyopathy", Circulation, 120: 1075-1083, 2009.
Jutkiewicz. The Antidepressant-Like Effects of Delta-Opioid Receptor Agonists, Molecular Interventions, 6(3): 162-169, 2006.
Kamdar et al., "Dystrophin-Deficient Cardiomyopathy", Journal of the American College of Cardiology, 67(21): 2533-2546, 2016.
Karlsson et al., "Insulin Gene Enhancer Binding Protein Is1-1 is a Member of a Novel Class of Proteins Containing Both a Homeo-and a Cys-His Domain", Nature. 344: 879-882, 1990.
Karoubi et al., "Single-Cell Hydrogel Encapsulation for Enhanced Survival of Human Marrow Stromal Cells", Biomaterials, 30: 5445-5455, 2009.
Kaspar et al., "Current Understanding and Management of Dilated Cardiomyopathy in Duchenne and Becker Muscular Dystrophy", Journal of the American Association of Nurse Practitioners, 21(5): 241-249, 2009.
Kawaguchi et al., "Cell Shape and Cardiosphere Differentiation: A Revelation by Proteomic Profiling", Hindawi Publishing Corporation, Biochemistry Research International, vol. 2013, Article ID 730874: 1-9, 2013.
Kim et al., "Generation of Human Induced Pluripotent Stem Cells by Direct Delivery of Reprogramming Proteins", Cell Stem Cell, 4(6): 472-476, 2009.
Kisselbach et al., "CD90 Expression on Human Primary Cells and Elimination of Contaminating Fibroblasts from Cell Cultures", Cytotechnology, 59: 31-44, 2009.
Kooijmans et al., "PEGylated and Targeted Extracellular Vesicles Display Enhanced Cell Specificity and Circulation Time", Journal of Controlled Release. 224: 77-85, 2016.
Kulm et al., "Periostin Induces Proliferation of Differentiated Cardiomyocytes and Promotes Cardiac Repair", Nature Medicine, 13(8): 962-969, 2007.
Kutschka et al., "Collagen Matrices Enhance Survival of Transplanted Cardiomyoblasts and Contribute to Functional Improvement of Ischemic Rat Hearts", Circulation, 114: 1167-11 73, 2006.
Kwon et al., "Cellular Manipulation of Human Embryonic Stem Cells by TAT-PDX1 Protein Transduction," Molecular Therapy, 12(1): 28-32, 2005.
Kyrtatos et al., "Magnetic Tagging Increases Delivery of Circulating Progenitors in Vascular Injury". Journal of the American College of Cardiology: Cardiovascular Interventions, 2(8): 794-802, 2009.
Laflamme et al., "Cardiomyocytes Derived from Human Embryonic Stem Cells in Pro-Survival Factors Enhance Function of Infarcted Rat Hearts", Nature Biotechnology, 25(9): 1015-1024, 2007.
Lai et al., "Exosome Secreted by MSC Reduces Myocardial Ischemia/Reperfusion Injury", Stem Cell Research, 4(3): 214-222, 2010.
Landazuri et al., "Complexation of Retroviruses with Charged Polymers Enhances Gene Transfer by Increasing the Rate that Viruses are Delivered to Cells", The Journal of Gene Medicine, 6: 1304-1319, 2004.
Lapchak et al., "Intravenous Xenogeneic Human Cardiosphere-Derived Cell Extracellular Vesicles (Exosomes) Improves Behavioral Function in Small-Clot Embolized Rabbits", Experimental Neurology, 307: 109-117, 2018.
Lavon et al., "Derivation of Euploid Human Embryonic Stem Cells from Aneuploid Embryos", Stem Cells. 26: 1874-1882, 2008.
Lee et al., "Antibody Targeting of Stem Cells to Infarcted Myocardium", Stem Cells: Translational and Clinical Research, 25: 712-717, 2007.
Lee et al., "Intramyocardial Injection of Autologous Cardiospheres or Cardiospliere-Derived Cells Preserves Function and Minimizes Adverse Ventricular Remodeling in Pigs With Heart Failure Post-Myocardial Infarction", Journal of the American College of Cardiology, 57(4): 455-465, 2011.
Leferovich et al., "Heart Regeneration in Adult MRL Mice". Proceedings of the National Academy of Sciences of the United States of America (PNAS), 98(17): 9830-9835, 2001.
Leor et al., "Transplantation of Fetal Myocardial Tissue Into the Infarcted Myocardium of Rat", Circulation, 94(9): 11-332-11336, 1996.
Levenberg et al., "Endothelial Cells Derived from Human Embryonic Stem Cells", Proceedings of the National Academy of Sciences of the United States of America (PNAS), Developmental Biology, 99(7): 4391-4396, 2002.
Levine et al., "Vitamin C Pharmacokinetics in Healthv Volunteers: Evidence for a Recommended Dietary Allowance", Proceedings of die National Academy of Sciences of the United States of America, 93: 3704-3709. 1996.
Li et al., "Cardiospheres Recapitulate a Niche-Like Microenvironment Rich in Stemness and Cell-Matrix Interactions, Rationalizing Their Enhanced Functional Potency for Myocardial Repair", Stem Cells: Translational and Clinical Research, 28: 2088-2098, 2010.
Li et al., "Direct Comparison of Different Stem Cell Types and Subpopulations Reveals Superior Paracrine Potency and Myocardial Repair Efficacy with Cardiospliere-Derived Cells", Journal of American College of Cardiology, 59(10): 942-953, 2012.
Li et al., "Expansion of Human Cardiac Stem Cells in Physiological Oxygen Improves Cell Production Efficiency and Potency for Myocardial Repair", Cardiovascular Research, 1-9, 2010.
Li et al., "IL-6 Contributes to the Defective Osteogenesis of Bone Marrow Stromal Cells from the Vertebral Body of the Glucocorticoid-Induced Osteoporotic Mouse", PLoS One, 11(4): 1, 2016.
Li et al., "Late-Breaking Basic Science Abstracts From the American Heart Association's Scientific Sessions 2009", Late-Breaking Basic Science Oral Abstracts: Translational Studies, Molecular, Cellular, and Functional Phenotypes of Human Cardiac Stem Cells Dependent Upon Monolayer Versus Three-Dimensional Culture Conditions. Abstract 5173. Circulation Research, 105(12): e56-e62, 2009.
Li et al., "Molecular, Cellular, and Functional Phenotypes of Human Cardiac Stem Cells Dependent Upon Monolayer Versus Three-Dimensional Culture Conditions", Circulation Research. 105(12): Abs. 5173, e58, 2009.
Li et al., "Physiological Levels of Reactive Oxygen Species Are Required to Maintain Genomic Stability in Stem Cells", Stem Cell, Stem Cell Technology: Epigenetics, Genomics, Proteomics, and Metabonomics, 28: 1178-1185, 2010.
Li et al., "Imaging Survival and Function of Transplanted Cardiac Resident Stem Cells", Journal of the American College of Cardiology, 53(14): 1229-1240, 2009.
Liao et al., "Enhanced Efficiency of Generating Induced Pluripotent Stem (iPS) Cells from Human Somatic Cells by a Combination of Six Transcription Factors", Cell Research, 18: 600-603, 2008.
Lin et al., "Accelerated Growth and Prolonged Lifespan of Adipose Tissue-Derived Human Mesenchymal Stem Cells in a Medium Using Reduced Calcium and Antioxidants", Stem Cells and Development, 14: 92-102, 2005.
Lindsay, "Peptide-Mediated Cell Delivery: Application in Protein Target Validation", Current Opinion in Pharmacology, 2: 587-594, 2002.
Lindsley et al., "The PI3K/Akt Pathway: Recent Progress in the Development of ATP-Competitive and Allosteric Akt Kinase Inhibitors", Current Cancer Drug Targets, 8: 7-18, 2008.
Lipinski et al., "Impact of Intracoronary Cell Therapy on Left Ventricular Function in the Setting of Acute Myocardial Infarction: A Collaborative Systematic Review and Meta-Analysis of Controlled Clinical Trials", Journal of the American College of Cardiology, 50(18): 1761-1767, 2007.
Liu et al. "Autologous Stem Cell Transplantation for Myocardial Repair", American Journal of Physiology, Heart and Circulatory Physiology, 287; H501-H511, 2004.
Liu et al., "Osteochondral Defect Repair with Autologous Bone Marrow-Derived Mesenchymal Stem Cells in an Injectable, In Situ, Cross-Linked Svnthetic Extracellular Matrix", Tissue Engineering, 12(12): 3405-3416. 2006.
Liu et al., "The Immunogenicity and Immune Tolerance of Pluripotent Stem Cell Derivatives", Frontiers in Immunology. 3(645) 1-6, 2017.

(56) References Cited

OTHER PUBLICATIONS

Lowry et al., "Generation of Human Induced Pluripotent Stem Cells from Dermal Fibroblasts", Proceedings of the National Academy of Sciences of the United States of America (PNAS). 105(8): 2883-2888, 2008.
Lum et al., "The New Face of Bispecific Antibodies: Targeting Cancer and Much More", Experimental Hematology, 34: 1-6, 2006.
Maitra et al, Genomic Alterations in Cultured Human Embryonic Stem Cells, Nature Genetics, 37(10): 1099-1103, 2005.
Makkar et al., "Intracoronary Cardiosphere-Derived Cells for Heart Regeneration After Myocardial Infarction (CADUCEUS): A Prospective, Randomised Phase 1 Trial" Lancet, 379: 895-904, 2012.
Malliaras et al., "Intracoronary Cardiosphere-Derived Cells After Myocardial Infarction", Journal of the American College of Cardiology, 63(2): 110-121, 2014.
Mangi et al., "Mesenchymal Stem Cells Modified with Akt Prevent Remodeling and Restore Performance of Infarcted Hearts," Nature Medicine, 9(9): 1195-1201, 2003.
Martens et al., "Percutaneous Cell Delivery Into the Heart Using Hydrogels Polymerizing In Situ", Cell Transplantation, 2009, 18(3): 297-304, 2009.
Matsumura, "Cardiaphal Association in Muscular Dystrophy", Nanbyo To Zaitaku Care (Intractable Diseases and Home Care), 19(8): 55-57, 2013.
Matsuura et al., "Adult Cardiac Sea-1-positive Cells Differentiate into Beating Cardiomyocytes", The Journal of Biological Chemistry, 2 79(12): 11384-11391, 2004.
Mehmel et al., "The Linearity of the End-Systolic Pressure-Volume Relationship in Man and its Sensitivity for Assessment of Left Ventricular Function", Circulation, 63: 1216-1222, 1981.
Middleton et al., "Newt Cells Secrete Extracellular Vesicles with Therapeutic Bioactivity in Mammalian Cardiomyocytes", Journal of Extracellular Vesicles, 7: 1-15, 2018.
Miller et al., Meta-Analysis: High-Dosage Vitamin E Supplementation May Increase All-Cause Mortality, Annals of Internal Medicine, 142: 37-46, 2005.
Miltenvi et al., "High Gradient Magnetic Cell Separation With MACS 1", Cytometry, 11: 231-238, 1990.
Mitsui et al., "The Homeoprotein Nanog is Required for Maintenance of Pluripotency in Mouse Epiblast and ES Cells", Cell, 113(5): 631-642, 2003.
Miyazono et al. "Latent High Molecular Weight Complex of Transforming Growth Factor β1", 263(13): 6407-6415, 1988.
Montessuit et al., "Regulation of Glucose Transporter Expression in Cardiac Myocytes: p38 MAPK is a Strong Inducer of GLUT4", Cardiovascular Research, 64(1): 94-104, 2004.
Montessuit et al., "Retinoic Acids Increase Expression of GLUT4 in Dedifferentiated and Hypertrophied Cardiac Myocytes", Basic Research in Cardiology, 101(1): 27-35, 2006.
Moss et al., "Conservation of the Heterochronic Regulator Lin-28, its Developmental Expression and MicroRNA Complementary Sites", Developmental Biology, 258(2): 432-442, 2003.
Moss et al., Prophylactic Implantation of a Defibrillator in Patients with Mvocardial Infarction and Reduced Ejection Fraction, The New England Journal of Medicine. 346(12): 877-883, 2002.
Murata et al., "C4d Deposition and Cellular Infiltrates as Markers of Acute Rejection in Rat Models of Orthotopic Lung Transplantation", Transplantation, 86(1): 123-129, 2008.
Naito-Matsui, "Lack of Neu5Gc Expression Contributes to the Severity of Duchenne Muscular Dystrophy in Humans", Trends in Glycoscience and Glycotechnology, 23(132): 194-196, 2011.
Naka et al, "Regulation of Reactive Oxygen Species and Genomic Stability in Hematopoietic Stem Cells", Antioxidants & Redox Signaling, 10(11): 1883-1894, 2008.
Nakagawa et al., "Generation of Induced Pluripotent Stem Cells without Myc from Mouse and Human Fibroblasts", Nature Biotechnology, 26(1): 101-106, 2008.

Nakasa et al., "Acceleration of Muscle Regeneration by Local Injection of Muscle-Specific MicroRNAs in Rat Skeletal Muscle Injury Model", Journal of Cellular and Molecular Medicine, 14(10): 2495-2505, 2010.
Nelson et al., "CXCR4+/FLK-1+ Biomarkers Select a Cardiopoietic Lineage from Embryonic Stem Cells", Stem Cells, 26: 1464-1473, 2008.
Nelson et al., "Repair of Acute Mvocardial Infarction with iPS Induced by Human Stemness Factors", Circulation, 120(5): 408-416, 2009.
Niethammer et al., "A Tissue-Scale Gradient of Hydrogen Peroxide Mediates Rapid Wound Detection in Zebrafish", Nature, 459: 996-999. 2009.
Noguchi et al., "Protein Transduction Technology: A Novel Therapeutic Perspective", Acta Medica Okayama, 60(1): 1-11. 2006.
North et al., "The Intersection Between Aging and Cardiovascular Disease", Circulation Research, 1097-1108, 2012.
Nussbaum et al., "Transplantation of Undifferentiated Murine Embryonic Stem Cells in the Heart: Teratoma Formation and Immune Response". The FASEB Journal. Research Communication, 21(7): 1345-1357, 2007.
Offord et al., "Photoprotective Potential of Lycopene, -Carotene, Vitamin E, Vitamin C and Carnosic in UVA-Irradiated Human Skin Fibroblasts", Free Radical Biology & Medicine,32(12): 1293-1303, 2002.
Okita et al., Generation of Mouse Induced Pluripotent Stem Cells Without Viral Vectors, 322: 949-953, 2008.
Ousaka et al., "Abstract 13881: Cardiac Progenitor Cell Infusion in Patients With Univentricular Heart Diseases in Heart Failure With Preserved Ejection Fraction", Circulation, Abstract 13881, vol. 132, <http://circ.ahajournals.org/content/132/Supp_3/A13881.short, 2015.
Owusu-Ansah et al., "Reactive Oxygen Species Prime Drosophila Haematopoietic Progenitors for Differentiation", Nature, 461: 537-541, 2009.
Park et al., "Reprogramming of Human Somatic Cells to Pluripotency with Defined Factors", Nature, 451: 141-146, 2008.
Passier et al., "Stem-Cell-Based Therapy and Lessons from the Heart", Nature, 453: 322-329, 2008.
Payne, "Using Immunomagnetic Technology and Other Means to Facilitate Stem Cell Homing". Medical Hypotheses, 62: 718-720, 2004.
Peterson et al., "Risk Stratification After Myocardial Infarction", Annals of Internal Medicine, 126(7): 561-582, 1997.
Pike et al., "Heparin-Regulated Release of Growth Factors In Vitro and Angiogenic Response In Vivo to Implanted Hvaluronan Hydrogels Containing VEGF and bFGF." Biomaterials. 27: 5242-5241, 2006.
Potapova et al., "Enhanced Recovery of Mechanical Function in the Canine Heart by Seeding an Extracellular Matrix Patch with Mesenchymal Stem Cells Committed to a Cardiac Lineage", American Journal of Physiology-Heart and Circulatory Physiology, 295: H2257-H2263, 2008.
Prestwich et al., "The Translational Imperative: Making Cell Therapy Simple and Effective", Acta Biomaterialia, 8: 4200-4207, 2012.
Prunier et al., "Delayed Erythropoietin Therapy Reduces Post-MI Cardiac Remodeling Only at a Dose that Mobilizes Endothelial Progenitor Cells", American Journal of Physiology-Heart and Circulatory Physiology, 292: H522-H529, 2007.
Puceat, "Role of Rac-GTPase and Reactive Oxygen Species in Cardiac Differentiation of Stem Cell", Antioxidants & Redox Signaling, 7(11-12): 1435-1439, 2005.
Qin et al., "ATM-Mediated Transcriptional Elevation of Prion in Response to Copper-Induced Oxidative Stress", The Journal of Biological Chemistry, 284(7): 4582-4593, 2009.
Quevedo et al., "Allogeneic Mesenchymal Stem Cells Restore Cardiac Function in Chronic Ischemic Cardiomyopathy via Trilineage Differentiating Capacity", Proceedings of the National Academy of Sciences of the United Statesof America (PNAS), 106(33): 14022-14027. 2009.
Rajasekaran et al., "Human αB-Crystallin Mutation Causes Oxido-Reductive Stress and Protein Aggregation Cardiomyopathy in Mice", Cell, 130(3): 427-439, 2007.

(56) References Cited

OTHER PUBLICATIONS

Ranghino et al., "Endothelial Progenitor Cell-Derived Microvesicles Improve Neovascularization in a Murine Model of Hindlimb Ischemia", International Journal of Immunopathology and Pharmacology, 25(1): 75-85, 2012.

Reiffel, "Ten Pearls for the Use of Antiarrhythmic Drugs for Atrial Fibrillation", Aug. 17, 2012, Retrieved from <http://www.acc.org/latest-in-cardiology/articles/2014/07/18/15/12/ten-pearls-for-the-use-of-antiarrhythmic-drugs-for-atrial-fibrillation>, pp. 17, 2012.

Riazifar et al., "Stem Cell Extracellular Vesicles: Extended Messages of Regeneration", Reviews in Advance, 14(1): 1-30, 2016.

Risebro et al., "Handl Regulates Cardiomyocyte Proliferation Versus Differentiation in the Developing Heart", Development, 133(22): 4595-4606, 2006.

Rossi et al., "Deficiencies in DNA Damage Repair Limit the Function of Haematopoietic Stem Cells with Age", Nature, 447: 725-729, 2007.

Rotwein et al., "Organization and Sequence of the Human Insulin-Like Growth Factor I Gene", The Journal of Biological Chemistry, 261(11): 4828-4832, 1986.

Saito et al., "Cell Death Caused by Selenium Deficiency and Protective Effect of Antioxidants", The Journal of Biological Chemistry, 278(41): 39428-39434, 2003.

Sareen et al., Chromosome 7 and 19 Trisomy7 in Cultured Human Neural Progenitor Cells, PLoS One, 4(10): e7630, 12, 2009.

Sasano et al., "Molecular Ablation of Ventricular Tachycardia after Myocardial Infarction", Natural Medicine, 12(11): 1256-1258, 2006.

Sasano et al., "Ventricular Tachycardia from the Healed Myocardial Infarction Scar: Validation of an Animal Model and Utility of Gene Therapy". Heart Rhythm. 6(8): S91-S97, 2009.

Scaria et al., "Host-Virus Genome Interactions: Marco Roles for MicroRNAs", Cellular Microbiology, 9(12): 2784-2794, 2007.

Seifried et al., "A Review of the Interaction Among Dietary Antioxidants and Reactive Oxygen Species", Journal of Nutritional Biochemistry, 18: 567-579, 2007.

Sempere et al., Expression Profiling of Mammalian MicroRNAs Uncovers a Subset of Brain-Expressed MicroRNAs with Possible Roles in Murine and Human Neuronal Differentiation, Genome Biology, 5(3): RI3.1- R13.11, 2004.

Sert et al., "The Radioprotective Effect of Vitamins C, E and Vitamin E + Glutathione on the Small Intestine and the Thyroid Gland in Rats Irradiated with X-Rays", Turkish Journal of Medical Sciences. 30: 417-425. 2000.

Sesso et al., "Vitamins E and C in the Prevention of Cardiovascular Disease in Men: The Physicians' Health Study II Randomized Controlled Trial", The Journal of the American Medical Association (JAMA), 300: 2123-2133, 2008.

Sharkey et al., "Stage-Specific Expression of Cytokine and Receptor Messenger Ribonucleic Acids in Human Preimplantation Embryos", Biology of Reproduction, 53: 95 5-962, 1995.

Sharma et al., "Cardiosphere Derived Cells from Pediatric End-Stage Heart Failure Patients Have Enhanced Functional Activity due to the Heat Shock Response Regulating the Secretome", Stem Cells, 33(4): 1213-1229, 2015.

Shen et al. "Isolation of an Insulin-Like Growth Factor II cDNA with a Unique 5' Untranslated Region from Human Placenta", Proceedings of the National Academy of Sciences of the United States of America (PNAS). 85: 1947-1951, 1988.

Shenje et al., "Lineage Tracing of Cardiac Explant Derived Cells", PLoS One, 3(4): cl 929, 10, 2008.

Shi et al., "3,3'-Diindolylmethane Stimulates Exosomal Wntl 1 Autocrine Signaling in Human Umbilical Cord Mesenchymal Stem Cells to Enhance Wound Healing", Theranostics. 7(6): 1674-1688, 2017.

Shimizu et al., "Fabrication of Pulsatile Cardiac Tissue Grafts Using a Novel 3-D Cell Sheet Manipulation Techniques and Temperature-Responsive Cell Culture Surfaces", Circulation Research, 90(3): 1-10, 2002.

Shu et al., "Disulfide-Crosslinked Hyaluronan-Gelatin Hydrogel Films: A Covalent Mimic of the Extracellular Matrix for In Vitro Cell Growth", Biomaterials, 24: 3825-3834, 2003.

Sigma-Aldrich, Inc., "Nutrient Mixture F12 Ham Kaighn's Modification (F12K)", Product Description, 2 pages, 2007.

Simpson et al., "A Tissue Engineering Approach to Progenitor Cell Delivery Results in Significant Cell Engraftment and Improved Myocardial Remodeling", Stem Cells, 25(9): 2350-2357, 2007.

Singh et al. "High-Dose α-Tocopherol Therapy Does Not Affect HDL Subtractions in Patients with Coronary Artery Disease on Statin Therapy", Clinical Chemistry, 53(3): 525-528, 2007.

Singh, "Enabling Technologies for Homing and Engraftment of Cells for Therapeutic Applications", JACC: Cardiovascular Interventions, 2(8): 803-804, 2009.

Slaughter et al., "Clinical Management of Continuous-Flow Left Ventricular Assist Devices in Advanced Heart Failure", The Journal of Heart and Lung Transplantation, 29(4S): S1-39, 2010.

Smart et al., "De Novo Cardiomyocytes from Within the Activated Adult Heart After Injury", Nature, 474: 640-646, 2011.

Smith et al., "Unique Phenotype of Cardiospheres Derived from Human Endomyocardial Biopsies", Circulation, Supplement II, 112(17): 2, 2005.

Smith et al., "Unselected Human Cardiosphere-derived Cells are Functionally Superior to c-Kit-or CD90-Purified Cardiosphere-Derived Cells", Circulation, Supplement 2, 118(17): I, 2008.

Smits, "Cell-Based Cardiac Repair", Thesis, Utrecht University, The Netherlands, 180, 2009.

Srivastava et al., "Thymosin β4 Is Cardioprotective after Myocardial Infarction", Annals of the New York Academy of Sciences, 1112: 161-170, 2007, Abstract only.

Stanczyk et al., "The Effect of Vitamin C and Glutathione on Ethanol Cytotoxicity and Selected Parameters of Pro- and Antioxidative Processes in Mouse Fibroblasts 3T3-L1", Polish Journal of Environmental Studies, 15(1): 131-137, 2005.

Stewart et al. "Revision of the 1990 Working Formulation for the Standardization of Nomenclature in the Diagnosis of Heart Rejection", The Journal of Heart and Lung Transplantation, 24(11): 1710-1720, 2005.

Takahashi et al., "Induction of Pluripotent Stem Cells from Adult Human Fibroblasts by Defined Factors," Cell, 131:861-872, 2007.

Takahashi et al., "Induction of Pluripotent Stem Cells from Fibroblast Cultures, Nature Protocols", 2(12): 3081-3089, 2007.

Takeda et al., "Human Oct3 Gene Family: cDNA Sequences, Alternative Splicing. Gene Organization, Chromosomal Location, and Expression at Low Levels in Adult Tissues", Nucleic Acids Research, 20(17): 4613-4620, 1992.

Takeda et al., "Induced Pluripotant Stem(IPS) Cell-Based Cell Therapy for Duchenne Muscular Dystrophy", History of Medicine, 239(14): 1440-1444, 2011.

Takehara et al., "Controlled Delivery of Basic Fibroblast Growth Factor Promotes Human Cardiosphere-Derived Cell Engraftment to Enhance Cardiac Repair for Chronic Myocardial Infarction" Journal of the American College of Cardiology. 52(23): 1858-1865, 2008.

Takeshita et al., "Osteoblast-Specific Factor 2: Cloning of a Putative Bone Adhesion Protein with Homology with the Insect Protein Fasciciin I", Biochemical Journal, 294: 271-278, 1993.

Trevethick et al., "Treating Lung Inflammation with Agonists from the Adenosine A2A Receptor: Promises, Problems and Potential Solutions", British Journal of Pharmacology, 155: 463-474, 208.

Tseliou et al., "Abstract 15925: Newt Exosomes are Bioactive on Mammalian Heart, Enhancing Proliferation of Rat Cardiomyocytes and Improving Recovery After Myocardial Infarction", Circulation, 132(3): 2, 2015.

Tseliou et al., "Allogeneic Cardiospheres Safely Boost Cardiac Function and Attenuate Adverse Remodeling After Myocardial Infarction in Immunologically Mismatched Rat Strains". Journal of the American College of Cardiology, 61(10): 1108-1119, 2013.

Ventura et al., "Hyaluronan Mixed Esters of Butyric and Retinoic Acid Drive Cardiac and Endothelial Fate in Term Placenta Human Mesenchymal Stem Cells and Enhance Cardiac Repair in Infarcted Rat Hearts", The Journal of Biological Chemistry. 282(19): 14243-14252, 2007.

(56) References Cited

OTHER PUBLICATIONS

Vrijsen et al., "Cardiomyocyte Progenitor Cell-Derived Exosomes Stimulate Migration of Endothelial Cells", Journal of Cellular and Molecular Medicine, 14(5): 1064-1070, 2010.
Walravens et al., "Cardiosphere-Derived Cell and Mesenchymal Stem Cell Extracellular Vesicles Contain Distinct RNA Cargo", Scientific Program, ISEV2017, 173, 2017.
Wang et al. "The LIM Domain Homeobox Gene isl-1: Conversation of Human, Hamster, and Rat Complementary Deoxyribonucleic Acid Sequences and Expression in Cell Types of Non-neuroendocrine Lineage", Endocrinology, 134(3): 1416-1422, 1994.
Wang et al., "Establishment of New Mouse Embryonic Stem Cell Lines is Improved by Physiological Glucose and Oxygen", Cloning and Stem Cells. 8(2): 108-116, 2006.
Wernig et al., "c-Myc Is Dispensable for Direct Reprogramming of Mouse Fibroblasts", Cell Stem Cell, 2: 10-12, 2008.
White et al., "Intrinsic Cardiac Origin of Human Cardiospliere-Derived Cells", European Heart Journal, 34: 68-75, 2013.
Wilmut et al., "Viable Offspring Derived from Fetal and Adult Mammalian Cells". Nature, 385: 810-813, 1997.
Wilson et al., "Bioluminescence Reporter Gene Imaging of Human Embryonic Stem Cell Survival, Proliferation, and Fate", Methods in Molecular Biology, 574: 87-103, 2009.
Wong et al., "Loss of the Y Chromosome: An Age-Related or Clonal Phenomenon in Acute Myelogenous Leukemia/Myelodysplastic Syndrome?" Archives of Pathology & Laboratory Medicine, 132: 1329-1332, 2008.
Wu et al., "Cell Delivery in Cardiac Regenerative Therapy", Ageing Research Reviews, 11: 32-40, 2012.
Yamada et al., "Type V Collagen-Induced Oral Tolerance Plus Low-Dose Cyclosporine Prevents Rejection of MHC Class I and II Incompatible Lung Allografts", The Journal Immunology, 183(1): 237-245, 2009.
Yang et al., "Human Cardiovascular Progenitor Cells Develop from a KDR+ Embryonic-Stem-Cell-Derived Population", Nature, 453: 524-528, 2008.
Yau et al., "Beneficial Effect of Autologous Cell Transplantation on Infarcted Heart Function: Comparison Between Bone Marrow Stromal Cells and Heart Cells", The Annals of Thoracic Surgery, 75(1): 169, 2003.
Yee et al. "Allogeneic Cardiospheres Delivered via Percutaneous Transendocardial Injection Increase Viable Myocardium, Decrease Scar Size, and Attenuate Cardiac Dilation in Porcine Ischemic Cardiomyopathy", Plos One, 1-29, 2014.
Yu et al., "Induced Pluripotent Stem Cell Lines Derived from Human Somatic cells," Science, 318: 1917-1920, 2007.
Yu et al., "miR-221 and miR-222 Promote Schwann Cell Proliferation and Migration by Targeting LASS2 after Sciatic Nerve Injury", Journal of Cell Science, 125(11): 2675-2683, 2012.
Zha et al., "Complementary Functions of ATM and H2AX in Development and Suppression of Genomic Instability", Proceedings of the National Academy of Sciences of the United States of America (PNAS), 105(27): 9302-9306, 2008.
Zhang et al., "Do Cardiac Stem Cells Arise from Cardiomyocyte Dedifferentiation?" Circulation Research, 99(11): 1278, 2006, Abstract only.
Zhao et al., "Targeting Human CD34+ Hematopoietic Stem Cells With Anti-CD45 x Anti-Myosin Light-Chain Bispecific Antibody Preserves Cardiac Function in Mvocardial Infarction", Journal of Applied Physiology, 104: 17934800, 2008.
Zhou et al., "Down-Regulation of microRNA-26a Promotes Mouse Hepatocyte Proliferation During Liver Regeneration", PLoS ONE, 7(4): e33577, 1-7, 2012.
Zhou et al., "Generation of Induced Pluripotent Stem Cells Using Recombinant Proteins", Cell Stem Cell, 4(5): 381-384, 2009.
Zuo et al., Assessment of Myocardial Blood Perfusion Improved by CD151 in a Pig Myocardial Infarction Model, Acta Pharmacologica Sinica, 30(1): 70-77, 2009.

Anastasiou-Nana et al., "Relative efficiency and risk of endomyocardial biopsy: comparisons in heart transplant and nontransplant patients," Cathet Cardiovasc Diagn, 1989;18(1):7-11.
Bryan et al., "Implications of Protein Fold Switching", Current Comments, posted Feb. 4, 2013, printed in 4 pages.https://web.archive.org/web/20160628060217/http://www.elsevierblogs.com/currentcomments/?p=962.
Carr et al., "Cardiosphere-Derived Cells Improve Function in the Infarcted Rat Heart for at Least 16 Weeks—anMRI Study", PLoS One, Oct. 2011, 6:10:1-10.
Cheng et al., "Focus on Mesenchymal Stem Cell-Derived Exosomes: Opportunities and Challenges in Cell-Free Therapy", Hindawi, Stem Cells International, 2017, Article ID 6305295, pp. 10.
Li et al., "Skeletal Myoblast-Seeded Vascularized Tissue Scaffolds in the Treatment of a Large Volumetric Muscle Defect in the Rat Biceps Femoris Muscle", Termis, Tissue Engineering: Part A, 2017, 23:17 & 18:989-1000.
Magarotto et al., "Muscle Functional Recovery is Driven by Extracellular Vesicles Combined with Muscle Extracellular Matrix in a Volumetric Muscle Loss Murine Model", Biomaterials, 2021, 269:1-15.
Maqbool et al., The Substrate-Binding Protein in Bacterial ABC Transporters: Dissecting Roles in the Evolution of Substrate Specificity, Biochemical Society Transactions, 2015, vol. 43, Part 5, pp. 1011-1017.
Mason, "Techniques for right and left ventricular endomyocardial biopsy," Arn J Cardiol 1978;41(5):887-92.
Pilia et al., "Transplantation and Perfusion of Microvascular Fragments in a Rodent Model of Volumetric Muscle Loss Injury", European Cells and Materials, 2014, 28:11-24.
Rachel Smith, PH.D.,"Curriculum Vitae," Exhibit A in U.S. Appl. No. 13/412,051, 13 pages, 2017.
Shimasakil et al., "Exosome Research and Co-culture Study", Biological and Pharmaceutical Bulletin, 2018, 40:9:1311-1321.
Sicari et al., "An Acellular Biologic Scaffold Promotes Skeletal Muscle Formation in Mice and Humans with Volumetric Muscle Loss", Science Translational Medicine, Apr. 30, 2014, 6:234:1-10.
USPTO Patent Trial and Appeal Board., "Decision on Appeal", in patent Application No. 2019-005766, U.S. Appl. No. 13/412,051, dated Jun. 8, 2020, 12 pages.
USPTO Patent Trial and Appeal Board., "Declaration of Rachel R. Smith, PH.D," in U.S. Appl. No. 13/412,051, dated Oct. 13, 2017, 32 pages.
Barile et al., "Beneficial Effects of Exosomes Secreted by Cardiac-Derived Progenitor Cells and Other Cell Types in Myocardial Ischemia", Stem Cell Investigation, Nov. 18, 2017, pp. 93-99.
Catalona, Mariadelva, "Engineering Exosomes Toward Folate Receptor Expressing Cells", Dec. 7, 2017, pp. 3.
Chen et al., "Transformation of Cell-Derived Microparticles into Quantum-Dot-Labeled Nanovectors for Antitumor siRNA Delivery", Angewandte Chemie International Edition, vol. 54, No. 3, Nov. 20, 2014, pp. 1036-1040.
Communication under Rule 71(3) EPC received for European Patent Application No. 05817349, dated Mar. 28, 2018, 7 pages.
De Couto et al., "Exosomal MicroRNA Transfer into Macrophages Mediates Cellular Postconditioning", Circulation, American Heart Association, vol. 136, No. 2, Jul. 11, 2017, pp. 200-214 (47 pages total).
Decision to grant a European patent received for European Patent Application No. 05817349, dated Aug. 2, 2018, 2 pages.
European Search Report and Search Opinion received for EP Application No. 05817349, dated Oct. 28, 2009, 10 pages.
European Search Report and Search Opinion received for EP Application No. 05817480, dated Dec. 7, 2009, 10 pages.
European Search Report and Search Opinion received for EP Application No. 12177594, dated Mar. 12, 2013, 8 pages.
European Search Report received for EP Application No. 12177594, dated Nov. 21, 2012, 7 pages.
Ex parte Eduardo Marban and Ke Cheng, decision of the Patent Trial and Appeal Board, U.S. Appl. No. 14/437,812, filed Jun. 19, 2020, pp. 1-21, https://casetext.com/admin-law/cedars-sinai-medical-center-13 (Year: 2020).

(56) References Cited

OTHER PUBLICATIONS

Girard et al., "A Germline-Specific Class of Small RNAs Binds Mammalian Piwi Proteins", Nature, Jul. 13, 2006, vol. 442, pp. 199-202.
Ibrahim et al., "Augmenting Canonical Wnt Signalling in Therapeutically Inert Cells Converts them into Therapeutically Potent Exosome Factories", Nature Biomedical Engineering, Sep. 2019, vol. 3, pp. 695-705.
Ibrahim et al., "Small Molecule Inhibitors and Culture Conditions Enhance Therapeutic Cell and EV Potency via Activation of Beta-Catenin and Suppression of THY1", Nanomedicine: Nanotechnology, Biology, and Medicine, Dec. 13, 2020, vol. 33, pp. 7.
Intention to grant (signatures) received for European Patent Application No. 05817349, dated Jul. 19, 2018, 5 pages.
International Preliminary Report on Patentability received for PCT Patent Application No. PCT/US05/40359, dated Mar. 17, 2009, 5 pages.
International Preliminary Report on Patentability received for PCT Patent Application No. PCT/US05/40361, dated May 30, 2007, 6 pages.
International Search Report and Written Opinion received for PCT Patent Application No. PCT/US05/40359, dated May 9, 2008, 5 pages.
International Search Report and Written Opinion received for PCT Patent Application No. PCT/US05/40361, dated May 11, 2007, 6 pages.
Kasai-Brunswick et al., "Cardiosphere-Derived Cells do not Improve Cardiac Function in Rats with Cardiac Failure," Stem Cell Research & Therapy, 2017, vol. 8, No. 36, 9 pages.
Kim, PhD et al., "Engineering Macrophage-Derived Exosomes for Targeted Paclitaxel Delivery to Pulmonary Metastases:in Vitroandin Vivoevaluations", Nanomedicine, Nanotechnology, Biology, and Medicine, vol. 14, 2018, pp. 195-204.
Kim, PhD et al., "Exosome Mediated Delivery of Paclitaxel for the Treatment of Multi Drug Resistant Pulmonary Metastases", Dissertation, Chapel Hill, Dec. 31, 2016, pp. 112.
Shen et al., "The Early Cryptic Transmission and Evolution of SARS-CoV-2 in Human Hosts", Available at SSRN 3724275, Aug. 2019, https://www.oyeyeah.com/wp-content/uploads/2020/11/SSRN-is3724275.pdf, pp. 22.
Smyth et al., "Surface Functionalization of Exosomes Using Click Chemistry", Bioconjugate Chemistry, vol. 25, No. 10, Sep. 30, 2014, pp. 1777-1784.
Vella et al., "PIWI-Interacting RNA (piRNA) Signatures in Human Cardiac Progenitor Cells", The International Journal of Biochemistry & Cell Biology, 2016, vol. 76, pp. 1-11.
Wan et al., "Aptamer-Conjugated Extracellular Nanovesicles for Targeted Drug Delivery", Cancer Research, vol. 78, No. 3, Dec. 7, 2017, pp. 798-808.
Wang et al., "The Use of RGD-Engineered Exosomes for Enhanced Targeting Ability and Synergistic Therapy Toward Angiogenesis", Nanoscale, vol. 9, No. 40, Jan. 1, 2017, pp. 15598-15605.
Wang et al., Challenges in the Development and Establishment of Exosome-Based Drug Delivery Systems, Journal of Controlled Release, 2021, vol. 329, pp. 894-906.
Zhang et al., "Magnetic and Folate Functionalization Enables Rapid Isolation and Enhanced Tumor-Targeting of Cell-Derived Microvesicles", ACS Nano, vol. 11, No. 1, Jan. 24, 2017, pp. 277-290.
Zhao et al., "Exosomes as Drug Carriers for Cancer Therapy and Challenges Regarding Exosome Uptake" Biomedicine & Pharmacotherapy, 2020, vol. 128, 9 pages.
Tateishi et al., "Clonally Amplified Cardiac Stem Cells are Regulated by Sca-1 Signaling for Efficient Cardiovascular Regeneration", Journal of Cell Science, 120(10): 1791-1800, 2007.
Ten Dijke et al., "Identification of Another Member of the Transforming Growth Factor Type β Gene Family", Proceedings of the National Academy of Sciences of the United States of America (PNAS), 85: 4715-4719, 1988.
Terrovitis et al., "Assessment and Optimization of Cell Engraftment after Transplantation into the Heart", Circulation Research. 106(3): 479-494, 2010.
Terrovitis et al., "Noninvasive Quantification and Optimization of Acute Cell Retention by In Vivo Positron Emission Tomography after Intramyocardial Cardiac-Derived Stem Cell Delivery", Journal of the American College of Cardiology, 54(17): 1619-1626, 2009.
The Exosomes Derived from CDCs Experimental Data to Show that Unexpectedly Improved Characteristics are Exhibited, p. 1., No Date.
Trevethick et al., "Treating Lung Inflammation with Agonists from the Adenosine A2A Receptor: Promises, Problems and Potential Solutions", British Journal of Pharmacology, 155: 463-474, 208, 2008.
Tsagalou et al., "Depressed Coronary Flow Reserve is Associated with Decreased Myocardial Capillary Density in Patients with Heart Failure Due to Idiopathic Dilated Cardiomyopathy", Journal of the American College of Cardiology, 52(17): 1391-1398, 2008.
Tseliou et al., "Abstract 15925: Newt Exosomes are Bioactive on Mammalian Heart, Enhancing Proliferation of Rat Cardiomyocytes and Improving Recovery After Myocardial Infarction", Circulation, 132(3): 2, 2015.
Tseliou et al., "Allogeneic Cardiospheres Safely Boost Cardiac Function and Attenuate Adverse Remodeling After Myocardial Infarction in Immunologically Mismatched Rat Strains", Journal of the American College of Cardiology, 61(10): 1108-1119, 2013.
Tsutsui, "Cardiomyopathy: Progress in Diagnosis and Treatments Topics: 1. New classification based on etiology of cardiomyopathy; 1. Classification of cardiomyopathy—its past and present status", The Japanese Society of Internal Medicine, February 103(2): 277-284, 2014.
Uemura et al., "Bone Marrow Stem Cells Prevent Left Ventricular Remodeling of Ischemic Heart Through Paracrine Signaling", Circulation Research, 98: 1414-1421, 2006.
Ueno et al., "Biphasic Role for Wnt/β-Catenin Signaling in Cardiac Specification in Zebrafish and Embryonic Stem Cells", Proceedings of the National Academy of Sciences of the United States of America (PNAS), 104(23): 9685-9690, 2007.
Ulloa-Montoya et al., "Culture Systems for Pluripotent Stem Cells", Journal of Bioscience and Bioengineering, 100(1): 12-27, 2005.
Van Der Geest et al., "Quantification in Cardiac MRI", Journal of Magnetic Resonance Imaging, 10: 602-608, 1999.
Van Gent et al., "Chromosomal Stability and the DNA Double-Stranded Break Connection", Nature, 2: 196-206, 2001.
Van Vliet et al., "Progenitor Cells Isolated from the Human Heart: a Potential Cell Source for Regenerative Therapy", Netherlands Heart Journal, 16(5): 163-169, 2008.
Vela et al., "Quest for the Cardiovascular Holy Grail: Mammalian Myocardial Regeneration", Cardiovascular Pathology, 17: 1-5, 2008.

* cited by examiner

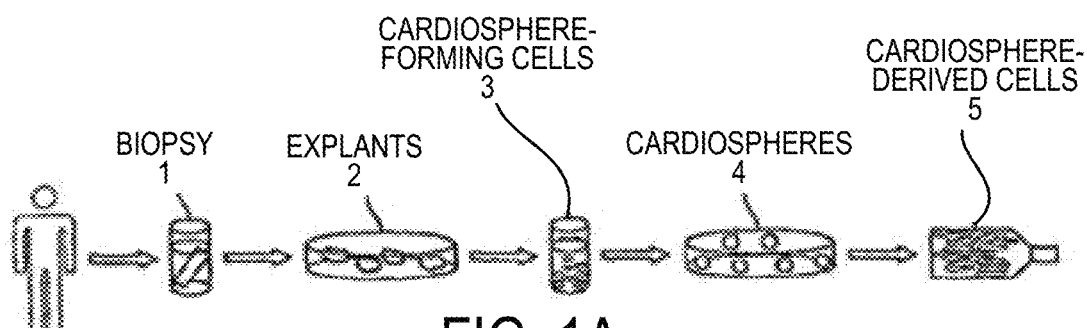
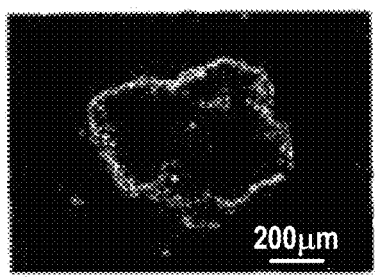
FIG. 1B
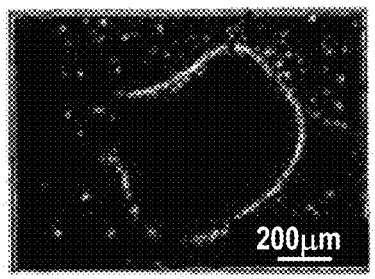
FIG. 1C
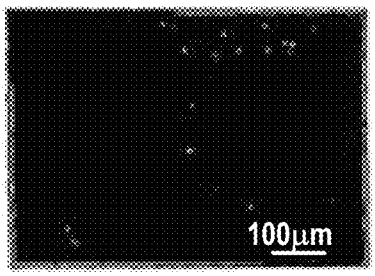
FIG. 1D
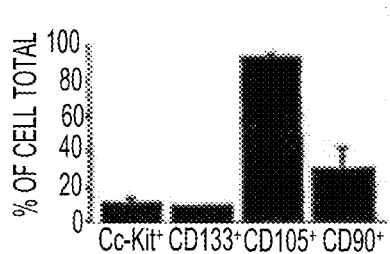
FIG. 1E
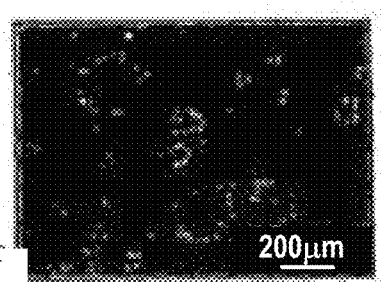
FIG. 1F
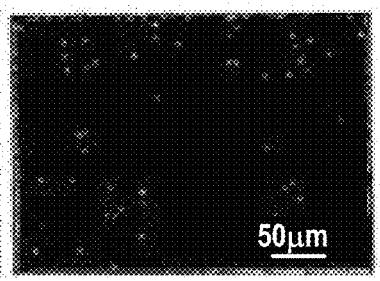
FIG. 1G
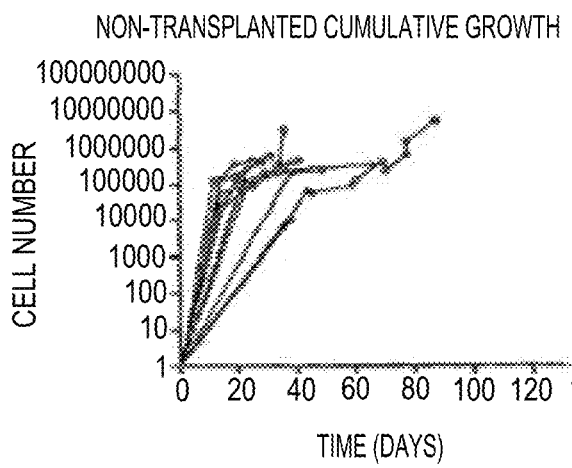
FIG. 1H
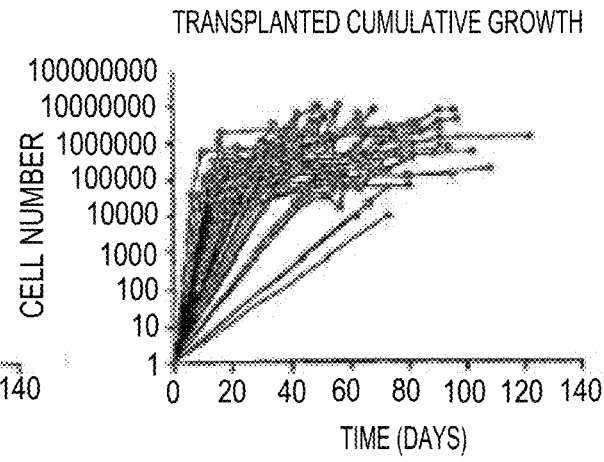
FIG. 1I

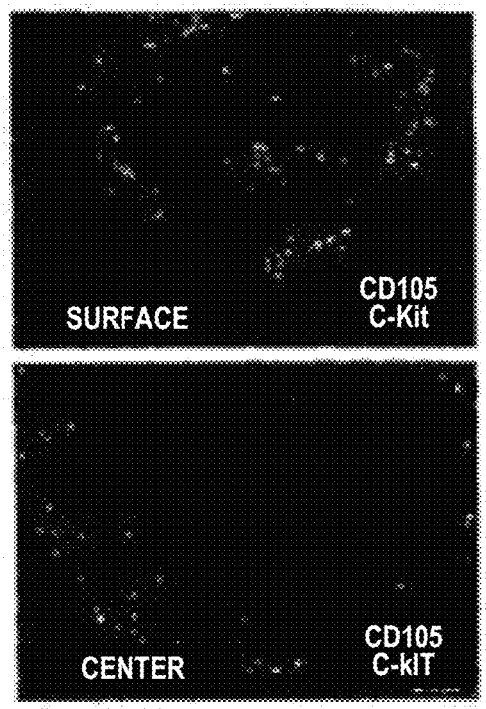
FIG. 2A
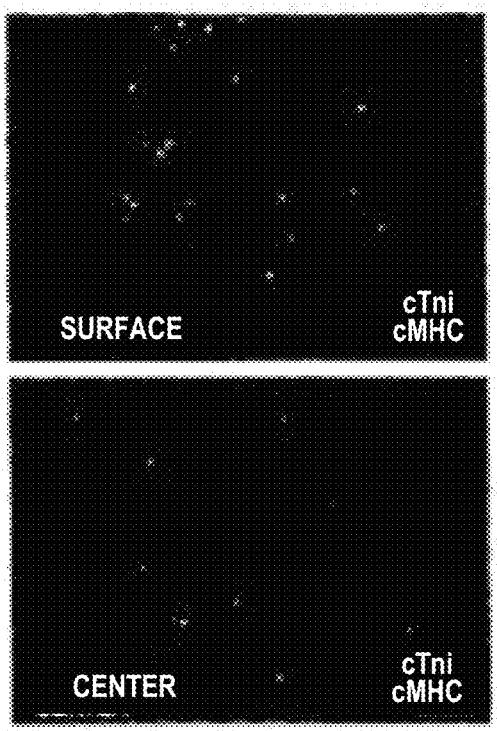
FIG. 2B
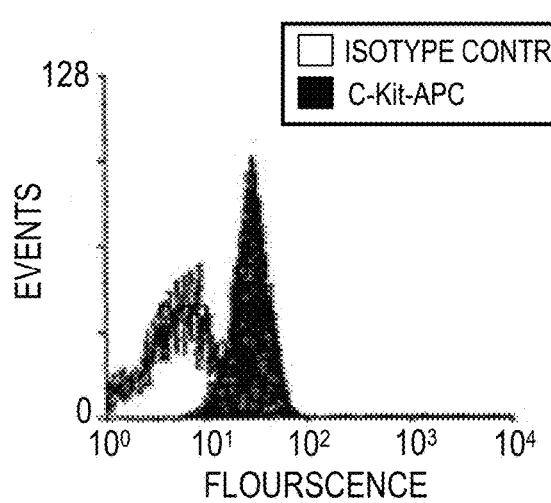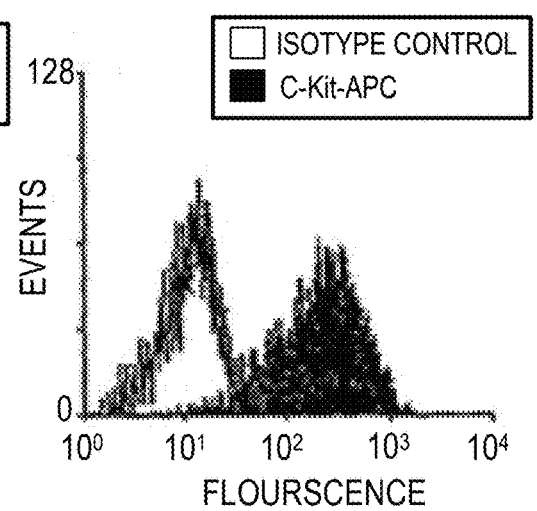
FIG. 2C

FIG. 10A
FIG. 10B

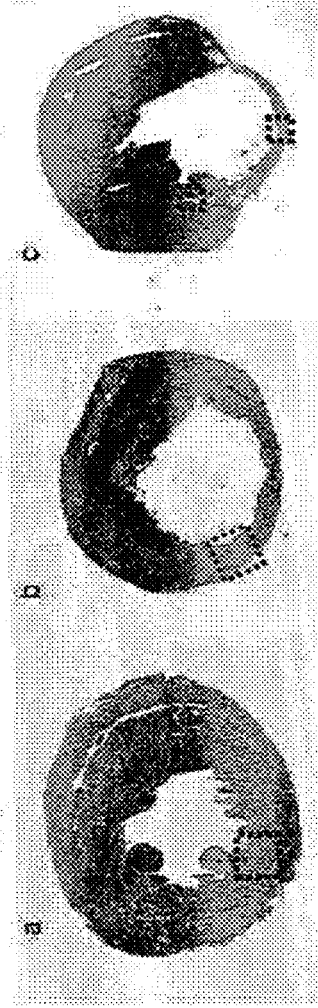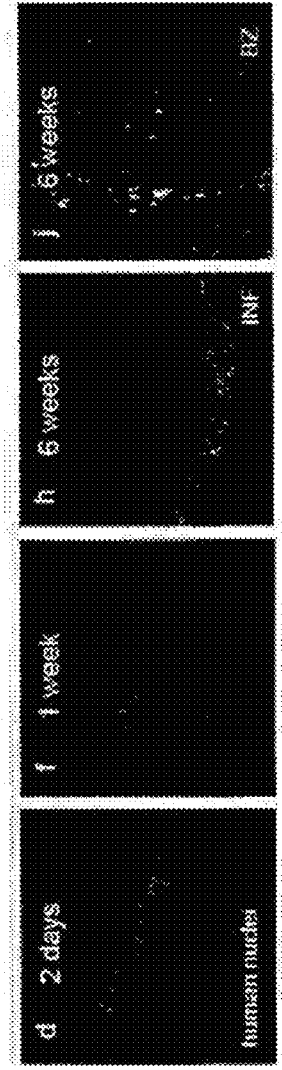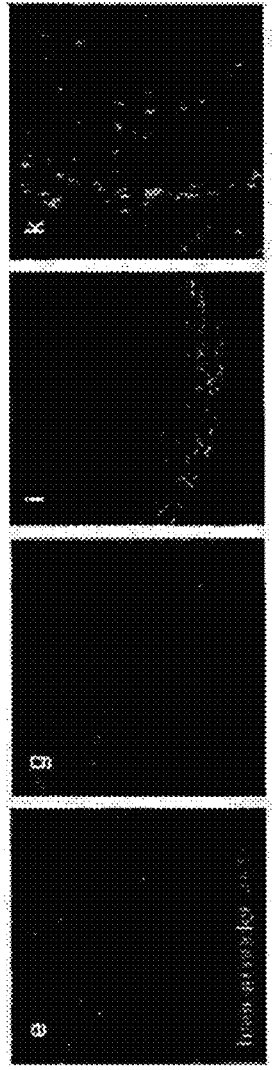

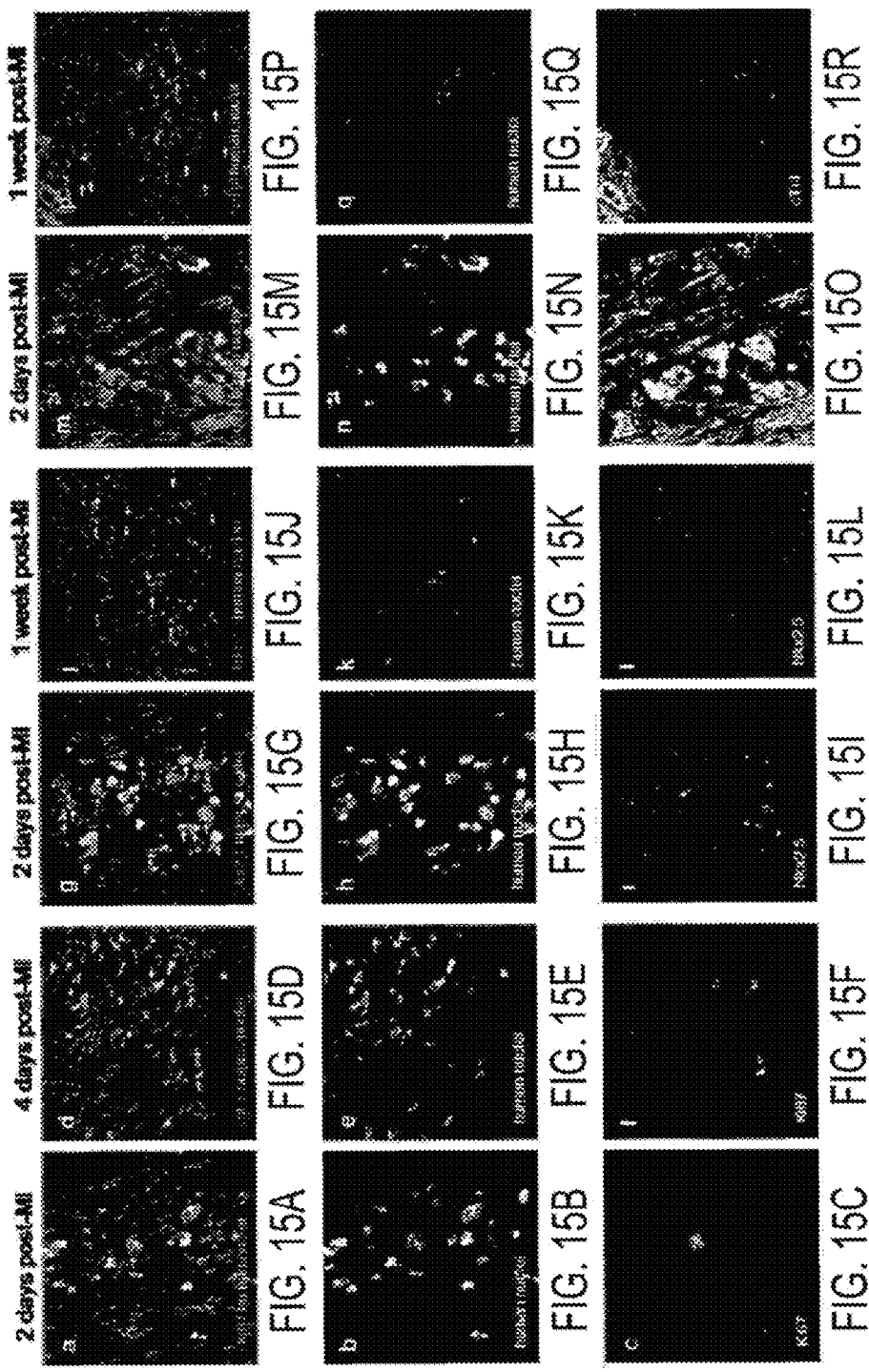

 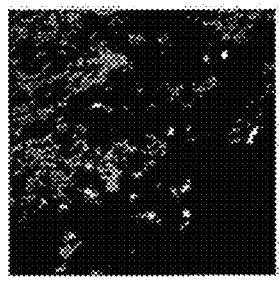 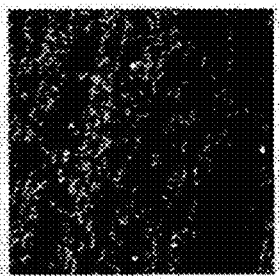 
FIG. 16A　　FIG. 16B　　FIG. 16C　　FIG. 16D
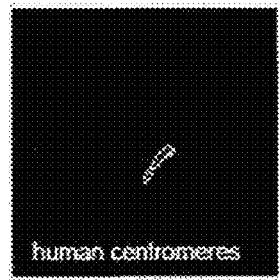 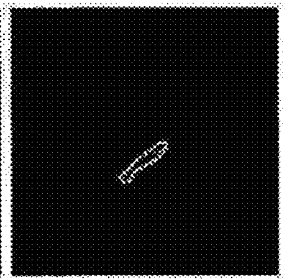 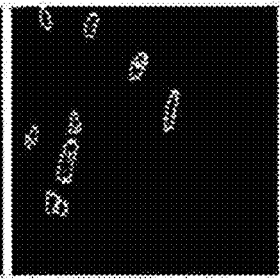 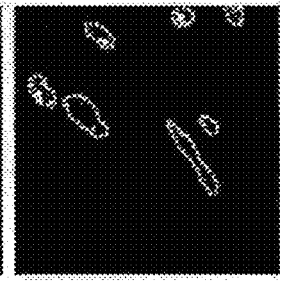
FIG. 16E　　FIG. 16F　　FIG. 16G　　FIG. 16H
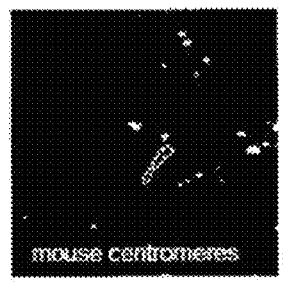 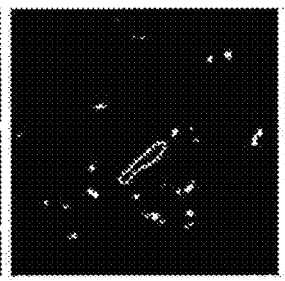 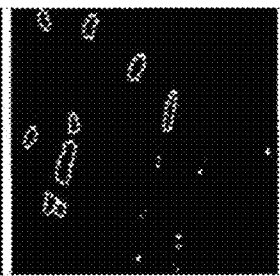 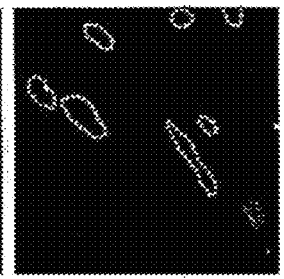
FIG. 16I　　FIG. 16J　　FIG. 16K　　FIG. 16L
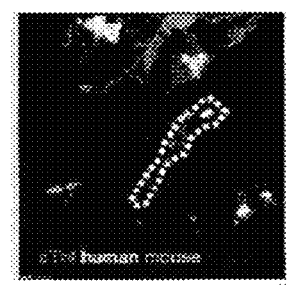 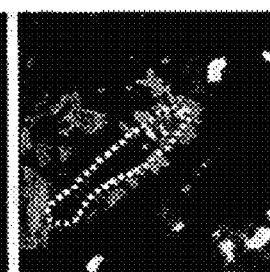 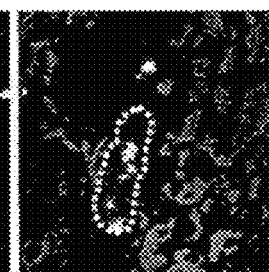 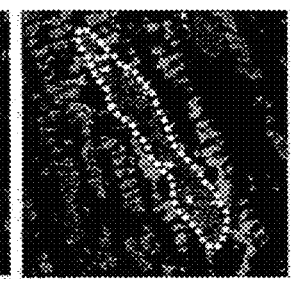
FIG. 16M　　FIG. 16N　　FIG. 16O　　FIG. 16P CSps                CDCs

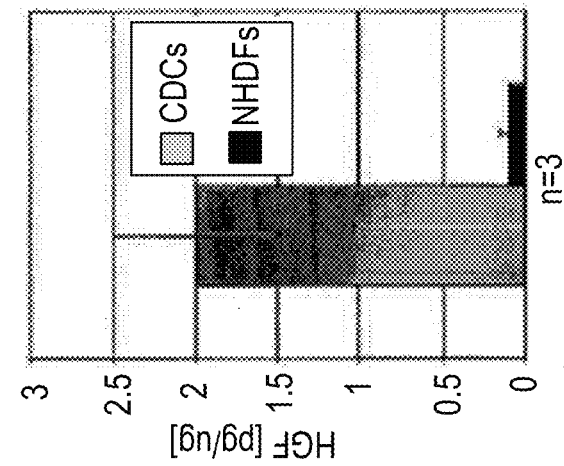
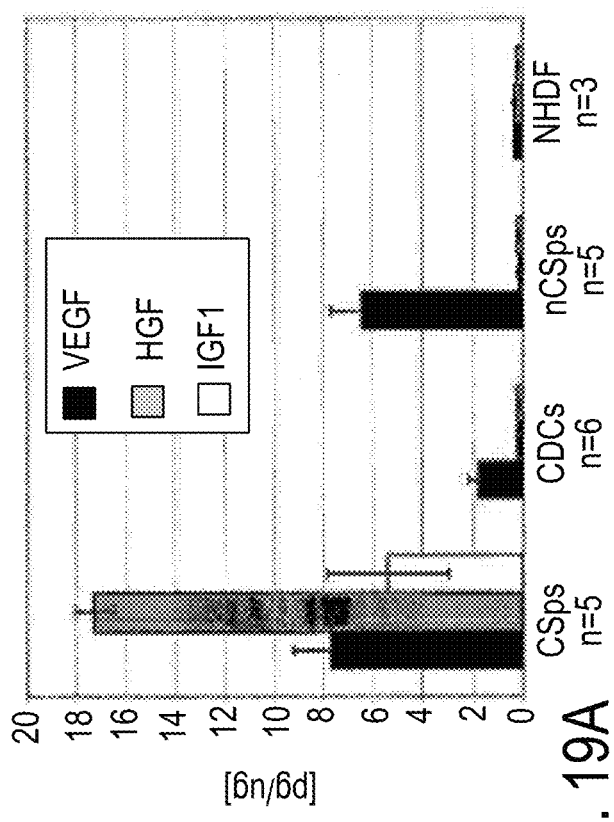
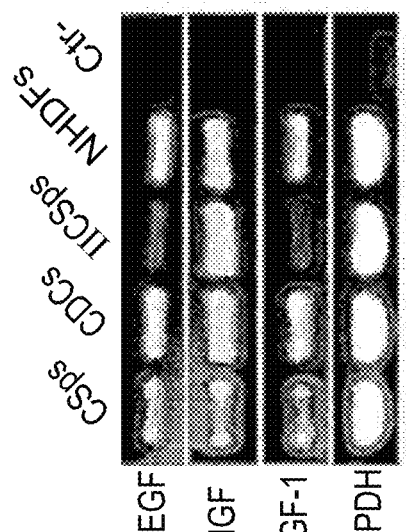
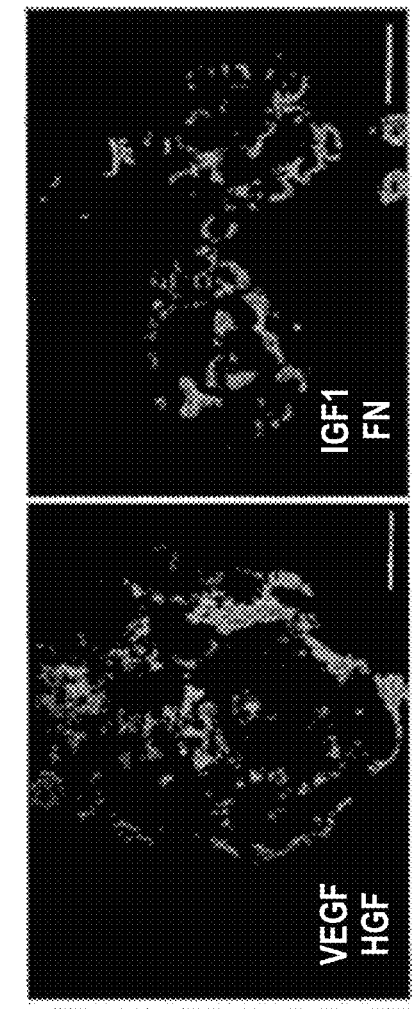
FIG. 19A  FIG. 19B  FIG. 19C  FIG. 19D  FIG. 19E

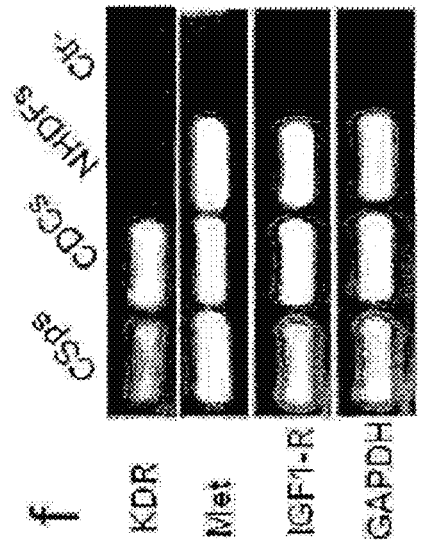
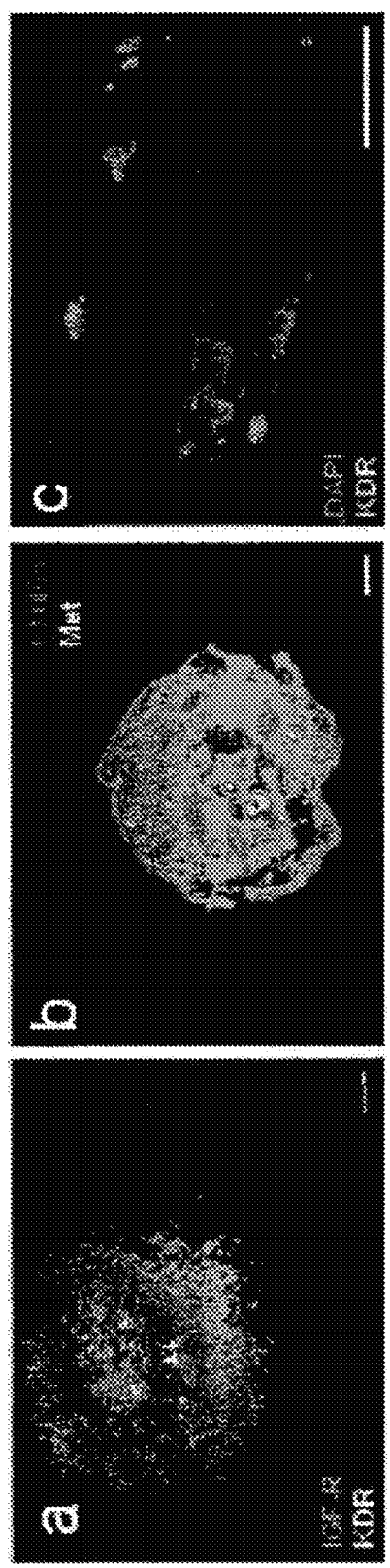
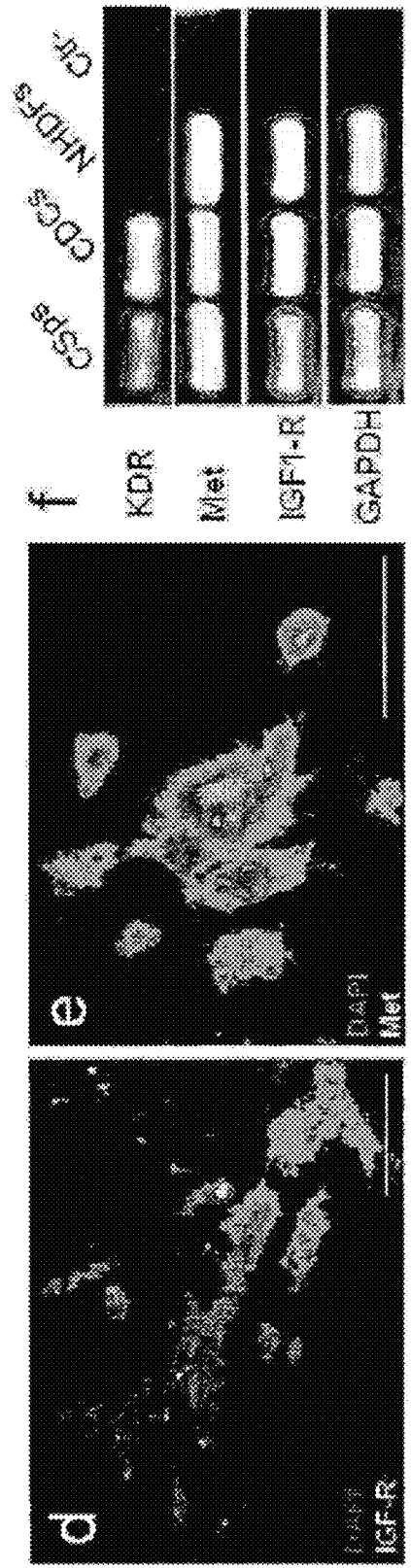
FIG. 20A  FIG. 20B  FIG. 20C
FIG. 20D  FIG. 20E  FIG. 20F

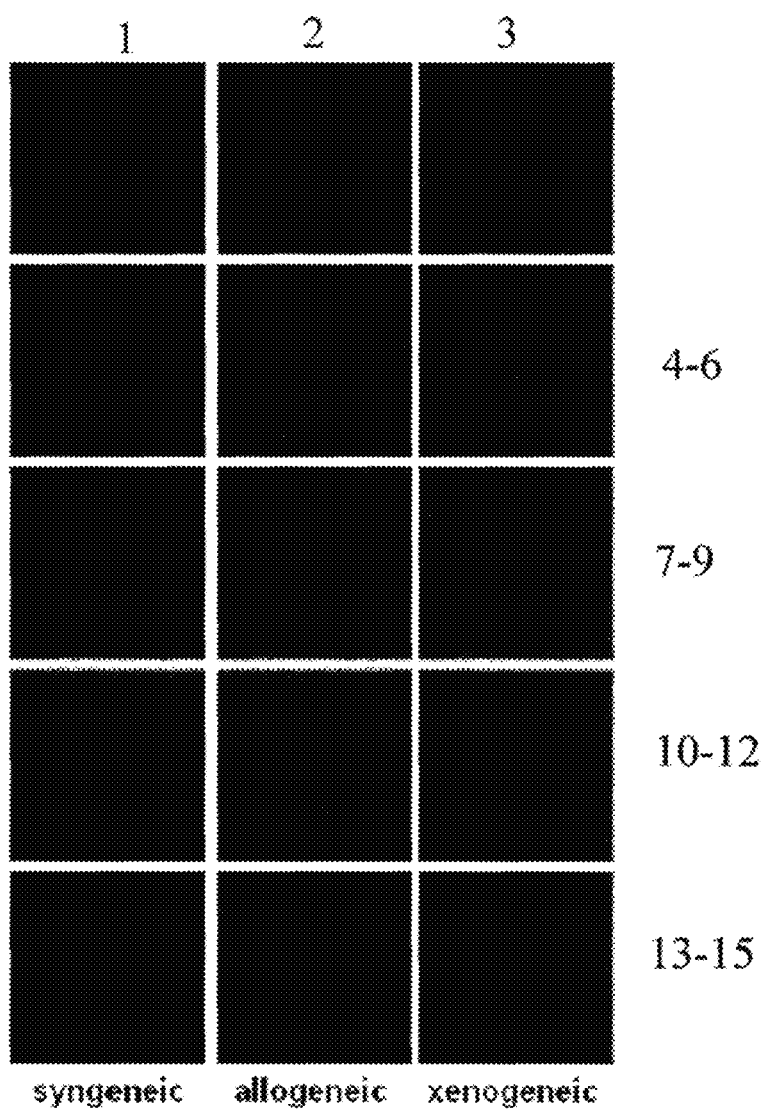

FIGS. 28L-M
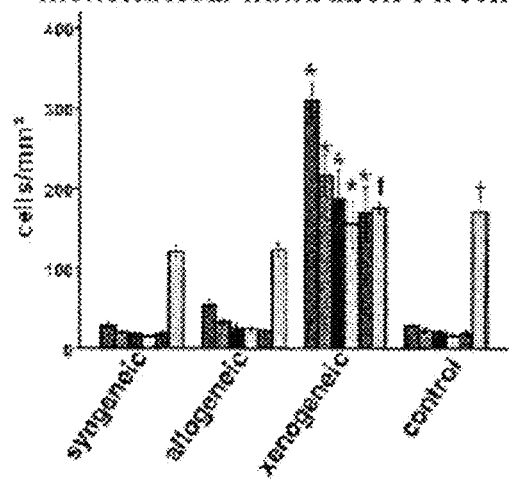
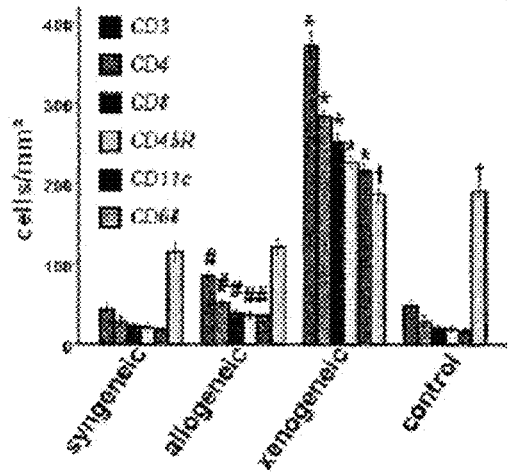

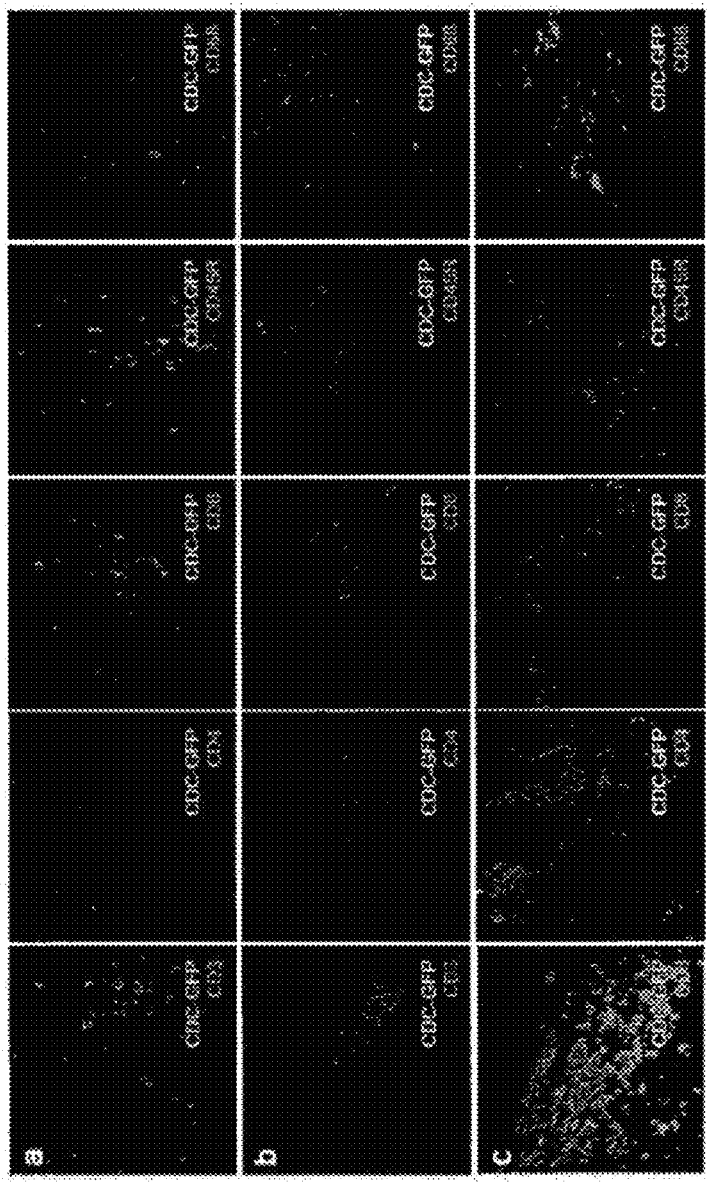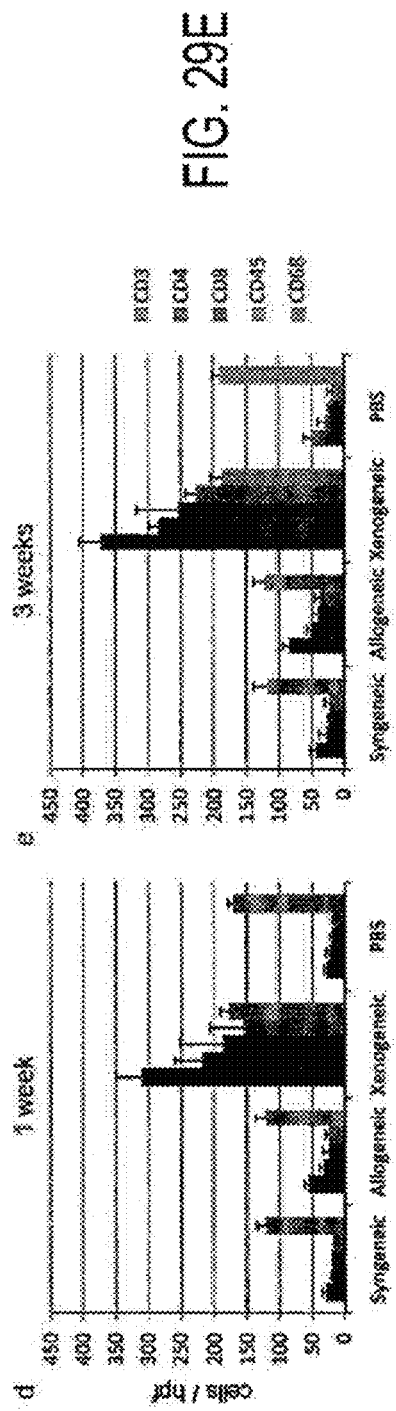
FIG. 29A
FIG. 29B
FIG. 29C
FIG. 29D
FIG. 29E

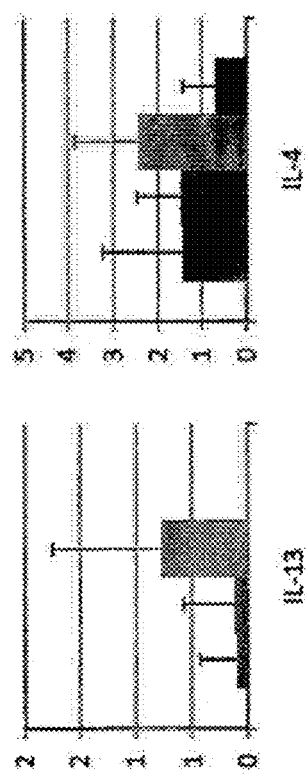 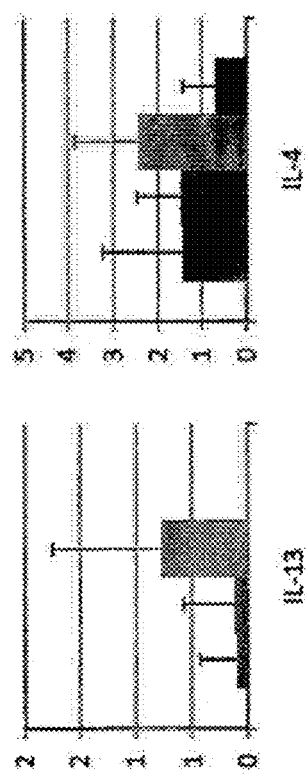 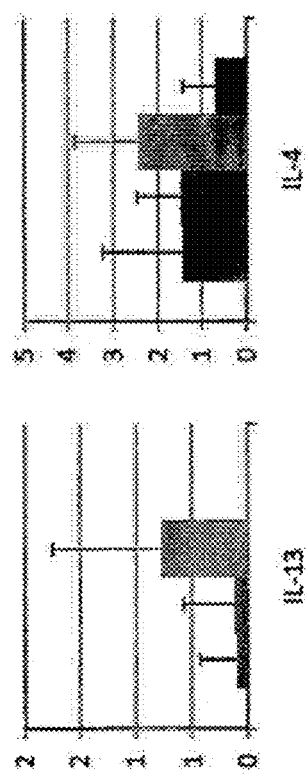 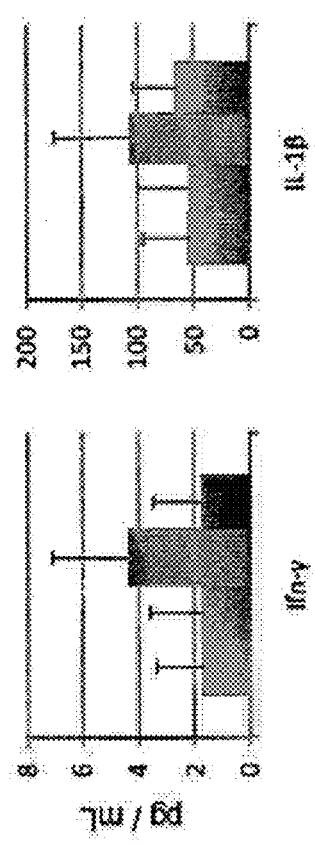 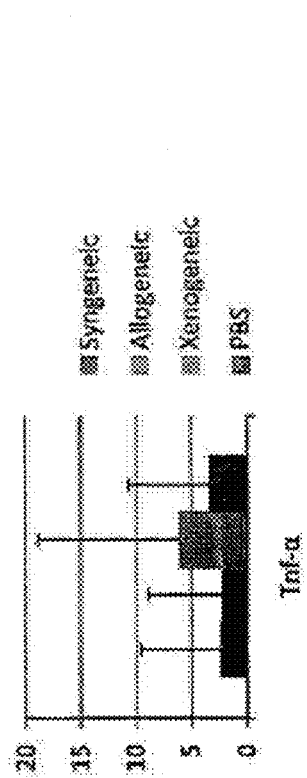 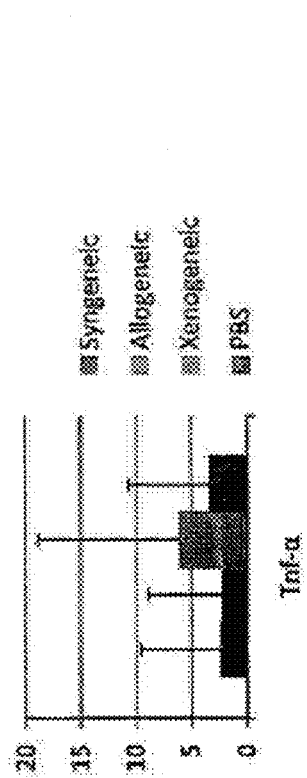 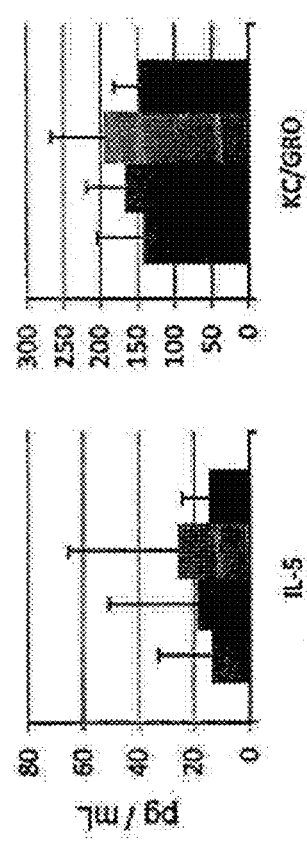
FIG. 30A FIG. 30B FIG. 30C FIG. 30D
FIG. 30E FIG. 30F FIG. 30G

Y

Z

FIGS. 31AA-31BB
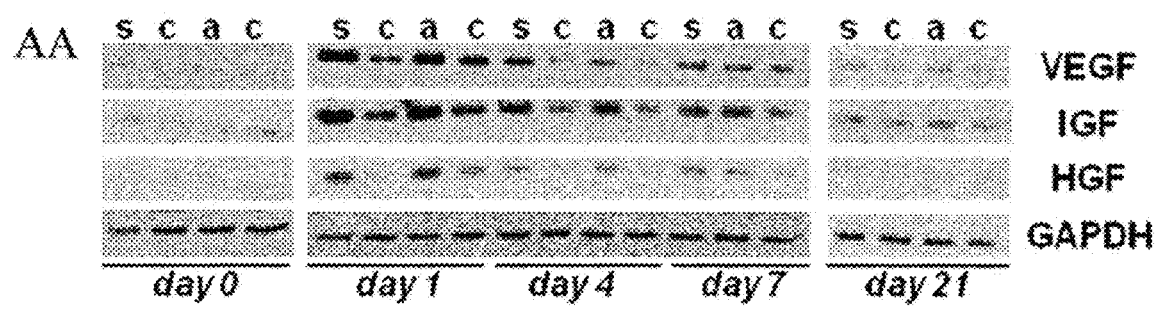
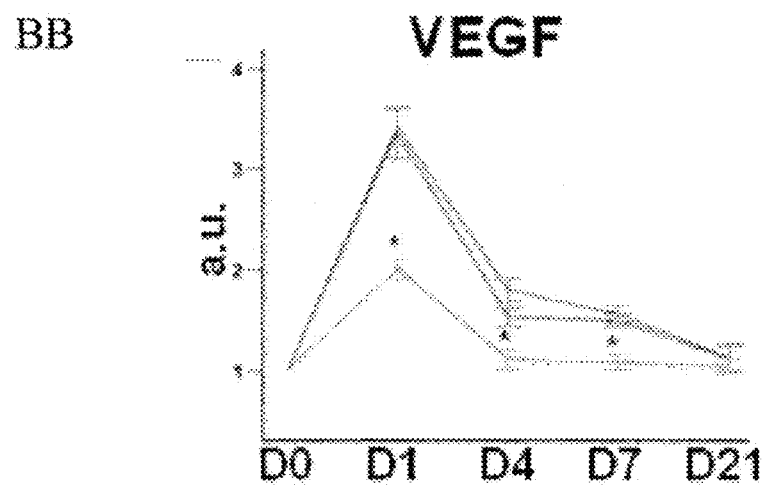

FIGS. 31CC-31DD
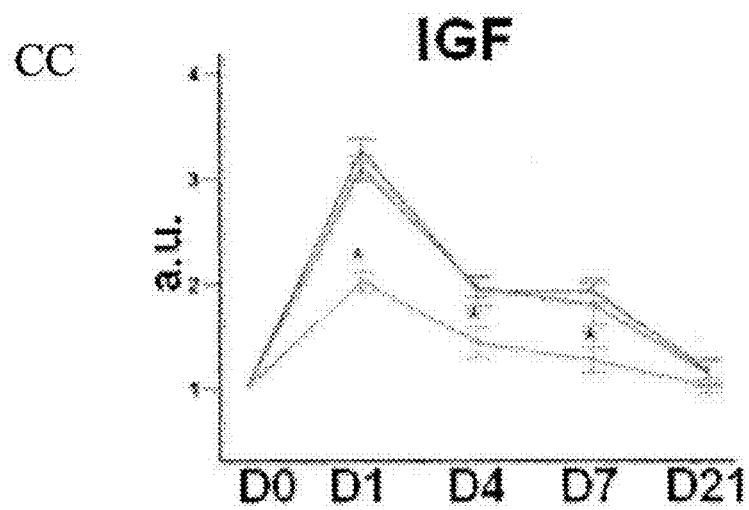
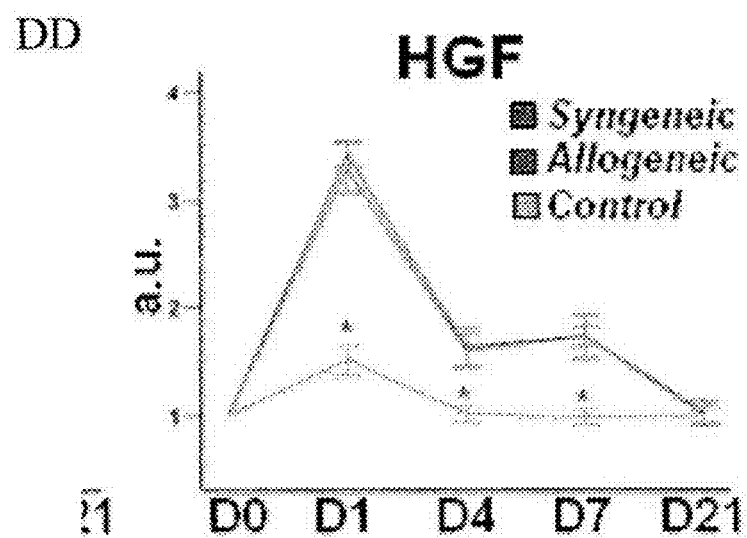

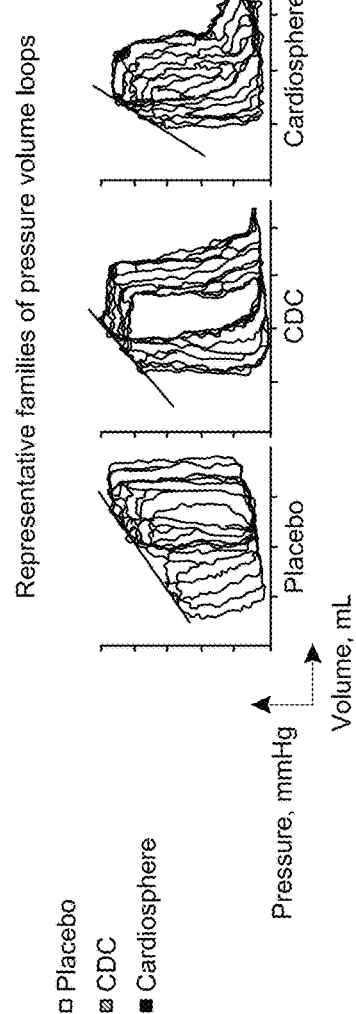
FIG. 35A
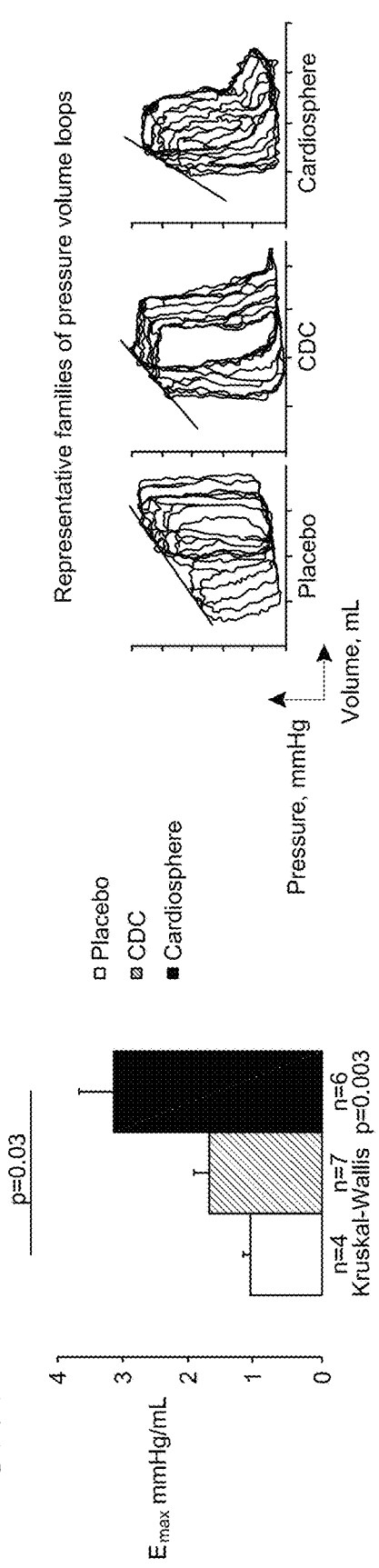
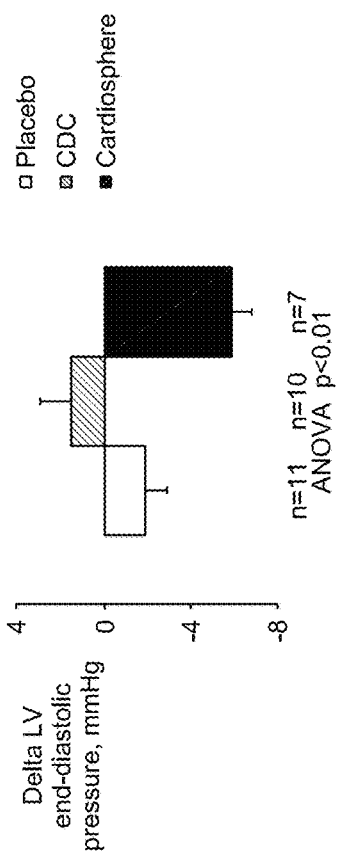
FIG. 35C
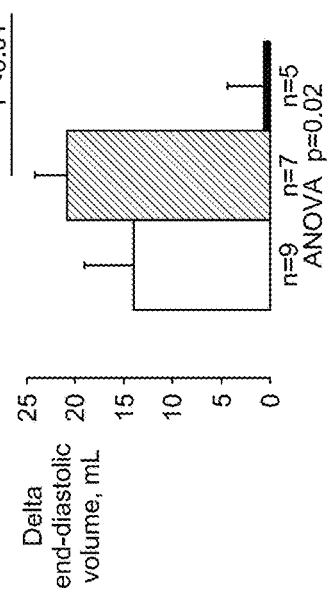
FIG. 35B

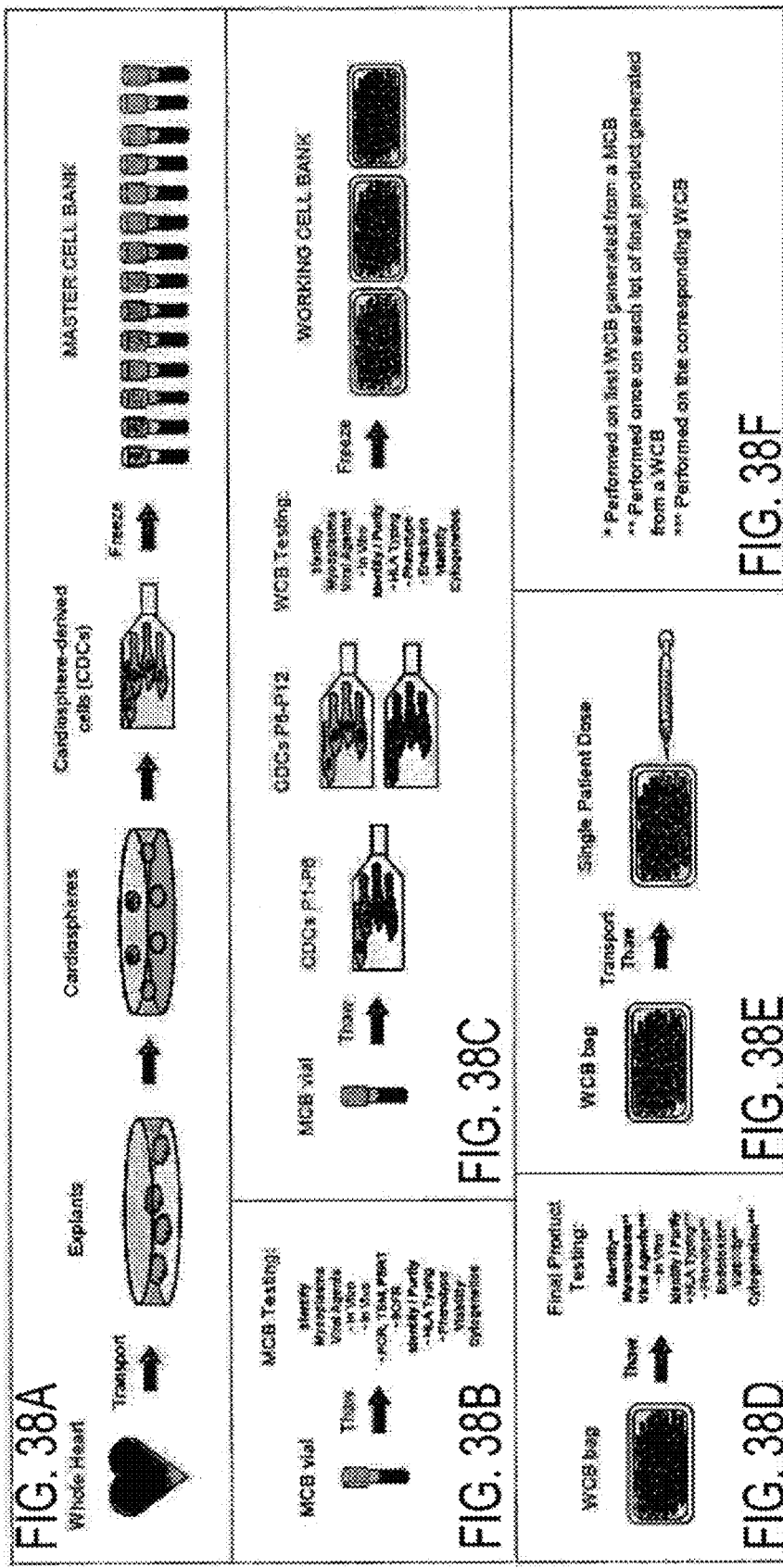

| Markers / Cell Types | CD29 | CD31 | CD34 | CD45 | CD90 | CD105 | CD117 (c-kit) | CD133 |
|---|---|---|---|---|---|---|---|---|
| CDC | 99.98% | 0.62% | 1.00% | 0.45% | 18.40% | 99.89% | 7.04% | 0.99% |
| BM-MSC | 99.95% | 0.74% | 1.23% | 0.54% | 99.0% | 99.37% | 5.60% | 1.24% |
| AD-MSC | 99.63% | 0.54% | 0.11% | 0.15% | 84.79% | 99.68% | 10.44% | 2.17% |
| BM-MNC | 94.54% | 19.88% | 3.76% | 74.72% | 4.21% | 24.54% | 3.73% | 2.17% |

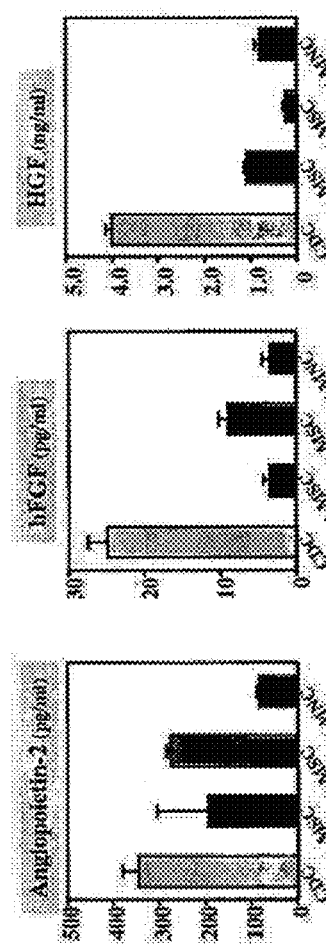
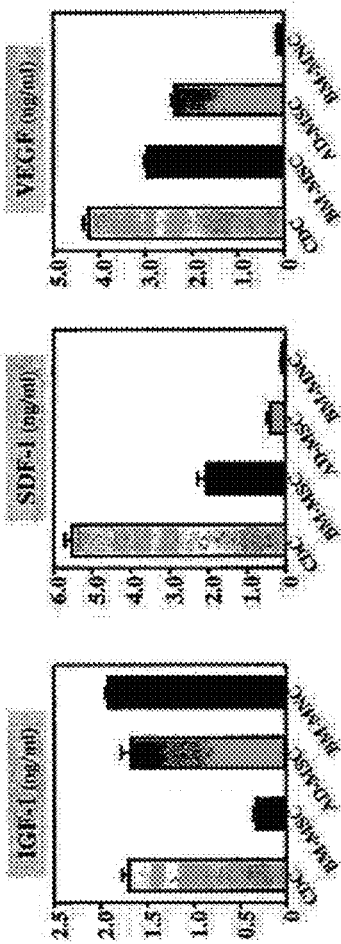
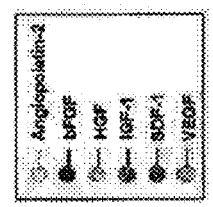
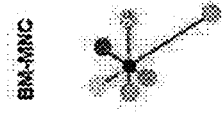
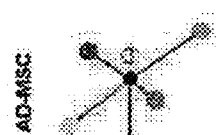
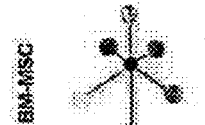
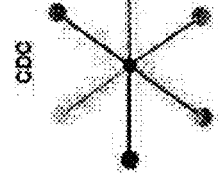
FIG. 41A  FIG. 41B  FIG. 41C
FIG. 41D  FIG. 41E  FIG. 41F
FIG. 41G  FIG. 41H  FIG. 41I  FIG. 41J

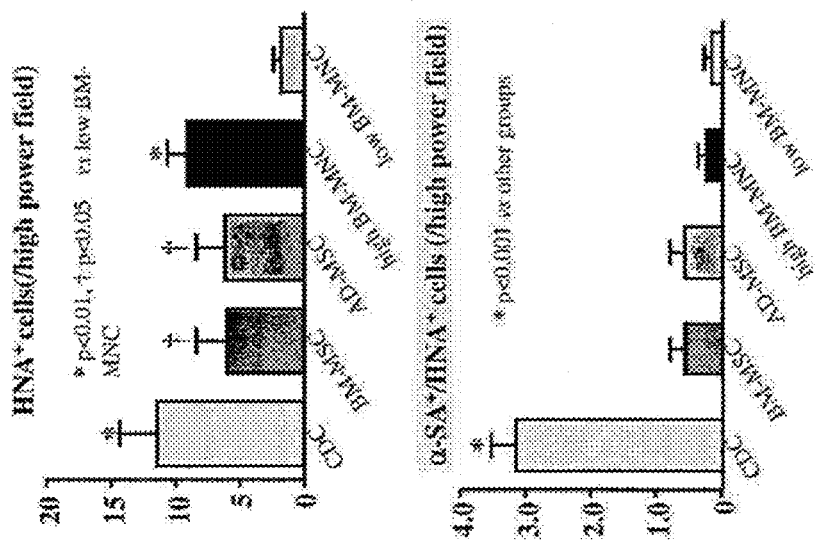
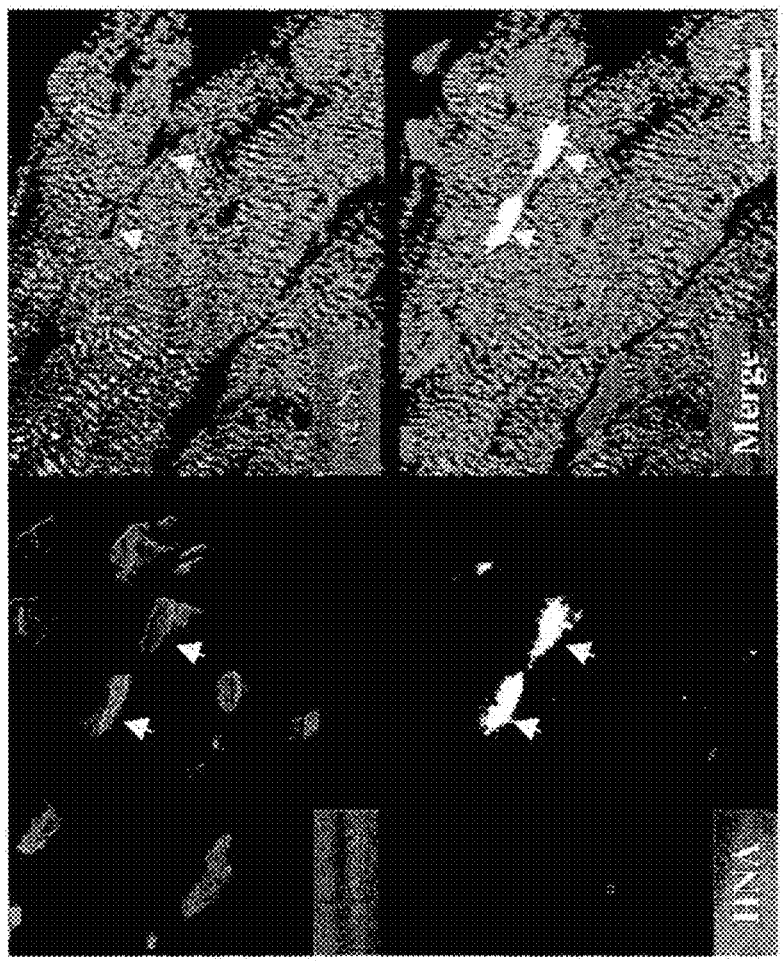

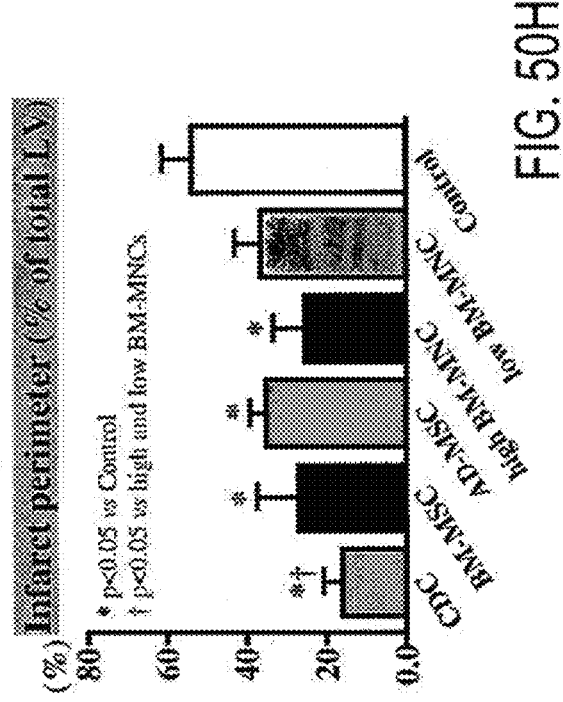
FIG. 50G
FIG. 50H
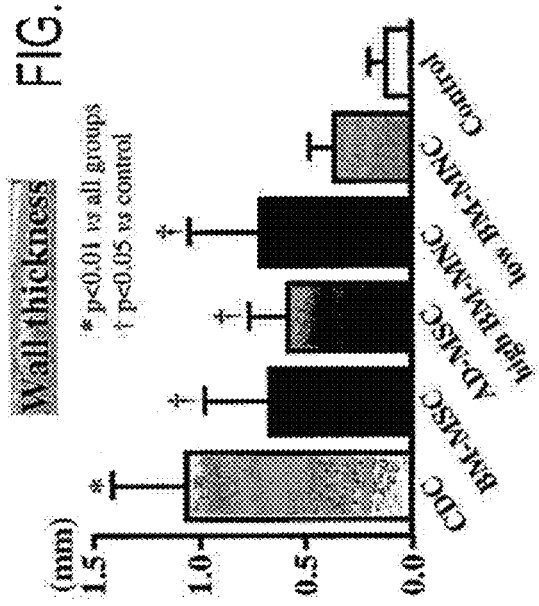
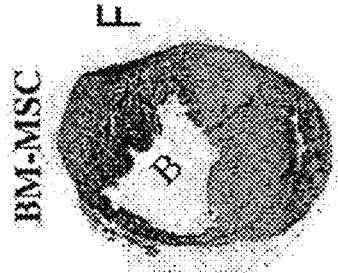
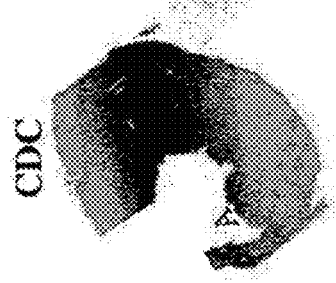
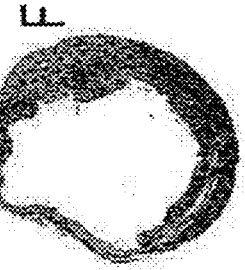
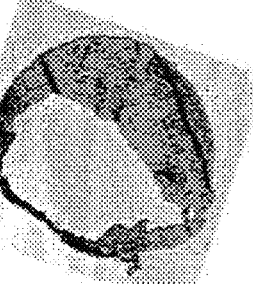
FIG. 50A CDC
FIG. 50B BM-MSC
FIG. 50C AD-MSC
FIG. 50D high BM-MNC
FIG. 50E low BM-MNC
FIG. 50F Control

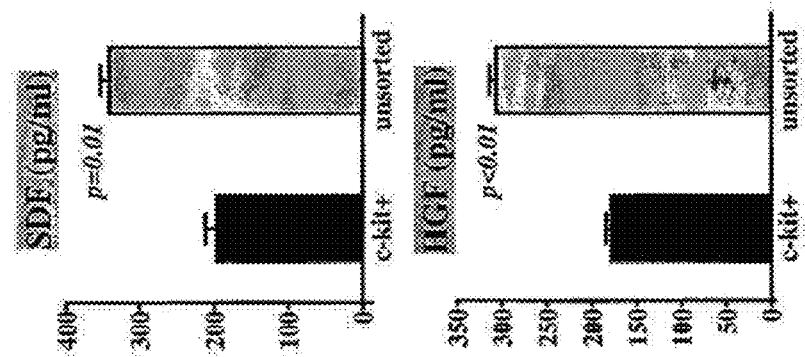
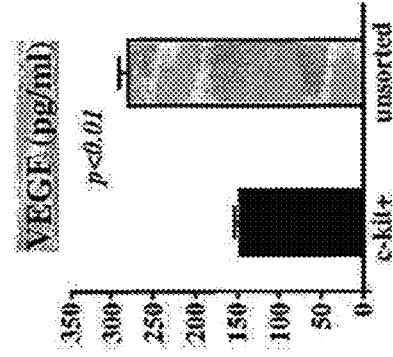
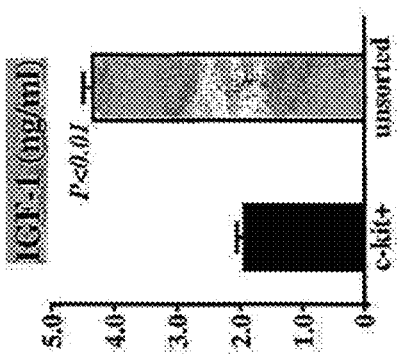
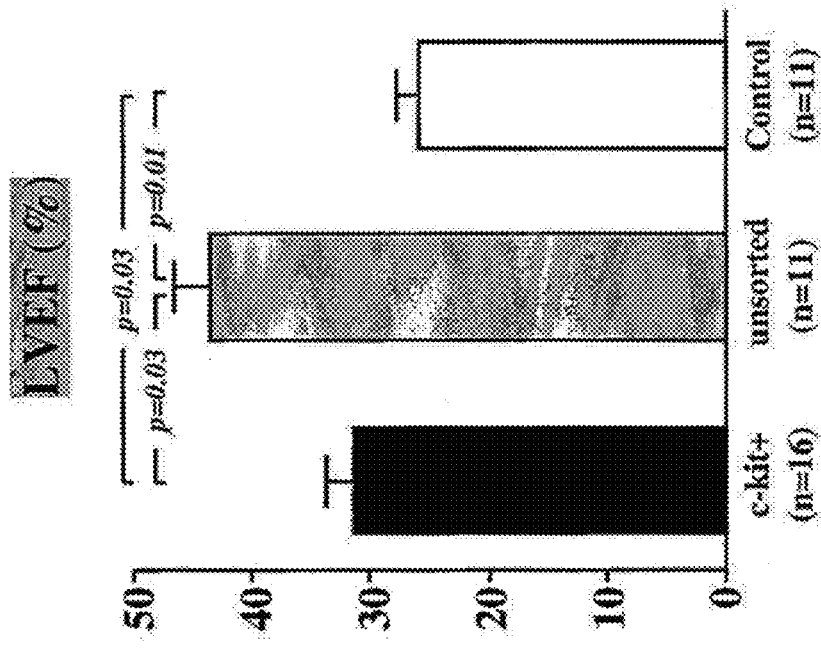

COMPOSITIONS COMPRISING CARDIOSPHERE-DERIVED CELLS FOR USE IN CELL THERAPY

RELATED CASES

This application is a continuation-in-part application of U.S. patent application Ser. No. 11/666,685, filed Apr. 21, 2008, which is the U.S. National Phase application under 35 U.S.C. § 371 International Application No. PCT/US2005/040359 filed on Nov. 8, 2005, which claims the benefit of U.S. Provisional Application No. 60/625,695 filed Nov. 8, 2004, the disclosures of each of which are expressly incorporated herein.

STATEMENT REGARDING GOVERNMENT SPONSORED GRANT

The studies disclosed herein were made with Government support under one or more of the National Institutes of Health Research Project Grants HL095203 HL103356, HL081028, and HL083109. The United States Government has certain rights in this invention.

BACKGROUND

Field of the Invention

Several embodiments of the present application relate generally to regenerative cells, methods of preparing regenerative cells, and compositions comprising regenerative cells for use in transplant for repair of damaged tissue. In one embodiment, regenerative cells isolated from donor heart tissue may be cultured, expanded, and administered to a recipient in order to repair damaged cardiac tissue of the recipient.

Description of the Related Art

Stem cells are characterized by the ability to renew themselves through mitotic cell division and the ability to differentiate into a diverse range of specialized cell types. The two primary types of mammalian stem cells are embryonic stem cells and adult stem cells (i.e., non-embryonic stem cells). Embryonic stem cells are isolated from the inner cell mass of blastocysts and are pluripotent, meaning that the cells have the capacity to differentiate into all of the specialized embryonic tissues. Adult stem cells are isolated from adult tissues and function as an ongoing repair system for adult organs.

Coronary heart disease is presently the leading cause of death in the United States, taking more than 650,000 lives annually. According to the American Heart Association, 1.2 million people suffer from a heart attack (or myocardial infarction, MI) every year in America. Of those who survive a first MI, many (25% of men and 38% of women survivors) will still die within one year of the MI. Currently, 16 million Americans are MI survivors or suffer from angina (chest pain due to coronary heart disease). Coronary heart disease can deteriorate into heart failure for many patients. 5 million Americans are currently suffering from heart failure, with 550,000 new diagnoses each year. Regardless of the etiology of their conditions, many of those suffering from coronary heart disease or heart failure have suffered long lasting and severe heart tissue damage, which often leads to a reduced quality of life.

SUMMARY

Given the vast potential of stem cell therapy to revolutionize medical treatment, there exists a need in for effective and efficient administration of stem cells, compositions comprising stem cells, or derivatives of stem cells to a recipient in order to elicit therapeutic effects, including, among others, tissue regeneration. In particular, in the context of coronary heart disease, there is a need for improved methods to isolate, prepare and administer cell-based compositions to recipients in order to ameliorate and/or treat the cardiac tissue damage that results from adverse cardiac events associated with coronary heart disease.

In several embodiments of the invention, a method of treating an adverse cardiac event (such as myocardial infarction) is provided, wherein the method comprises obtaining a cardiac biopsy sample from a first patient, culturing the sample to obtain regenerative cells, and implanting the regenerative cells into a second patient. This type of allogeneic transplant, according to several embodiments, is particularly advantageous because the regenerative cells do not evoke a significant chronic immune response that is adverse to the patient. Instead, the regenerative cells trigger a cascade of therapeutic signaling effects (e.g., a paracrine effect) prior to destruction via an acute immune response that destroys the regenerative cells. In this manner, according to several embodiments, "off-the-shelf" regenerative cells can be produced to treat patients suffering from cardiac diseases. Thus the patient need not have healthy tissue from which to harvest his or her own cells (as is the case for an autologous transplant). Moreover, even when a patient has healthy heart tissue for biopsy, the patient need not have to wait for the culturing process. Instead, the "off-the-shelf" allogeneic cells may be available with little or no time delay.

According to several embodiments, methods for increasing function of a damaged or diseased heart of a mammal are provided. In one embodiment, a population of cells is administered to the mammal, wherein the population of cells increases cardiac function in the mammal. The population of cells, in one embodiment, is obtained by the process of culturing cells obtained from cardiospheres on a surface as a monolayer. In several embodiments, a population of in vitro-expanded cells is administered to the mammal. In some embodiments, the cells have the capacity to form cardiospheres in suspension culture. According to one embodiment, the cells are not, however, in the form of cardiospheres when administered.

Methods for treating a mammal with a damaged or diseased heart are provided which comprise, in some embodiments, obtaining heart tissue from the damaged or diseased heart of the mammal. In several embodiments, heart tissue is obtained from a heart of a donor. In some embodiments, the heart tissue is obtained by way of a percutaneous endomyocardial biopsy. In some embodiments, the heart tissue is treated to obtain and expand a population of cardiac stem cells and the cardiac stem cells and/or their progeny are subsequently introduced into the damaged or diseased heart.

In some embodiments, methods are provided for treating a mammal with a damaged or diseased organ (e.g., not necessarily the heart). In one embodiment, tissue is obtained from the damaged or diseased organ of the mammal or from a healthy organ of a donor by, for example, a percutaneous biopsy. In several embodiments, the tissue is treated to obtain and expand a population of stem cells. The stem cells and/or their progeny are introduced into the damaged or diseased organ of the mammal. In one embodiment, a method of treating kidney damage is provided. In one embodiment, a kidney biopsy specimen is incubated in the presence of a protease. The cells liberated from the biopsy specimen by the protease incubation are collected. The collected cells are cultured on a surface as a monolayer to expand number of cells, which are then introduced to the damaged kidney.

In several embodiments, cells (e.g., stem cells) are obtained from allogeneic donor tissue, including but not limited to donated organs having tissue that is at least partially healthy and harvestable. In some embodiments, cardiac tissue is obtained from hearts deemed unsuitable for transplantation. Accordingly, in several embodiments, the methods provided herein are particularly advantageous because they utilize donor hearts that would otherwise have been discarded or under-utilized.

In some embodiments, methods for treating tissue (including but not limited to a cardiac biopsy specimen) are provided. In several embodiments, the tissue is incubated in the presence of a protease. The cells that are liberated from the tissue by the protease incubation are collected. In some embodiments, the collected cells are cultured on a surface as a monolayer to expand number of cells.

In some embodiments, methods for expanding a population of cells (including but not limited to cardiac stem cells) are provided. In several embodiments, one or more bodies (e.g., cardiospheres) are disaggregated to individual cells or smaller aggregates of cells. The individual cells or smaller aggregates of cells are cultured on a surface as a monolayer, in some embodiments. In one embodiment, a population of in vitro-expanded cells in a monolayer is provided. The cells have the capacity to form cardiospheres in suspension culture. The cells are not, however, in the form of cardiospheres in some embodiments. In still another embodiment, a population of cells made by the process of culturing cells on a surface as a monolayer is provided. In some embodiments, the cells are obtained from disaggregated cardiospheres.

Although several embodiments of the invention are used for autologous administration, many embodiments are suitable for allogeneic administration. Allogeneic administration is advantageous in several embodiments because it is readily available for immediate administration to patients.

Use of certain types of cells for cellular therapy may be hampered by the unwanted differentiation and growth of administered cells into cell types that are distinct (and in some cases not functionally complementary) to the target tissue. Teratoma formation is thus a potential concern with certain types of cell therapy. To address such concerns, in several embodiments, there is provided a method for the reduction of teratoma formation following the delivery of non-self cells to a first subject (e.g., cells isolated from a tissue source harvested from a second subject, wherein the second subject is an adult) comprising delivering to a first subject a population of regenerative cells, wherein the at least a portion of the regenerative cells engraft into a target tissue of the first subject after delivery to the subject, wherein the regenerative cells express one or more factors that reduce teratoma formation (e.g., in comparison to the delivery of embryonic cells to a subject). In some embodiments, it is the engraftment of the regenerative cells that reduces teratoma formation, at least in part due to the retention of the cells at the desired target site. In some embodiments, the period of engraftment reduces teratoma formation. For example, in some embodiments the period of engraftment is short term (e.g., a few days to several weeks) and insufficient for teratoma formation to occur. In some embodiments, whether engrafted or not, death and/or destruction of the regenerative cells reduces teratoma formation. In several embodiments, it is the combination of two or more of engraftment of the cells, the period of engraftment, the destruction of the cells, and/or the factors released by the cells that reduces teratoma formation.

In several embodiments, there is provided a method of treating a first subject having damaged cardiac tissue with allogeneic cells from a second subject, the method comprising obtaining a plurality of regenerative cells (e.g., CDCs) harvested from the cardiac tissue of a second subject, wherein the administered CDCs generate one or more cytokines, chemokines or diffusible factors, wherein, after administration, at least a portion of the administered CDCs engraft into the cardiac tissue of the first subject; and wherein the one or more generated cytokines, chemokines or diffusible factors or the engraftment improves the function of the damaged cardiac tissue, thereby treating the first subject. In several embodiments, the cells have been expanded in culture to yield a population of cardiosphere-derived cells (CDCs). In one embodiment, the CDCs are not pluripotent and are committed to differentiating into cardiac tissue, thereby reducing the risk of producing undesired tissue growth.

In several embodiments, the engraftment of administered cells persists for a time period ranging from about 1 week to about 6 weeks. In several embodiments, during the period of engraftment at least a portion of the regenerative cells are destroyed by the immune system of the first subject. In several embodiments, the destruction of cells by the immune system is, at least in part, responsible for the reduced teratoma formation as a result of the reduced residence time of the cells.

In several embodiments, during the period of engraftment, the regenerative cells induce endogenous cells to express one or more factors that reduce teratoma formation. Thus, in some embodiments, the combination of factors generated from the regenerative cells and the factors induced to be generated by the endogenous cells is responsible for the reduction in teratoma formation. In several embodiments, expression of the factors comprises cell-surface expression. In several embodiments, expression of the factors comprises release of the factors from the cells.

In several embodiments, the delivery of the regenerative cells is for the purpose of repairing a damaged or diseased tissue of the first subject. In several such embodiments, the damaged or diseased tissue of the first subject comprises damaged or diseased cardiac tissue. In some embodiments, the population of regenerative cells comprises cardiac stem cells. In several embodiments, the cardiac stem cells are selected from the group consisting of cardiospheres, cardiosphere-derived cells, and a subsequent generation of cardiospheres.

In several embodiments, the regenerative cells express one or more stem cell markers selected from the group consisting of c-kit, CD90, and sca-1. In several embodiments, the regenerative cells express one or more endothelial cell markers selected from the group consisting of KDR, flk-1, CD31, von Willebrand factor, Ve-cadherin, and smooth muscle alpha actin. In several embodiments, the regenerative cells express one or more of the stem cell markers or one or more of the endothelial cell markers, but are not selected for, enriched, purified or otherwise preferentially obtained based on the expression of the one or more expressed markers. In several embodiments, the isolated regenerative cells are expanded in culture prior to delivery. In several embodiments, the culturing of the cells is performed in order to induce the expression of one or more of the markers above.

In several embodiments, the isolated regenerative cells generate teratoma-reducing factors in culture. In one embodiment, the method further comprises isolating the teratoma-reducing factors from the culture. In one embodiment, the method also comprises delivering the isolated teratoma-reducing factors from the culture to the first subject. In one embodiment, delivery of the isolated teratoma-reducing factors is prior to delivery of the regenerative cells. In one embodiment, delivery of the isolated teratoma-reducing factors is concurrent with delivery of the regenerative cells. In one embodiment, delivery of the isolated teratoma-reducing factors is after delivery of the regenerative cells. In several embodiments, delivery of the isolated teratoma-reducing factors is at multiple time points throughout the period of engraftment of the regenerative cells. In several embodiments, the delivery of factors isolated in culture supplements the expressed (and/or the induced) generation of teratoma-reducing factors.

In one embodiment, between about $1 \times 10^6$ and about $100 \times 10^6$ of the CDCs, or the regenerative cells, are administered to first subject.

In several embodiments, there is provided a method of treating a first subject having diseased or damaged cardiac tissue with allogeneic regenerative cells obtained from a second subject, the method comprising obtaining a plurality of regenerative cells for administration to a first subject and administering at least a portion of the population of expanded regenerative cells to the first subject.

In several embodiments wherein the regenerative cells are harvested from cardiac tissue obtained from a second subject and subsequently expanded in culture to yield a population of expanded regenerative cells, at least a portion of which are suitable for administration. In several embodiments, after administration, at least a portion of the administered regenerative cells is destroyed by the first subject's immune system. However, in some embodiments, the administered regenerative cells generate one or more paracrine signals post-administration and prior to the destruction. In several embodiments, the one or more paracrine signals improve one or more of the viability or function of the damaged cardiac tissue, thereby treating the first subject. In one embodiment, the regenerative cells are cardiosphere-derived cells (CDCs). In one embodiment, the regenerative cells are cardiospheres. In one embodiment, a mixture of CDCs and cardiospheres is used.

In several embodiments, the regenerative cells are harvested from cardiac tissue obtained from a second subject and subsequently expanded in culture to yield CDCs. In some embodiments, after administration, at least a portion of the CDCs is destroyed by the immune function of the first subject. In several embodiments, the administered CDCs generate one or more paracrine signals post-administration and prior to the destruction. In several embodiments, the one or more paracrine signals improve one or more of the viability or function of the damaged cardiac tissue, thereby treating the first subject.

In several embodiments, the viability or function of the damaged cardiac tissue is improved directly by the paracrine signals. In several embodiments, the viability or function of the damaged cardiac tissue is improved by an indirect mechanism induced by the paracrine signals. In some embodiments, the indirect mechanism comprises recruitment of endogenous cells that repair cardiac tissue. In some embodiments, the indirect mechanism comprises induction of production of paracrine factors by endogenous cells. As a result, in some embodiments, a feed forward repair cascade is initiated, wherein administered cells and their paracrine signals induce further paracrine signal generation by endogenous cells, and effect a more robust repair (e.g., viability or function) of cardiac tissue.

In several embodiments, the administration of the cells results in an increase in at least one of left ventricular percent fractional area and left ventricular ejection fraction. In several embodiments, increases of at least about 5%, 10%, 15%, or more are realized. In other embodiments (e.g., myocardial infarction) scar tissue formation is reduced. In some embodiments, administration of the cells induces pro-survival paracrine signals that improve the viability and/or function of the damaged cardiac tissue. Thus, in such embodiments, the administration induces anti-apoptotic (or other cell death pathways) signals or cascades that result in improved viability, despite an injurious event or disease that affected or is affecting the cardiac tissue. In several embodiments, the pro-survival paracrine signals decrease apoptosis in the damaged cardiac tissue. In several embodiments the pro-survival paracrine signals increase capillary density in the damaged or diseased cardiac tissue. In some such embodiments, the increased capillary density increases the flow of oxygenated blood the regions of the cardiac tissue, thereby improving the viability of the tissue by reducing periods of ischemia, for example.

In several embodiments, the paracrine signals comprise one or more growth factors or cytokines. In one embodiment, the growth factors or cytokines comprise one or more of VEGF, HGF, and IGFI. In the alternative or in conjunction with these factors, other growth factors or cytokines are released (or presented on the surface) by the cells, in other embodiments.

In several embodiments the destruction of the cells is accomplished via phagocytosis. In some embodiments, immune responses (humoral or complement mediated) act to destroy the regenerative cells. In several embodiments, natural death of the administered cells (e.g., apoptosis) occurs, thereby accounting for destruction of the administered cells.

In several embodiments, the cells express one or more stem cell markers selected from the group consisting of: CD105, c-kit, CD90, and sca-1 and one or more endothelial cell markers selected from the group consisting of KDR, flk-1, CD31, von Willebrand factor, Ve-cadherin, and smooth muscle alpha actin. In some embodiments, other cardiac, vascular, or endothelial markers are expressed within or on the cells. In some embodiments, the cells may be selected for by the presence or expression of certain markers. However, in several embodiments, no selection or enrichment based on marker selection is made.

In one embodiment, the diseased or damaged cardiac tissue is the result of one or more of acute heart failure (e.g., a stroke or MI) or chronic heart failure (e.g., congestive heart failure). In several embodiments, about $1 \times 10^5$ to about $1 \times 10^7$ of the cells are administered. In several embodiments, the dose is varied depending on the size and/or age of a subject receiving the cells. In some embodiments (e.g., those that induce feed-forward effects in endogenous cells), smaller numbers of cells are optionally administered. Different routes of administration are also used, depending on the embodiment. For example, the regenerative cells may be administered by intravenous, intra-arterial, intracoronary, or intramyocardial routes (or other routes) of administration.

In one embodiment, there is provided a method of treating a first subject having diseased or damaged cardiac tissue with allogeneic regenerative cells obtained from a second subject, the method comprising obtaining a plurality of regenerative cells for administration to a first subject, administering the expanded regenerative cells to a first subject having damaged cardiac tissue, wherein the regenerative cells are harvested from cardiac tissue obtained from a second subject and subsequently expanded in culture to yield the population of expanded regenerative cells, wherein, after administration, at least a portion of the expanded regenerative cells engraft into the cardiac tissue of the first subject; wherein the administered regenerative cells generate one or more paracrine signals; and wherein the one or more paracrine signals improve one or more of the viability or function of the damaged cardiac tissue, thereby treating the first subject. In one embodiment, the regenerative cells comprise cardiosphere-derived cells (CDCs), wherein the CDCs are about 5 and 20 microns in diameter. In one embodiment, the CDCs are delivered to the first subject via intracoronary administration. In some embodiments, other administration routes are used, for example, intravenous, direct myocardial injection, etc. Selection of the optimal administration route is based upon, among other factors, dose of cells to be delivered, location of the area of damaged tissue, severity of tissue damage, and the like.

In addition to the methods disclosed above, there is also provided a population of allogeneic cells for administration to a subject for the repair of damaged cardiac tissue, comprising cardiosphere derived cells (CDCs) isolated from a first subject, and suitable for administration to a second subject that is allogeneic with respect to the first subject, and expanded in culture.

In several embodiments, there is provided a population of allogeneic cells isolated from a first subject and suitable for administration to a second subject for the repair of damaged cardiac tissue of the second subject comprising cardiosphere derived cells (CDCs) isolated from a first subject and expanded in culture, wherein the CDCs express the stem cell markers CD105 and c-kit, but are not screened, subfractionated, or otherwise selected based on the expression of the markers, wherein the CDCs express one or more products that improve the viability or functionality of the damaged cardiac tissue of the second subject, In several embodiments, the CDCs have a diameter of between about 5 and 20 microns. In some embodiments, the size of the CDCs is advantageous in that a greater variety of delivery routes are available with reduced risk of inducing embolization of the microcirculation upon administration. In several embodiments, administration of the CDCs to a second subject results in engraftment of the CDCs in the cardiac tissue of the second subject for at least about 3 weeks. During that period of engraftment, in several embodiments, the CDCs generate one or more paracrine signals (or expressed products) that yield improvements in the viability or function of the damaged cardiac tissue. In several embodiments, generation of paracrine factors persists beyond the period of engraftment (e.g., the administered cells induce a cascade of events that results in the propagation of paracrine signal production, even in the absence of some or all of the originally administered cells). As discussed above, in several embodiments, the administered cells induce paracrine factor production in endogenous cells.

In several embodiments, the CDCs express a variety of markers that identify the cell types that comprise a CDC population. In several embodiments, the CDCs express the stem cell marker CD105. In several embodiments, the CDCs further express one or more stem cell markers selected from the group consisting of: c-kit, CD90, and sca-1. In several embodiments the CDCs further express one or more endothelial cell markers selected from the group consisting of: KDR, flk-1, CD31, von Willebrand factor, Ve-cadherin, and smooth muscle alpha actin. As discussed herein, in several embodiments, while the CDCs express one or more of the stem cell markers and/or one or more of the endothelial cell markers, the cells are screened, subfractionated, or otherwise selected for based on the expression of the one or more expressed markers.

The beneficial effects of the administration of cells, as disclosed herein, is attributable to the cells themselves, one or more of the paracrine factors produced by the cells, or combinations thereof. In several embodiments, the paracrine signals comprise one or more growth factors or cytokines. In several embodiments, the growth factors or cytokines comprise one or more growth factors or cytokines selected from the group consisting of: ENA-78, G-CSF, GM-CSF, GRO, GRO-alpha, I-309, IL-1 alpha, IL-1 beta, IL-2, IL-3, IL-4, IL-5, IL-6, IL-7, IL-8, IL-10, IL-12, IL-13, IL-15, interferon gamma, MCP-1, MCP-2, MCP-3, M-CSF, MDC, MIG, MIP-1 beta, MIP-1 delta, RANTES, SCF, SDF-1, TGF-beta 1, TNF-beta, EGF, IGF-1, angiogenin, oncostatin M, thrombopoeitin, VEGF, PDGF-BB, leptin, BDNF, BLC, Ck beta 8-1, eotaxin, eotaxin-2, eotaxin-3, FGF-4, FGF-6, FGF-7, Flt-3 ligand, fractalkine, GCP-2, GDNF, HGF, IGFBP-1, IGFBP-2, IGFBP-3, IGFBP-4, IL-16, IP-10, LIF, LIGHT, MCP-4, MIP-3 alpha, NAP-2, NT-3, NT-4, osteopontin, osteoprogenerin, PARC, PIGF, TGF beta 2, TGF beta 3, TIMP-1 and TIMP-2. In several embodiments, the growth factors or cytokines comprise one or more of VEGF, HGF, and IGFI.

The beneficial effects of administration of the population of allogeneic CDCs are multi-fold, and include both functional improvements and improvements in viability of the damaged, diseased, and/or surrounding cardiac tissue. In some embodiments, administration of the CDCs results in at least a 5%, at least a 10%, or at least a 15% improvement in left ventricular function. In some embodiments, the improvement in left ventricular function persists for at least about 6 weeks after administration of the CDCs. In some embodiments, longer term functional improvement is achieved (e.g., 2-3 months, 3-5 months, or greater). In some embodiments, functional improvement is essentially indefinite (e.g., the treatment methods disclosed herein are one-time methods in that additional doses of cells are not required). However, in some embodiments, a serial dosing regimen is preferred. In several embodiments, administration of the CDCs results in at least a 2-fold improvement cardiac cell viability. In some embodiments, similar to the functional improvements, the increased viability is also for longer period (e.g., the damaged cells live longer and/or endogenous cells live longer). In some embodiments, the increased viability is due to a reduction in apoptosis. In some embodiments, apoptosis still occurs naturally, but cells have an altered threshold for committing to an apoptotic pathway (e.g., a greater degree of damage or longer period of ischemia is required). As discussed herein, in several embodiments, the damaged cardiac tissue of the first subject is a result of myocardial infarction, chronic ischemia, or congestive heart disease. In some such embodiments wherein an infarct caused the damage, administration of the CDCs results in a decrease in infarct size. In some embodiments, the reduction in infarct size ameliorates the increased cardiac function (a greater amount of functionally contractile cardiac tissue) and/or the viability (reduction in scar size allows for better overall tissue perfusion and better tissue viability).

In some instances, damage or disease affects cardiac tissue to such a degree that cardiac function cannot be maintained at a level sufficient to support the continued viability of a subject. There is therefore provided a method of supplementing the cardiac function of a first subject, the method comprising obtaining a plurality of cardiac stem cells from a second subject for administration to a first subject, and administering the cardiac stem cells to the first subject. In several embodiments, the first subject has reduced cardiac function due to damaged cardiac tissue. In some embodiments, the obtained cardiac stem cells are optionally expanded in culture in order to achieve a certain population density prior to administration to the first subject. In several embodiments, the administered cardiac stem cells produce one or more diffusible factors and the one or more diffusible factors improve the left ventricular ejection fraction of the heart of the first subject, thereby, supplementing the cardiac function of the first subject.

In some instances, damage or disease affects cardiac tissue to such a degree that an assist device is required in order to maintain normal cardiac functionality. Even with an assist device (e.g., an implanted pacemaker), in some circumstances, cardiac functionality is still too low for some individuals. Therefore, there is provided, in several embodiments, a method of supplementing the function of an implanted left ventricular assist device (LVAD) in a subject, comprising identifying a subject having damaged cardiac tissue and an implanted LVAD and delivering a plurality of cardiac stem cells to the subject, wherein the damaged cardiac tissue is functionally assisted by the implanted LVAD. In several embodiments, the plurality of cardiac stem cells is isolated from healthy donor cardiac tissue, wherein the healthy donor tissue is either from the subject with the LVAD, or preferably from a subject that is allogeneic to the subject with the LVAD. In several embodiments, at least a portion of the delivered cardiac stem cells engraft into the damaged cardiac tissue, although, in some embodiments, at least a portion of the engrafted cardiac stem cells are destroyed by the subject's immune system. The engrafted cardiac stem cells release one or more factors prior to the destruction, and as a result, the one or more factors improve the function of the damaged cardiac tissue, thereby supplementing the function of the LVAD.

In several embodiments, the factors comprise one or more of VEGF, HGF, and IGFI. Other factors, as disclosed herein, are produced by the cells (either the administered cells or the endogenous cells, post-administration) in some embodiments.

In some embodiments, the combination of the direct effect of the engrafted cells (e.g., new healthy functional cardiac cells) with the factors serves to increase the LVAD supplementation. Moreover, in several embodiments, the factors improve the viability of the damaged cardiac tissue. A greater degree of viable cardiac tissue also ameliorates the functionality of the cardiac tissue as a whole, in several embodiments.

In one embodiment, the donor cardiac tissue is allogeneic with respect to the subject. In one embodiment, the donor cardiac tissue is autologous with respect to the subject. In additional embodiments, combinations of allogeneic and autologous cells are used. Such combinations may be beneficial in certain patient populations, such as for example, the extremely immunocompromised. Allogeneic cells produced by the methods herein induce only a limited immune response, if any. However, extremely immunosuppressed individuals may still be susceptible to minor immune reactions from fully allogeneic cell populations. Thus, combinations of autologous and allogeneic may be used in such cases.

In several embodiments, the cardiac stem cells are selected from the group consisting of: cardiospheres, cardiosphere-derived cells (CDCs), and a subsequent generation of cardiospheres. The choice of which cell type is used may be made based on the target location. The size of the CDCs versus the cardiospheres may impact the delivery route and/or the dose delivered. In some embodiments, about $1 \times 10^5$ to about $1 \times 10^7$ cardiac stem cells per kilogram of body weight of the subject are delivered. In some embodiments, the regenerative cells are delivered by injection. In some cases, the regenerative cells are delivered during the process of implanting an LVAD. In such cases, a simple direct injection may be used. Also, in such cases, the degree of damage or disease (which corresponds to the degree of reduced functionality of the heart) can be used to tailor the dose of cells administered. For example, moderate damage may be primarily addressed by an LVAD, with the administration of CDCs minorly supplementing the overall cardiac function. In contrast, severe damage may require both the LVAD and the administration of cells in order to maintain sufficient cardiac function to support the viability of the recipient.

In some embodiments, a subject has an implanted LVAD as a result of at least one prior myocardial infarction. A single infarction may not require the use of a LVAD, depending on its severity. However, as discussed above, in several embodiments, even a minor infarction may optionally be treated with the cells and methods disclosed herein and/or an LVAD. In some such embodiments, delivery of the cardiac stem cells reduces the infarct size, which allows a greater supplementation of LVAD function, as the LVAD is not forced to assist the same amount of stiff, non-contractile scar tissue. Moreover, in several embodiments, the delivery of the cardiac stem cells increase the left ventricular ejection fraction of the subject by about 15%, thereby supplementing the function of the LVAD. In some embodiments, greater or lesser increases in left ventricular function are achieved, which can be tailored to the amount of assistance provided by the LVAD. In some embodiments, however, the administration of cells according to several embodiments herein negates the need for an LVAD, as discussed below.

In several embodiments, the damage or disease to a subject's heart is so severe that the subject is suitable for undergoing a cardiac transplant. In some embodiments, the cardiac stem cells are delivered as a bridge to maintain left ventricular function until the subject receives a cardiac transplant. In other words, such a great degree of the cardiac tissue is damaged, diseased, or otherwise compromised, that the administration of the cells temporarily maintains cardiac viability and function, until such time as a complete heart transplant can be performed. However, in cases with less severe damage, the supplementation of the implanted LVAD negates the need for a cardiac transplant.

In several embodiments, the engrafted cardiac stem cells express one or more stem cell markers selected from the group consisting of CD105, CD90, c-kit, and sca-1. In some embodiments, the engrafted cardiac stem cells express one or more endothelial cell markers selected from the group consisting of KDR, flk-1, CD31, von Willebrand factor, Ve-cadherin, and smooth muscle alpha actin. Despite the wide variety of markers that may be expressed on the cells, e.g., one or more of the stem cell markers CD105 and c-kit, the cells are not screened, subfractionated, or otherwise selected based on the expression of the markers. In other words the markers are used to characterize the cells, not selectively choose the cells. However, in some embodiments, selection based one or more of such markers is optionally performed.

In some embodiments, autologous cells are administered to patients with left ventricular dysfunction and a recent myocardial infarction with delivery occurring by intracoronary infusion via an over-the-wire balloon catheter. In other embodiments, allogeneic cells are administered to patients undergoing ventricular assist device placement, via intramyocardial injection using a standard needle and syringe and an epicardial approach during LVAD placement. In some embodiments, the allogeneic cells produce an immune response that is similar to the autologous cells.

In several embodiments, regenerative cells (autologous and/or allogeneic) are administered to patients via epicardial injection (or other delivery mechanism) in conjunction with LVAD implantation.

Given the widespread use of LVADs to treat reduced cardiac function, certain subject's that are treated by the methods disclosed herein may already have an LVAD implanted. However, there is also provided a method of reducing the dependence of a subject on an implanted left ventricular assist device (LVAD) comprising administering to the cardiac tissue of the subject a population of regenerative cells, wherein, after administration, at least a portion of the administered regenerative cells are removed from the subject's cardiac tissue by endogenous mechanisms of the subject, and wherein, prior to the removal, the administered regenerative cells generate one or more signals that induce improvement in one or more of the viability or function of the cardiac tissue of the subject, thereby reducing the dependence of the subject on the LVAD.

As discussed herein, certain subjects present with widespread and severe cardiac damage and/or decreased functionality as a result of a cardiac injury (e.g., a myocardial infarction) or disease (e.g., congestive heart failure). Often, such subjects are likely candidates for heart transplants. However, the costs, and complications, associated with transplants mean that such an approach is not a viable solution for all subjects. There is, therefore, also provided a method of reducing a first subject's likelihood of having a cardiac transplant, the method comprising, obtaining a plurality regenerative cells from a second subject that are suitable for administration to the first subject, wherein the regenerative cells are expanded in culture to generate a population of regenerative cells prior to administration to the first subject, and administering at least a portion of the population of expanded regenerative cells to the first subject; wherein the administered regenerative cells produce one or more diffusible factors, wherein the administered regenerative cells and the one or more diffusible factors induce one or more of stimulation of resident cardiac cells to grow, stimulation of resident cardiac cells to reproduce, or stimulation of resident cardiac cells to improve functionally, thereby reducing the likelihood of the first subject requiring a cardiac transplant.

In some embodiments, the first subject has reduced cardiac function and either has an LVAD or is a candidate for a heart transplant (or both) due to one or more of an acute ischemic event, chronic ischemia, or congestive heart disease. In several embodiments, the first subject receives cells isolated from the first subject's own tissue (e.g., an autologous transplant). In other embodiments, the first subject is allogeneic with respect to the donor of the tissue from which the regenerative cells are isolated. In several embodiments, the administration increases the function of the cardiac tissue of the first subject thereby reducing the likelihood of the first subject requiring a cardiac transplant.

In several embodiments, the regenerative cells are harvested from healthy donor cardiac tissue. In several embodiments, the donor cardiac tissue is allogeneic with respect to the subject.

In several embodiments, the dose of cells to be administered may be determined by virtue of the severity of the cardiac damage or disease, the age of the subject, the subject's overall general health, and other factors. However, in several embodiments, about $1\times10^5$ to about $1\times10^7$ regenerative cells per kilogram of body weight of the subject are administered. In other embodiments, other doses are used. In some embodiments, the regenerative cells are administered by local intramyocardial injection. In some embodiments, the regenerative cells are administered by epicardial injection. Other routes of administration are used, in some embodiments, for example, depending on the precise location of a LVAD and/or the damaged cardiac tissue. In some embodiments, the regenerative cells are administered during the process of implanting the LVAD. In other embodiments, the regenerative cells are administered during the process of explanting an implanted LVAD.

While various mechanisms, both direct and indirect, may be involved, in some embodiments, the regenerative cells increase the incidence of angiogenesis in the subject's cardiac tissue. In some embodiments, the regenerative cells increase the left ventricular ejection fraction of the subject by at least about 5%, at least about 10%, at least about 15%, or more, thereby reducing the dependence of the subject on the implanted LVAD.

As discussed herein, in several embodiments, at least a portion of the administered cells engraft into the target tissue. Additionally, in several embodiments, at least a portion of the cells are removed from the target tissue by endogenous mechanisms of the subject receiving the cells. In one embodiment, the endogenous mechanisms comprise recruitment of at least a portion of the subject's immune system. In one embodiment, the endogenous mechanisms comprise induction of apoptosis of the administered regenerative cells.

In several embodiments, the regenerative cells are selected from the group consisting of: cardiospheres, cardiosphere-derived cells (CDCs), and a subsequent generation of cardiospheres. In one embodiment, the regenerative cells are CDCs. In several embodiments, the regenerative cells express one or more of the stem cell markers CD105 and c-kit, but are not screened, subfractionated, or otherwise selected based on the expression of the markers.

As a result of acute injury to the heart (e.g., a myocardial infarction) or long-term damage there may be an associated increase in cell death as a result, in particular, apoptotic cell death. Therefore, there is provided a method of decreasing apoptosis in a heart having been affected by myocardial infarction, comprising administering a population of cardiac stem cells to a subject having a heart affected by a myocardial infarction, wherein, after administration, at least a portion of the administered population of cardiac stem cells is destroyed by endogenous mechanisms of the subject, wherein the administered population of cardiac stem cells generate one or more paracrine signals post-administration and prior to the destruction, and wherein the one or more paracrine signals reduce the incidence of apoptosis in the cardiac tissue affected by the myocardial infarction.

There is also provided a method of decreasing apoptosis in a heart having been affected by myocardial infarction, comprising administering a population of cardiac stem cells to a subject having a heart affected by a myocardial infarction, wherein the administered cardiac stem cells generate one or more paracrine signals, and wherein the one or more paracrine signals act on the administered cardiac stem cells and resident cardiac stem cells to increase the viability of the administered cardiac stem cells and the resident cardiac stem cells, thereby reducing the incidence of apoptosis in the cardiac tissue affected by the myocardial infarction.

In several embodiments the administration reduces the expression of apoptotic markers on cardiac cells affected by the myocardial infarction, thereby indicating a reduction in one or more portions of the apoptotic cascade. For example, in one embodiment, the decrease in apoptosis is associated with reduced Caspase 3 expression. In some embodiments, administration reduces the amount of plasma membrane damage on the cardiac cells affected by the myocardial infarction. In still additional embodiments, anti-apoptotic signals or markers are increased. For example, in one embodiment, the decrease in apoptosis is associated with an increase in Akt expression. As a result, in several embodiments, apoptosis is decreased by about 5% about 10%, about 15%, about 20%, or more. In several embodiments, the decrease in apoptosis occurs within several hours after administration of the cardiac stem cells. However, in several embodiments, the decrease in apoptosis occurs within several days after administration of the cardiac stem cells. In some embodiments, the decrease in apoptosis is associated with increased cardiac function.

In some embodiments, damaged or diseased cardiac tissue is the result of a reduced blood supply to a region of the cardiac tissue. For example, a myocardial infarction may result from the partial or total blockage of a vessel providing oxygenated blood to one or more regions of the heart. In some embodiments, the major vessels may be affected, while in some embodiments, minor blockages (e.g., to the arterioles) may also damage the cardiac tissue. Thus, in order to combat the deleterious effects of reduced blood supply, there is provided a method for increasing angiogenesis in a heart having been affected by a myocardial infarction, comprising administering cardiac stem cells to a subject having a heart affected by a myocardial infarction, wherein the administered population of cardiac stem cells generate one or more paracrine signals post-administration and prior to the destruction, and wherein the one or more paracrine signals increase the level of angiogenesis in the cardiac tissue affected by the myocardial infarction.

In several embodiments, at least a portion of the administered population of cardiac stem cells is destroyed by the subject's immune system. As a result, there may not be long-term survival of the entire population of administered cells. However, as a result of the paracrine signals, at least a portion of the beneficial effects of the administered cells carries on beyond the time at which the cells are destroyed. In some embodiments, the administered cells die on their own time frame, and are simply removed from the tissue by endogenous mechanisms (e.g., phagocytosis). In some embodiments, the combination of the administered cells themselves (a direct repair mechanism) works in concert with the induced paracrine cascade (either from the administered cells or from the endogenous cells) to effect the increased angiogenesis.

In several embodiments, the increased angiogenesis results in an increase in vessel density in the cardiac tissue of the subject. In some embodiments, the vessel density is increased by about 2-fold, about 3-fold, about 5-fold, or greater. In some embodiments, a 10% increase, a 15% increase, a 20% increase, or greater is achieved. In several embodiments, the increased angiogenesis increases the length of existing blood vessels. In some embodiments, the vessel length is increased by about 2-fold, about 3-fold, about 5-fold, or greater. In some embodiments, a 10% increase, a 15% increase, a 20% increase, or greater is achieved. In several embodiments, combinations of increased vessel density length and increased density are achieved. In addition to the effects on existing vessels, in several embodiments, the increased angiogenesis increases the formation of new blood vessels. In some embodiments, a 5%, 10%, 15% or greater increase in new vessels is achieved. In combination with the positive effects on existing vessels, blood supply is increased to the region of damaged or diseased cardiac tissue, which, in several embodiments, provides increased function and/or viability to the region. In several embodiments, the increased vessel density, increased vessel length, and/or the new vessels are associated with improved function of about 5%, 10%, 15%, or greater in at least one of left ventricular percent fractional area and left ventricular ejection fraction.

In several embodiments, the paracrine signal comprises release of VEGF from the cardiac stem cells. In some embodiments, additional pro-angiogenic factors are also generated by the cardiac stem cells, including endogenous cardiac stem cells.

In several embodiments, the plurality of cardiac stem cells is harvested from healthy donor cardiac tissue. Depending on the amount of cells desired or required for administration, the plurality of the harvested cardiac stem cells is expanded in culture to yield the population of cardiac stem cells. While in several embodiments, the cardiac stem cells are allogeneic with respect to the subject, in other embodiments, the cardiac stem cells are autologous with respect to the subject.

In addition to the administration of regenerative cells to a subject, there is also provided a method of regenerating cardiac tissue in an individual having damaged cardiac tissue, comprising isolating a population of regenerative cells from cardiac tissue of a donor, expanding the population of regenerative cells in culture, wherein the regenerative cells in culture generate one or more paracrine factors, isolating the one or more paracrine factors from the culture, wherein the isolated paracrine factors are suitable for administration to a damaged heart of an individual, and wherein, after administration, one or more paracrine factors facilitate the formation of new cardiac tissue in the individual. In several embodiments, said damaged cardiac tissue is a result of myocardial infarction. In some embodiments, administration of said one or more paracrine factors results in a decrease in infarct size. In additional embodiments, the one or more paracrine factors improves one or more of the viability or function of the damaged cardiac tissue. In one embodiment, administration of one or more paracrine factors results in at least a 15% improvement in left ventricular function In several embodiments, there is also provided a method of improving the cardiac function of an individual having damaged cardiac tissue, comprising identifying a subject having damaged cardiac tissue and administering to said subject one or more paracrine factors, wherein said paracrine factors are obtained from a population of regenerative cells in culture, wherein said regenerative cells were isolated from the cardiac tissue of a donor, wherein said population of regenerative cells comprises cardiac stem cells and, wherein, after administration, said one or more paracrine factors induce formation of new functional cardiac tissue and/or improve the function of the damaged cardiac tissue of said subject.

In several embodiments, said cardiac stem cells are selected from the group consisting of cardiospheres, cardiosphere-derived cells, and a subsequent generation of cardiospsheres. In one embodiment, said one or more paracrine factors comprise one or more of VEGF, HGF, and IGFI.

Additionally, there is provided a method of increasing the function of cardiac tissue in an individual having damaged cardiac tissue, comprising identifying a subject having damaged cardiac tissue, administering to said subject one or more paracrine factors selected from the group consisting of VEGF, HGF, and IGFI, wherein said paracrine factors are obtained from a population of regenerative cells in culture, wherein said regenerative cells were isolated from the cardiac tissue of a donor, wherein said population of regenerative cells comprises cardiac stem cells, wherein said cardiac stem cells comprise one or more of cardiospheres, cardiosphere-derived cells, and a subsequent generation of cardiospsheres, wherein, after administration, said one or more paracrine factors recruit endogenous cardiac cells to the damaged cardiac tissue, wherein said recruited cells repair said damaged cardiac tissue, thereby improving the function of the damaged cardiac tissue of said subject. In several embodiments, the one or more paracrine factors induce production of paracrine factors by endogenous cells at or near the site of administration, thereby further increasing repair of said damaged cardiac tissue. In several embodiments, such method result in at least a 15% improvement in left ventricular function.

In several embodiments, the donor is allogeneic with respect to the individual, while in other embodiments, the donor and the recipient individual are the same. Thus, there are provided herein both cell-based and cell-free methods of generating and/or repairing cardiac tissue.

BRIEF DESCRIPTION OF THE FIGURES

FIGS. 1A-1I depict specimen processing for cardiosphere growth and Cardiosphere-Derived Cell (CDC) expansion. FIG. 1A depicts a schematic of the steps involved in certain embodiments of specimen processing. FIG. 1B depicts a human endomyocardial biopsy fragment on day 1. FIG. 1C depicts a human explant 3 days after plating. FIG. 1D depicts the edge of a human explant 13 days after plating and showing stromal-like and phase-bright cells. FIG. 1E depicts results of sub-population selection performed using cardiosphere-forming cells. c-kit$^+$ cells were 90.0±4.7% CD105$^+$, and c-kit$^-$ cells were 94.0±0.8% CD105$^+$ (n=3). FIG. 1F depicts human cardiospheres on day 25, 12 days after collection of cardiosphere-forming cells. FIG. 1G depicts human CDCs during passage 2, plated on fibronectin for expansion. FIG. 1H depicts cumulative growth curves for 11 specimens from untransplanted patients over the course of 4 months. FIG. 1I depicts growth for 59 specimens from transplanted patients. Day 0 corresponds to the date the specimen was collected and cell number on that day is plotted as 1 on the log scale, since no cardiosphere-forming cells had yet been harvested from the specimen.

FIGS. 2A-2C depict cardiosphere and CDC phenotypes. FIG. 2A depicts expression of c-kit throughout the core of a cardiosphere and CD105 on the periphery. FIG. 2B depicts expression of cardiac MHC and TnI primarily on cardiosphere periphery. FIG. 2C depicts c-kit and CD105 expression levels in CDCs at passage 2 shown for one representative specimen (n=3 and n=2).

FIG. 3E depicts the percent of viable myocardium found within the infarcted area in CDC (n=8), PBS (n=4), and fibroblast-injected (n=4) groups (* p<0.01).

FIG. 4A depicts end-diastole while FIG. 4B depicts end-systole. Yellow lines trace around the left ventricular area used for the calculation of LVEF and LVFA. (FIG. 4C and FIG. 4D). FIG. 4E shows the left ventricular ejection fractions (LVEF) for the three experimental groups after 20 days (CDC n=8, PBS n=7, Fibroblast n=4; *p<0.01). LVEF was calculated as $$100 \times (LVVolume_{diastole} - LVVolume_{systole})/LVVolume_{diastole}$$

and left ventricular volume (LVVolume) was calculated from long-axis views assuming a prolate ellipsoid. FIG. 4F depicts left ventricular percent fractional area (LVFA) for the three experimental groups after 20 days. *p<0.01. LVFA was calculated as:

$$100 \times (LVArea_{diastole} - LVArea_{systole})/LVArea_{diastole}$$

Figure 5A:
Figure 5B:
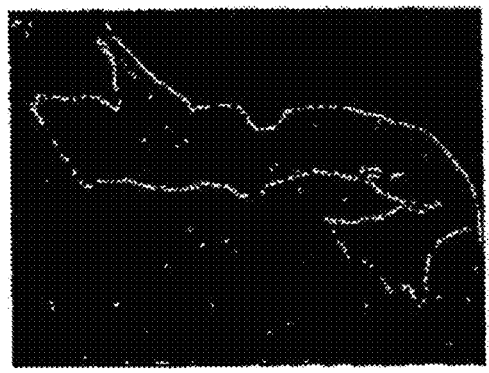
Figure 5C:

FIGS. 5A-5C depict quantification of cardiac tissue regeneration. FIG. 5A shows Masson's trichrome staining for a representative CDC-injected mouse. The total infarct zone is outlined in yellow in FIG. 5B and FIG. 5C. FIG. 5B depicts areas of fibrosis in red after image processing. FIG. 5C depicts areas of viable myocardium in red after image processing. Six sections were analyzed per animal and an average taken.

Figure 6A:
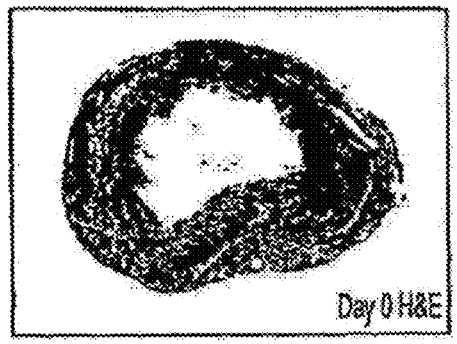
Figure 6B:
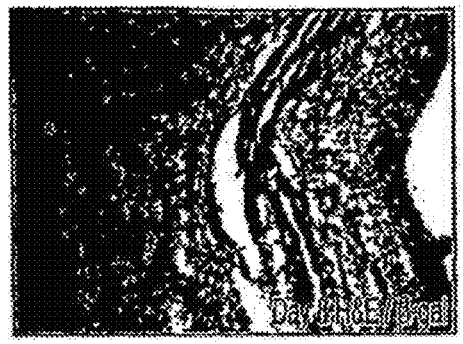
Figure 6C:
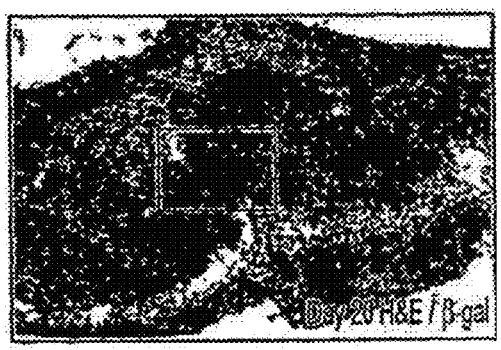
Figure 6D:
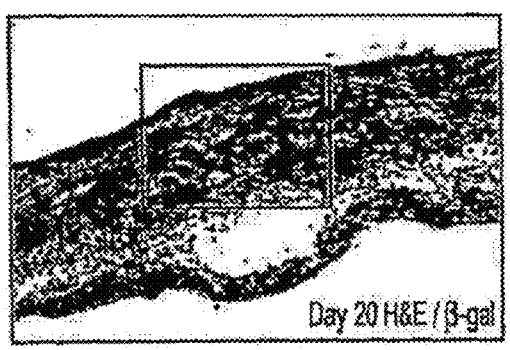
Figure 6E:
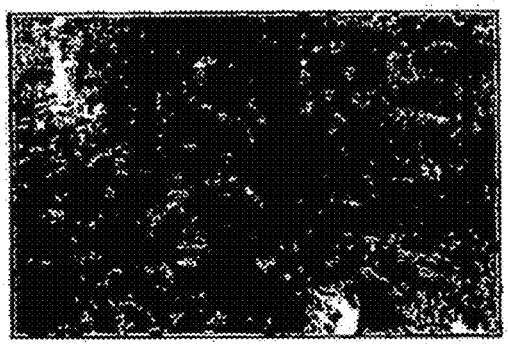
Figure 6F:
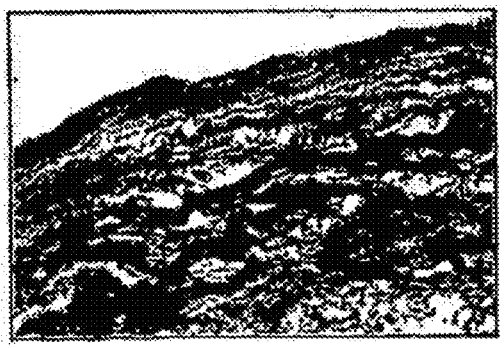

FIGS. 6A-6F depict an engraftment time course. FIG. 6A depicts the bolus of injected cells on day 0 in an H&E stained section of cardiac tissue. FIG. 6B depicts engraftment of CDCs 8 days after injection. FIG. 6C and FIG. 6D depict engraftment of CDCs 20 days after injection. FIG. 6E and FIG. 6F depict corresponding higher magnification views of FIG. 6C and FIG. 6D demonstrating colocalization of lac-Z-positive CDCs and viable myocardium.

Figure 7A:
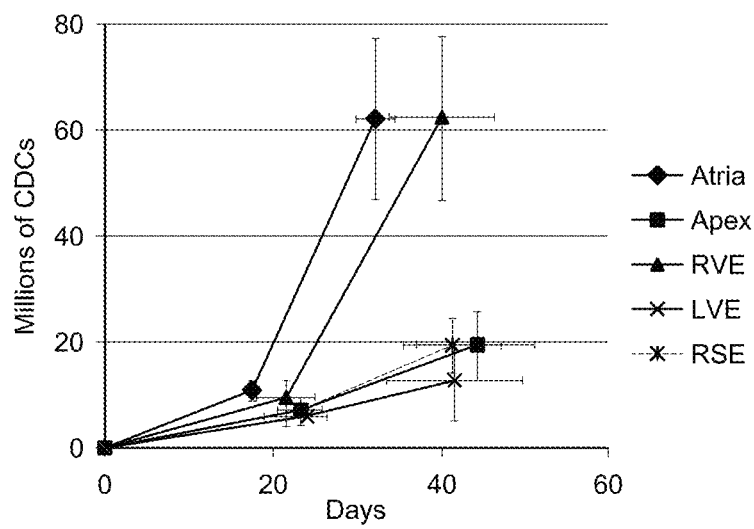
Figure 7B:
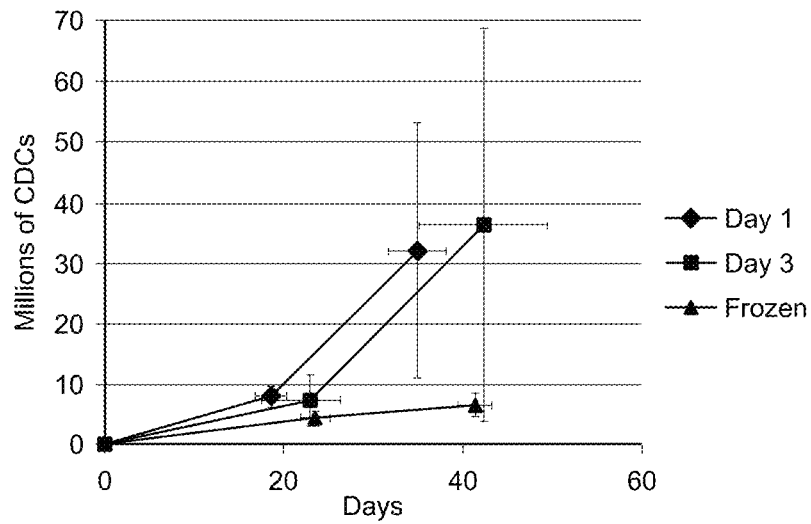
Figure 7C:
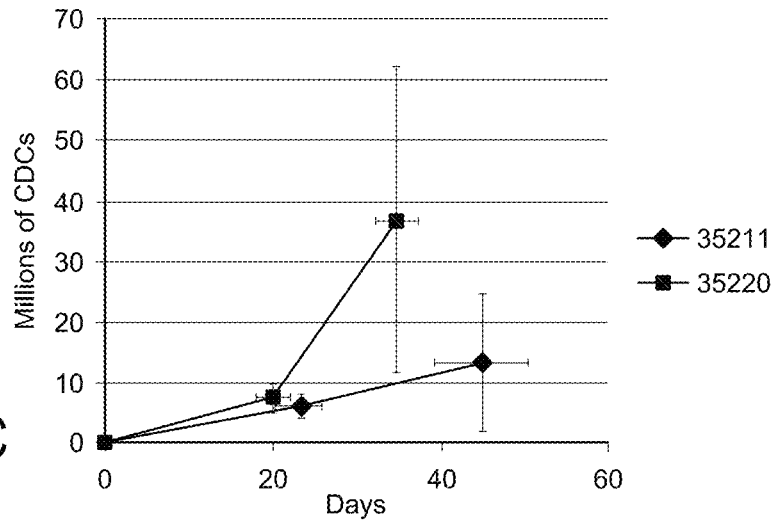

FIGS. 7A-7C depict the growth of CDCs generated from 2 whole hearts and subjected to various growth conditions. FIG. 7A depicts CDC yield from samples taken from different regions of the heart. FIG. 7B depicts the effect of tissue storage in cold cardioplegia for up to 6 days or freezing and thawing. FIG. 7C depicts a comparison of yield of CDCs from each of the sample hearts grown under the same conditions.

Figure 8A:
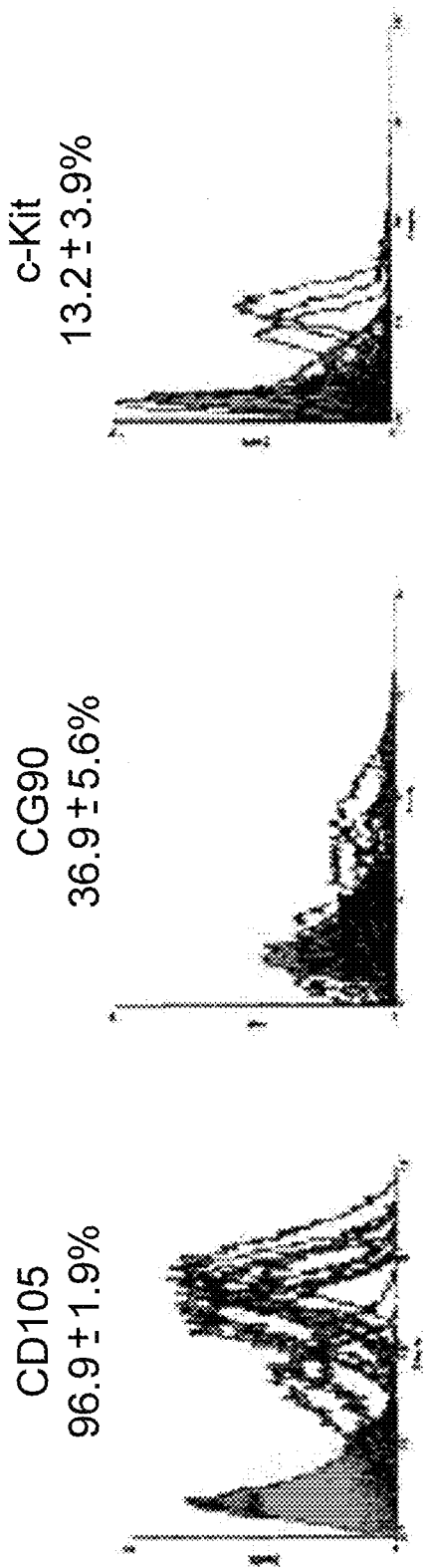
Figure 8B:
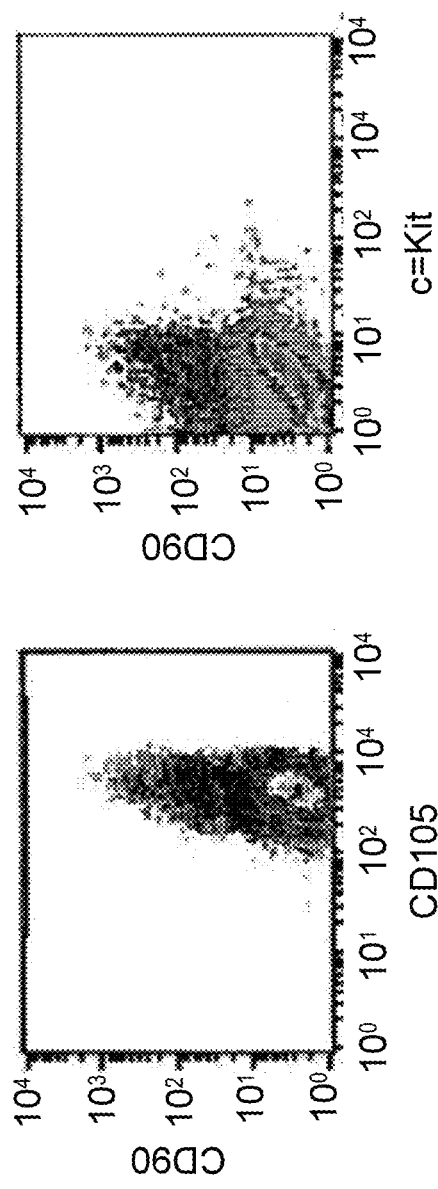

FIGS. 8A-8B depict phenotypic identity of human CDCs. FIG. 8A depicts surface immunophenotype by flow cytometry of human CDCs from multiple patients. Dual-labeled analysis depicting mesenchymal and progenitor CDC subpopulations is shown in FIG. 8B.

Figure 9A:
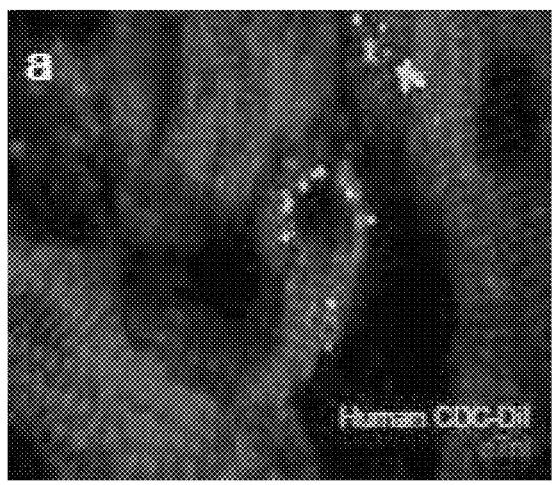
Figure 9B:
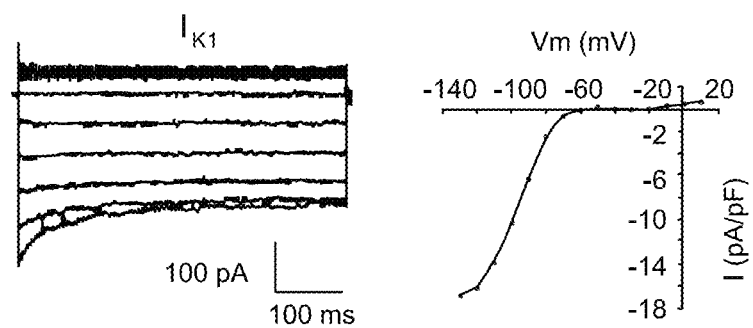
Figure 9C:
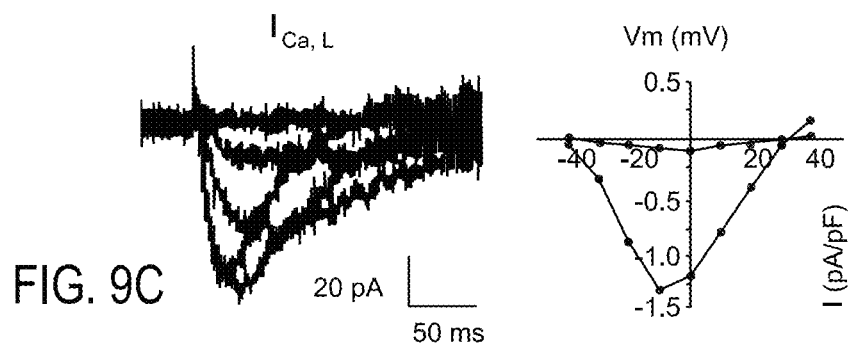

FIGS. 9A-9C depict characteristics of differentiating CDCs. FIG. 9A depicts sarcomeric organization in human CDCs co-cultured with rat neonatal ventricular myocytes. FIG. 9B depicts inwardly rectifying potassium current recorded form CDCs, which is consistent with cardiomyocyte ventricular phenotype. FIG. 9C depicts L-type calcium current $I_{Ca,L}$ recorded from CDCs transduced with the beta subunit of the L-type calcium channel, indicating the presence of the pore-forming alpha subunit.

FIGS. 10A-10B depict CDCs forming tube matrices in an angiogenesis assay. Human CDCs (FIG. 10A) form tubelike networks at early timepoints and undergo complex morphological changes at late timepoints. This is in comparison to human umbilical vein endothelial cells (HUVECs) (FIG. 10B) which form distinct tube networks.

Figure 11A:
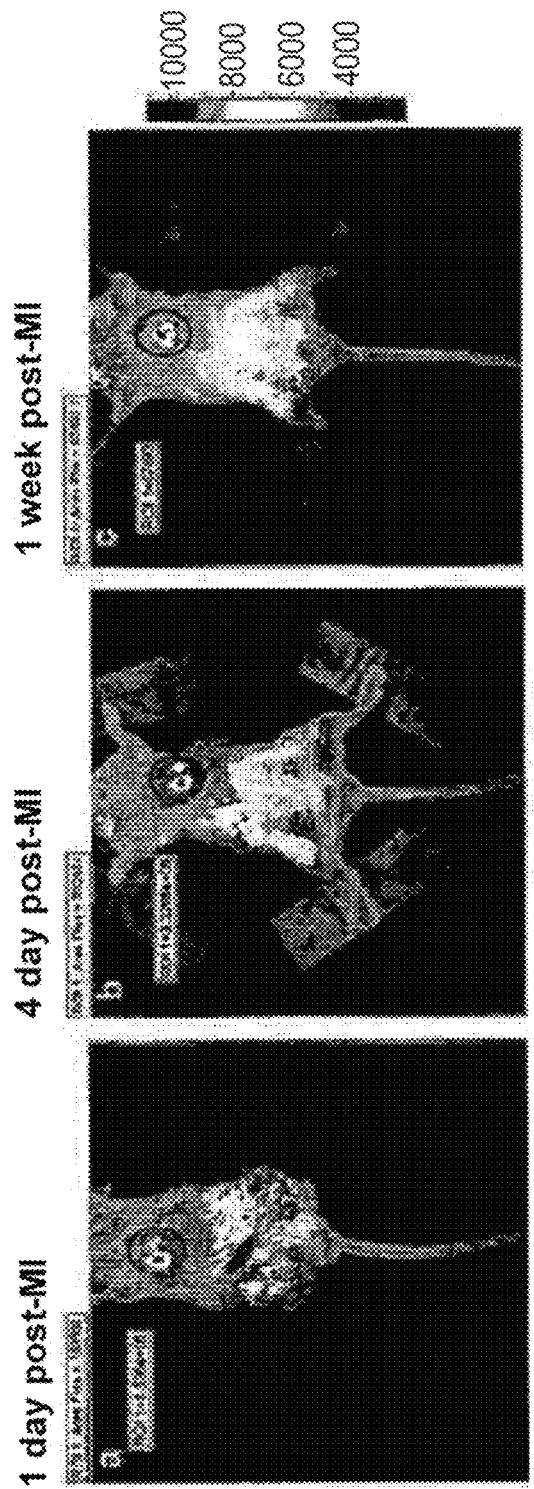
Figure 11B:
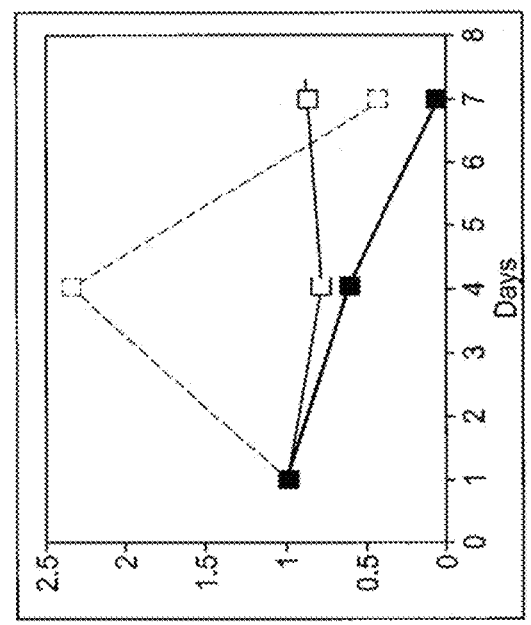

FIGS. 11A-11B depict engraftment of human CDCS. FIG. 11A depicts luciferase-labeled cells detected in the heart at 1 day, 4 days, and 1 week post-administration. FIG. 11B depicts peak signals detected for each of 3 mice.

FIGS. 12A-12K depict detection of human CDCs in injected mouse hearts. Mouse hearts excised at different timepoints following MI and delivery of human CDCs are shown in FIGS. 12A-12C. Human nuclei are identified at each timepoint by green fluorescence overlaid on the blue fluorescence of all nuclei (FIGS. 12D-12K). INF=infarct. BZ=border zone.

Figure 13:
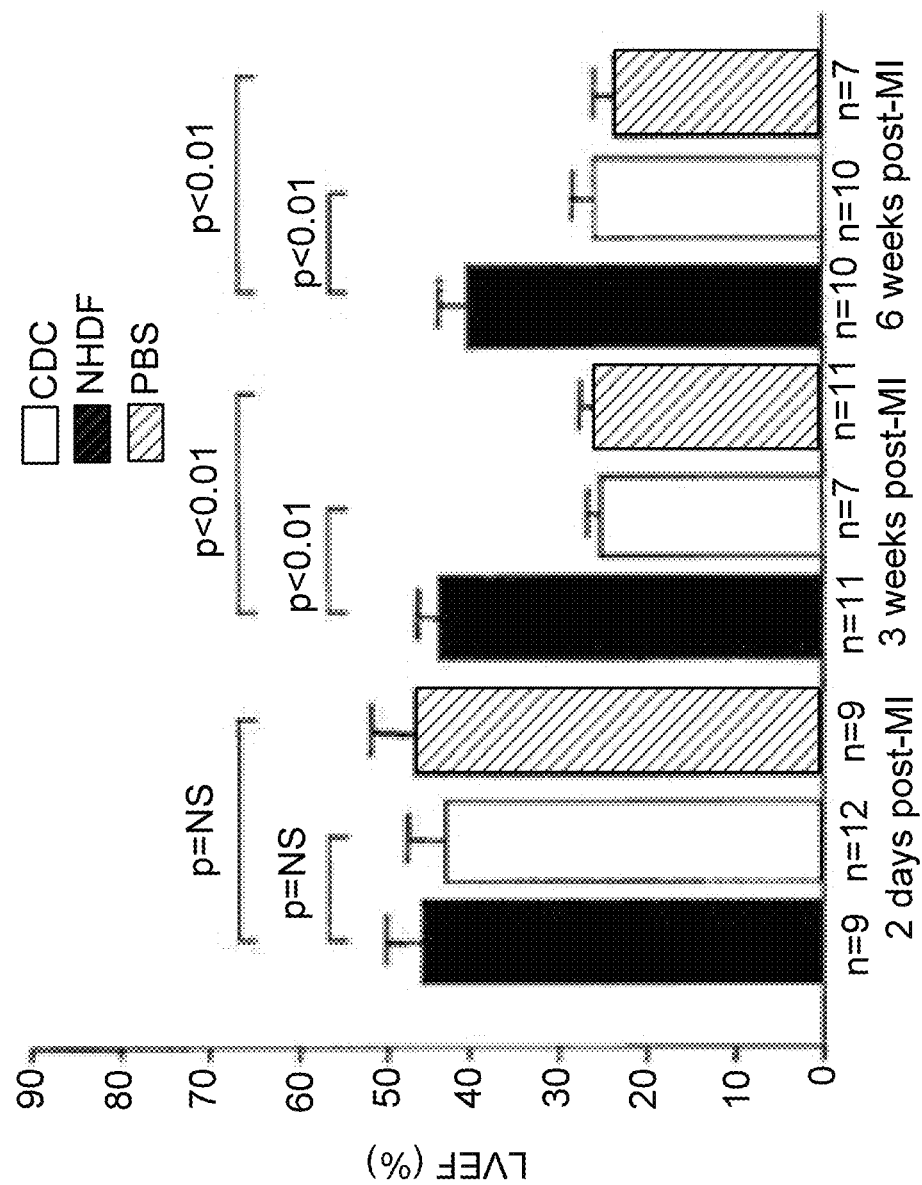

FIG. 13 depicts a summary of echocardiography on mice injected with CDCs, normal human derived fibroblasts, or phosphate buffered saline. CDC-injected animals maintained function after MI, while NHDF- and PBS-injected declined.

Figure 14:
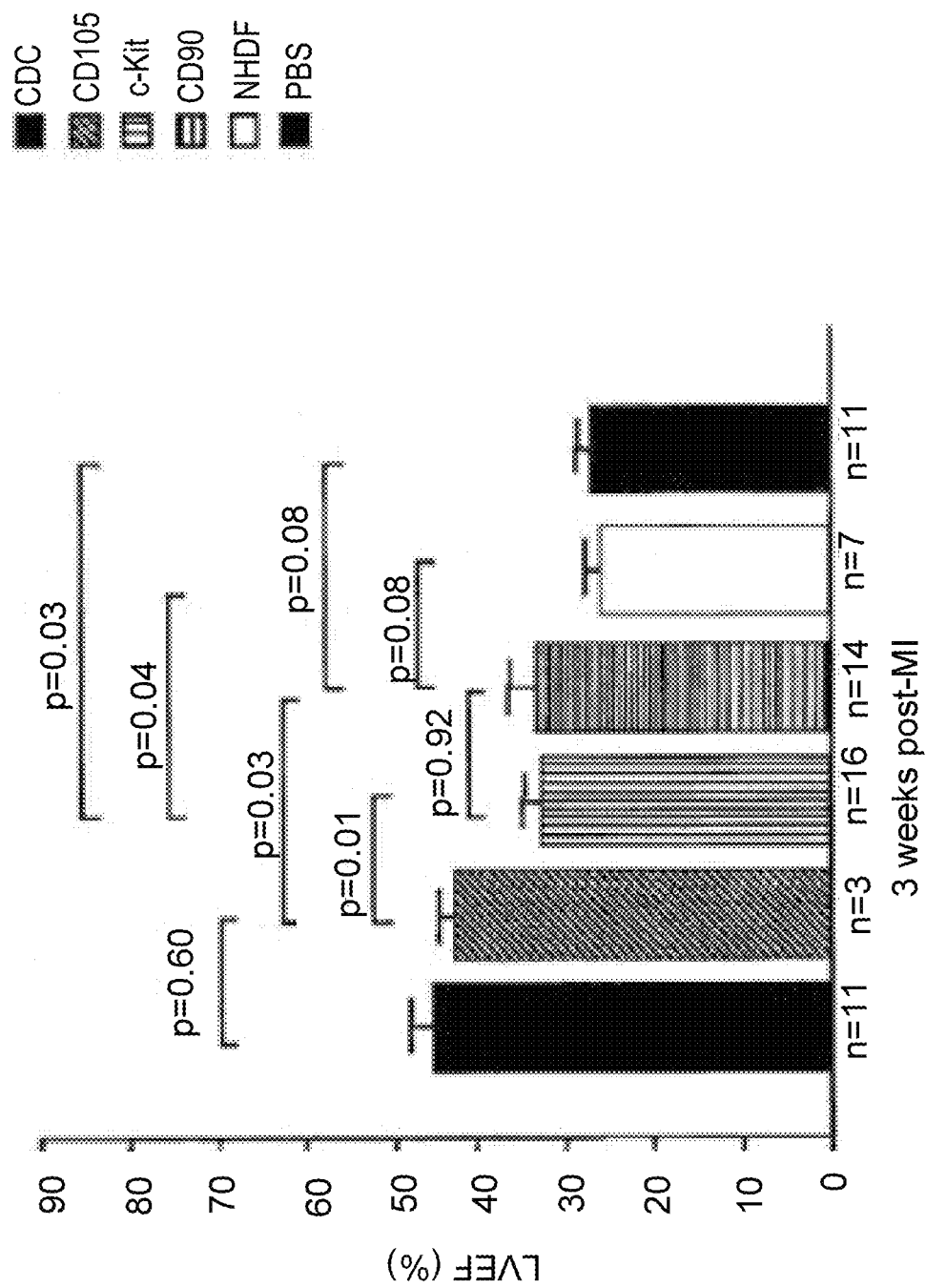

FIG. 14 depicts the effect of various CDC subpopulations on murine cardiac function. CDC-injected animals outperformed animals injected with either c-kit or CD90 subpopulations.

FIGS. 15A-15R depict differentiation of human CDCs at various time-points in infarcted mice.

FIGS. 16A-16P depict formation of cardiomyocytes and non-cardiomyocytes from human CDCs at 6 weeks post-MI. Human nuclei of interest are outlined in FIGS. 16E-16H. Example cardiomyocyte nuclei are shown in FIGS. 16M-16P at higher magnification.

Figure 17:
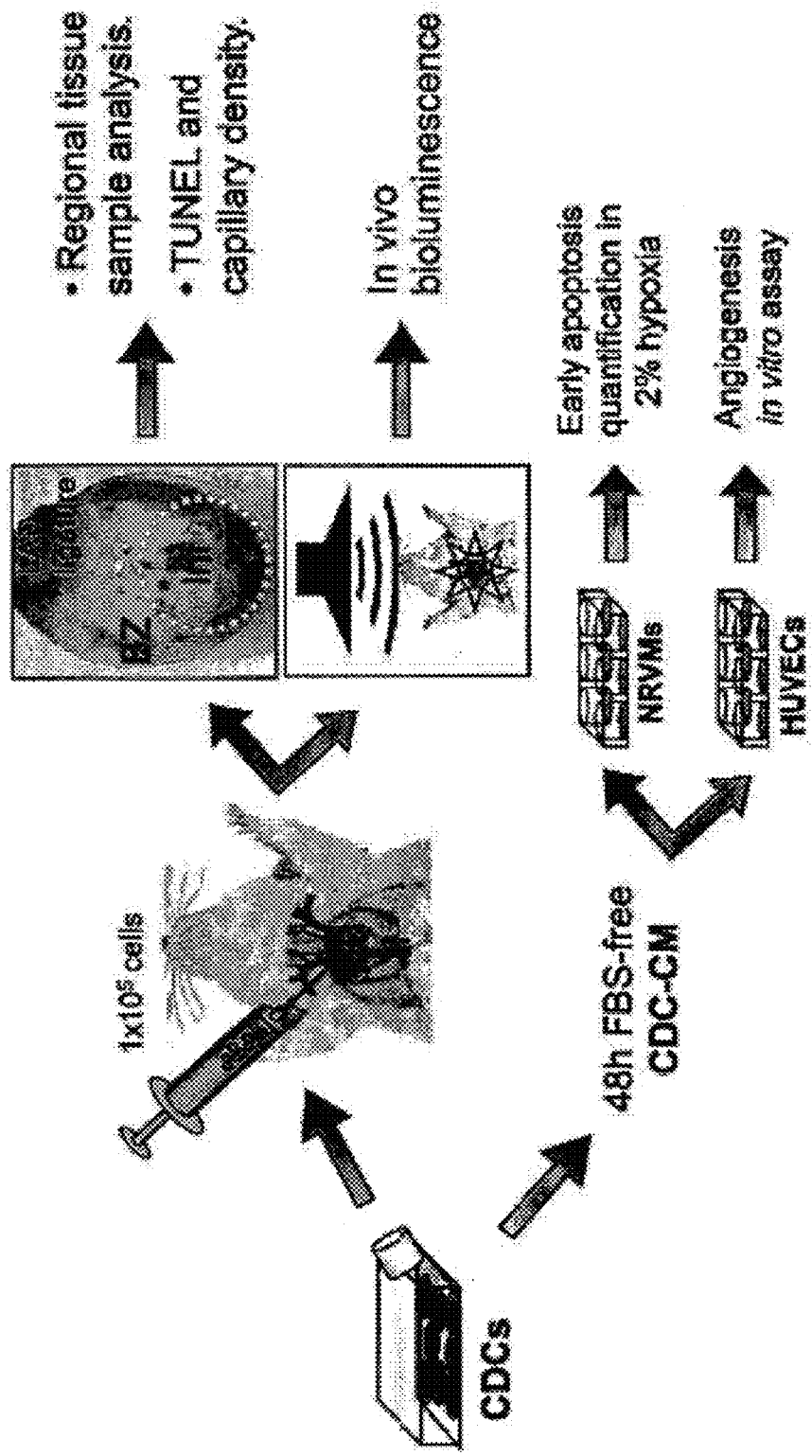

FIG. 17 depicts a schematic of in vitro and in vivo experimental designs to evaluate functional effects of paracrine signals released from regenerative cells.

Figure 18A:
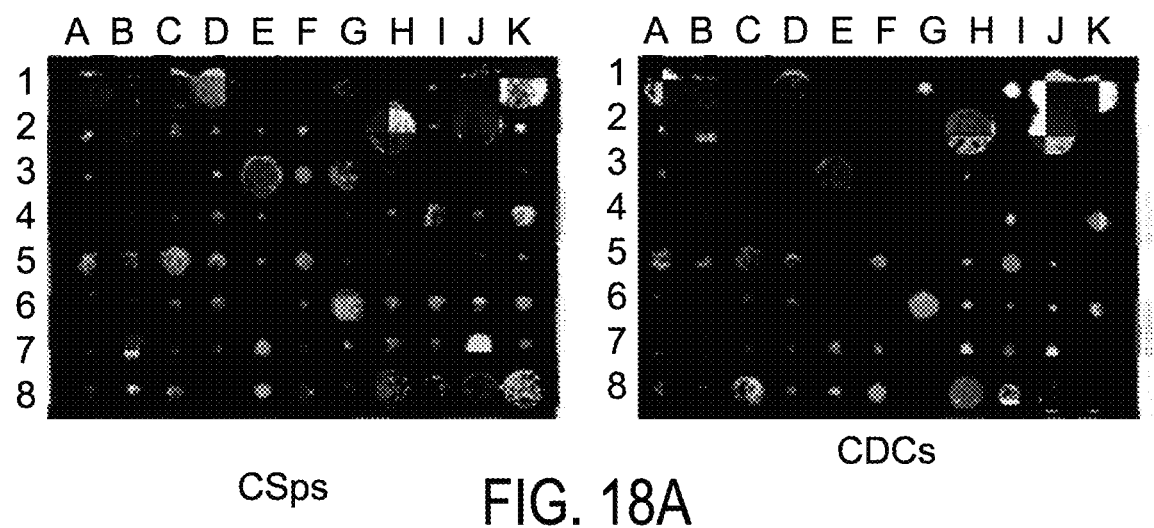
Figure 18B:
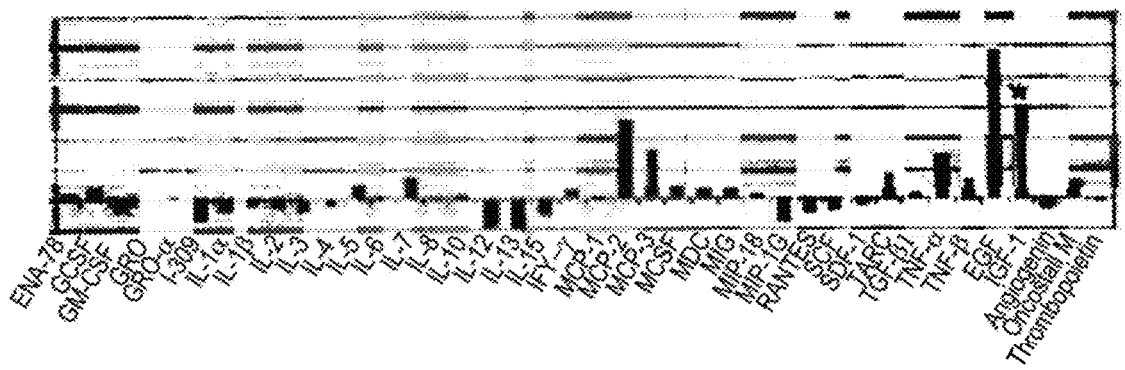
Figure 18C:
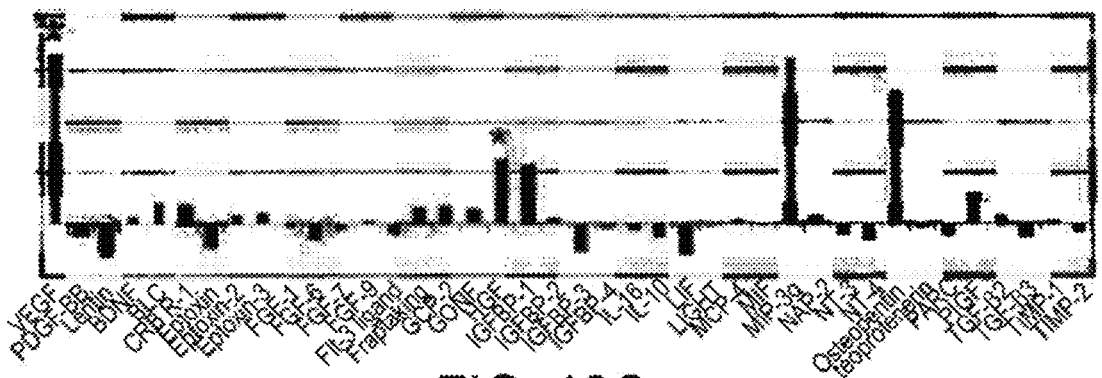

FIGS. 18A-18C depict protein array analysis of serum free conditioned media collected from the culture of regenerative cells, specifically cardiospheres and CDCs.

FIGS. 19A-19E depict in vitro analysis of VEGF, HGF and IGFI secretion.

FIGS. 20A-20F depict the gene expression profiles of various growth factor receptors on cardiospheres and CDCs.

FIGS. 21A-21K depict the effects of conditioned media from regenerative cells on cultured cells. FIGS. 21A-21E depict the pro-survival effects of conditioned media from regenerative cells on neonatal rat ventricular myocytes (NVRMs) and pro-angiogenic (FIGS. 21F-21K) effects of conditioned media from regenerative cells on cultured HUVEC cells.

Figure 22:
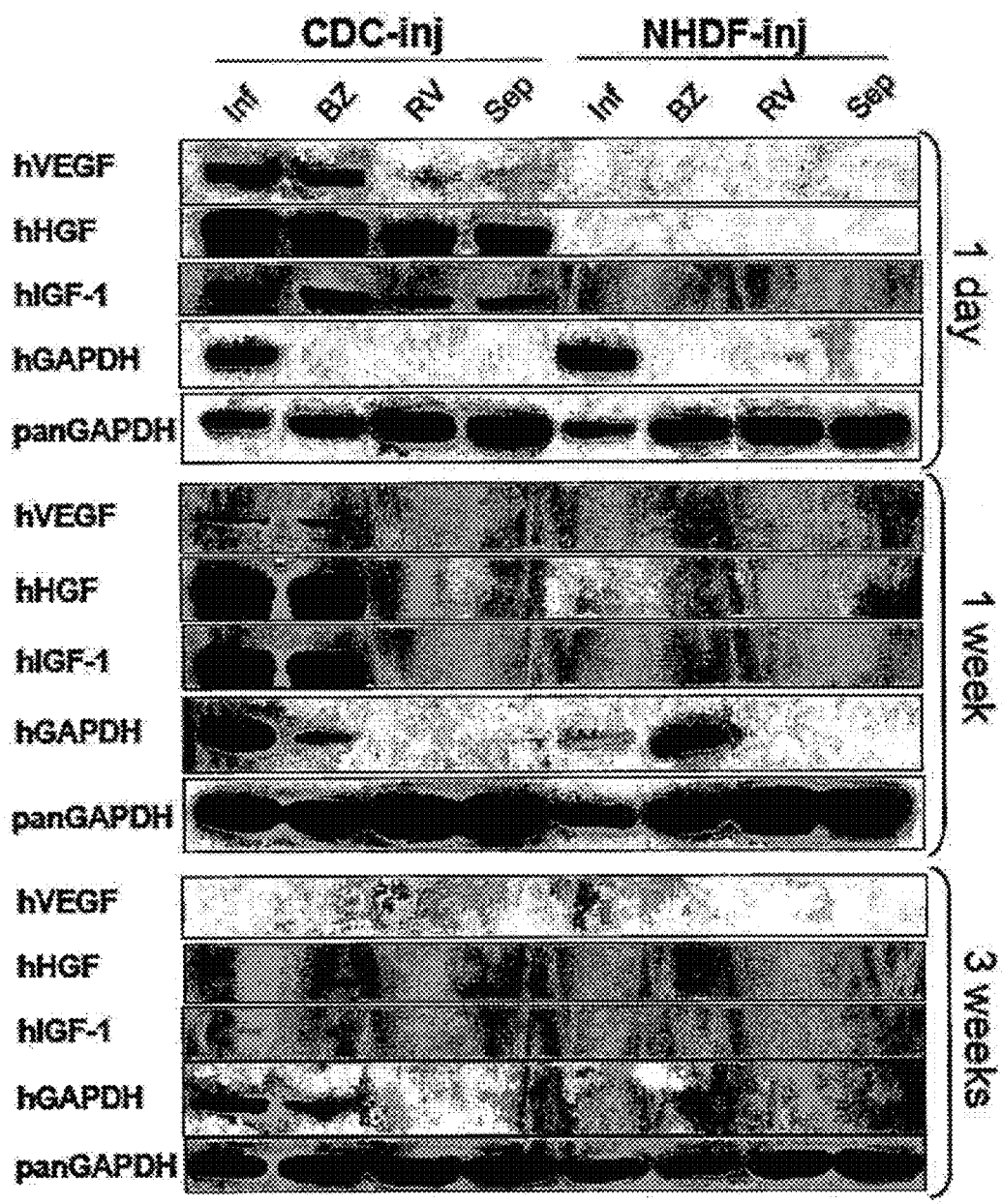

FIG. 22 depicts results of growth factor and cytokine protein expression analysis in infarcted regenerative cell-injected mouse hearts.

FIGS. 23A-23D depict assessment of tissue viability and cardiac tissue perfusion after administration of regenerative cells.

FIGS. 24A-24D depict an evaluation of the amount of regenerative cell contribution to capillaries and muscle tissue formed in the border zone of an induced infarction.

Figures 25A, 25B:
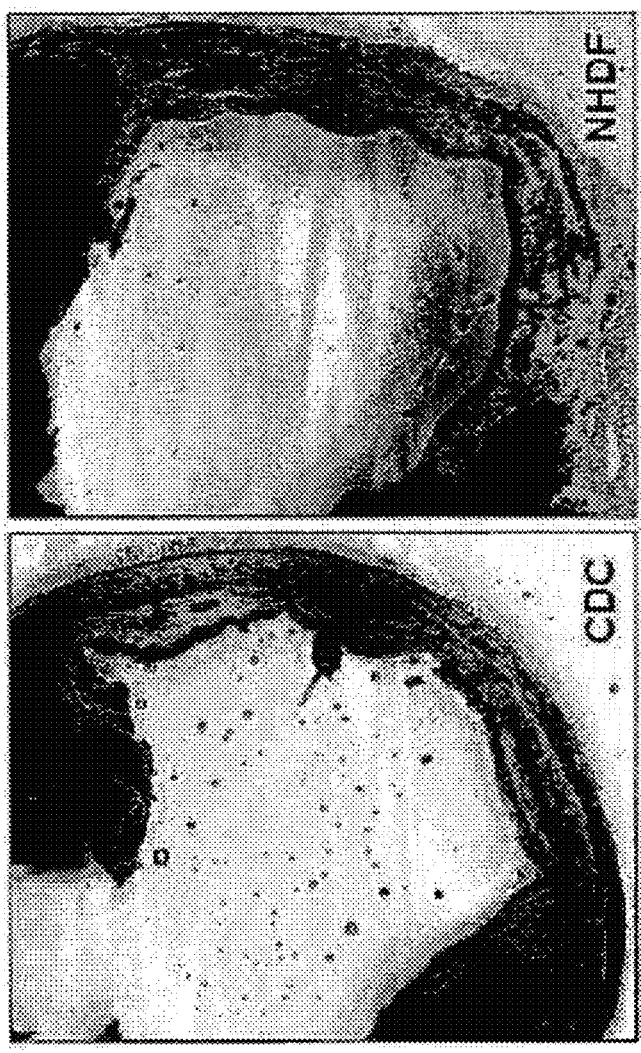
Figure 25C:
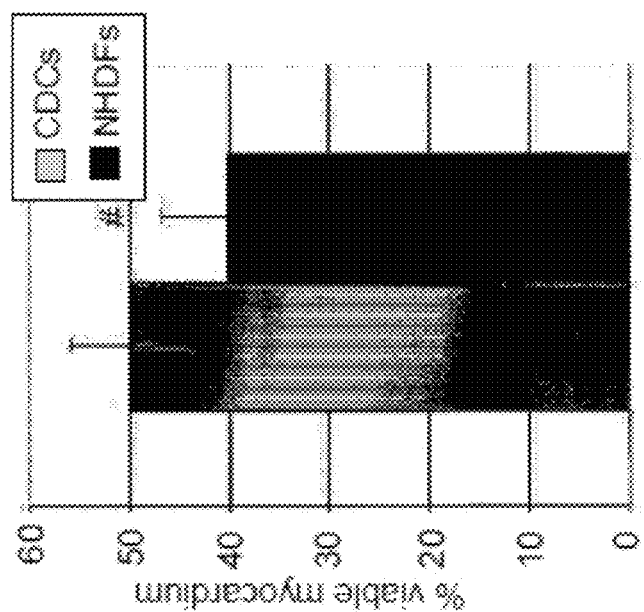

FIGS. 25A-25C depict an analysis of infarct size evaluated by Masson's trichrome staining.

FIGS. 26A-26H depict MHC Class I and II expression for human CDCs before and after interferon stimulation.

Figures 26A, 26B, 26C, 26D, 26E, 26F, 26G, 26H:
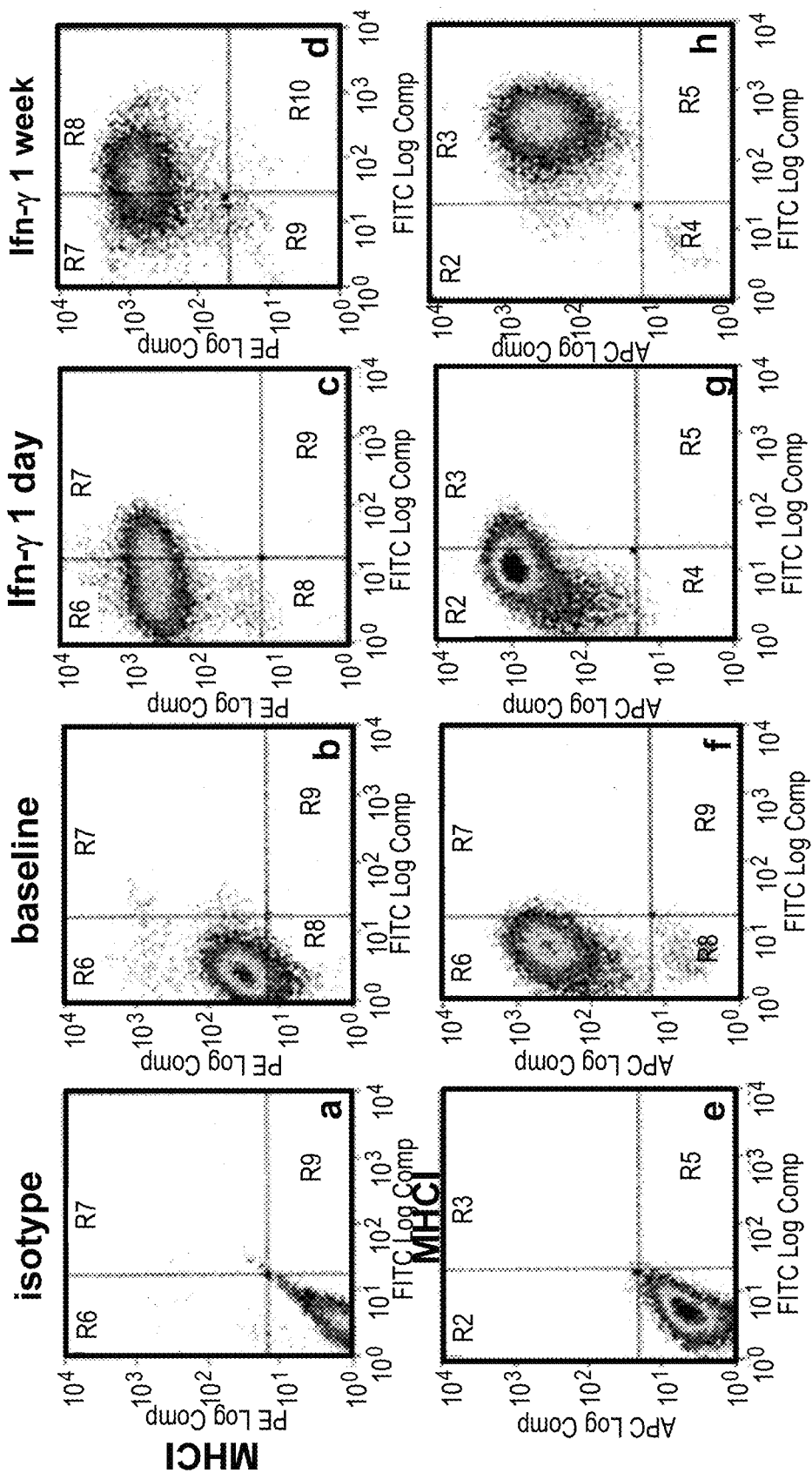
Figures 26I, 26J:
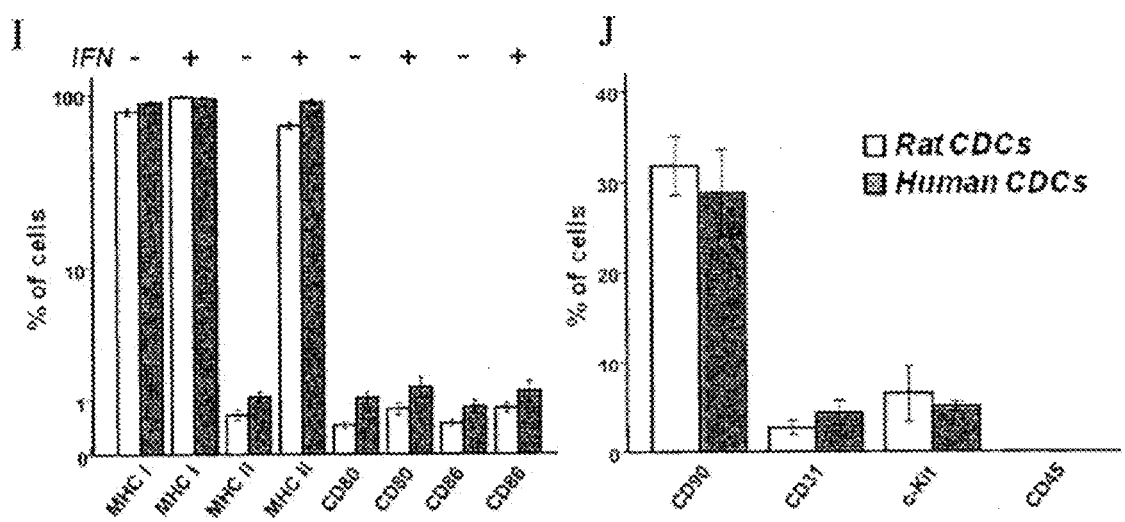

FIGS. 26I-26J depict the fractional change in lymphocyte proliferation normalized to syngeneic co-culture for allogeneic and xenogeneic co-cultures.

Figures 26K, 26L, 26M:
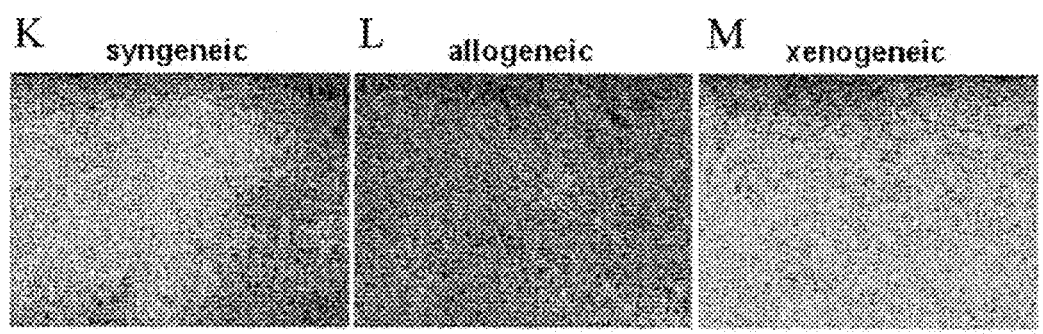

FIGS. 26K-26M depict the associated lymphocyte infiltration in syngeneic, allogeneic, and xenogeneic co-cultures.

Figures 26N, 26O:
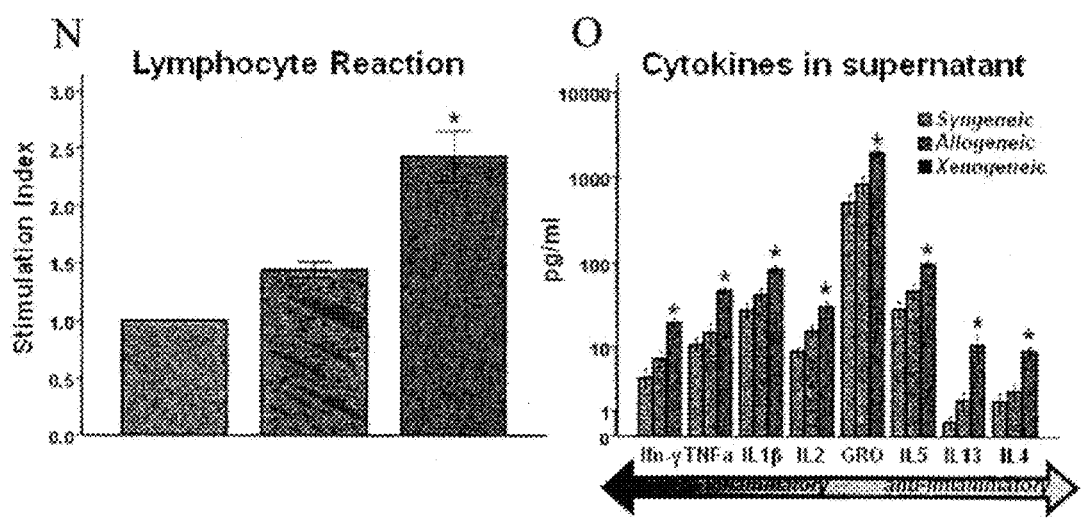

FIG. 26N depicts the index of lymphocyte proliferation induced by various co-cultures.

FIG. 26O depicts data related to the quantification of inflammatory cytokines after co-culture.

Figures 27A, 27B:
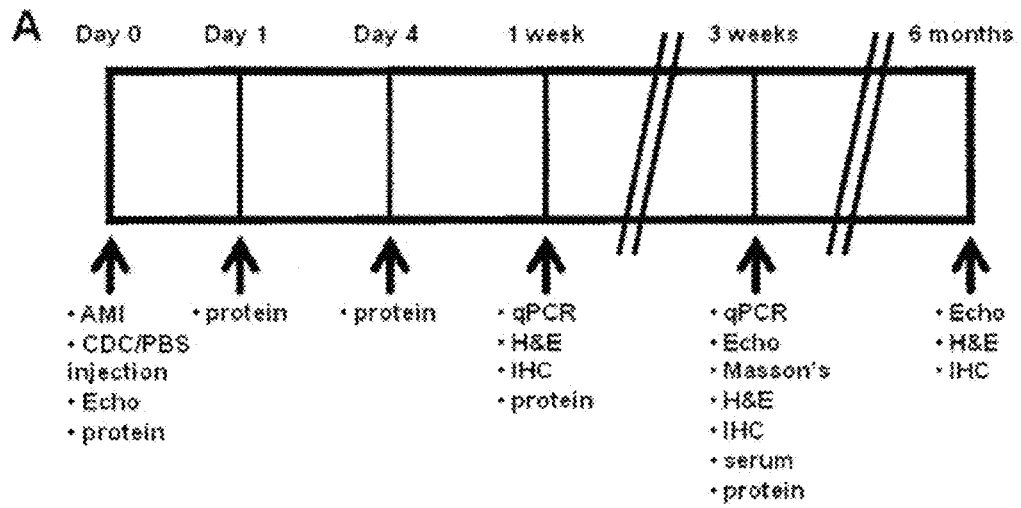

FIG. 27A depicts a graphical experimental scheme employed to study engraftment and function of CDCs.

FIG. 27B depicts the experimental and control groups used to evaluate engraftment and function.

Figure 27C:
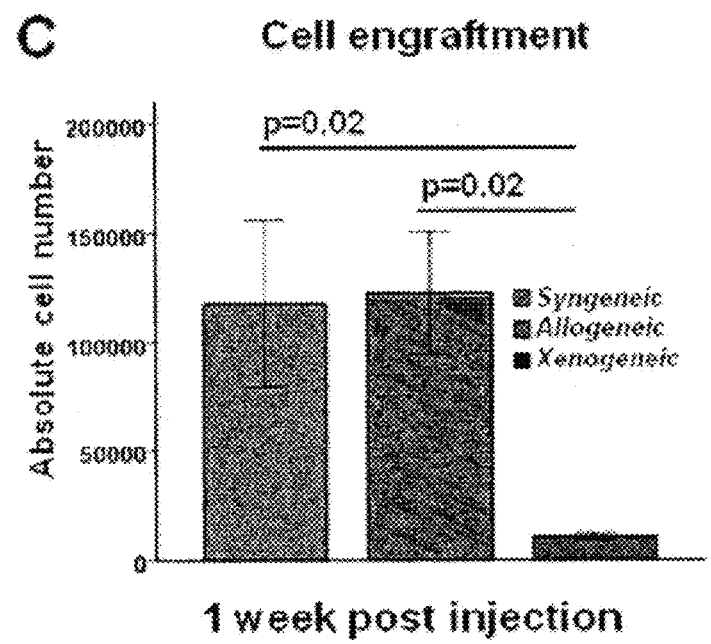

FIG. 27C depicts data related to 1-week cell engraftment in various transplant groups.

Figure 27D:
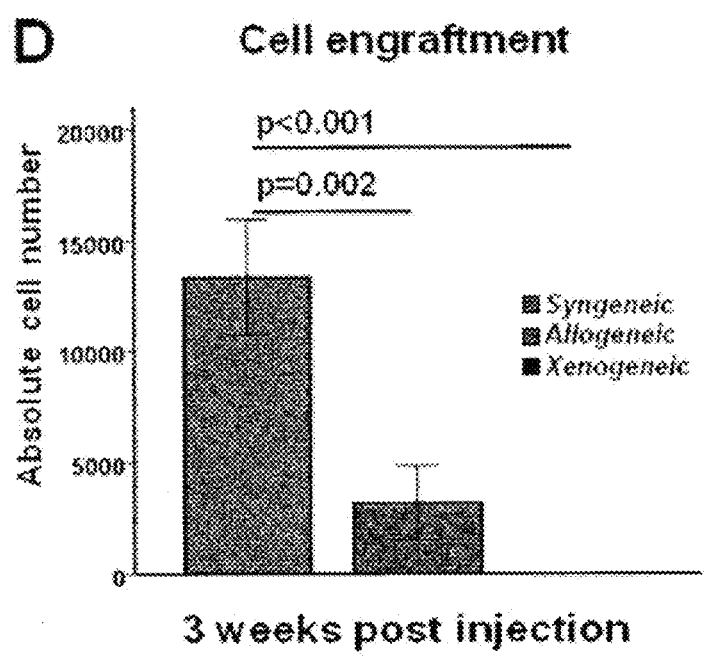

FIG. 27D depicts data related to 3-week cell engraftment in various transplant groups.

Figures 28A, 28B, 28C:
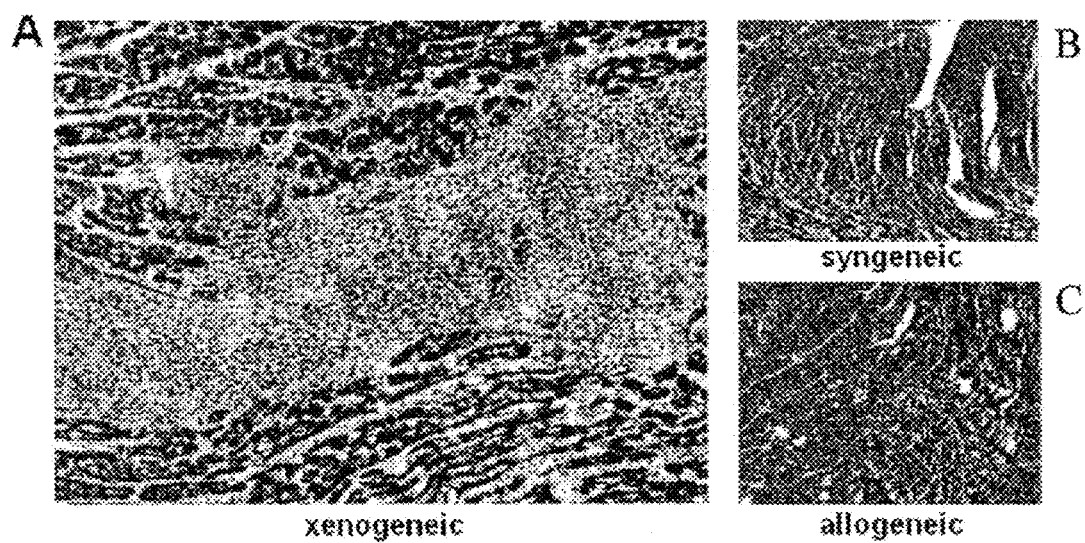
Figures 28D, 28E, 28F, 28G:
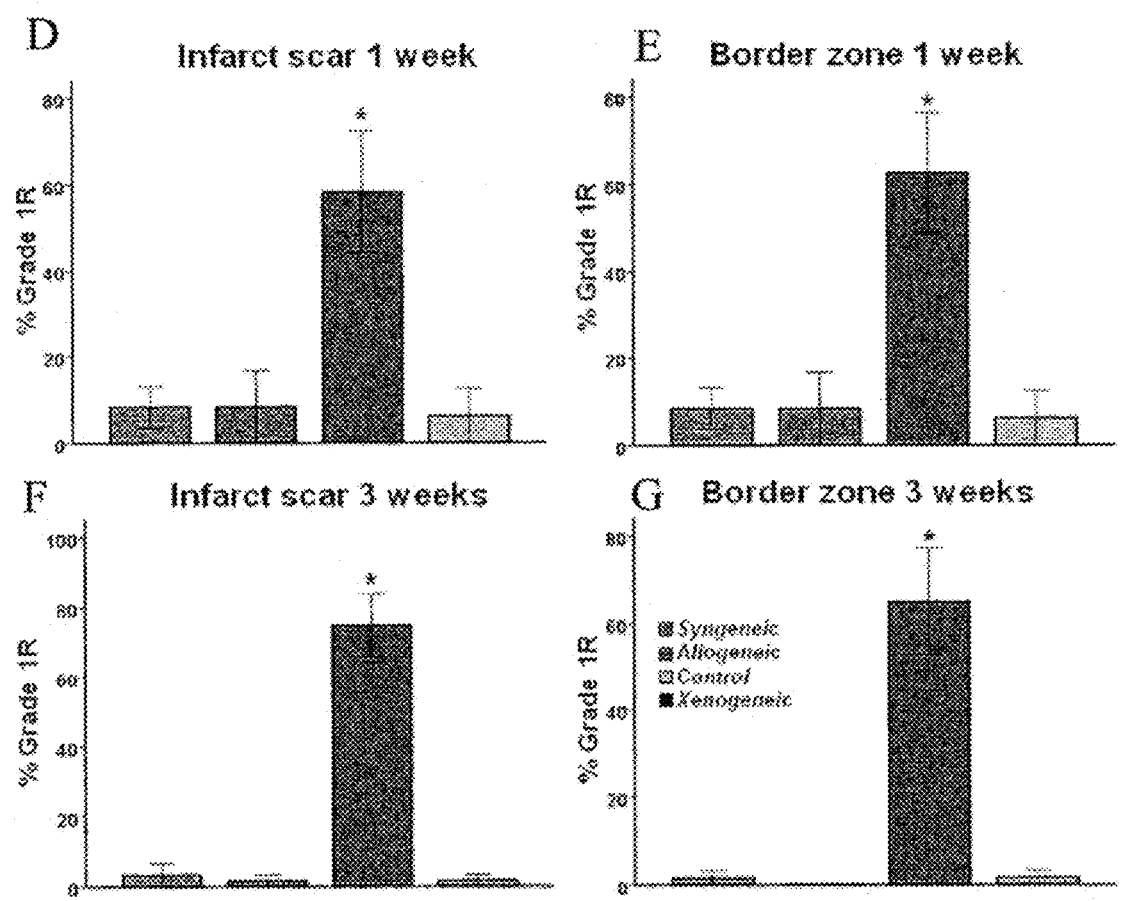

FIGS. 28A-28C depict hematoxylin and eosin staining of syngeneic, allogeneic, or xenogeneic treated cardiac tissue. Analysis revealed significant evidence of an immune reaction in xenogeneic (28A) heart sections, but very little in syngeneic (28B) or allogeneic (28C) sections. Example images are shown at 3 weeks post-MI.

FIGS. 28D-28G depict 1-week and 3-week data related to the rejection score for various transplant types at various regions throughout the infarct scar or border zone.

Figures 28H, 28I, 28J:
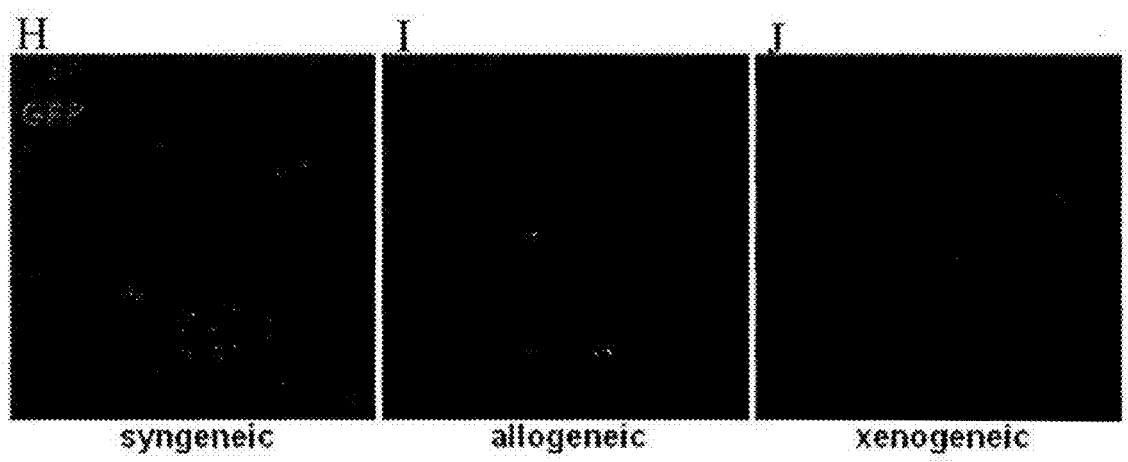

FIGS. 28H-28J depict immunohistochemistry data related to cell infiltration post-transplant.

FIGS. $28K_1$-$28K_{15}$ depict immunohistochemistry further defining the types of infiltrating lymphocytes in each transplant.

FIGS. 28L-28M depict data related to monocyte infiltration in each transplant type at 1 and 3 weeks.

FIGS. 29A-29E represent data and analysis of T-cell, B-cell, and macrophage infiltration in various treatment groups at 1 and 3-weeks post-MI. Engraftment of GFP-labeled CDCs and the level of T cell ($CD3^+$, $CD4^+$, or $CD8^+$), B cell ($CD45R^+$), or macrophage ($CD68^+$) infiltration surrounding the cells 3 weeks post-MI is shown for animals who received syngeneic (29A), allogeneic (29B), or xenogeneic (29C) CDCs. The number of cells per high power field is quantified 1 week (29D) and 3 weeks post-MI (29E).

FIGS. 30A-30G depict quantification of serum concentrations of pro-inflammatory cytokines IFN-γ, IL-1β, KC/GRO, TNF-α, (FIGS. 30A, 30B, 30F, and 30G, respectively), or the anti-inflammatory cytokines IL-13, IL-4, and IL-5 (FIGS. 30C, 30D, and 30E, respectively).

Figure 31A:
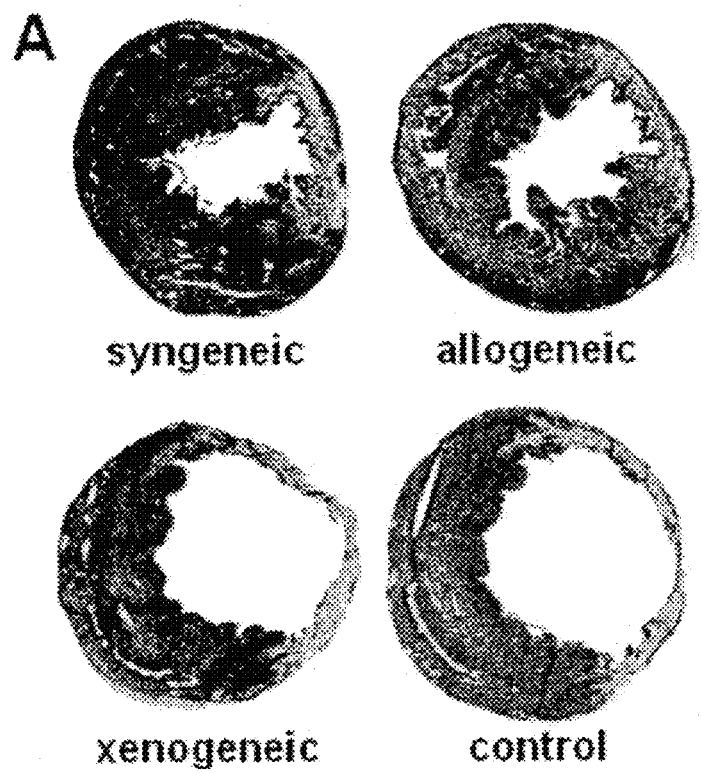

FIG. 31A depicts morphometric analysis of explanted hearts 3 weeks post infarction in syngeneic (upper left), allogeneic (upper right), xenogeneic (lower left) and control (lower right) groups.

Figure 31B:
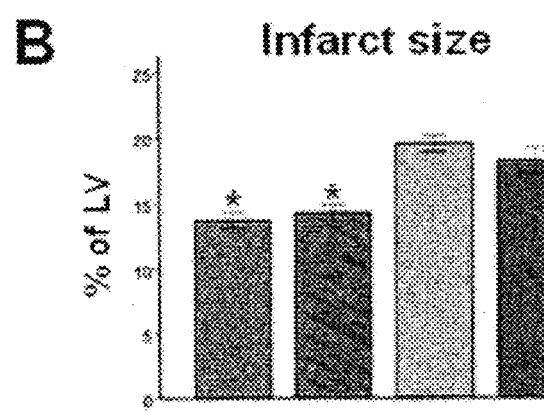
Figure 31C:
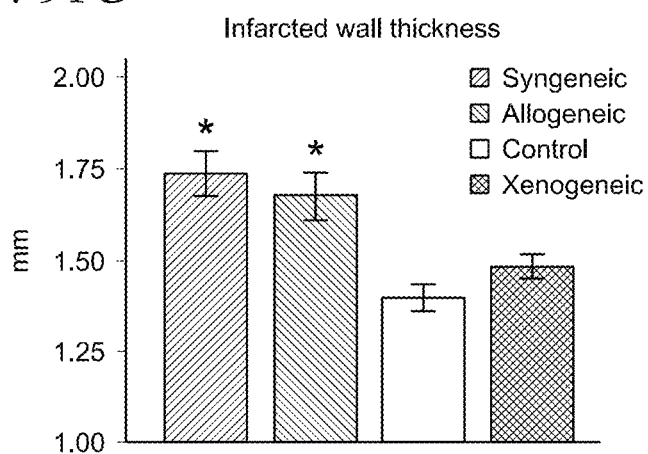

FIG. 31B depicts infarct size in the various transplant groups while FIG. 31C depicts infarcted wall thickness.

FIGS. 31D-31G depict fractional area change (31D), ejection fraction (31E), fractional shortening (31F), and treatment effect (31G) for the various transplant groups.

Figure 31D:
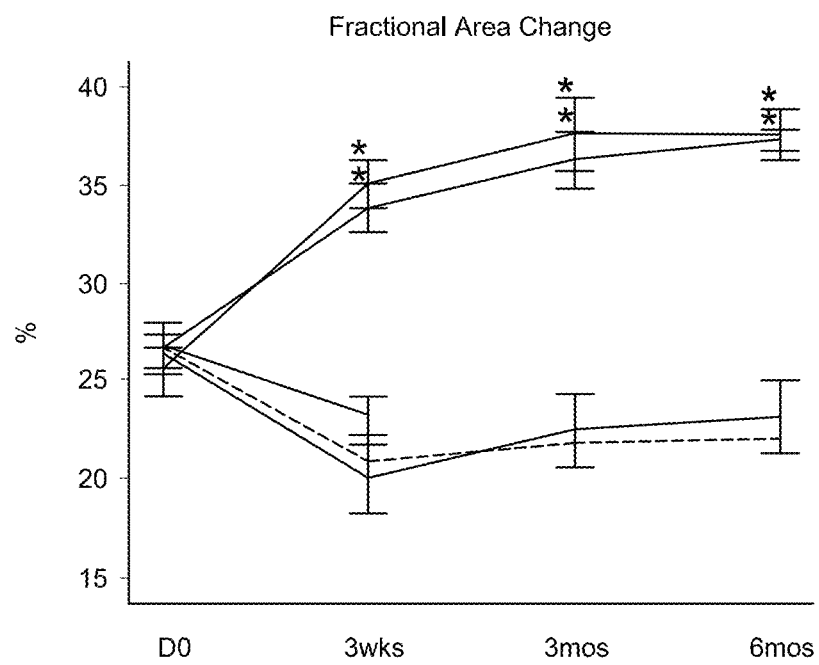
Figure 31E:
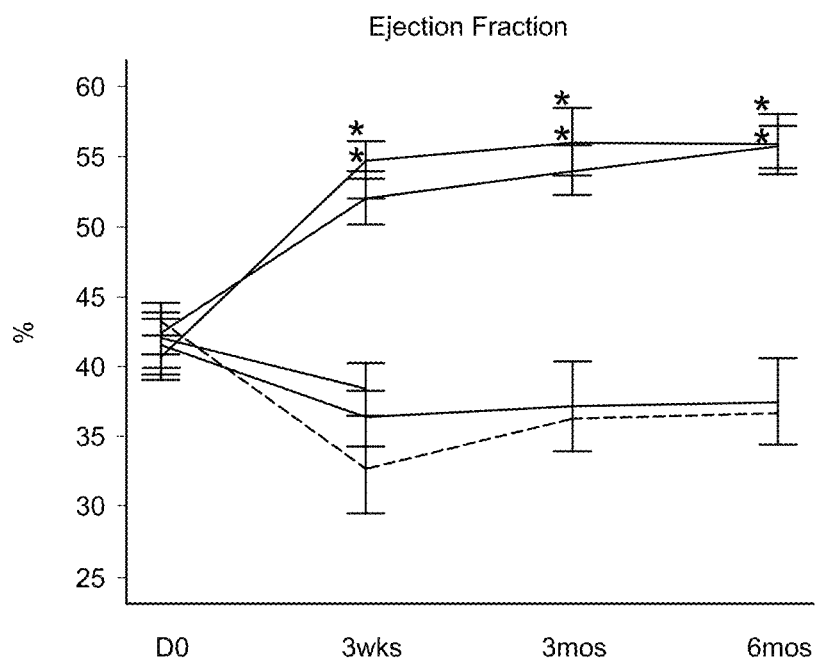
Figure 31F:
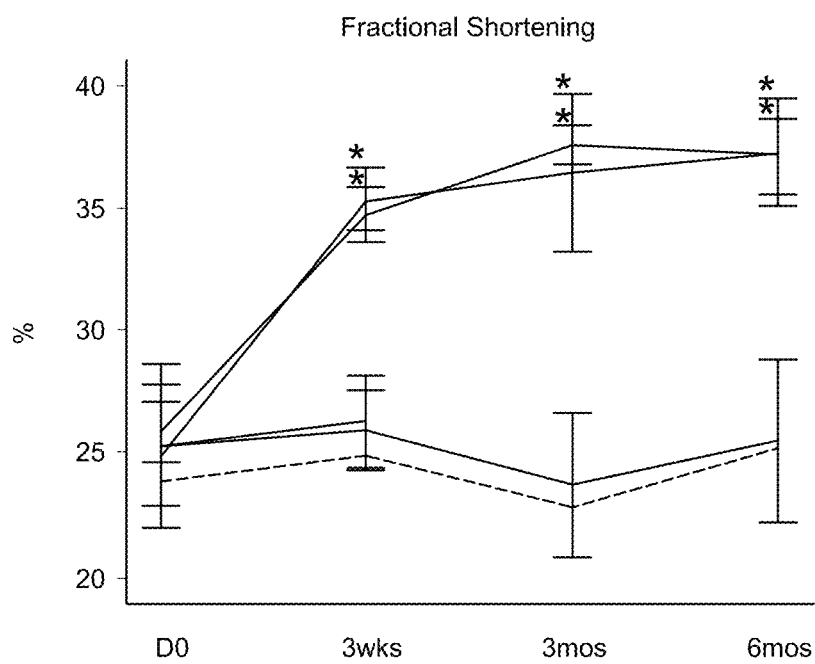
Figure 31G:
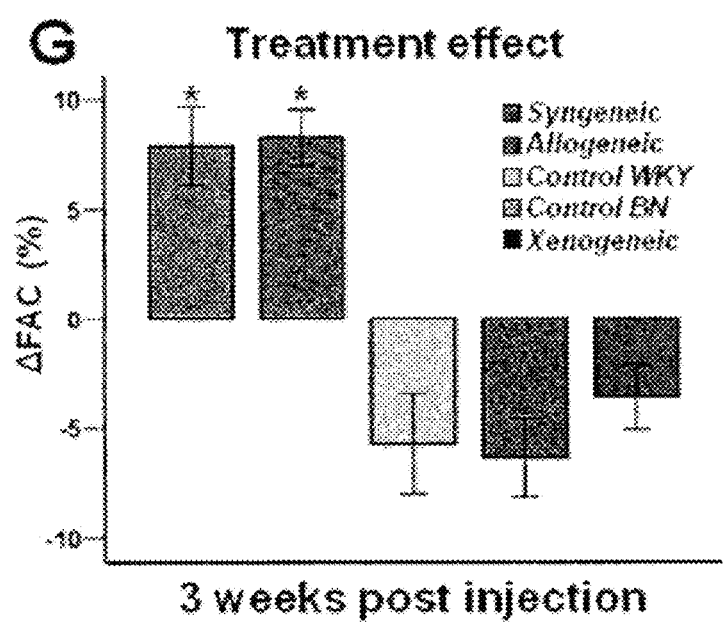
Figures 31H, 31V:
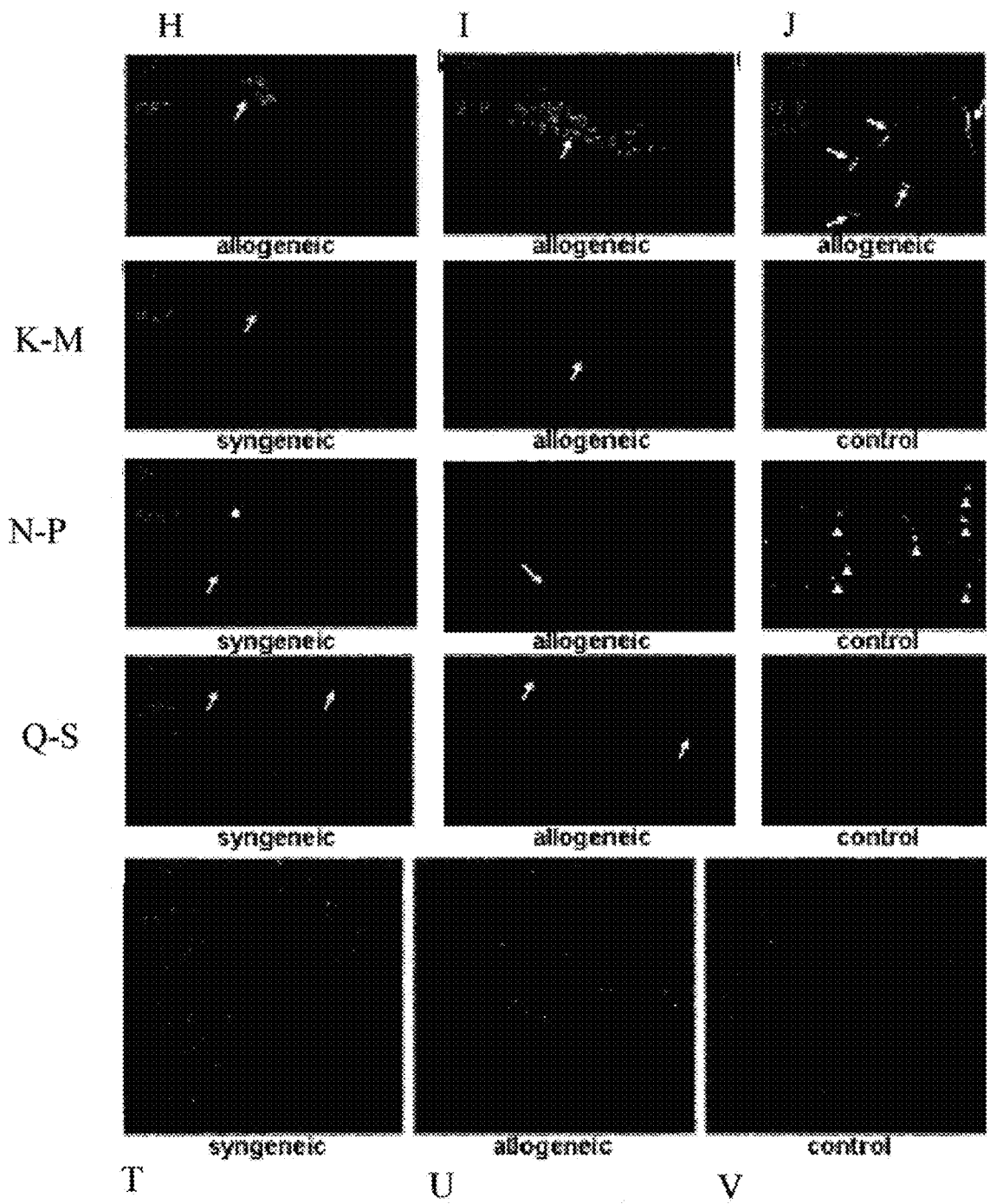
Figure 31W:
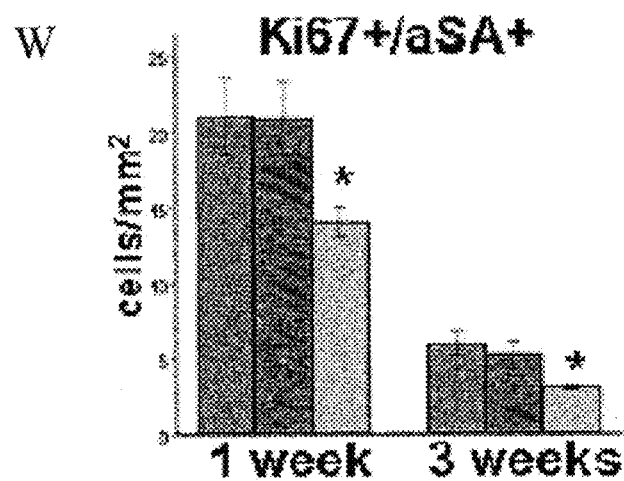
Figure 31X:
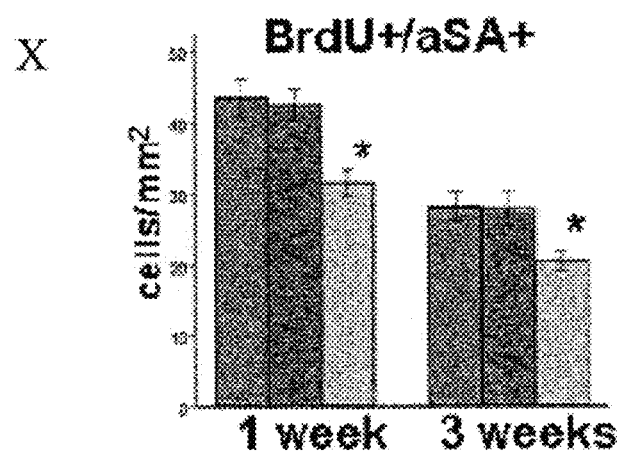
Figure 31Y:
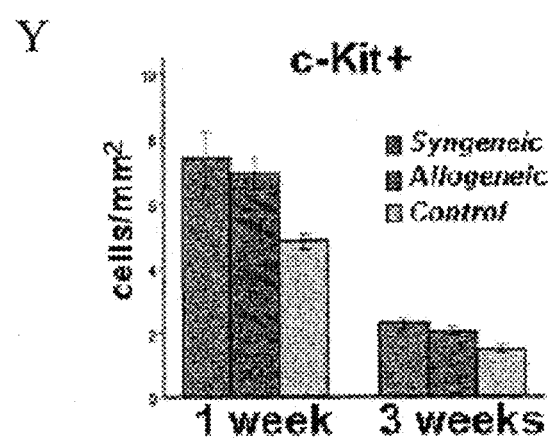
Figure 31Z:
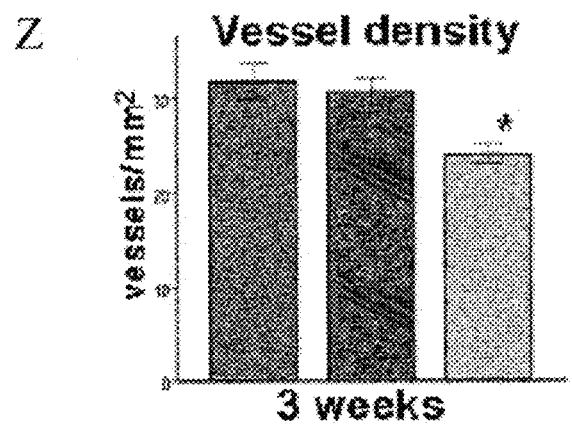

FIGS. 31H-31V depict immunohistochemistry related to the location of transplanted cells as well as markers for cell cycle, stem cell markers, and endothelial cell markers.

FIGS. 31W-31Z depict data at 1 and 3 weeks for, respectively, Ki67/smooth muscle actin, BrdU expression/smooth muscle actin expression, cKit expression, and vessel density.

FIG. 31AA depicts protein analysis of growth factor secretion at various time points post-MI.

FIGS. 31BB-31DD depict data for VEGF (31BB), IGF (31CC), and HGF (31DD) in syngeneic, allogeneic, or control groups.

Figure 32A:
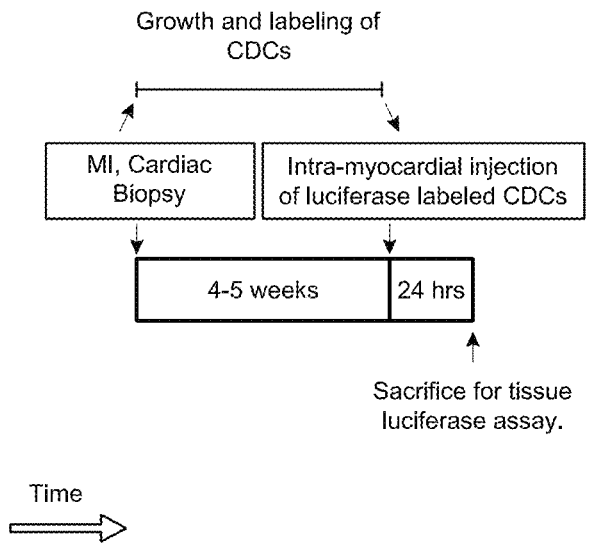
Figure 32B:
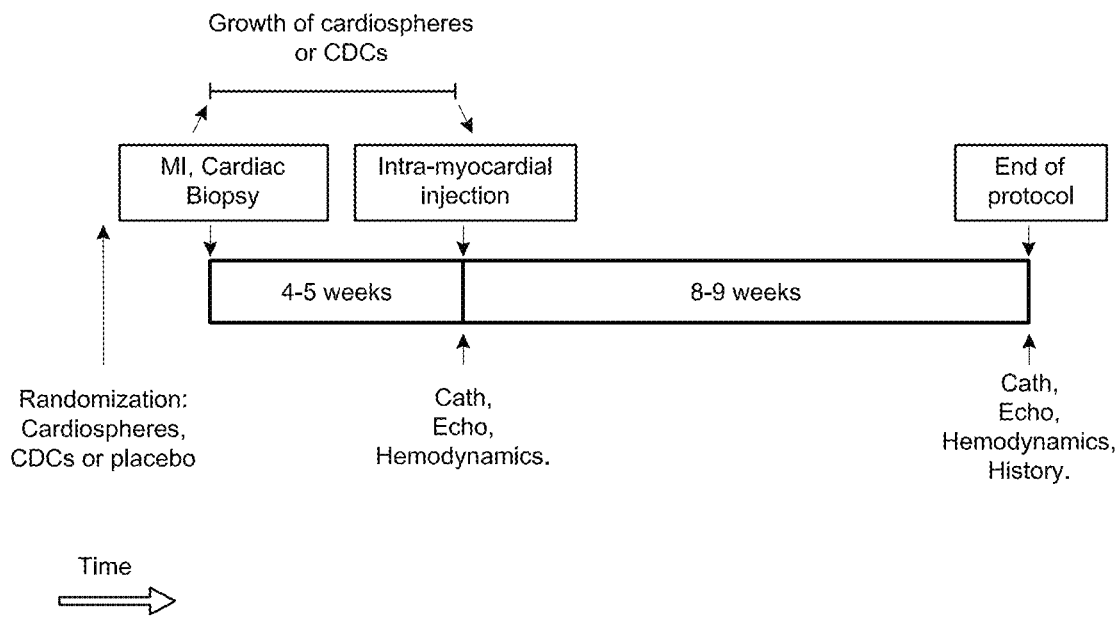

FIGS. 32A-32B depict schematics of two study designs disclosed herein.

Figure 33:
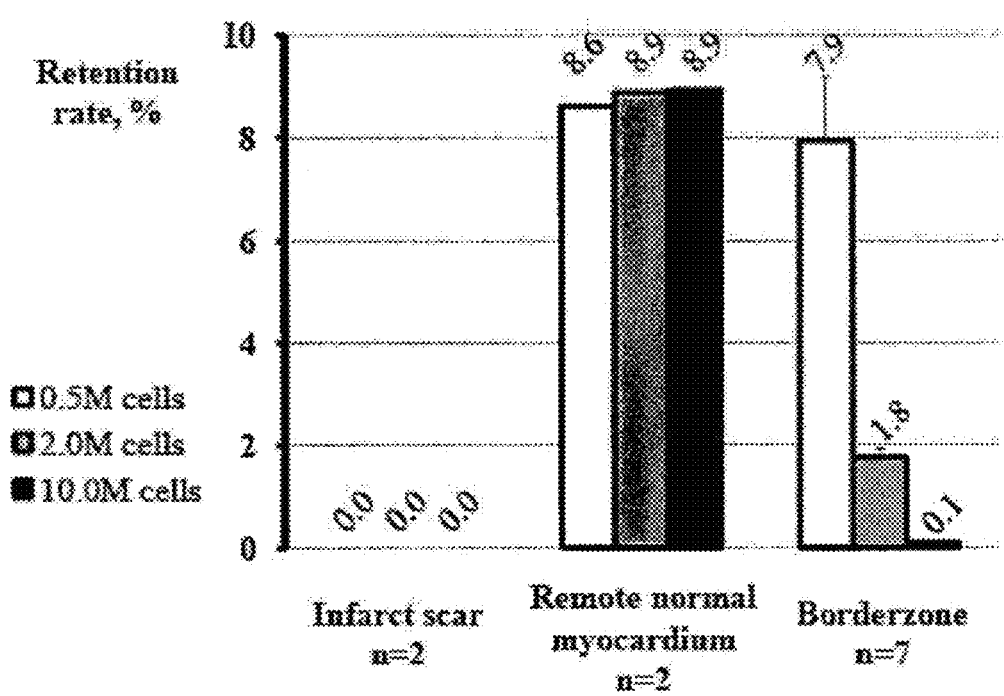

FIG. 33 depicts the percentage of CDCs retained, after injecting into three different areas of pig heart, as determined by an in vitro luciferase assay 24 hours after injection.

Figures 34A, 34B, 34C:
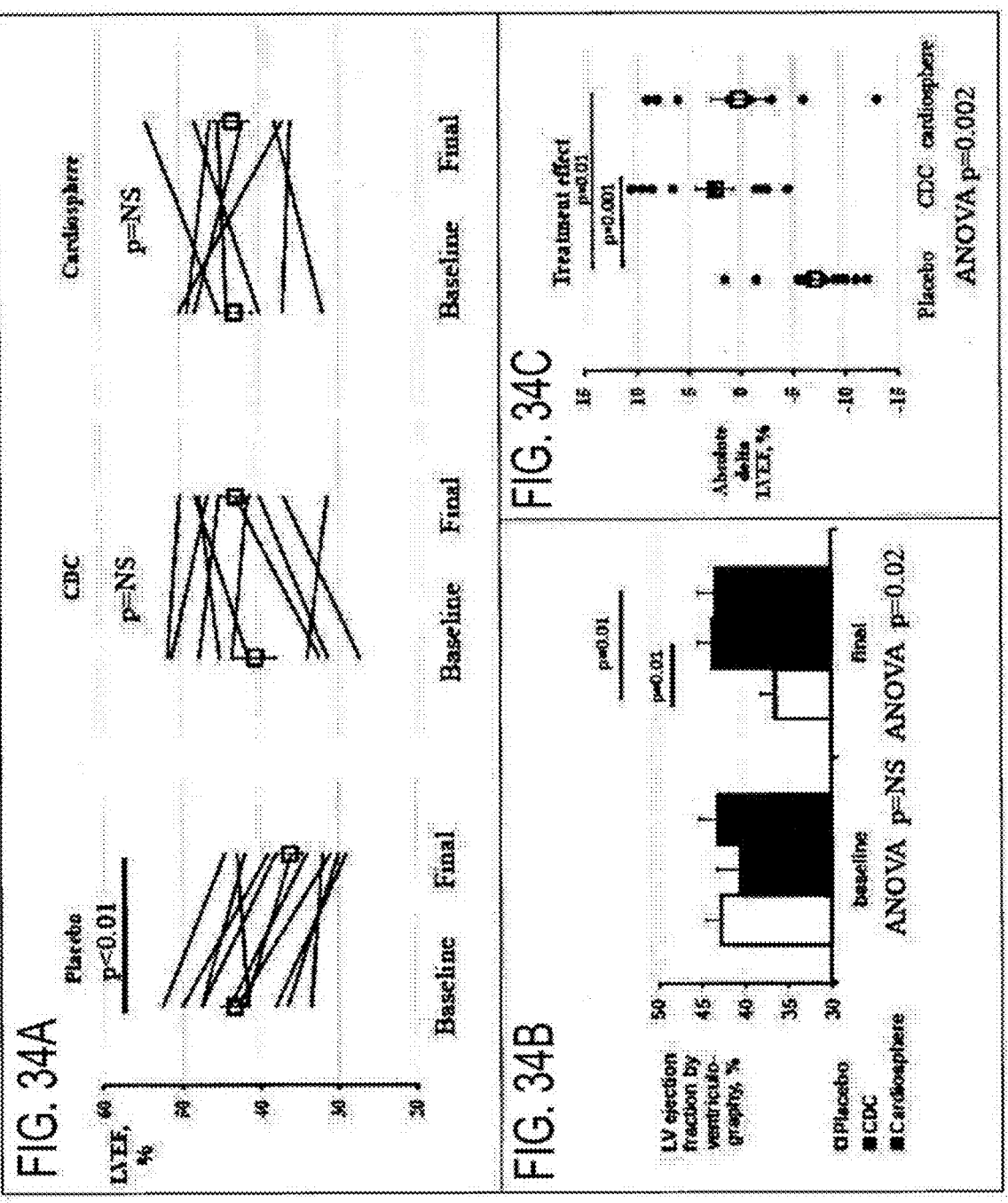

FIGS. 34A-34C depict changes in LV function as measured by ventriculography. Paired analysis of LVEF before injection and 8 weeks later in controls and CDC-injected pigs is shown (34A). Average LVEF for pigs in the CDC-injected group was significantly higher than those in the control group 8 weeks after injection (34B). Treatment effects in the two groups as absolute change in LVEF (34C).

FIGS. 35A-35C depict various echocardiographic measurements. FIG. 35A shows that Emax in the cardiosphere group was significantly higher than in placebo-injected pigs. Emax in the CDC group was not significantly higher than placebo-treated animals. (Levene's test p<0.05, Kruskal-Wallis comparison p=0.003. Placebo vs. CDC, p=NS; Placebo vs. cardiosphere, p=0.03). Representative families of PV loops are shown below the graph for placebo, CDC and cardiosphere-treated animals. FIG. 35B shows the change in diastolic volume (Final EDV-Baseline EDV) is significantly lower in the cardiosphere treated group than the CDC treated group, with a trend to being lower than the placebo group. (ANOVA p=0.02). FIG. 35C shows that the changes in end-diastolic pressure measurements demonstrated a significantly higher fall in end-diastolic pressure in cardiosphere-injected animals compared to CDC treated animal (ANOVA p<0.01; cardiospheres vs. CDCs p=0.001). This indicates that, in some embodiments, the ventricles of cardiosphere-injected hearts are more responsive to treatment after infarction CDC-treated hearts. However, in some embodiments, CDC-treated hearts are responsive to an equal or greater degree.

Figure 36A:
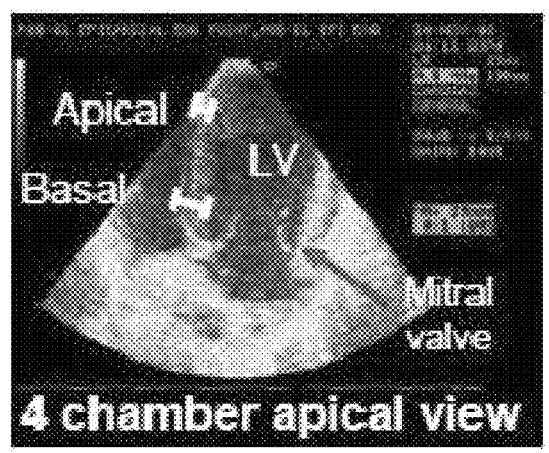
Figure 36B:
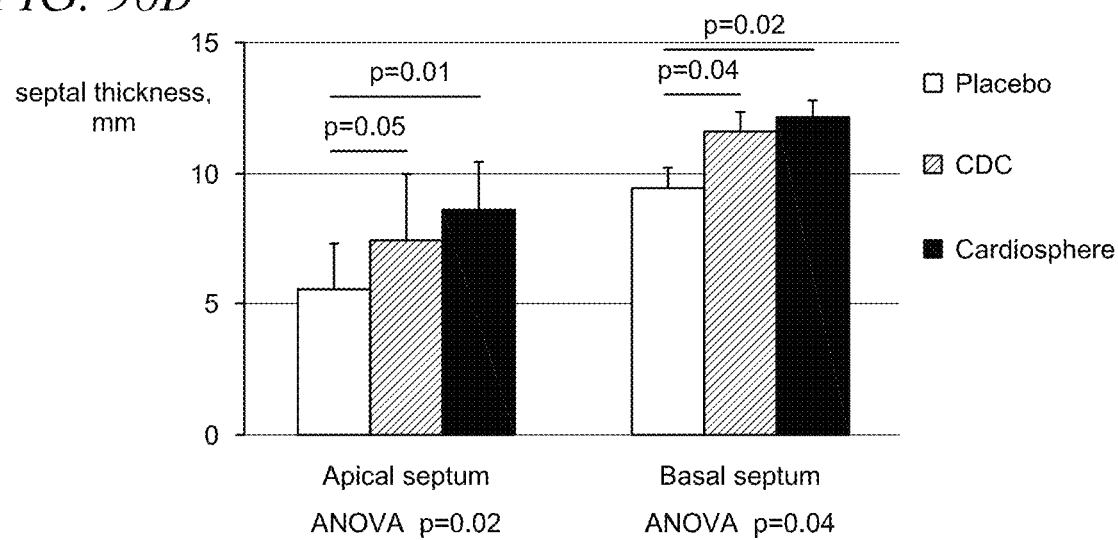
Figure 36C:
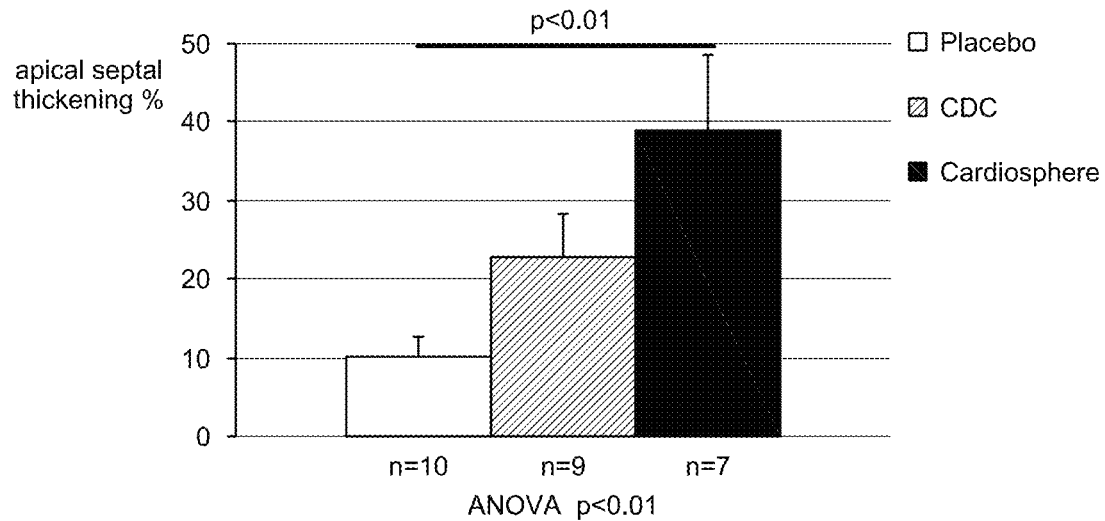

FIGS. 36A-36C depict improved regional contractility in cardiosphere-injected pigs relative to sham-injected controls.

Figure 37A:
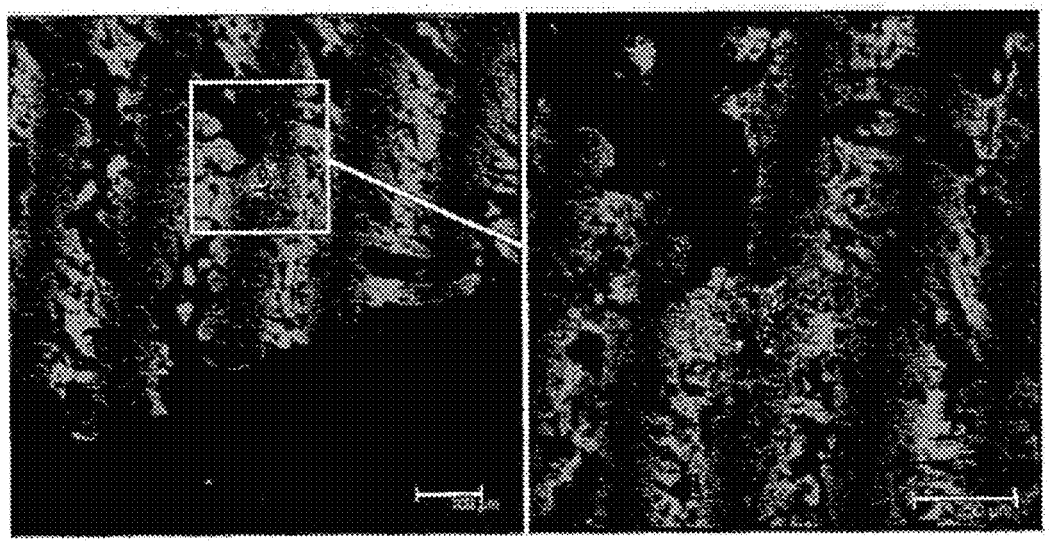
Figure 37B:
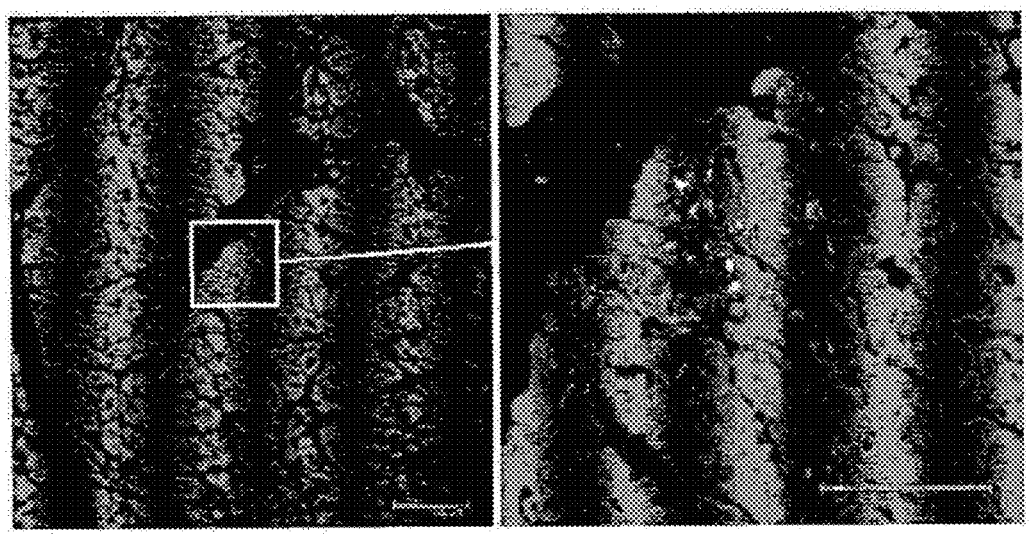

FIGS. 37A-37B depict two examples of islands of cardiomyocytes with lacZ-positive nuclei in the periinfarct zone, one from each animal that received intramyocardial genetically-labeled CDCs.

FIGS. 38A-38F depict schematics of various cell processing and cell banking procedures disclosed herein.

Figures 39A, 39B:
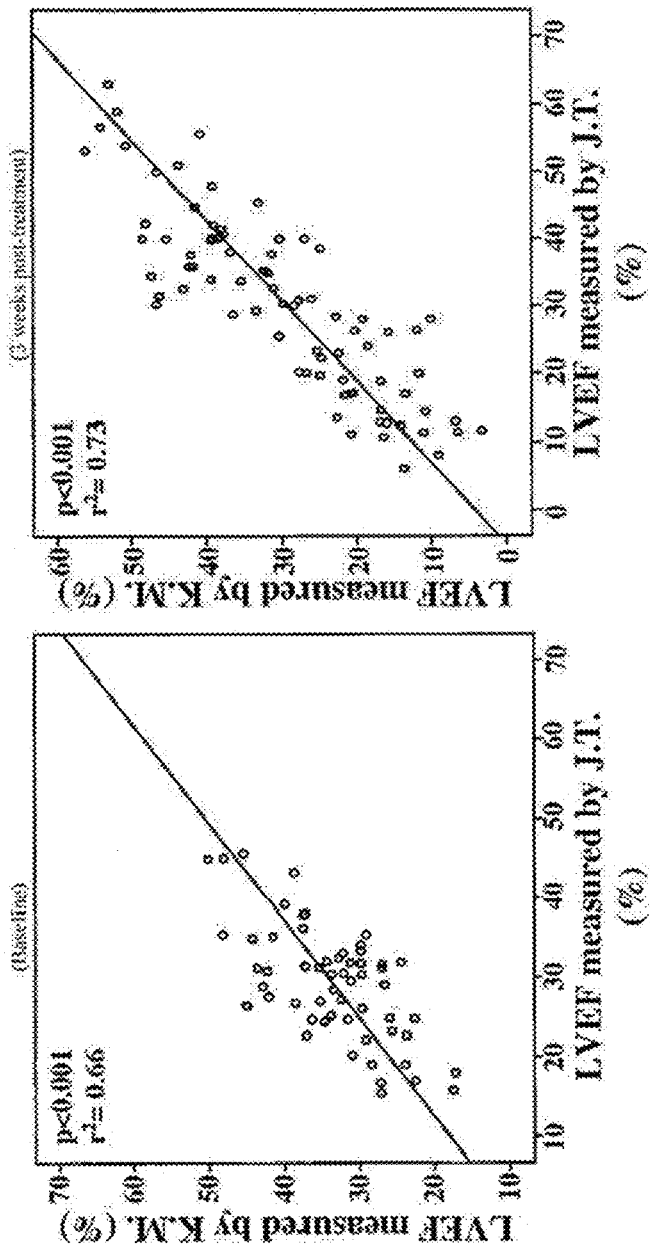

FIGS. 39A-39B depict correlation of LVEF values measured independently by two blinded, experienced echocardiographers. Measurements for each animal from the two readers show good correlation at baseline (39A) and 3 weeks after treatment (39B).

Figures 40A, 40B, 40C, 40D, 40E:
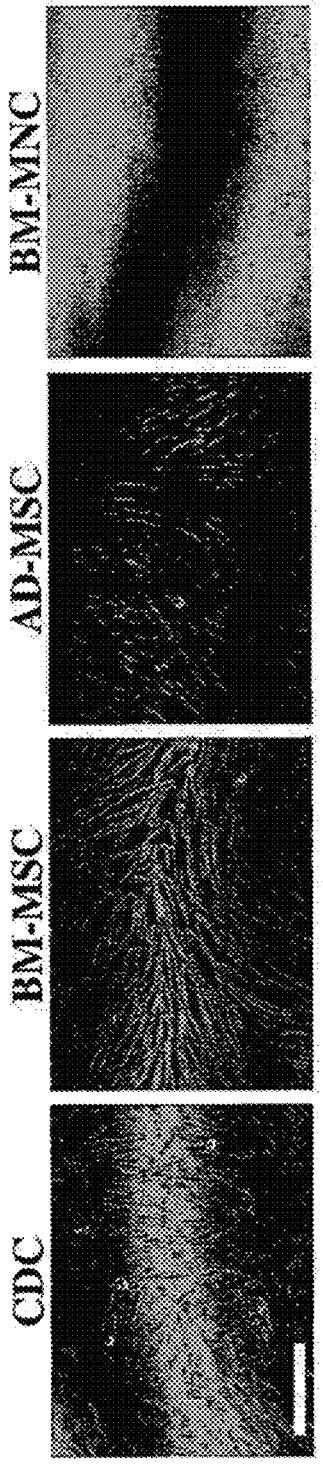

FIGS. 40A-40E depict characteristics of the various stem cell types evaluated. FIGS. 40A-40D depict phase-bright images of CDCs (shown in 40A), bone marrow-derived mesenchymal stem cells (BM-MSC, shown in 40B), adipose tissue-derived mesenchymal stem cells (AD-MSC, shown in 40C), and bone marrow mononuclear cells (BM-MNC, shown in 40D) in culture. FIG. 40E displays the expression of certain surface markers on each cell type.

FIGS. 41A-41J depict the secretion of a variety of paracrine factors by various stem cell types. FIGS. 41A-41F display the concentrations of each factor by each cell type. FIGS. 41G-41K display a relative paracine factor profile for each cell type.

Figures 42A, 42B, 42C:
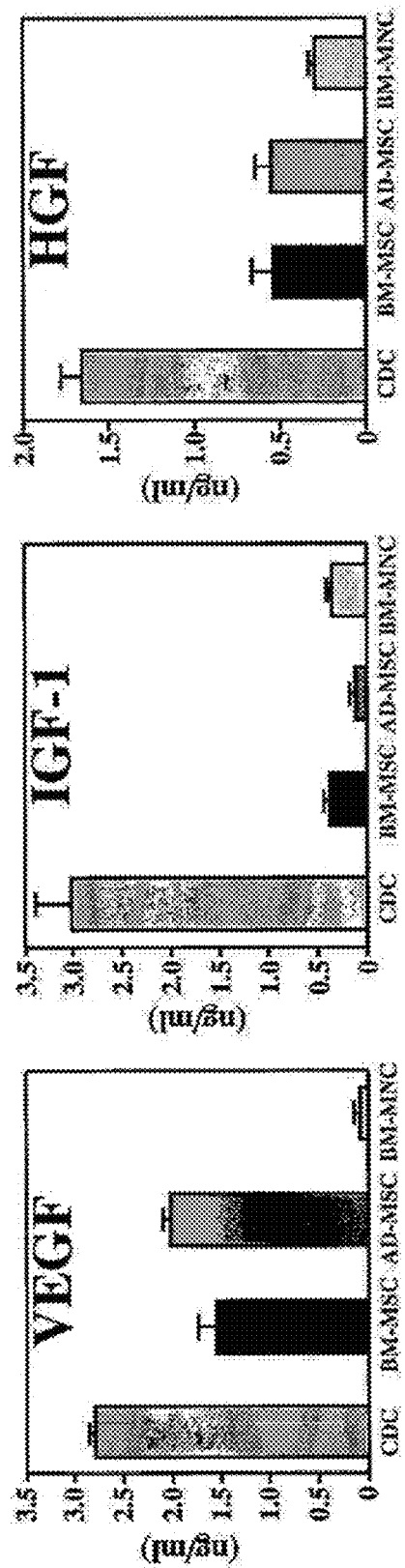

FIGS. 42A-42C depict the in vitro production of growth factors from rat cells. The concentrations of VEGF (42A), IGF-1 (42B), and HGF (42C) measured by ELISA are shown.

Figure 43B:
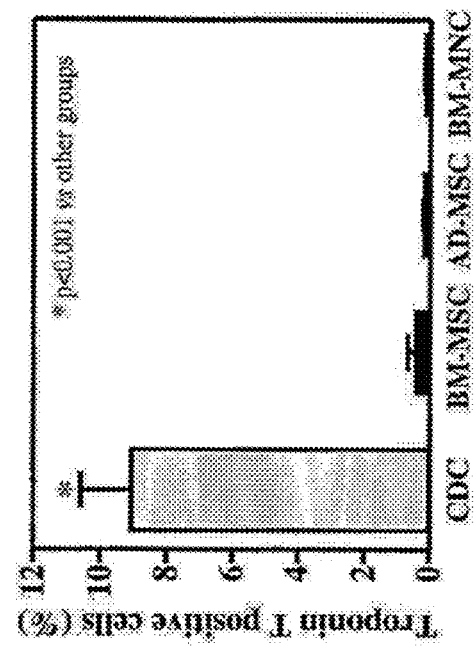
Figure 43D:
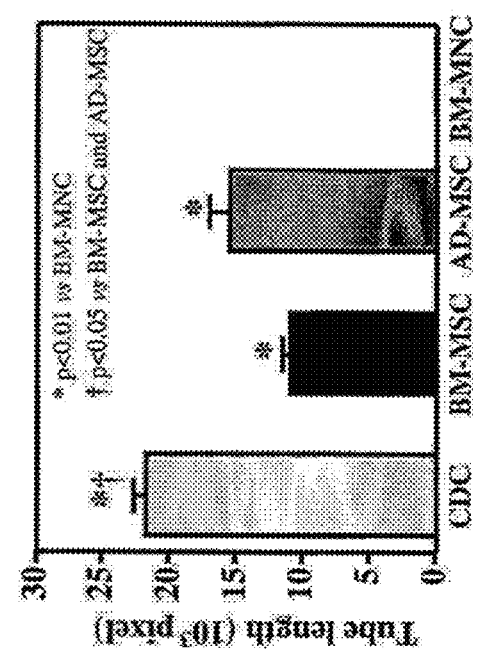
Figure 43A:
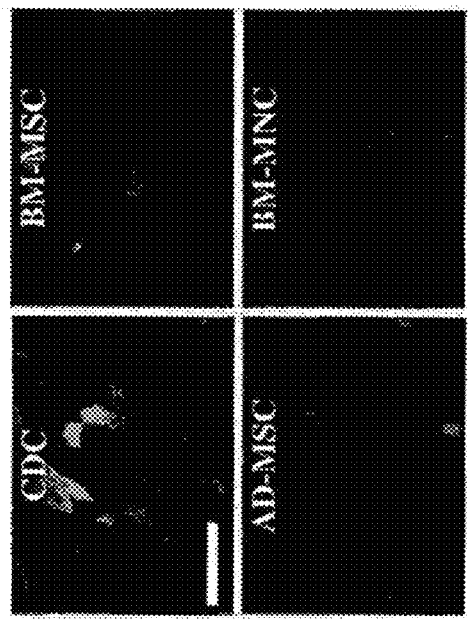
Figure 43C:
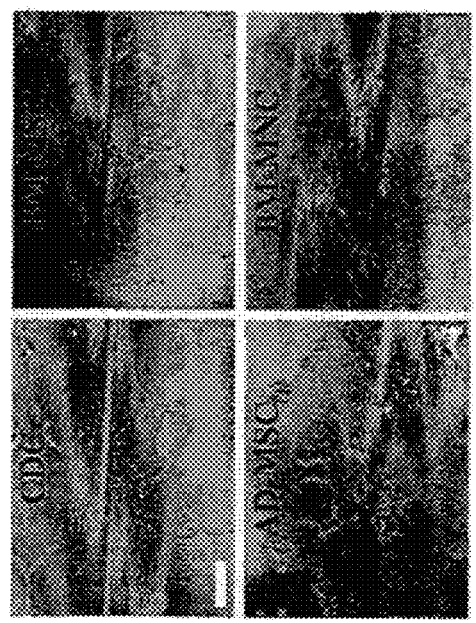

FIGS. 43A-43D depict analysis of in vitro myogenic differentiation and angiogenesis assay. FIG. 43A shows that Troponin T, with distinct myocyte-like appearance, was expressed spontaneously in a fraction of CDCs cultured for 7 days. This cardiac-specific marker was rarely expressed in BM-MSCs, AD-MSCs, and BM-MNCs. FIG. 43B depicts quantitative analysis of Troponin T expression in CDCs (9% of the cells positive), BM-MSCs (0.4% positive) and AD-MSCs and BM-MNCs (approximately 0.1% positive). FIG. 43C depicts CDCs, BM-MSCs, and AD-MSC-derived production of capillary-like tube formations in extracellular matrix. BM-MNCs did not form similar structures under these conditions. FIG. 43D depicts quantitation and comparison of tube formation capacity by the different cell types. Bars=50 um.

Figure 44B:
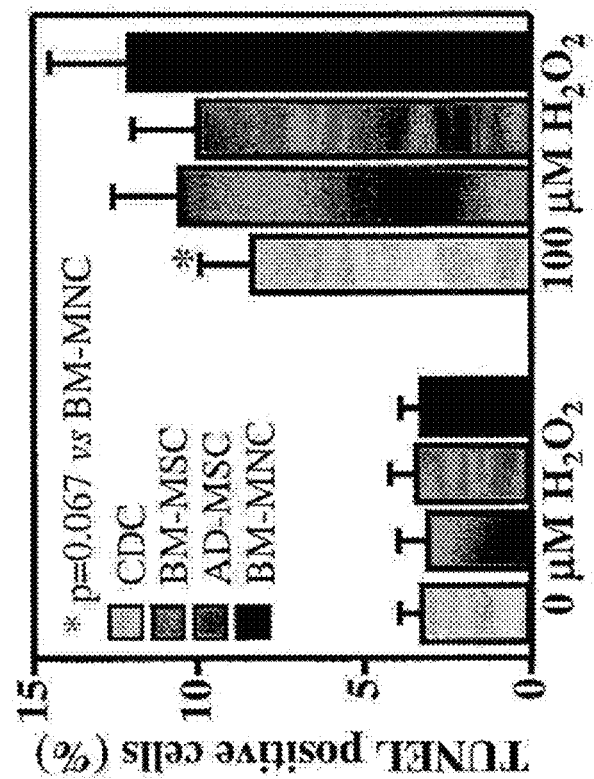
Figure 44A:
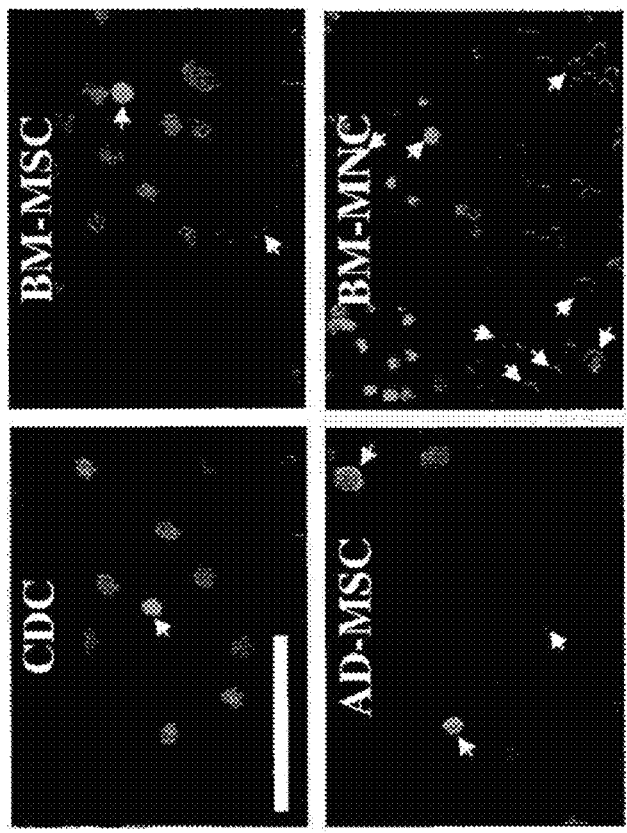

FIGS. 44A-44B depict the in vitro resistance of different types of human cells to oxidative stress. FIG. 44A shows representative images of TUNEL-positive cells (red) after 24 hours exposure to 100 mM H2O2. FIG. 44B depicts quantitative assessment of apoptotic cells. The number of TUNEL-positive cells was lower in CDC group compared to BM-MNC group with 100 mM H2O2. Bar=50 mm.

Figure 45B:
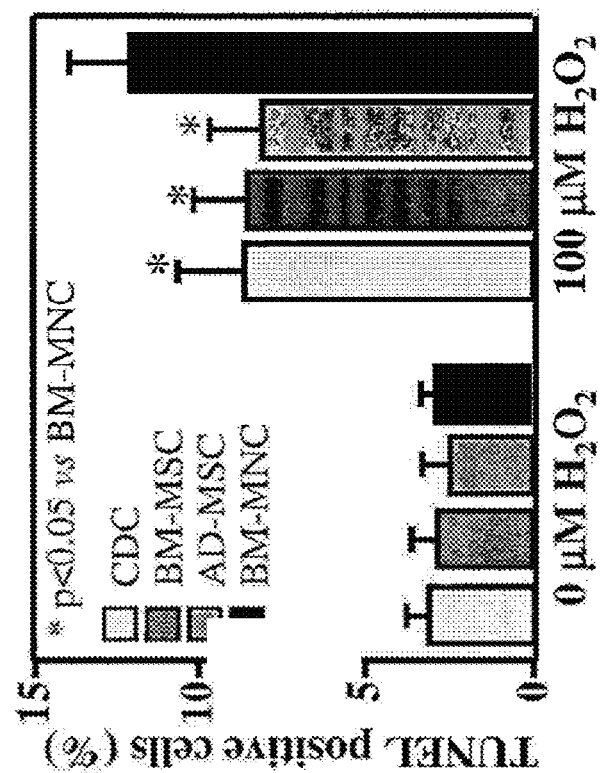
Figure 45A:
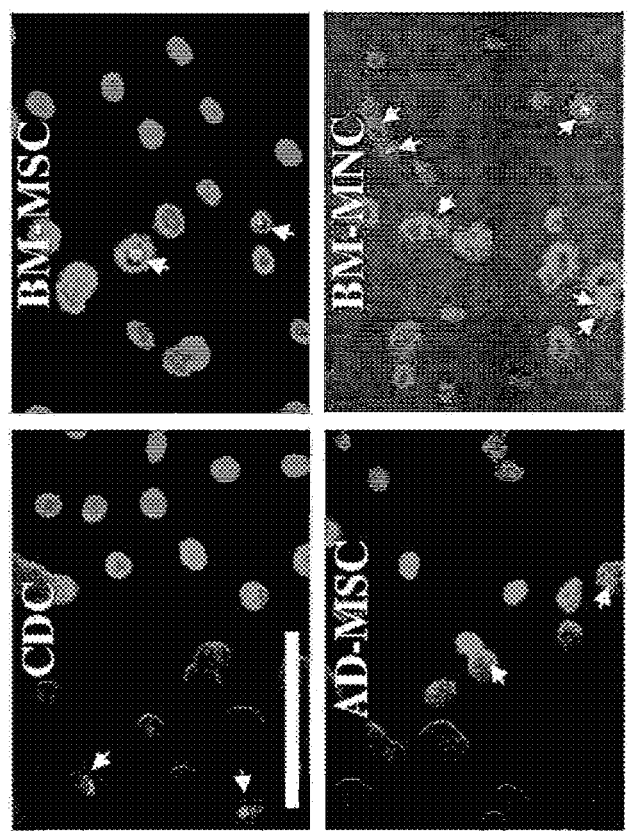

FIGS. 45A-45B depict in vitro resistance of different cell types isolated from the same rat, to oxidative stress. FIG. 45A shows representative images of TUNEL-positive cells (red) after 24 hours' exposure to 100 mM H2O2. FIG. 45B shows quantitative analysis showed that the number of apoptotic cells was significantly lower in CDCs, BM-MSCs, and AD-MSCs than in BM-MNCs with 100 mM $H_2$. Bar=50 mm.

Figure 46B:
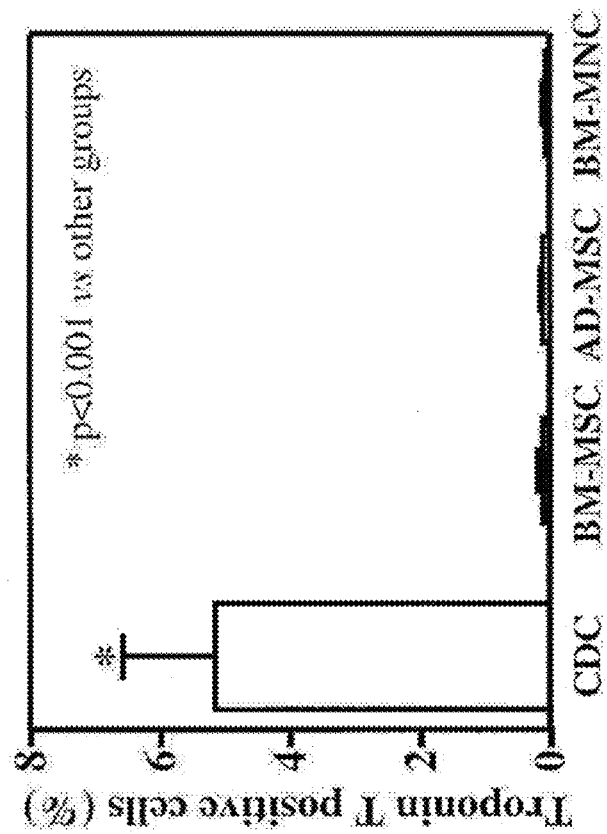
Figure 46A:
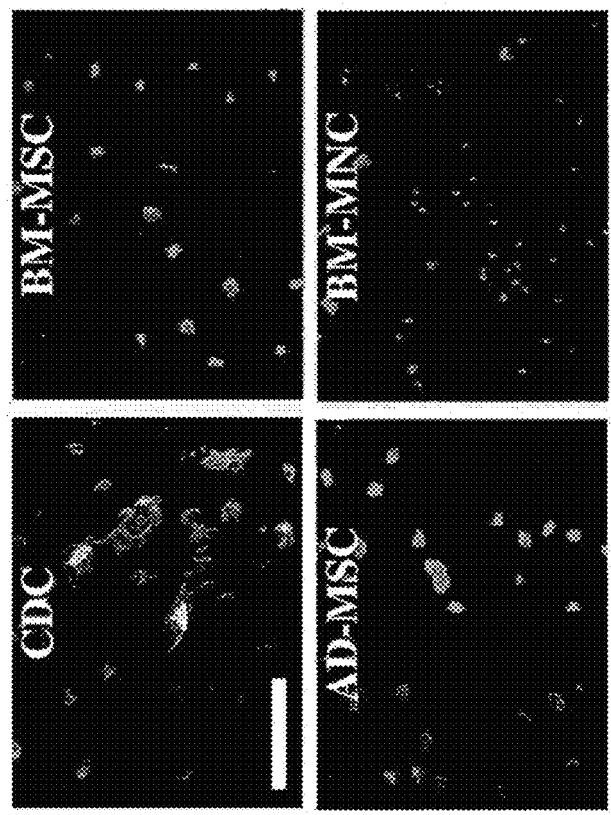

FIGS. 46A-46B depict in vitro myogenic differentiation of different cell types (all isolated from the same rat). FIG. 46A shows a fraction of the CDCs positively expressed the cardiac specific marker Troponin T, with distinct myocyte-like appearance. Troponin T expression was rarely observed in BM-MSCs, AD-MSCs, and BM-MNCs. FIG. 46A depicts the quantitative assessment of Troponin T expression in different cell types is shown. Bar=50 mm.

FIGS. 47A-47C depict cell engraftment and in vivo myogenic differentiation. FIG. 47A Immunostaining shows some human CDCs (green, HNA) expressing α-sarcomeric actin, indicating myogenic differentiation, 3 weeks after implantation into infarcted mice hearts. FIG. 47B Quantitation of engraftment (HNA+ cells). C) Quantitation of cardiomyocytes differentiated from transplanted human cells (HNA+/αSA+ cells). Bar=20 μm.

Figures 48A, 48B, 48C:
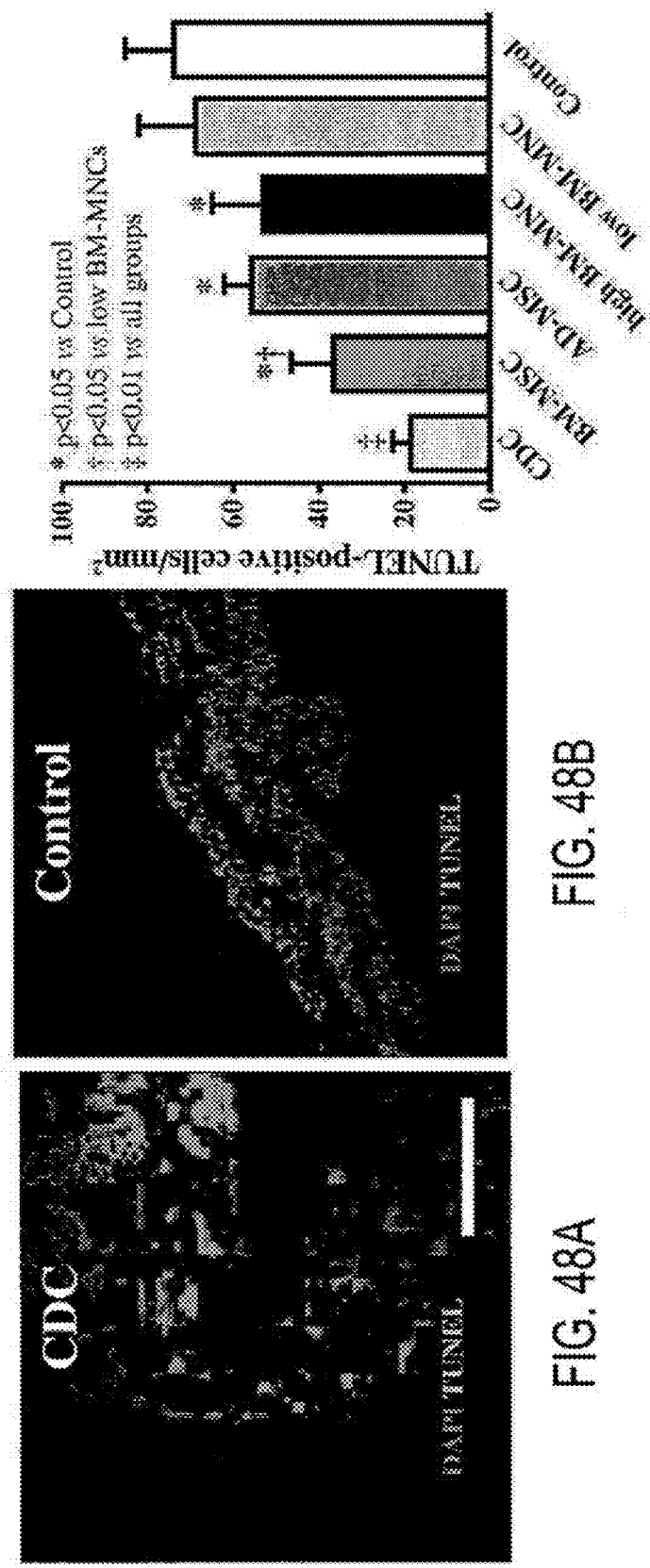

FIGS. 48A-48C depict results of cell apoptosis studies. FIGS. 48A and 48B are representative images of TUNEL-positive cells in the infarcted hearts of mice 3 weeks after cell treatment with CDCs (48A) and PBS (48B). FIG. 48C depicts quantitative assessment of TUNEL-positive cells in the myocardium of mice treated with different cell types and control, is shown. Bar=500 μm.

Figure 49:
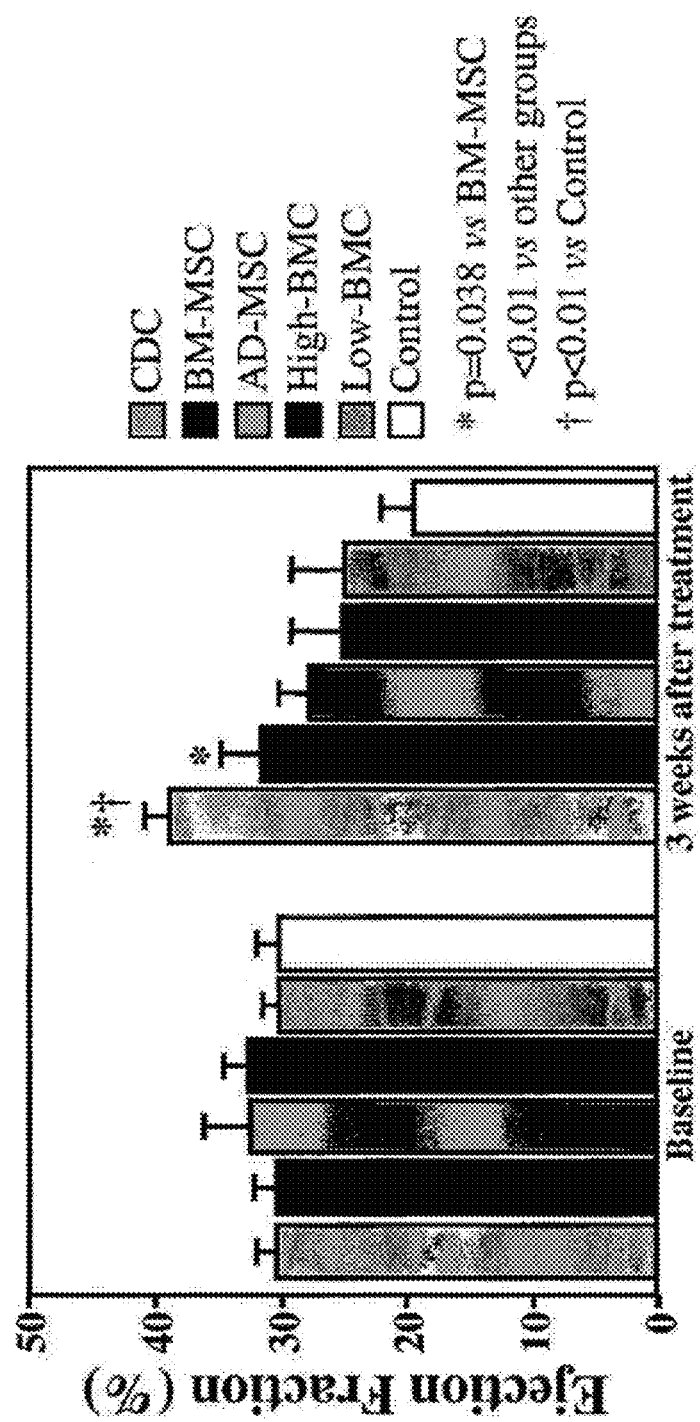

FIG. 49 depicts cardiac function of mice treated with the various cell types. LVEF at baseline (4 hrs post-MI) did not differ among groups, indicating a similar infarct size in animals of all groups. After 3 weeks, LVEF was higher in mice implanted with CDCs, compared to animals treated with cells of non-cardiac origin. Implantation of BM-MSCs also improved cardiac function, compared to controls injected with saline only. Data are presented as mean±SEM.

FIGS. 50A-50H depict Ventricular remodeling after treatment with various cell types. FIGS. 50A-50F are representative images of Masson's staining of infarcted mice hearts, after implantation of different types of human cells or saline injection only. Quantitative analyses of LV wall thickness (50G) and infarct perimeter (50H) show that remodeling was attenuated more efficiently by CDC implantation, compared with BM-MSCs, AD-MSCs, and BM-MNC treatment, although implantation of BM-MSCs, AD-MSCs, and BM- MNCs resulted in less remodeling compared to control treatment with saline injection only.

FIGS. 51A-51E depict a comparison of purified c-kit+ stem cells and unsorted CDCs. FIG. 51A shows LVEF 3 weeks after infarction. LVEF was higher in mice that received unsorted CDCs than those with c-kit+ cells purified from the same CDCs. FIGS. 51B-51E show that although the same number of cells was used for culture, the purified c-kit+ stem cells released less VEGF, SDF, IGF-1, and HGF than the unsorted CDCs.

DETAILED DESCRIPTION

Cell therapy, the introduction of new cells into a tissue in order to treat a disease, represents a promising new method for repairing or replacing diseased tissue with healthy tissue. Therefore, in several embodiments described herein, methods of isolating, culturing, preparing, and introducing regenerative cells into a recipient are provided and result in one or more of treatment of symptoms of a cardiac disease, improvement in cardiac function, and/or regeneration of cardiac tissue in the recipient. In several embodiments, the cardiac disease is the result of one or more of an acute heart failure or chronic heart failure. In some embodiments, the disease creates damaged to the cardiac tissue due to one or more of ischemia, reperfusion, or infarction.

As used herein, the term "regenerative cells" shall be given its ordinary meaning and shall include mixed cell populations (e.g., cardiospheres) and derivatives thereof (e.g., CDCs and secondary generations of cardiospheres (IICSps)), unless explicitly indicated otherwise. Regenerative cells include cells that directly repair tissue (e.g., stem cells) and cells that promote tissue repair (e.g., through paracrine effects or other signaling events).

General

Several embodiments disclosed herein provide methods for expanding populations of resident stem cells from organs, such that only small initial samples are required. Such small initial samples can be obtained relatively non-invasively, for example, by a simple percutaneous entry. Such samples can be obtained using a percutaneous bioptome, in some embodiments. The bioptome can be used to access a tissue sample from any organ source, including heart, kidney, liver, spleen, and pancreas. Particularly suitable locations within the heart which can be accessed using a bioptome include, but are not limited to, the crista terminalis, the right ventricular endocardium, the septal or ventricle wall, and the atrial appendages. These locations have been found to provide abundant stem or progenitor cells. Accessing such locations is facilitated by use of a bioptome which is more flexible than the standard bioptome used for accessing the right ventricular endocardium for diagnostic purposes. Preferably the bioptome is also steerable by an external controller. Such procedures are enable collection of tissue on an out-patient basis without major surgery or general anesthesia. While percutaneous biopsy is employed in some embodiments, in other embodiments, several embodiments employ explanted tissues (e.g., those removed from a subject and under evaluation for transplantation).

One of the advantages of several embodiments disclosed herein that enables use of a small biopsy sample (or small non-biopsy samples) as a starting material is the collection of a cell population which has previously been ignored or discarded. In one embodiment, this cell population is formed by treating the sample with a protease and harvesting or collecting the cells that are liberated from the sample. The use of these liberated cells enhances the rate of cell population expansion. Non-limiting examples of proteases which can be employed include collagenase, matrix metalloproteases, trypsin, and chymotrypsin. This technique can be applied to any organ from which resident stem cells are desired, including, for example, heart, kidney, lung, spleen, pancreas, and liver. In some embodiments, the mass of tissue collected to isolated resident stem cells is roughly equivalent, regardless of the manner in which the tissue was obtained. For example, in some embodiments, the amount of tissue collected ranges from about 10 mg of tissue to about 1000 mg of tissue. For example, in some embodiments, the amount of tissue collected ranges from about 20 mg of tissue to about 500 mg of tissue. In some embodiments, the amount of tissue collected ranges from about 10-50 mg of tissue, about 50-100 mg of tissue, about 100-150 mg of tissue, about 150-200 mg of tissue, about 200-250 mg of tissue, about 250-300 mg of tissue, about 300-350 mg of tissue, about 350-400 mg of tissue, about 400-450 mg of tissue, about 450-500 mg of tissue, and overlapping ranges thereof. In some embodiments, a total of no more than 20 mg of tissue is collected. In some embodiments, a total of no more than 30 mg of tissue is collected. In some embodiments, a total of no more than 40 mg of tissue is collected. In some embodiments, a total of no more than 50 mg of tissue is collected. In some embodiments, a total of no more than 60 mg of tissue is collected. In some embodiments, a total of no more than 70 mg of tissue is collected. In some embodiments, a total of no more than 80 mg of tissue is collected. In some embodiments, a total of no more than 90 mg of tissue is collected. In some embodiments, a total of no more than 100 mg of tissue is collected. In several embodiments, the mass of tissue collected from any single biopsy or collection ranges between about 10-20 mg, including about 11, 12, 13, 14, 15, 16, 17, 18, and 19 mg. In several embodiments, the mass of tissue collected from any single biopsy or collection ranges between about 20-30 mg, including about 21, 22, 23, 24, 25, 26, 27, 28, and 29 mg. In several embodiments, the mass of tissue collected from any single biopsy or collection ranges between about 30-40 mg, including about 31, 32, 33, 34, 35, 36, 37, 38, and 39 mg. In several embodiments, the mass of tissue collected from any single biopsy or collection ranges between about 40-40 mg, including about 41, 42, 43, 44, 45, 46, 47, 48, and 49 mg.

Resident stem cells are those which are found in a particular organ. As discussed below in more detail, it is believed that the stem cells found in a particular organ are not necessarily pluripotent, but rather, are committed to a particular branch of differentiation. Thus in the heart, one expects to find cardiac stem cells, and in the kidney one expects to find kidney stem cells. Despite this, in several embodiments some of the stem cells isolation and expanded using the methods disclosed herein are able to develop into cells of an organ other than the one from which they were obtained.

Cardiospheres are self-associating aggregates of cells which have been shown to display certain properties of cardiomyocytes. Cardiospheres have been shown to "beat" in vitro. They are excitable cells and contract in synchrony. In one embodiment, the cells which form the cardiospheres have been obtained from heart biopsies. In one embodiment, the cells which form the cardiospheres have not been obtained from heart biopsies, but rather have been obtained from a whole heart, or a portion thereof. The cardiospheres can be disaggregated using standard means known in the art for separating cell clumps or aggregates, including, but not limited to trituration, agitation, shaking, blending. In one embodiment, cardiospheres are disaggregated to single cells.

In several embodiments they are disaggregated to smaller aggregates of cells. In several embodiments, after disaggregation, the resultant cells are grown on a solid surface, such as a culture dish, a vessel wall or bottom, a microtiter dish, a bead, flask, roller bottle, etc. The surface can be glass or plastic, for example. In one embodiment, the cells are capable of adhering to the material of the solid surface. The solid surface is optionally coated with a substance which encourages adherence in some embodiments. Several such substances are known in the art and include, without limitation, fibronectin. hydrogels, polymers, laminin, serum, collagen, gelatin, and poly-L-lysine. In several embodiments, growth on the surface is monolayer growth. These cells are cardiosphere-derived cells (CDCs).

In several embodiments, after growth of CDCs, they are directly administered to a mammal in need thereof. In one embodiment the CDCs are optionally grown under conditions which favor formation of cardiospheres. In one embodiment, the cells themselves are not administered, but one or more substances contacted with or released from the cells are administered. Repeated cycling between surface growth and suspension growth (cardiospheres) leads to a rapid and exponential expansion of desired cells. In one embodiment the cardiosphere phase is eliminated and CDCs are repeatedly expanded through growth on a surface without forming cardiospheres at each passage.

Several embodiments, of the culturing processes disclosed herein (whether culturing CDCs on surfaces or cardiospheres in suspension) are performed in the absence of exogenous growth factors. In one embodiment, fetal bovine serum is used, but other factors are viewed as expendable. For example the cells of the present invention are readily cultured in the absence of added EGF, bFGF, cardiotrophin-1, and thrombin.

Mammals which can be the donors and recipients of cells are not limited. Thus, while in several embodiments, humans provide both the cells and are the recipients, often other mammals will be useful. Pig cells can be transplanted into humans, for example. Such cross-species transplantation is known as xenogeneic transplantation. The transplantation can also be allogeneic, syngeneic, or autologous, all within a single species. Suitable mammals for use in such transplants include pets, such as dogs, cats, rabbits; agricultural animals, such as horses, cows, sheep, goats, pigs, as well as humans.

Administration of cells to a mammal can be by any means known in the art. Cardiac cells can be delivered systemically or locally to the heart. In several embodiments, the administered cells are not in the form of cardiospheres, but rather are CDCs. In some embodiments, cardiospheres are delivered. As discussed above, they have the capacity to form cardiospheres under suitable conditions. Local administration can be by catheter or direct (e.g., during surgery). Systemic administration can be by intravenous or intraarterial injections, perfusion, or infusion. In those embodiments, employed systemic administration, the administered cells migrate to the appropriate organ, e.g., the heart, if the cells are derived from resident heart stem cells.

The beneficial effects which are observed upon administration of the cells to a mammal may be due to the cells per se in some embodiments. For example, in some embodiments the engraftment of cells produces a favorable outcome. However, in some embodiments, the beneficial effects are due to products which are expressed by the cells (e.g., a surface marker that interacts with host tissue) or secreted, released or otherwise delivered to the recipient tissue by the cells. In several embodiments cytokines or chemokines or other diffusible factors, including but not limited to paracrine factors (e.g., growth factors) stimulate resident cells to grow, reproduce, or perform better. In some embodiments, the combination of the cells and diffusible factors provide the beneficial effects.

As discussed below, in some embodiments, an effective dose of cardiac stem cells will typically be between $1 \times 10^6$ and $100 \times 10^6$. In some embodiments, the dose is between $10 \times 10^6$ and $50 \times 10^6$. Depending on the size of the damaged region of the heart, more or less cells may be used. For example, when treating a larger region of damage, a larger dose of cells may be used, and a small region of damage may require a smaller does of cells. On the basis of body weight of the recipient, an effective dose may be between 1 and $10 \times 10^6$ per kg of body weight, preferably between $1 \times 10^6$ and $5 \times 10^6$ cells per kg of body weight. Patient age, general condition, and immunological status may be used as factors in determining the dose administered.

Diseases which can be treated using the methods and compositions disclosed herein include acute and chronic heart disease. For example, hearts having been subjected to an ischemic incident, subjected of chronic ischemia, or congestive heart disease are treated in some embodiments. In some embodiments, patients are candidates for heart transplants or recipients of heart transplants. In additional embodiments, hearts which are damaged due to trauma, such as damage induced during surgery or other accidental damage, are treated according to the methods disclosed herein.

The cell populations which are collected, expanded, and/or administered according to the present invention can optionally be genetically modified, according to several embodiments. In one embodiment, they are transfected with a coding sequence for a protein, for example. The protein can be beneficial for diseased organs, such as hearts. Non-limiting examples of coding sequences which can be used include without limitation akt, connexin 43, other connexins, HIF1-alpha, VEGF, FGF, PDGF, IGF, SCF, myocardin, cardiotrophin, L-type calcium channel alpha-subunit, L-type calcium channel beta-subunit, and Nkx2.5. The cells may be conveniently genetically modified before the cells are administered to a mammal. Techniques for genetically modifying cells to express known proteins are well known in the art. As discussed herein, in several embodiments, genetic modification is not necessary as the beneficial effects which are observed upon administration of the cells to a mammal are due to the engraftment of the administered cells, due to products which are expressed by the cells (e.g., a surface marker that interacts with host tissue) or secreted, released or otherwise delivered to the recipient tissue by the cells (e.g., cytokines or chemokines or other diffusible factors, such as paracrine factors) or combinations thereof.

As discussed below, CDCs were easily harvested and readily expanded from biopsy specimens as well as from transplant-ready hearts, and after administration regenerated myocardium and improve function in several acute MI models. 69 of 70 patients had biopsy specimens that yielded cells by the methods disclosed herein, making the goal of autologous cellular cardiomyoplasty attainable. In some embodiments, autologous cells are used, as the cells are a perfect genetic match and thus present fewer potential safety concerns than allogeneic cells. However, practical limitations with the use of autologous cells may arise from the delay from tissue harvesting to cell transplantation. To avoid the delay, cell banks can be created of cardiac stem cells from patients with defined immunological features. These should permit matching of immunological antigens of donor cells and recipients for use in allogeneic transplantation.

Antigens for matching are known in the art of transplantation. Likewise, as disclosed below, in several embodiments allogeneic cells need not be matched, as they present limited immune responses when administered. In some embodiments, this is due a short residence time of the cells themselves. In some embodiments, the choice of cardiospheres or CDCs determines the residence time. In several embodiments, CDCs reside in host tissues for about 3-6 weeks, and then are destroyed by host mechanisms. However, despite the loss of some or all of the originally administered cells, beneficial effects are still observed, likely due to paracrine effects set in motion by the cells. In several embodiments, the relatively short residence time of the administered cells limits the immune response.

Previous clinical studies in which bone marrow-derived stem cells were injected into patients within 2 weeks following acute MI, resulted in significantly improved LVEF with intracoronary infusion of $5\text{-}80 \times 10^6$ cells. As such, several million CDCs may constitute an effective therapeutic dose, in certain embodiments. From single bioptome or non-biopsy specimens, millions of CDCs can be derived after just two passages; if biopsies or sample collection were performed specifically for therapeutic purposes, the amount of starting material could easily be scaled upwards by ten-fold or more, further improving the overall cell yield. In several embodiments, however, other variables, such as culture conditions, can increase the yield while allowing reduction in the amount of starting material required.

In some embodiments, minimizing the number of passages for expansion will minimize the risk of cancerous transformation of CDCs, a problem which has been observed in mesenchymal stem cells, typically after about 6 or more passages. Another prominent risk of cell transplantation lies in the potential for arrhythmogenicity. Arrhythmias have not been documented with cardiac stem cells. Teratoma formation is also a concern, though in several embodiments, teratoma formation is reduced or non-existent. In one embodiment, teratoma formation can occur when cells are not committed to forming a specific type of tissue.

In several embodiments, CDCs are derived from human biopsies (or non-biopsy samples) without antigenic selection (including but not limited to c-kit). In several embodiments, all cells that are shed from the initial heart specimen and which go on to contribute to the formation of cardiospheres. Thus, in several embodiments, cells according to several embodiments of the invention differ fundamentally from cardiac "stem cells" which have been isolated by antigenic panning for one or another putative stem cell marker, for example c-kit. Nevertheless, CDCs include a sizable population of cells that exhibit stem cell markers, and the observed regenerative ability in vivo further supports the notion that CDCs include a number of resident stem cells. In some embodiments, a subfraction of CDCs suffices to produce the beneficial effects; however, subfractionation may delay transplantation and raise regulatory concerns by introducing an artificial selection step. Thus, in several embodiments CDC or cardiosphere populations that have not been enriched for any one marker (including but not limited to c-kit) are particularly advantageous, as the required manipulation and handling of the cells is reduced and the resultant beneficial effects are equivalent.

Adult human cardiac stem cells have been shown to respond to a limited degree to a state of cardiac hypertrophy by proliferation and myocardial regeneration and to acute ischemia by mobilization to the injury border zone and subsequent regeneration, but often ultimately succumb to apoptosis in a chronic ischemic setting. Significant progress is currently being made identifying means of enhancing in vivo survival, mobilization, proliferation, and subsequent differentiation of CSCs using animal models. The methods disclosed herein for ex vivo expansion of resident stem cells for subsequent autologous or allogeneic transplantation may give these cell populations, the resident and the expanded, the combined ability to mediate myocardial regeneration to an appreciable degree. If so, cardiac stem cell therapy may well change the fundamental approach to the treatment of disorders of cardiac dysfunction.

Transplant and Regenerative Cell Types

With respect to the recipient of administered regenerative cells, several embodiments use allogeneic regenerative cells. In such a transplant, the donor and recipient are different individuals within the same species. For example, a first mammal is the donor of the cells and a second mammal is the recipient of the cells. In several embodiments, the mammals are humans. In several embodiments, autologous stem cells (donor and recipient are the same) are used. In such embodiments, a donor's own regenerative cells are re-administered to the same individual. In several other embodiments xenogeneic (donor and recipient are different individuals from different species) regenerative cells are used. In some such embodiments, closely related phylogenetic species are used, such as humans and chimpanzees. In other embodiments, individuals from more distantly related species may be the donor and recipient, but immunological compatibility is still possible. In several embodiments, syngeneic (genetically identical and thus, immunologically compatible) regenerative cells are used. Although adult regenerative cells are provided in several embodiments of the invention, embryonic regenerative cells are used in one embodiment. However, many embodiments of the invention obviate the need for embryonic stems cells. In some embodiments, other cell types are used, for example, myoblasts or peripheral blood-derived endothelial progenitors may be used. Additionally, induced pluripotent stem cells are used in some embodiments.

The Major Histocompatibility Complex (MHC) is large, gene-dense region of the mammalian genome, which plays and important role in immune system function. The proteins encoded by the MHC are expressed on the surface of cells and thus are involved in antigen presentation as well as lymphocyte recognition. MHC molecules effectively control the initiation of an immune response through identification of cells as "self" or "non-self." Thus, MHC molecules are key targets in transplantation rejection.

The most well-known genes in the MHC region are the subset that encode antigen-presenting proteins on the cell surface. In humans, these genes are referred to as human leukocyte antigen (HLA) genes. In humans, the MHC is divided into three regions: Class I, II, and III. HLA class I antigens (A, B, and C) present peptides from inside the cell (including viral peptides if present). HLA class II antigens (DP, DM, DOA, DOB, DQ, and DR) present antigens from outside of the cell to T-lymphocytes. HLA class III antigens encode components of the complement system.

While class I and class II MHC molecules are structurally similar and both present antigens to T-cells, their functions in the immune response cascade are different. Class I molecules are found on virtually every cell in the human body while Class II molecules, in contrast, are only found on B-cells, macrophages and other antigen-presenting cells. Class I molecules present antigens to cytotoxic T-cells (CTLs) while class II molecules present antigen to helper T-cells. This specificity of antigen presentation leads into another difference, the type of antigen presented. Class I molecules present endogenous antigens while class II molecules present exogenous antigens. For example, an endogenous antigen could be a viral protein fragment or tumor protein. These endogenous antigens indicate internal cellular alterations that need to be controlled so that they don't spread throughout the body. In contrast, exogenous antigens may comprise fragments of bacterial cells or viruses, e.g., non-self antigens, which are engulfed and processed by, for example, a macrophage, and then presented to helper T-cells. The helper T-cells, in turn, activate B-cells to produce antibody that may lead to the destruction of the cell. Thus, recognition of a newly administered cell or tissue as non-self is one aspect of the cascade of events giving rise to transplant rejection.

Autologous cell therapies are attractive, and commonly used, as the "self" immune profile of administered cells/tissues will rarely elicit an immune response upon re-administration to the donor/recipient. Autologous transplant with embryonic tissue is not feasible in the vast majority of cases, as harvesting embryonic tissue for later use in the same individual is technologically and temporally challenging. Thus, embryonic cells are typically allogeneic with respect to the recipient. As a result, rejection of transplanted embryonic cells may be a significant concern. Additionally, the pluripotency of embryonic stem cells does not guarantee differentiation of implanted/administered cells into cells related to the target tissue. In other words, an embryonic stem cell implanted into the heart may not necessarily yield heart tissue, but rather may yield other, unwanted cell types or result in teratoma formation.

According to several embodiments of the present invention, adult stem cells, whether allogeneic, autologous, xenogeneic, or syngeneic develop into cell types closely related to the originating tissue type. In other words, adult cardiac regenerative cells will differentiate into cardiac related cell types, such as cardiomyocytes or cardiac endothelial cells and vasculature, among other cardiac cell types. Several embodiments of the invention are especially advantageous because the risk that adult stem cells will develop into undesired cell types is less than when embryonic stem cells are used and can be further reduced by isolating adult stem cells from the tissue that is to be treated or repaired.

The determination of whether to use autologous or allogeneic regenerative cells may not be driven primarily by temporal difficulties with respect to cell isolation, but by other clinical implications. Tissue collection for isolation of adult regenerative cells is commonly accomplished by simple biopsy procedures. In many cases, the current state of a donor's tissue is a determining factor on whether to use autologous or allogeneic regenerative cells. For example, a donor who suffered from extensive tissue damage may have insufficient or non-ideal tissue from which to isolate regenerative cells. In such cases, allogeneic regenerative cells may present a preferred alternative.

Allogeneic regenerative cells do present the possibility of immune rejection by the recipient, thereby potentially limiting the long term survival of the administered regenerative cells. However, allogeneic regenerative cells also present numerous benefits. They can be harvested from healthy donors, expanded in culture, and stored for future use, meaning there is a ready availability of regenerative cells for use in therapies. In the cardiac context in particular, this ready supply of stored regenerative cells would enable administration of cells in the critical post-injury period, where beneficial therapeutic outcomes may be maximal.

Additionally, because the donor and recipient are distinct from one another, allogeneic regenerative cells can be obtained from healthy tissue of a healthy donor. This may improve the survival of the regenerative cells in long term storage, as well as during the post-administration period. In addition, regenerative cells from a healthy donor may simply induce a more robust and positive therapeutic effect than regenerative cells taken from a recipient in a state of compromised health. Additionally, even though adult regenerative cells can be isolated via a simple biopsy procedure, allogeneic transplants decrease risk to the recipient, such as infection risk, as the recipient need not undergo the tissue isolation procedure. Moreover, these advantages have the potential to increase the number of recipients that can receive allogeneic transplants and simultaneously reduce the cost of providing such therapies.

Several embodiments described herein provide for methods of isolating, methods of culturing, methods of preparing, and methods of introducing regenerative cells into a recipient in need of amelioration of the symptoms associated with and/or treatment of a cardiac condition. In several embodiments, the regenerative cells are cardiac tissue-derived. In certain such embodiments, the regenerative cells are adult regenerative cells. As used herein, the term adult shall be given its ordinary meaning and shall also refer to all stages of life extending from birth to death, (e.g., adult cells are non-embryonic/non-fetal cells). Additionally, in several embodiments, adult cells or adult tissues also refer to cells or tissues collected after death of an adult individual.

In several embodiments the regenerative cells are allogeneic. In some embodiments, allogeneic regenerative cells are harvested from healthy donors, expanded in culture, and stored for future use. In certain such embodiments, a pool of allogeneic regenerative cells for acute therapy is available. Thus, in some embodiments, an allogeneic source of regenerative cells and allogeneic transplant reduces overall risk to the recipient. In some embodiments, the allogeneic regenerative cells are stored in a manner that allows for rapid preparation and administration to a recipient in need of cell therapy. In certain embodiments, such regenerative cells are administered to a recipient as soon as possible after the recipient has suffered an adverse cardiac event. However, in other embodiments, the regenerative cells are administered over a period of time, multiple times, or after a certain period of time, depending on the severity and nature of an adverse cardiac event.

In several allogeneic embodiments, the donor regenerative cells have not been immunologically matched with respect to the subject. In other embodiments, donor regenerative cells are known to be immunologically mismatched with respect to the recipient. In such embodiments, the donor regenerative cells are mismatched (with respect to the recipient) at one or more HLA antigens. However, in certain embodiments, the degree of mismatch does not necessarily predict a severity of immune response. In other words, in some embodiments involving a donor and recipient having a larger degree of immunological mismatch there is a less severe immune response as compared to a donor and recipient who are more immunologically similar.

In several embodiments the regenerative cells are autologous. In some embodiments, autologous regenerative cells are harvested from a donor at a point when the donor is healthy, expanded in culture, and stored for future use. In certain such embodiments, a pool of autologous regenerative cells for personally tailored cell therapy is available. In certain embodiments, the autologous regenerative cells are stored in a manner that allows for rapid preparation and re-administration to the donor/recipient when the donor/recipient is in need of cell therapy. In certain embodiments, such regenerative cells are administered to the donor/recipient as soon as possible after the recipient has suffered an adverse cardiac event. However, in other embodiments, the regenerative cells are administered over a period of time, multiple times, or after a certain period of time, depending on the severity and nature of an adverse cardiac event.

In several embodiments the stem cells are xenogeneic. In certain such embodiments, a large pool of xenogeneic regenerative cells isolated from a donor organism is available. In certain embodiments, the xenogeneic regenerative cells are stored in a manner that allows for rapid preparation and administration to the recipient when the recipient is in need of cell therapy. In certain embodiments, such regenerative cells are available and ready for administration to the recipient as soon as possible after the recipient has suffered an adverse cardiac event. However, in other embodiments, the regenerative cells are administered over a period of time, multiple times, or after a certain period of time, depending on the severity and nature of an adverse cardiac event.

In several embodiments of the invention, the regenerative cells are syngeneic. In some embodiments, syngeneic regenerative cells are harvested from a healthy donor, expanded in culture, and stored for future use in either the donor (in which case the transplant would be autologous) or a genetically related recipient. In certain such embodiments, a pool of syngeneic regenerative cells for cell therapy tailored to a specific genetic and/or immunological background is available. In certain embodiments, the syngeneic regenerative cells are stored in a manner that allows for rapid preparation and re-administration to the donor/recipient when the donor/recipient is in need of cell therapy. In certain embodiments, such regenerative cells are administered to the donor/recipient as soon as possible after the recipient has suffered an adverse cardiac event. However, in other embodiments, the regenerative cells are administered over a period of time, multiple times, or after a certain period of time, depending on the severity and nature of an adverse cardiac event.

As used herein, the term "adverse cardiac event" shall be given its ordinary meaning and shall also be read to include, but not be limited to myocardial infarction, ischemic cardiac tissue damage, congestive heart failure, aneurysm, atherosclerosis-induced events, cerebrovascular accident (stroke), and coronary artery disease.

In several embodiments, the regenerative cells, whether allogeneic, autologous, xenogeneic, or syngeneic, are multipotent. In certain embodiments, the regenerative cells advantageously present a decreased risk of abnormal tissue or teratoma formation, and depending on the transplant type, a reduced risk of immunological rejection. Despite these advantages, in certain other embodiments, pluripotent regenerative cells are used.

The Role Model Effect—Signals and Cellular Recruitment Induced by Regenerative Cells Depending on the cell types involved, and the type of signal to be conveyed, multiple varieties of cell signaling are used. Autocrine signaling involves the generation of a signal that acts back on the same cell (or same type of cell). In contrast paracrine signaling involves a target cell which is near, but distinct from the signal-releasing cell. Among other events, paracrine signaling is involved in allergic and immune responses, tissue growth and repair, and blood clotting.

The beneficial effects which are observed upon administration of the cells to a mammal may be due to the cells per se in some embodiments. For example, in some embodiments the engraftment of cells produces a favorable outcome. However, in some embodiments, the beneficial effects are due to products which are expressed by the cells (e.g., a surface marker that interacts with host tissue) or secreted, released or otherwise delivered to the recipient tissue by the cells. In several embodiments cytokines or chemokines or other diffusible factors, including but not limited to paracrine factors (e.g., growth factors) stimulate resident cells to grow, reproduce, or perform better. In some embodiments, the combination of the cells and diffusible factors provide the beneficial effects.

In several embodiments, the regenerative cells administered to a recipient produce paracrine signals that affect the surrounding target tissue during or after administration. However, in several embodiments, the direct administration of regenerative cells is not necessary, in that the culturing of isolated regenerative cells results in release of the paracrine signaling molecules into the culture media, which can then be harvested and administered in place of the regenerative cells. In some embodiments, regenerative cells and their paracrine signaling molecule-enriched media are co-administered. In other embodiments, stem cells and their paracrine signaling molecule-enriched media are sequentially administered. In still other embodiments, regenerative cells (in a pharmaceutically acceptable carrier) are administered alone.

In several embodiments, paracrine signals from the administered regenerative cells have multiple positive effects on the surrounding target tissue. In certain embodiments, the effects of the paracrine signals persist, even after the administered regenerative cells are no longer viable. In other words, the regenerative cells create a "Role Model" effect or a "butterfly effect", in that they set in motion a cascade of events that carries on, even when the regenerative cells are no longer present. In some embodiments, the paracrine signals generated improve the viability of the surrounding target tissue (e.g. signals are pro-survival). In certain such embodiments, paracrine signals act on both damaged and healthy target tissue. In some embodiments, paracrine signals enhance the recovery of damaged cells in the target tissue. In some embodiments, paracrine signals enhance the function of damaged and/or healthy cells in the target tissue. In some embodiments, paracrine signals induce the regeneration of new target tissue. In some embodiments, paracrine signals enhance the recovery of damaged cells in the target tissue.

In several embodiments, the paracrine signals reduce the amount of induced programmed cell death (apoptosis). In some embodiments, reduction in apoptosis is manifest by a reduction in the expression of certain apoptotic markers in the target tissue. In other embodiments, anti-apoptotic markers are increased. In some embodiments, apoptotic markers are simultaneously reduced while anti-apoptotic markers are increased. In some embodiments, reduction in apoptosis is manifest by a reduction in the number of cells in target tissue that are permeable to certain molecules (i.e. fewer cells have the characteristic plasma membrane damage associated with apoptosis). In some embodiments, reduction in apoptosis in the target tissue occurs rapidly after administration of regenerative cells. In other embodiments, reduction apoptosis in the target tissue occurs after several hours or days post-administration of regenerative cells. In some such embodiment, reductions in apoptosis are detected between about 24 and about 72 hours post-administration. In some embodiments, apoptosis is reduced after 1 week. In other embodiments, apoptosis remains low for several weeks. In some embodiments, apoptosis is reduced by up to 20%. In some embodiments, apoptosis is reduced by about 20%. In other embodiments, apoptosis is reduced by about 30%. In some embodiments, apoptosis is reduced by about 35%. In some embodiments apoptosis is reduced by about 40%. In certain embodiments, apoptosis is reduced by about 20-30%, including 21, 22, 23, 24, 25, 26, 27, 28, and 29%.

In several embodiments, paracrine signals induce formation of new blood vessels, which thereby improves function and/or survival of the target tissue (e.g., signals are pro-angiogenic). In some embodiments, new blood vessel formation is manifest by an increase in the length of existing vessels (e.g., into the infarcted area). In some embodiments, new blood vessel formation is manifest by an increase in the density of vessels or in an area of tissue. In some embodiments, vessel density increases by up to about 4-fold (as compared to damaged tissue not receiving regenerative cells). In other embodiments, vessel density increases by about 2-fold. In some embodiments, vessel density increases by about 3-fold. In some embodiments, vessel density increases by about 1.5-fold. In certain embodiments, vessel density increases by about an amount ranging from about 1.1 to 2.5-fold, including 1.2, 1.4, 1.6, 1.8, 2.2, and 2.4-fold.

In several embodiments, the paracrine signals generating the new blood vessels are carried to more remote locations in the target tissue, and induce positive effects in the remote tissue. In some embodiments, paracrine signals recruit endogenous stem cells from the surrounding tissue. In certain other embodiments, paracrine signals from the administered stem cells initiate a signaling cascade, causing other local cells to generate additional paracrine signals. In still other embodiments, paracrine signals from the administered regenerative cells act both on endogenous cells in a paracrine manner as well in an autocrine manner on the stem cells themselves. In several embodiments wherein two or more paracrine signals are generated, the signals function in a synergistic manner to generate one or more of the positive effects described herein. Thus, it shall be appreciated that the administration of regenerative cells, in several embodiments as described above, yield positive effects in the target tissue through either a direct effect (e.g., tissue regeneration), indirect effect (e.g., increase blood supply to new and endogenous tissue), or a combination thereof.

In several embodiments, the type of regenerative cells administered plays a role in determining one or more of the type, duration, or intensity of paracrine signals generated. For example, in certain embodiments, a first type of regenerative cells may release a particular amount of a first paracrine signal upon administration, while in other embodiments, a different type of regenerative cells may release less of the first paracrine signal, and more of a second (or additional) paracrine signal. It shall be appreciated that while the types of regenerative cells are genetically related, their differing structures, compositions, and/or state of differentiation make it possible that the paracrine signals released by one type of regenerative cells are quite different than those released by its derivatives. For example, the microenvironment surrounding certain stem cells is known to play a role in the regulation of stem cells. Thus, differentiation of embryonic stem cells is both spatially and temporally regulated by the distinct environments, or "cellular niches" created during development. As discussed above, removal of an embryonic stem cell and placement of the cell in a distinct niche disrupts the signals of the native microenvironment, often resulting in teratoma formation.

Certain regenerative cells have a multicellular, 3-dimenensional structure, thus creating the possibility of numerous microenvironments or niches within the regenerative cells. For example, based on the 3-dimensional structure of some regenerative cells, a gradient of cellular oxygen exists that decreases from the outer to the inner cell layers. Thus in some embodiments, certain cells in the inner layers are stimulated to release paracrine signals by the level of hypoxia the cells experience in their immediate environment. In some embodiments, the close physical proximity of certain cell types within the regenerative cells create a contact-based microenvironment, which subsequently directs the function and fate of the regenerative cells. In several embodiments, the paracrine signals produced by the cells comprising the regenerative cells create a distinct microenvironment which subsequently directs the function and fate of the regenerative cells. Thus, in certain embodiments, regenerative cells having a 3-D structure are preferred. However, non-3-dimensional regenerative cells are used in other embodiments.

In several embodiments, certain regenerative cells release more or less of the paracrine signals released by other regenerative cells, and may release one or more additional paracrine signals not released by other regenerative cells. In some such embodiments, each type of regenerative cells has the capacity to generate any or all of the paracrine signals generated by the other types (and vice versa) but is not stimulated to do so.

In several embodiments, the generation of paracrine signals from regenerative cells varies over time (either during in vitro culture or in vivo, post-administration). In some embodiments, generation of paracrine signals continues for at least a week after administration or culturing begins. In other embodiments, generation of paracrine signals continues for two, three or four weeks, several months, or for several years. In several embodiments, the paracrine signals, either alone or in combination with the signals generated by endogenous tissue, promote the engraftment and/or long term survival of the administered regenerative cells. In other embodiments, the engraftment and survival are relatively short-lived, but the resultant effects are long-term. In some embodiments, the survival of administered regenerative cells is due to their ability to differentiate into multiple types of cardiac tissue, thus efficiently adapting to the local environment. In some embodiments, the adaptability of regenerative cells functions in combination with paracrine signals to effectuate the survival of the administered cells.

In several embodiments, the administration of regenerative cells results in engraftment of the regenerative cells into host tissue. In some embodiments, as discussed herein, the amount of detectable engraftment of the regenerative cells changes over time. In some embodiments, a higher degree of regenerative cells have engrafted a short period of time after administration as compared to later times after administration (i.e. engrafted numbers decrease). In some embodiments, engraftment peaks at an intermediate time point. In some embodiments, the type of regenerative cells used (i.e., allogeneic v. autologous, etc.) is a factor in engraftment. In some embodiments, allogeneic regenerative cells engraft as well as other types, while in other embodiments, allogeneic regenerative cells show lesser engraftment. In some embodiments, engraftment of allogeneic regenerative cells is equivalent to that of other regenerative cells types at a first time point, but decreases more rapidly post-administration. However, in several embodiments, the functional effect of allogeneic regenerative cells is equivalent, or greater than, that of other cell types, despite the lesser degree of engraftment. In certain embodiments, engraftment is correlated with survival of regenerative cells. In some embodiments, the administered regenerative cells survive for several days post-administration. In some embodiments, administered regenerative cells survive for about a week to about two weeks. In some embodiments, administered regenerative cells survive for several weeks, or one, two, three or more months. As discussed above, in certain embodiments, the effects of the paracrine signals, and in some embodiments the signals themselves, persist after administered regenerative cells are no longer viable. In several embodiments, this "butterfly effect", the persistence of the signals that result from the engrafted cells, despite the limited term of the engraftment, is responsible for the long-term beneficial anatomical and functional recovery of the cardiac tissue.

In several embodiments, the paracrine signals comprise one or more growth factors, hormones, cytokines, or other signaling molecule that are released from the administered regenerative cells. In certain embodiments the paracrine signals comprise one or more of the following signaling molecules: ENA-78, G-CSF, GM-CSF, GRO, GRO-alpha, I-309, IL-1 alpha, IL-1 beta, IL-2, IL-3, IL-4, IL-5, IL-6, IL-7, IL-8, IL-10, IL-12, IL-13, IL-15, interferon gamma, MCP-1, MCP-2, MCP-3, M-CSF, MDC, MIG, MIP-1 beta, MIP-1 delta, RANTES, SCF, SDF-1, TGF-beta 1, TNF-beta, EGF, IGF-1, angiogenin, oncostatin M, thrombopoeitin, VEGF, PDGF-BB, leptin, BDNF, BLC, Ck beta 8-1, eotaxin, eotaxin-2, eotaxin-3, FGF-4, FGF-6, FGF-7, Flt-3 ligand, fractalkine, GCP-2, GDNF, HGF, IGFBP-1, IGFBP-2, IGFBP-3, IGFBP-4, IL-16, IP-10, LIF, LIGHT, MCP-4, MIP-3 alpha, NAP-2, NT-3, NT-4, osteopontin, osteoprogenerin, PARC, PIGF, TGF beta 2, TGF beta 3, TIMP-1 and TIMP-2. In several preferred embodiments, the paracrine signals comprise one or more of VEGF, HGF, and IGFI. In some embodiments, a single paracrine signal is responsible for the beneficial therapeutic effects, while in other embodiments, one or more paracrine signals work synergistically to produce the effects. As discussed above, several embodiments described herein reduce the risk of teratoma formation. In certain embodiments, the paracrine signals from the regenerative cells (or those induced in the target tissue) reduce, minimize, and/or eliminate the risk of teratoma formation.

In several embodiments, various types of regenerative cells have different paracrine potencies. In other embodiments, the paracrine potency of a single type of regenerative cells varies over time. In some embodiments, regenerative cells express one or more receptors for the paracrine signals generated by the regenerative cells. As such, in some embodiments the regenerative cells act in a paracrine manner on other co-administered regenerative cells. In some embodiments, the regenerative cells act in a paracrine manner on endogenous tissue. In still other embodiments, the regenerative cells act in an autocrine manner. In some embodiments, the regenerative cells express one or more of the KDR, Met, and IGFI receptors (the receptors for receptors for VEGF, HGF and IGFI, respectively).

In several embodiments, endogenous cells are recruited by the administration of the regenerative cells. In some embodiments, the presence of the administered regenerative cells induces the recruitment of endogenous cells. In other embodiments, paracrine signals released from the regenerative cells induce the recruitment of endogenous cells. In still other embodiments, the presence of the regenerative cells and the paracrine signals produced thereby work in combination to induce the recruitment of endogenous cells.

In several embodiments, the recruited endogenous cells improve the viability of the surrounding target tissue. In certain embodiments, the recruited cells engraft into the damaged tissue and generate new, healthy tissue. In certain embodiments, the recruited endogenous cells generate paracrine signals that act on both damaged and healthy target tissue. In some embodiments, these paracrine signals enhance the recovery of damaged cells in the target tissue. In certain embodiments, these paracrine signals reduce the amount of programmed cell death. In some embodiments, paracrine signals from the recruited endogenous cells enhance the function of damaged and/or healthy cells in the target tissue. In some embodiments, these paracrine signals induce the regeneration of new target tissue. In some embodiments, these paracrine signals enhance the recovery of damaged cells in the target tissue. In some embodiments, paracrine signals from the recruited endogenous cells induce formation of new blood vessels, which thereby improves function and/or survival of the target tissue. In certain such embodiments, these paracrine signals generating the new blood vessels are carried to more remote locations in the target tissue, and induce positive effects in the remote tissue.

In certain other embodiments, paracrine signals from the recruited endogenous cells initiate a signaling cascade, causing other local cells to generate additional paracrine signals. In still other embodiments, paracrine signals from the recruited endogenous cells act both on other endogenous cells in a paracrine manner as well in an autocrine manner on the recruited endogenous cells themselves. In several embodiments wherein two or more paracrine signals are generated, the signals function in a synergistic manner to generate one or more of the positive effects described herein. Thus, it shall be appreciated that the recruitment of endogenous cells, in several embodiments as described above, yield positive effects in the target tissue through either a direct (e.g., tissue regeneration of increased function traceable to the endogenous cells), indirect effect (e.g., paracrine signals induce increased blood supply to new and endogenous tissue), or a combination thereof.

In several embodiments, the regenerative cells are used in the preparation of a medicament. In some embodiments, the medicament is suitable for administration to an individual having damaged or diseased tissue, in particular damaged or diseased cardiac tissue. In some embodiments, administration of the medicament results in one or more of alleviation of symptoms of a cardiac disease, improvement in cardiac function, and/or regeneration of cardiac tissue in the recipient individual.

Methods of Harvesting Cardiac Tissue and Producing Regenerative Cells

It shall be appreciated that the term "regenerative cells" as used herein refers to each of the mixed cell populations described herein (cardiospheres) and derivatives thereof (CDCs and IICSps). In describing the isolation methods, and the methods to produce derivatives of certain regenerative cells, the individual type of regenerative cells is used for clarity.

Donor tissue may be obtained from embryonic or adult sources. Adult sources are preferred for several embodiments. In some embodiments, donor cardiac tissue is obtained during a surgical procedure, such as bypass surgery. In other embodiments, donor tissue is obtained during a percutaneous endomyocardial biopsy procedure. In still other embodiments, large quantities of tissue are obtained from recently deceased organ donors, processed, and stored for use in allogeneic transplants. While a typical human adult heart weighs about 200 to 300 g, sufficient amounts of regenerative cells can be obtained from cardiac tissue samples of about 1 mg to about 50 mg. In some embodiments, the mass of the cardiac tissue sample is about 25 mg or less. The tissue sample may be obtained from a variety of locations in the heart, including but not limited to, the crista terminalis, the right ventricular endocardium, the right ventricular septum, the septal or ventricle wall, the atrioventricular groove and the right and left atrial appendages.

In one embodiment, the tissue sample is obtained from donor hearts that are transplant quality, but are unable to be transplanted into a human patient (e.g., because of unavailability of a matched recipient, etc.). In one embodiment, the tissue sample is obtained from hearts that are not transplant quality because (e.g., of tissue damage in the donor heart, the age of the heart, suspected cardiovascular disease in the donor, etc.). In several embodiments, the entire heart is processed to obtain a tissue sample for culture. In other embodiments, tissue is extracted from one or more of the following: atria, atrial appendages and apex.

According to several embodiments, percutaneous endomyocardial biopsy specimens are harvested using the following procedure. Under local anesthesia, a guide catheter is introduced into a vein, such as the jugular vein, in the patient's neck if tissue samples are to be taken from the right ventricle. Alternatively, the guide catheter can be introduced into an artery if tissue samples are to be taken from the left ventricle. The guide catheter is guided to the heart with the aid of visualization provided by a standard imaging technique, such as fluoroscopy. Once the guide catheter is in place, a bioptome can be introduced into the guide catheter and threaded to the heart. Once the bioptome is within the heart, the flexible distal end of the bioptome can be manipulated by the surgeon to extract a tissue sample from the desired location. The bioptome can be removed from the patient so that the tissue sample can be retrieved and then the bioptome can be reintroduced so that another sample can be taken from the same or different location. In another embodiment, the bioptome can extract multiple samples before being withdrawn, thereby reducing the time needed to collect the tissue samples.

In one embodiment, the invention comprises harvesting a piece of myocardial tissue about 0.25-about 1 cm in length and width through a catheter placed in the jugular vein of a subject under local anesthesia. In one embodiment, the weight of the sample is about 0.25-about 1 gram. The heart biopsy sample is then cultured over a period of about 3 to about 6 weeks (e.g., about 4 weeks) until approximately 10 to 25 million cells are available for implantation into the coronary arteries. As disclosed herein, the biopsy sample may be obtained from a first subject and then implanted into the same subject. Alternatively, the biopsy sample may be obtained from a first subject and then implanted into a different subject.

In several embodiments, the processing of a biopsy sample yields regenerative cells that comprise a mixed population of cells that comprises, for example, stem cells, cardiac cells, and/or vascular cells, among other cell types. In some embodiments, the mixed population of cells expresses various stem cell markers. In some embodiments, stem cells of the mixed population may be identified by expression of stem cell-related markers including one or more of CD-105, CD90, CD34, Sca-1, and c-kit, among others. In certain embodiments, the stem cells do not express one or more of the stem cell markers identified above. In certain embodiments, the stem cells are CD45 negative. In some embodiments, the vascular cells of the mixed cell population express at least one of KDR, flk-1, CD31, von Willebrand factor, Ve-cadherin, and smooth muscle alpha actin, among others.

In vitro, the mixed cell populations are clonogenic and can give rise to immature cardiomyocytes (heart muscle cells) and endothelial and smooth muscle cells (blood vessel components). In addition, in some embodiments, CDCs may be grown on a solid surface to produce a second (or greater) generation of cardiospheres (IICSps).

In one embodiment of the invention, regenerative cells are isolated and cultured as according to the schematic in FIG. 1. Briefly, cardiac tissue samples are weighed, cut into small fragments and cleaned of gross connective tissue, and washed in a sterile solution, such as phosphate-buffered saline. In some embodiments, the tissue fragments are at least partially digested with protease enzymes such as collagenase, trypsin, and the like. In certain embodiments, the digested pieces are placed in primary culture as explants on sterile tissue culture dishes with a suitable culture media. The digested pieces of tissue range in size from about 0.1 mm to about 2.5 mm. In several embodiments, the digested pieces of tissue range 0.25 mm to about 1.5 mm. Smaller or larger pieces of tissue can be used in other embodiments. The tissue culture dish and culture media are selected so that the tissue fragments adhere to the tissue culture plates. In some embodiments, the tissue culture plates are coated with fibronectin or other extracellular matrix (ECM) proteins, such as collagen, elastin, gelatin and laminin, for example. In other embodiments, the tissue culture plates are treated with plasma. In certain embodiments, the dishes are coated with fibronectin at a final concentration of from about 10 to about 50 µg/mL. In still other embodiments, the fibronectin dishes are coated with fibronectin at a final concentration of from about 20 to 40 µg/mL, with still other embodiments employing a final fibronectin concentration of about 25 µg/mL.

In certain embodiments, the base component of the complete explant medium comprises Iscove's Modified Dulbecco's Medium (IMDM). In some embodiments, the culture media is supplemented with fetal calf serum (FCS) or fetal bovine serum (FBS). In certain embodiments, the media is supplemented with serum ranging from 5 to 30% v/v. In other embodiments, the culture media is serum-free and is instead supplemented with specific growth factors or hydrolyzed plant extracts. In other embodiments, the media us supplemented with serum, but no additional exogenous growth factors. In yet other embodiments, the media is further supplemented with antibiotics, essential amino acids, reducing agents, or combinations thereof. In one embodiment, the complete explant medium comprises IMDM supplemented with about 20% fetal bovine serum, about 50 µg/mL gentamicin, about 2 mM L-glutamine, and about 0.1 mM 2-mercaptoethanol. In some embodiments, the explant media is changed every 2-4 days while the explants culture.

The tissue explants are cultured until a layer of stromal-like cells arise from adherent explants. This phase of culturing is further identifiable by small, round, phase-bright cells that migrate over the stromal-cells. In certain embodiments, the explants are cultured until the stromal-like cells grow to confluence. At or before that stage, the phase-bright cells are harvested. In certain embodiments, phase-bright cells are harvested by manual methods, while in others, enzymatic digestion, for example trypsin, is used. The phase-bright cells may be termed cardiosphere-forming cells, and the two phrases are used interchangeably herein.

Cardiosphere-forming cells may then be seeded on sterile dishes and cultured in cardiosphere media. In certain embodiments, the dishes are coated with poly-D-lysine, or another suitable natural or synthetic molecule to deter cell attachment to the dish surface. In other embodiments, for example, laminin, fibronectin, poly-L-orinthine, or combinations thereof may be used.

In certain embodiments, the base component of the cardiosphere medium comprises Iscove's Modified Dulbecco's Medium (IMDM). In some embodiments, the culture media is supplemented with fetal calf serum (FCS) or fetal bovine serum (FBS). In certain embodiments, the media is supplemented with serum ranging from 5 to 30% v/v. In other embodiments, the culture media is serum-free and is instead supplemented with specific growth factors or hydrolyzed plant extracts. In certain other embodiments, the media is further supplemented with antibiotics, essential amino acids, reducing agents, or combinations thereof. In one embodiment the cardiosphere medium comprises IMDM supplemented with about 10% fetal bovine serum, about 50 µg/mL gentamicin, about 2 mM L-glutamine, and about 0.1 mM 2-mercaptoethanol.

According to one embodiment, cardiospheres will form spontaneously during the culturing of the cardiosphere forming cells. Cardiospheres are recognizable as spherical multicellular clusters in the culture medium. Cells that remain adherent to the poly-D-lysine-coated dishes are discarded. In certain embodiments, the cardiospheres are collected and used to seed a biomaterial or synthetic graft. In other embodiments, the cardiospheres are further cultured on coated cell culture flasks in cardiosphere-derived stem cell (CDC) medium.

In some embodiments used to culture cardiospheres into CDCs, the culturing flasks are fibronectin coated, though in other embodiments other cellular attachment promoting coatings are employed. The cultured cardiospheres attach to the surface of the flask and are expanded as a monolayer of CDCs. CDC medium comprises IMDM, and in certain embodiments is supplemented with fetal calf serum (FCS) or fetal bovine serum (FBS). In some embodiments, the media is supplemented with serum ranging from 5 to 30% v/v. In other embodiments, the culture media is serum-free and is optionally supplemented with specific growth factors or hydrolyzed plant extracts. In certain other embodiments, the media is further supplemented with antibiotics, essential amino acids, reducing agents, or combinations thereof. In one embodiment, the CDC medium comprises IMDM supplemented with about 10% fetal bovine serum, about 2 mM L-glutamine, and about 0.1 mM 2-mercaptoethanol. CDCs may be repeatedly passaged by standard cell culture techniques. In some embodiments, CDCs are detached from the culturing surface and plated on poly-D-lysine-coated dishes to form a second generation of cardiospheres (IICSps). This process of generating cardiospheres followed by CDCs followed by a subsequent generation of cardiospheres may be repeated as needed to expand the population of any of the regenerative cell types.

Administration of Regenerative Cells

In several embodiments, regenerative cells are administered to recipients systemically. In some such embodiments, the systemically administered cells migrate to the recipient's heart, particularly to the area of damaged tissue. In several embodiments, regenerative cells are delivered systemically via an intravenous route. In several embodiments, the regenerative cells are delivered locally. In certain embodiments, local delivery is achieved by direct myocardial injection. In certain embodiments, local delivery is achieved via a biopsy procedure. In some embodiment, delivery is accomplished during a surgical procedure. Delivery may be accomplished with specific injection site guidance in certain embodiments. In one embodiment, NOGA is employed. In certain embodiments, regenerative cells are delivered alone, while in other embodiments regenerative cells are delivered in associated with an additional therapeutic agent. In still other embodiments, the paracrine agents produced by regenerative cells are administered, either alone or in conjunction with the regenerative cells.

In certain embodiments, the regenerative cells are used to seed a biomaterial or synthetic graft. In certain embodiments, the graft comprises a biocompatible biomaterial such as hyaluronan, alginate, or fibrin. In some embodiments, the biomaterial or synthetic graft is injectable. In other embodiments, the biomaterial or synthetic graft is painted or directly placed onto the target tissue.

In several embodiments, the regenerative cells are delivered at a dose of about $1 \times 10^5$ to about $1 \times 10^7$ regenerative cells per kilogram of body weight of the recipient. However, in some embodiments, lower numbers of cells may be used, due to the butterfly effect described herein (e.g., the persistence of positive effects on the target tissue even after some or all of the delivered cells are removed by host mechanisms).

Immune Responses and Functional Effects of Regenerative Cells

As discussed above, the various transplant types, and cells used in each have advantages and disadvantages. Autologous transplants are advantageous due to limited risk for immune rejection of transplanted cells. Thus in some embodiments, autologous regenerative cells are used. However, in certain instances, autologous transplants are expensive, and somewhat time consuming (since tissue must be harvested, processed into regenerative cells, and re-administered), especially in circumstances where the donor/recipient requires immediate administration of therapy (e.g., they are within a critical post-injury period, typically within a few hours of an adverse event). Therefore, an ideal cellular therapy would be available "off the shelf", and preferably would not induce severe immune responses in the recipient, or at least be able to initiate or yield a therapeutic response despite an immune response. Thus, in some embodiments, allogeneic regenerative cells are used.

Immune responses mounted by a recipient may lead to rejection of transplanted cells that are immunologically distinct. Such cells, for example, allogeneic regenerative cells, may be rejected through a direct or indirect pathway. Direct rejection by the recipient involves either antigen presenting cells (APCs) that were transplanted from the donor or their donor APC precursor cells that have differentiated into APCs after transplantation. When a recipient T-cell (also known as T-lymphocytes, immune cells that play a central role in cell-mediated immunity) recognizes a donor APC as "non-self" (via expression of donor HLA molecules or other donor-derived antigens), the recipient T-cell becomes activated, recruits other recipient immune co-stimulatory molecules become involved (such as CD80 or CD86 with CD28, and CD40 with CD40 ligand), and an immune response is initiated.

Indirect rejection may occur due to the "shedding" various antigens from transplanted donor cells or tissues. These donor antigens are taken up by recipient APCs, and subsequently presented to recipient T cells. This can result in the activation of donor-reactive recipient T cells, which then initiate an immune response.

In several embodiments, an immune response is initiated against transplanted allogeneic regenerative cells. In several embodiments, the grade of any immune response is higher than the grade of a corresponding autologous or syngeneic transplant, however, in such embodiments, the severity of the immune response does not eliminate all of the transplanted regenerative cells, or their effect on the target tissue. In some embodiments, the grade of immune response in an allogeneic transplant scenario is equivalent to or less than that of an autologous or syngeneic transplant. In certain embodiments, as discussed herein, some of the administered regenerative cells survive for several days post-administration. In some embodiments, some of the administered regenerative cells survive for about a week to about three weeks. In some embodiments, a local immune effect is initiated against transplanted regenerative cells. In certain such embodiments, the local immune response does not destroy or render non-functional the transplanted regenerative cells until after a series of signal or events have been initiated that lead to a beneficial therapeutic effect. In some embodiments, a systemic immune response is initiated against transplanted regenerative cells. In certain such embodiments, the systemic immune response does not destroy or render non-functional the transplanted regenerative cells until after a series of signal or events have been initiated that lead to a beneficial therapeutic effect. In still other embodiments, there is little or no systemic immune response. Thus, in certain embodiments, the effects initiated by the administration of the regenerative cells persist after some, or all, of the administered regenerative cells are no longer viable.

In several embodiments, the transplant of regenerative cells (regardless of transplant type) results in a beneficial therapeutic effect in the recipient. As discussed above, the beneficial therapeutic effect may comprise one or more of treatment of symptoms of a cardiac disease, improvement in cardiac function, and/or regeneration of cardiac tissue in the recipient.

In several embodiments, transplanted regenerative cells result in significantly increased fractional area. In some embodiments, fractional area is increased by about 5%. In some embodiments, fractional area is increased by about 10%. In some embodiments, fractional area is increased by about 15%. In some embodiments, fractional area is increased by about 20%. In some embodiments, fractional area is increased by about 5-10%, including 6, 7, 8, and 9%. In some embodiments, fractional area is increased by about 10-20%, including 11, 12, 13, 14, 15, 16, 17, 18, and 19%. In still additional embodiments, greater increases are realized.

In several embodiments, transplanted regenerative cells result in significantly increased ejection fraction. In some embodiments, ejection fraction is increased by about 5%. In some embodiments, ejection fraction is increased by about 10%. In some embodiments, ejection fraction is increased by about 15%. In some embodiments, ejection fraction is increased by about 20%. In some embodiments, ejection fraction is increased by up to about 25%. In some embodiments, ejection fraction is increased by about 6-12, 12-18, or 19-25% In some embodiments, ejection fraction is increased by about 5-20%, including 6, 7, 8, 9, 10, 11, 12, 13, 14, 15, 16, 17, 18, and 19%.

In several embodiments, transplanted regenerative cells result in a decrease in infarct size (i.e. an increase in viable tissue in and around the infarct). In some embodiments, infarct size is reduced by about 5%. In some embodiments, infarct size is reduced by about 10%. In some embodiments, infarct size is reduced by about 15%. In some embodiments, infarct size is reduced by about 1-3, 4-7, or 7-11%. In some embodiments, infarct size is reduced by 5-15%, including 6, 7, 8, 9, 10, 11, 12, 13, and 14%.

In several embodiments, the beneficial therapeutic effect of transplanting regenerative cells (regardless of the transplant type) lasts for several weeks. In some embodiments, the beneficial therapeutic effect last for up to three weeks. In some embodiments, the beneficial therapeutic effect lasts for a period of time from about 3 weeks to about 12 weeks. In some embodiments, the beneficial therapeutic effect lasts for about 3 months to about 1 year. In still other embodiments, the beneficial therapeutic effect lasts for several years.

In several embodiments of the invention, a method of treating an adverse cardiac event is provided, wherein the method comprises implanting regenerative cells into a recipient patient. The regenerative cells are obtained from one or more different donor subjects, and have been obtained by obtaining a cardiac biopsy sample from said donor(s), and culturing the sample(s) to obtain the regenerative cells. Such allogeneic transplant methodology, according to several embodiments, is particularly beneficial because the regenerative cells do not evoke a significant chronic immune response that is adverse to the patient. Instead, the regenerative cells trigger a cascade of therapeutic signaling effects (e.g., a paracrine effect) prior to destruction via an acute immune response that destroys the regenerative cells. Thus, "off-the-shelf" regenerative cells can be produced to treat patients suffering from cardiac diseases. Further, the patient need not have healthy tissue from which to harvest his or her own cells (for an autologous transplant). Moreover, even when a patient has viable heart tissue for biopsy, the patient need not have to wait for the culturing process when his or her own tissue is not used. Instead, the "off-the-shelf" allogeneic cells may be available with little or no time delay. In one embodiment, the donor cells are obtained from the recipient patient plus at least one different donor. In one embodiment, the donor cells are obtained from a single donor (different than the recipient patient). In one embodiment, the donor cells are obtained from a two or more different donor (different than the recipient patient and each other). The recipient patient and donor(s) may be race, age, sex, blood-type, and/or HLA-matched in some embodiments. In other embodiments, the recipient patient and donor(s) need not be matched in any of the categories identified above. In several embodiments, the allogeneic cells and/or the patient need not be treated with immune suppressants prior to (or during or after) implantation of the regenerative cells. In some embodiments, the allogeneic cells and/or the patient need not be treated with radiation prior to (or during or after) implantation of the regenerative cells.

EXAMPLES

Examples provided below are intended to be non-limiting embodiments of the invention.

Example 1—Specimen Processing and Cardiosphere Growth

Following institutional guidelines, and with patient consent, human biopsy specimens were obtained from patients undergoing clinically-indicated percutaneous endomyocardial biopsy and processed as described above, with certain modifications. Specimens consisted of whole or partial bioptome "bites", stored on ice in high-potassium cardioplegic solution and processed within two hours (FIG. 1A, step 1). As discussed, herein, samples, in some embodiments, are taken from whole donor hearts (e.g., not collected via biopsy). Samples were cut into fragments from which gross connective tissue was removed. The fragments were then washed, partially-digested enzymatically, and the single cells discarded. In several embodiments, partial digestion is accomplished using trypsin. In some embodiments, collagenase is used. In some embodiments, other proteases may be used. The remaining tissue fragments were cultured as "explants" on dishes coated with fibronectin (FIG. 1A, step 2). In some embodiments, other surface coatings may be used (e.g., collagen or other extracellular matrix proteins. After several days, a layer of stromal-like cells arose from adherent explants over which small, round, phase-bright cells migrated. Once confluent, the loosely-adherent cells surrounding the explants were harvested by gentle enzymatic digestion (FIG. 1A, step 3). These cells were seeded at $2-3 \times 10^4$ cells/mL on poly-D-lysine-coated dishes in media designed for optimal growth of cardiospheres (FIG. 1A, step 4). Detached cardiospheres were then plated on fibronectin-coated flasks and expanded as adherent monolayers (FIG. 1A, step 5), which could be subsequently passaged by trypsinization. Single cells were counted under phase microscopy using a hemocytometer as cardiosphere-forming cells and during CDC passaging to track cell growth for each specimen. Isolation of the cardiosphere-forming cells was repeated up to 3 more times from the same specimen.

Sub-Population Selection and Flow Cytometric Analysis

To characterize the antigenic features of cells that form cardiospheres, cells obtained during the first harvesting (FIG. 1A, step 3) were sub-selected by magnetic-activated cell separation with an APC-conjugated monoclonal antibody against c-kit, followed by labeling with a microbead-conjugated anti-APC, followed by separation using Octo-MACS. $CD105^+$ populations were then sub-selected with a second antibody directly conjugated to a microbead. As discussed herein, in several embodiments, selection is used for analysis of the cell population only, and the cells that are administered have not been selected for expression of a particular marker, including, but not limited to c-kit.

CDCs were passaged two times as adherent monolayers and then used for flow cytometry experiments. c-kit-APC, CD105-PE, and similarly conjugated isotype-matched control monoclonal antibodies were utilized. Gates were established by 7-AAD fluorescence and forward scatter. Data were collected using a FACScalibur cytofluorometer with CellQuest software.

Adenovirus Creation and Cell Transduction

The *E. coli* beta-galactosidase (lacZ) gene was cloned into an adenoviral shuttle vector pAd-Lox to generate pAd-Lox-LacZ by Cre-Lox recombination in Cre-4 293HEK cells as described. CDCs were passaged two times and transduced with virus as adherent monolayers. Transduction efficiencies of 90% were achieved with an MOI of 20 for 12 hours.

Myocardial Infarction and Cell Injection

Adenovirally-transduced CDCs were injected into adult male SCID-beige mice 10-16 weeks of age. Myocardial infarction (MI) was created by ligation of the mid-left anterior descending coronary artery and cells or vehicle injected under direct visualization at two peri-infarct sites. As disclosed herein, other delivery routes (e.g., intracoronary, IV, etc.) are used in some embodiments. CDCs ($10^5$) were injected in a volume of 10 µL of PBS (5 µL at each site), with $10^5$ primary human skin fibroblasts or 10 µL of PBS as controls. All mice underwent echocardiography prior to surgery (baseline) and again 20 days post-surgery. Ejection fractions (EFs) were calculated using V1.3.8 software from 2D long-axis views taken through the infarcted area. Mice were then euthanized at 0, 8, or 20 days, and the excised hearts prepared for histology.

Immunostaining, Immunohistochemistry, and Microscopy

Cardiospheres were collected for immunostaining when they had reached 100-1000 cells in size. Primary antibodies against c-kit, CD105, cardiac myosin heavy chain (cMHC), and cardiac troponin I (cTnI) were used for immunostaining Secondary antibodies conjugated with Alexa fluorochromes were utilized. Immunostaining was performed as previously described. Confocal fluorescence imaging was performed on an Eclipse TE2000-U equipped with a krypton/argon laser using UltraVIEW software.

Mouse hearts were excised, embedded in OCT compound, frozen, and sectioned in 5 µm slices. Tissue sections were stained with hematoxylin-eosin and b-galactosidase reagent or Masson's trichrome. Tissue viability within the infarct zone was calculated from Masson's trichrome stained sections by tracing the infarct borders manually and then using ImageJ software to calculate the percent of viable myocardium within the overall infarcted area.

Statistics

All results are presented as means±SEM. The significance of differences between any two groups was determined by the Student's t-test. Multiple groups were compared using GB-Stat software using one-way ANOVA and group pairs compared by the Bonferroni-Dunn method if a significant F value was obtained. A value of $p<0.05$ was considered significant.

The generalized estimation equation (GEE) approach was employed to identify parameters that were independently associated with high cell yield. Data from patients who donated multiple specimens were treated as repeated measures. Those parameters that were significant ($p<0.1$) in the univariate models were included in the final, multivariate models. The analysis was performed with the use of SAS software. A final value of $p<0.05$ was considered significant. All p-values reported are 2-sided.

Statistics

Product manufacturers, recipes, and reagents used in several embodiments are shown in Table 1.

TABLE 1

Products and Manufacturers and Media Recipes

Explant and CDC media

IMDM
20% FBS
1% penicillin-streptomycin
1% L-glutamine
0.1 mM 2-mercaptoethanol

Cardiosphere media

35% IMDM and 65% DMEM/F-12 Mix
3.5% FBS
1% penicillin-streptomycin
1% L-glutamine
0.1 mM 2-mercaptoethanol
Thrombin, B-27, bFGF, EGF and Cardiotrophin-1
at final working concentrations

| Product: | Working concentration: | Manufacturer: |
| --- | --- | --- |
| IMFM | | Invitrogen |
| DMEM/F-12 Mix | | Invitrogen |
| Thrombin | 1 unit/mL | Sigma |
| B-27 | 1:50 | Invitrogen |
| bFGF | 80 ng/mL | PeproTech |
| EGF | 25 ng/mL | PeproTech |
| Cardiotrophin-1 | 4 ng/mL | PeproTech |
| Fibronectin | 25 µg/mL | BD Biosciences |
| Poly-D-lysine | 20 µg/mL | BD Biosciences |
| c-kit-APC | 1:10 | BD Pharmingen |
| CD105 MicroBeads | 1:5 | Miltenyi Biotec |
| Anti-APC MultiSort | 1:4 | Miltenyi Biotec |
| CD105-PE | 1:10 | R&D Systems |
| 7-AAD | 20 µg/mL | Calbiochem |

TABLE 1-continued

Products and Manufacturers and Media Recipes

| | | |
|---|---|---|
| SCID-beige mice | | Harlan |
| Dermal fibroblasts | | ATCC |
| c-kit pAb | 1:100 | Abcam |
| CD105 mAb | 1:50 | R&D Systems |
| cMHCpAb | 1:100 | (6) Rome, Italy |
| cTaImAb | 1:200 | Chemicon |
| Alexa 488, 568 | 1:400 | Invitrogen |
| OCT | | VWR Scientific |

| Equipment and Software: | Manufacturer: |
|---|---|
| OctoMACS | Miltenyi Biotec |
| FACScalibur | BD Biosciences |
| Vevo 660 Echo | VisualSonics |
| Eclipse TE2000-U | Nikon |
| CellQuest | BD Biosciences |
| V.1.3.8 software | VisualSonics |
| UltraVIEW software | Perkin Elmer |
| ImageJ software | NIH |
| GB-Stat V10 | Dynamic Microsystems Inc. |
| SAS software v9.1 | SAS Institute Inc. |

Example 2—Specimen Processing and Cardiosphere-Forming Sub-Populations

FIG. 1B shows a typical explant, after mincing and partial enzymatic digestion, on the day it was obtained and also on days 3 (FIG. 1C) and 13 (FIG. 1D), immediately prior to first harvest. Harvesting of cardiosphere-forming cells (FIG. 1A, step 3) was initially performed 8 or more days after obtaining a specimen and at 4-12 day intervals thereafter. Panel E summarizes the results of sub-population selection experiments performed using cells harvested from 3 different patient specimens. The large majority of the cells that generate cardiospheres are CD105$^+$, those that are c-kit$^+$ and those that are c-kit$^-$. Typical cardiospheres are shown in FIG. 1F, 12 days after harvest. Floating cardiospheres were plated for expansion (FIG. 1A, step 5) 4-28 days after step 3 and passaged at 2-7 day intervals thereafter. FIG. 1G shows CDCs plated on fibronectin during expansion at passage 2, when those cells were harvested for injection.

Example 3—Patient Specimens and Cardiosphere Growth 83 patient specimens (21.0±1.9 mg) were obtained for analysis. 72 of the specimens were obtained from patients who had received a heart transplant and 11 were from patients awaiting transplant. Nine transplanted patients donated multiple specimens. 78 of 83 specimens were processed, and 4 of those specimens never harvested were from repeat patients, yielding growth data from 69 of 70 patients. Cumulative growth curves for each specimen are depicted in FIG. 1, Panels H and I. The growth curves from patients awaiting transplant (FIG. 1H) are similar to those from transplanted patients (FIG. 1I), showing a wide range of growth potential among specimens. Patient parameters are summarized in Table 2 for the non-transplanted and transplanted groups. A GEE analysis involving all patient parameters listed in the table revealed no independent predictors for high cell yield within the non-transplanted group. Within the transplanted group, specimens from patients with a higher EF tended to yield more cells, but the effect was weak (final $R^2$ estimate=0.04, $p<0.05$).

TABLE 2

Patient Population Summary

| | Non-transplanted Patients: | Transplanted Patients: |
|---|---|---|
| Patient age | 47.2 ± 3.7 years | 53.6 ± 1.7 years |
| Patient sex | 63% male, 37% female | 73% male, 27% female |
| Patient ejection fraction | 36.9 ± 4.7% | 61.9 = 0.8% |
| Donor age | | 31.4 ± 1.6 years |
| Donor sex | | 69% male, 31% female |
| Time out from transplant | | 4.5 ± 0.6 years |
| Donor ischemic time | | 173.9 ± 7.8 minutes |
| Pathological rejection level* | | 0.5 ± 0.1 |
| Immunosupportive level** | | 31% normal, 43% low, 26% high |

*grade 0 = 0, grade 1A = 0.5, grade 1B = 1, grade 2 = 2, grade 3A = 3
**considered for Cyclosporine and FK506 (±Rapamycin) relative to time out from transplant.

Example 4—Cardiosphere and Cardiosphere-Derived Cell Phenotypes

Part of the rationale for using CDCs lies in the unique biology of cardiospheres and their cell progeny. The self-organizing cardiospheres create a niche environment favoring the expression of stem cell antigens (e.g., c-kit and CD105, FIG. 2A) and frequently manifest a surface phenotype marked by mature cardiac-specific antigens (cMHC and cTnI, FIG. 2B) with retention of internal "stemness". In fact, c-kit and CD105 were present in all cardiospheres examined (10 or more from each of 10 patients), with c-kit either localized to the core or expressed throughout the sphere, and CD105 typically localized to the periphery or expressed throughout. CDCs after two passages retain high levels of c-kit and CD105 antigen expression (FIG. 2C, representative of expression profiles of CDCs from 3 and 2 different patients respectively).

Example 5—Cardiosphere-Derived Cell Engraftment, Regeneration, and Functional Improvement CDCs from 4 different patients were utilized for in vivo experiments. To assess engraftment and cell migration, mice were injected with lac-Z-expressing CDCs and sacrificed at each of 3 time points (0, 8, and 20 days following injection). At day 0, CDCs were located at injection sites in the border zone, but at day 8 and day 20 injected cells were distributed mainly within the MI area, forming islands or continuous bands of β-galactosidase positive tissue (see e.g., FIG. 5).

Figure 3A:
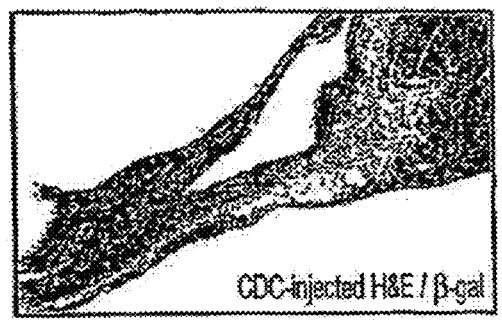
FIGS. 3A-3E depict engraftment and regeneration. Engraftment of CDCs (FIG. 3A) or fibroblasts (FIG. 3B) is depicted 20 days after injection in heart sections double stained for H&E and beta-galactosidase. Infiltration of CDCs is seen as a distinct band, while a rare group of a few fibroblasts can be detected in some sections. Masson's trichrome staining was used to calculate myocardial regeneration is shown for a representative CDC-injected mouse (FIG. 3C) and fibroblast-injected mouse (FIG. 3D).
Figure 3B:
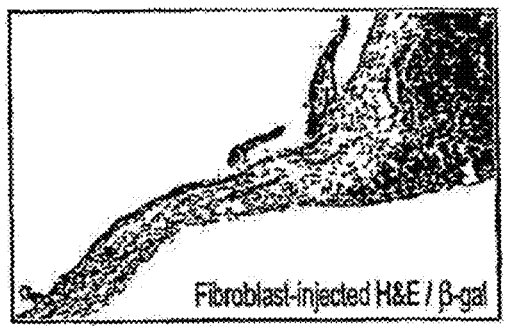
Figure 3C:
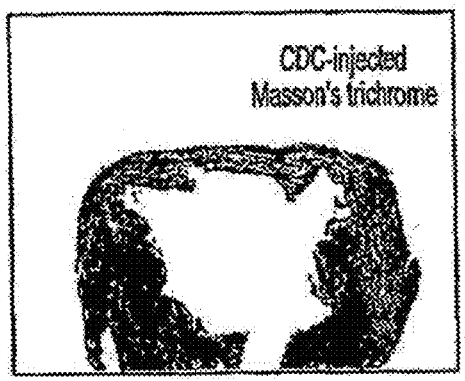
Figure 3D:
Figure 3E:
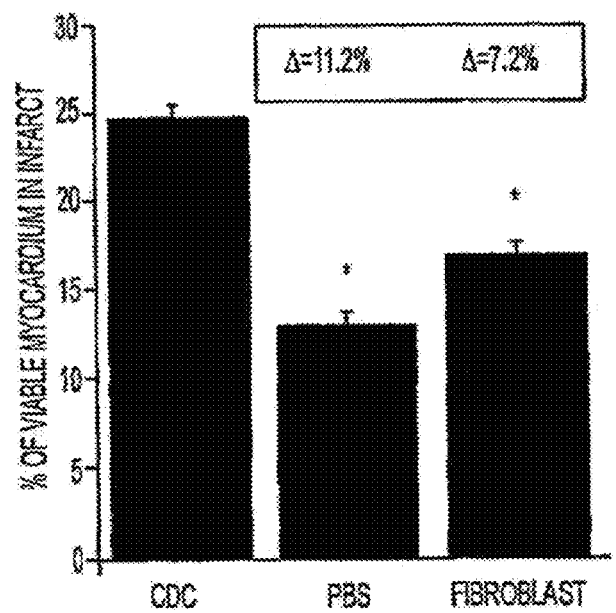
Figure 4A:
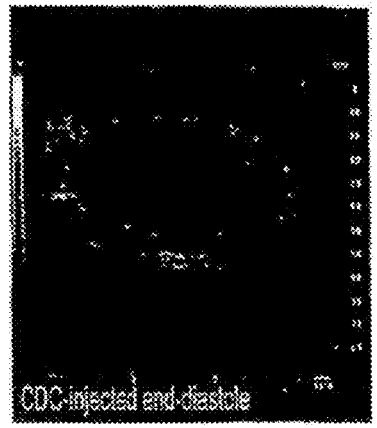
FIGS. 4A-4F depicts functional cardiac improvement. Long-axis views from an echocardiogram performed after 20 days in a CDC-injected mouse are shown.
Figure 4B:
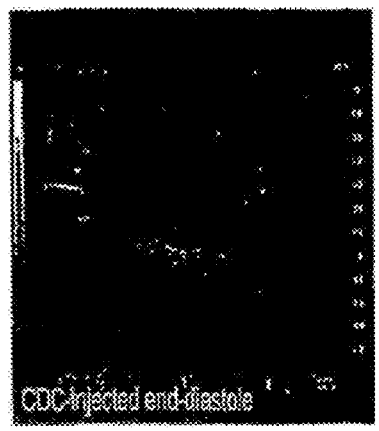
Figure 4C:
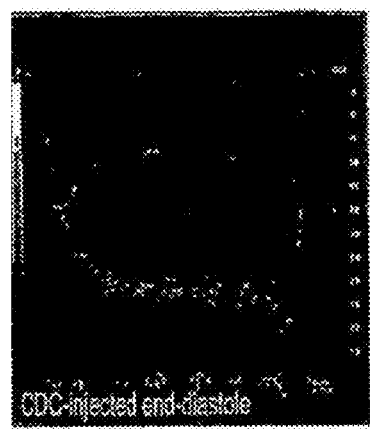
Figure 4D:
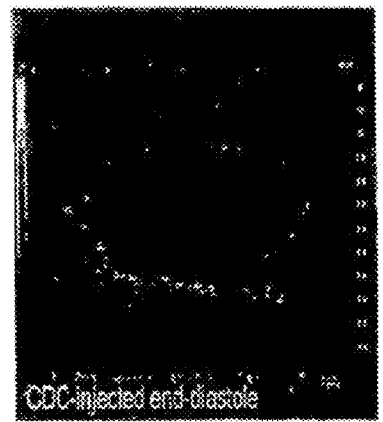
Figure 4E:
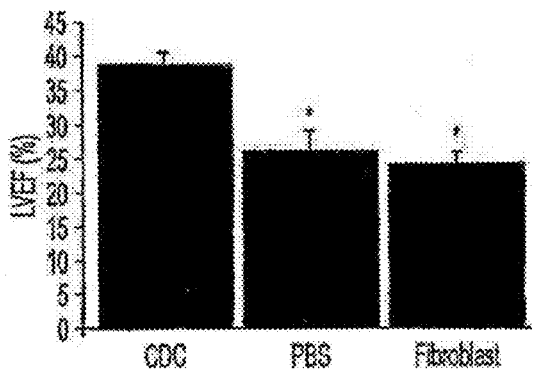
Figure 4F:
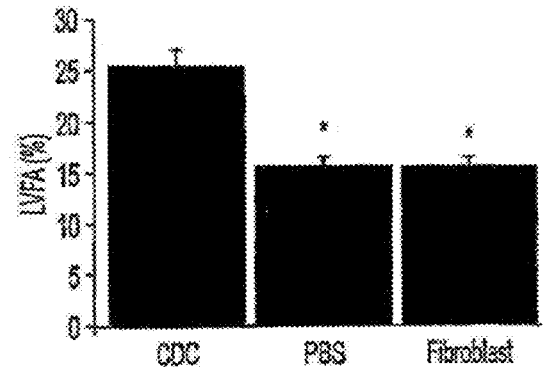

Eight mice were injected with CDCs and followed for 20 days; 11 mice served as controls (4 with fibroblasts, and 7 with PBS). FIG. 3A shows a typical beta-galactosidase staining pattern indicating the distribution of injected human cells after 20 days in vivo. Note the band of blue cells infiltrating the infarct zone, which was not apparent in the fibroblast-injected mice (FIG. 3B) or the PBS-injected mice. Masson's trichrome-stained sections were used to quantify regeneration (FIG. 3, C and D). Panel C, from a CDC-injected heart, shows a number of obvious red regions within the blue infarct zone; fewer such regions are evident in the fibroblast-injected heart (FIG. 3D). CDC-injected mice had a higher fraction of viable fuchsin-positive tissue within the MI zone (24.9±1.1%) compared to fibroblast-injected mice (17.7±1.8%, p<0.01) or PBS-injected mice (13.7±0.7%, p<0.01), but the overall total infarct area was similar to that in the two control groups (60.6±6.4 CDC, 76.9±7.0 fibroblast, 75.7±2.7 PBS, units in $10^4$ pixels; p=NS). The differences between the CDC group and each of the control groups in percent viable myocardium within the MI zone, 7.2% and 11.2%, represent the extents of myocardial regeneration attributable to the CDCs.

Echocardiograms were performed for all groups at 20 days; FIG. 4 shows examples from the CDC and fibroblast-treated groups at end-diastole and end-systole. Pooled data for left ventricular EF (LVEF, FIG. 4E) and left ventricular fractional area (LVFA, FIG. 4F) reveal a higher LVEF in the CDC-treated group (38.8±1.7%) as compared to either the fibroblast-treated (24.5±1.8%, p<0.01) or the PBS-treated group (26.4±3.0%, p<0.01), but the two control groups were indistinguishable. There was no difference among the LVEFs at baseline.

Example 6—Process for the Isolation of Cardiac Stem Cells from Cardiac Biopsy Specimens Pluripotent stem cells may be isolated from cardiac biopsy specimens or other cardiac tissue using a multi-step process (see FIG. 1A for schematic). First, cardiac tissue is obtained via percutaneous endomyocardial biopsy or via sterile dissection of the heart. Once obtained, tissue specimens are stored on ice in a high-potassium cardioplegic solution (containing 5% dextrose, 68.6 mmol/L mannitol, 12.5 meq potassium chloride, and 12.5 meq sodium bicarbonate, with the addition of 10 units/mL of heparin) until they are processed (up to 12 hours later). For processing, specimens are cut into 1-2 mm.sup.3 pieces using sterile forceps and scissors; any gross connective tissue is removed. The fragments are then washed with $Ca^{++}Mg^{++}$ free phosphate buffered saline (PBS) and typically digested for 5 min at room temperature with 0.05% trypsin-EDTA. Alternatively the tissue fragments may be digested in type IV collagenase (1 mg/mL) for 30 minutes at 37 degrees C. Preliminary experiments have shown that cellular yield is greater per mg of explant tissue when collagenase is used.

Once digestion is complete, the remaining tissue fragments are washed with "Complete Explant Medium" (CEM) containing 20% heat-inactivated fetal calf serum, 100 Units/mL penicillin G, 100 μg/mL streptomycin, 2 mmol/L L-glutamine, and 0.1 mmol/L 2-mercaptoethanol in Iscove's modified Dulbecco medium to quench the digestion process. The tissue fragments are minced again with sterile forceps and scissors and then transferred to fibronectin-coated (25 μg/mL for at least 1 hour) tissue culture plates, where they are placed, evenly spaced, across the surface of the plate. A minimal amount of CEM is added to the plate, after which it is incubated at 37° C. and 5% $CO_2$ for 30 minutes to allow the tissue fragments, now referred to as "explants", to attach to the plate (FIG. 1B). Once the explants have attached, enough CEM is added to the plate to cover the explants, and the plates are returned to the incubator.

After a period of 8 or more days, a layer of stromal-like cells begins to arise from adherent explants, covering the surface of the plate surrounding the explant. Over this layer a population of small, round, phase-bright cells is seen (FIG. 1C, 1D). Once the stromal cell layer becomes confluent and there is a large population of bright phase cells, the loosely-adherent cells surrounding the explants are harvested. This is performed by first washing the plate with $Ca^{++}Mg^{++}$-free PBS, then with 0.48 mmol/L EDTA (for 1-2 min) and finally with 0.05% trypsin-EDTA (for 2-3 min). All washes are performed at room temperature under visual control to determine when the loosely adherent cells have become detached. After each step the wash fluid is collected and pooled with that from the other steps. After the final wash, the explants are covered again with CEM and returned to the incubator. Each plate of explants may be harvested in this manner for up to four times at 5-10 day intervals. The pooled wash fluid is then centrifuged at 1000 rpm for 6-8 minutes, forming a cellular pellet. When centrifugation is complete, the supernatant is removed, the pellet is resuspended, and the cells are counted using a hemacytometer. The cells are then plated in poly-d-lysine coated 24-well tissue culture plates at a density ranging from 3-5×$10^4$ cells/well (depending on the species) and returned to the incubator. The cells may be grown in either "Cardiosphere Growth Media" (CGM) consisting of 65% Dulbeco's Modified Eagle Media 1:1 with Ham's F-12 supplement and 35% CEM with 2% B27, 25 ng/mL epidermal growth factor, 80 ng/mL basic fibroblast growth factor, 4 ng/mL Cardiotrophin-1 and 1 Unit/mL thrombin, or in CEM alone.

In either media, after a period of 4-28 days, multicellular clusters ("cardiospheres") will form, detach from the tissue culture surface and begin to grow in suspension (FIG. 1E, 1F). When sufficient in size and number, these free-floating cardiospheres are then harvested by aspiration of their media, and the resulting suspension is transferred to fibronectin-coated tissue culture flasks in CEM (cells remaining adherent to the poly-D-lysine-coated dishes are not expanded further). In the presence of fibronectin, cardiospheres attach and form adherent monolayers of CDCs (FIG. 1G). These cells will grow to confluence and then may be repeatedly passaged and expanded as CDCs, or returned to poly-d-lysine coated plates, where they will again form cardiospheres. Grown as CDCs, millions of cells can be grown within 4-6 weeks of the time cardiac tissue is obtained, whether the origin of the tissue is human (FIG. 1I), porcine or from rodents (data not shown). When collagenase is used, the initial increase in cells harvested per mass of explant tissue results in faster production of large numbers of CDCs.

Example 7—Evaluation of Processing and Culture Conditions

Optionally, changes in processing or culture methods and or reagents disclosed herein may be made in order to promote generation of cardiospheres, CDCs, or IICSps in sufficient numbers and having sufficient viability for use in allogeneic (or autologous) therapies In several embodiments a commercially-available cardioplegic solution is used to store the biopsy or donor tissue until processing begins. In some embodiments, the initial biopsy digestion step is modified through the used of with collagenase rather than trypsin. In some embodiments, the number of mincing steps is minimized.

In several embodiments the presence of recombinant human proteins and/or cytokines in cardiosphere medium are eliminated, and fetal bovine serum used in their place. However, in some embodiments, recombinant human proteins and/or cytokines are used in combination with fetal bovine serum. In several embodiments, gentamicin is used as an antibiotic. In some embodiments, gentamicin is preferred as compared to penicillin and streptomycin, or combinations thereof. In several embodiments, antibiotics are removed from the culture media in the final phase of CDC culture. In several embodiments, trypsin is replaced with TrypLE Select during the harvesting of cardiosphere-forming cells and passaging of CDCs.

Tissue collected sites were also compared for CDC yield. The sites were the right ventricular septal wall (RVS), the atria, the apex, the right ventricular epicardium (RVE), and the left ventricular epicardium (LVE). As shown in FIG. 7A, yields from the atria and RVE are somewhat greater than yields from the other regions. Thus in some embodiments these sites are preferred (whether from biopsy or whole heart). However, these data also show that CDCs can reliably be produced using tissue from each of the collection regions tested. In some embodiments, other regions of the heart are used.

Because several embodiments involve the use of a heart that is in condition for transplant, there may be a delay from the collection of the heart itself and the initiation of processing the heart to generate CDCs. Therefore, the effect of tissue storage on CDC yield was examined. Specimens were taken from two transplant quality human hearts. Specimens processed immediately after collection were compared to those stored for 3 or 6 days in cold cardioplegia solution or to those cryopreserved and subsequently thawed. For each of the two hearts, 6-12 specimens were processed following each storage condition. Four out of 12 specimens taken from the first heart and stored for 6 days did not yield CDCs, and therefore, in some embodiments, tissue is preferably stored for less than 6 days (e.g., 1, 2, 3, 4, or 5 days). However, in several embodiments, storage for 6 days is acceptable, as the possibility of generating CDCs from such a sample exists.

Data demonstrate a slight effect of 3 days of cold storage in terms of the time required to achieve a similar CDC yield, and a larger effect seen after freezing and thawing the specimen (FIG. 7B). Freezing and thawing decreased the average yield and increased processing time required. However, following either 3 days of cold storage or cryopreservation CDCs were reliably generated. Thus in several embodiments, tissue is processed for CDCs immediately, while in some embodiments, a storage time of 1-2 or 2-3 days (or longer) is allowed. In some embodiments, cold storage is used, while in other embodiments, cryopreservation is used.

Tissue samples from the RVS and cultured in conditions such as those described above are used, in some embodiments, to generate a master cell bank (MCB). CDCs were passaged to P1 to create the MCB. A fraction of CDCs underwent further passaging to P6 in order to generate a working cell bank (WCB). The yields presented for the WCB (Table 3) represent the potential yield extrapolated from the growth seen with the fraction of cells expanded. In some embodiments, greater passage numbers are used for either the MCB or the WCB. For example, the MCB is optionally generated at P2, P3, P4, P5, or P6. Likewise, the WCB is optionally generated at P7, P8, P9, P10, P11, P12, or more. In some embodiments, CDCs are expanded just prior to the point of to the point of in vitro senescence). The WCB is then split into multiple doses, e.g., single cryopreserved doses.

These data taken as a whole, demonstrate the feasibility of generating CDCs and cell banks from the CDCs from transplant-quality hearts.

TABLE 3

Cell Banks Generated from Whole Hearts

| Source | MCB Yield | WCB Yield |
|---|---|---|
| Donor Heart 1 | 116 million | 8.72 billion |
| Donor Heart 2 | 185 million | 42.0 billion |

Example 8—Characterization of Human CDCs

The markers expressed on CDCs, in several embodiments, are related to the "sternness" of the cells. In some embodiments, markers are used to select, screen, isolate, or enrich a sample for cells bearing one or more markers. In some embodiments, however, cells are isolated without preference to a given marker or set of markers. The vast majority of CDCs (derived from 13-27 different preclinical patient endomyocardial biopsy specimens) were CD105$^+$, with significant pluralities that were CD90$^+$ and c-kit$^+$ (FIG. 8A). CDCs were largely negative for CD45 (0.1±0.1%). FIG. 8B demonstrates that CDCs contain distinct sub-populations of cells that are CD105$^+$CD90$^+$c-kit$^-$. These particular profiles, in some embodiments are suggestive of cardiac mesenchymal cells or fibroblasts. CDCs also, in some embodiments, contain distinct cardiac progenitor populations (c-kit$^+$CD90). In several embodiments, all populations express CD105, the regulatory component of the TGF-β receptor complex important in angiogenesis and hematopoiesis. In several embodiments all populations also lack CD45. In some embodiments, CD45 is used to screen for contaminating blood-derived cells to ensure purity of the CDCs to be administered.

Data presented in Example 10 illustrate the potency of the sub-populations in comparison to the total population in an animal model.

Example 9—In Vitro Differentiation of Human CDCs

Cardiomyocyte Differentiation

In order to examine the ability of human CDCs to differentiate fully into functional cardiomyocytes, an in vitro co-culture system was utilized. DiI-labeled or lentivirally-transduced GFP$^+$ CDCs were identified in co-cultures with neonatal rat ventricular myocytes (NRVMs) which spontaneously contract in culture. Cocultures were subjected to immunostaining or whole-cell patch clamp in order to record voltage-sensitive currents. Co-cultured CDCs demonstrated biophysical features characteristic of cardiomyocytes, including: contractions as early as 24 hours after the start of co-culture, sarcomeric organization (FIG. 9A), expression of the inwardly-rectifying potassium current $I_{K1}$ which is consistent with a cardiomyocyte ventricular phenotype (FIG. 9B), and when transduced with the β-subunit of the L-type calcium channel expression of the calcium current $I_{Ca,L}$ indicating the presence of the pore-forming α-subunit (FIG. 9C). Thus, in several embodiments, CDCs differentiate into cardiomyocytes having normal functional characteristics. Therefore, such CDCs, upon administration, are used in some embodiments to effectuate cardiac repair.

Endothelial Differentiation

Human CDCs were also challenged to an endothelial tube-forming assay by culturing them on MATRIGEL™ in endothelial differentiation media. Within 4-6 hours, human CDCs formed complex tube networks (FIG. 10A) resembling those created by human umbilical vein endothelial cells (HUVECs) (FIG. 10B). Unexpectedly, CDCs display a unique morphology between about 24 and about 72 hours after the start of the assay. CDCs contract toward one another within about 24 hours and then begin to migrate into the underlying gel substrate within 72 hours. This response could be reversibly inhibited by including HERCEPTIN® in the endothelial media (data not shown), a factor known to inhibit angiogenesis. Thus, in several embodiments, CDCs are capable of forming endothelial cells, and in some embodiments, such endothelial cells are related to angiogenesis. These data demonstrate the potential for administered CDCs to generate not only cardiomyocytes, but also to generate supporting endothelial cells and, in some embodiments, new vasculature to supply newly generated cardiomyocytes with blood.

Example 10—Mouse Model of Allogeneic Cardiac Repair

Protocols for Testing Human Cdcs in Mouse Model

As a supplement to the Examples described above, myocardial infarction was created in adult male SCID-beige mice by permanent ligation of the left anterior descending (LAD) coronary artery, as described above. Cells were delivered intramyocardially by direct injection at two peri-infarct sites immediately following ligation. CDCs ($10^5$) were injected in calcium-free PBS (5-7 µL at each site), with $10^5$ normal human dermal fibroblasts (NHDFs) or PBS as controls. During the course of the study, mice underwent echocardiography prior to surgery (baseline), and at 2 days, 3 weeks, and 6 weeks post-surgery. Left ventricular ejection fraction was evaluated by manual planimetry of the endocardial border in end-diastolic and end-systolic frames. Mice were euthanized at the end of the study for histology. Human cells were identified in histological sections using a human-specific monoclonal antibody and a human-specific DNA probe.

Time Course of Engraftment of Human Cdcs in Infarcted Mice

In order to track the time course of migration of human CDCs injected into infarcted mice, an in vivo bioluminescence study was performed, with treated animals being sacrificed at various time points for histology. To investigate acute cell retention in the heart and to visualize the biodistribution of the cells over the short term, CDCs were transduced with a lentivirus containing the luciferase gene. Animals were given an injection of D-luciferin intraperotineally and subjected to optical imaging on an IVIS® SPECTRUM (Xenogen) 1 day, 4 days, and 1 week after cell delivery. Images were acquired every 4 minutes with a 1 minute exposure time until the peak signal was obtained and the signal began to decline. FIG. 11A depicts a strong luminescent signal present in the heart out to 1 week in a representative animal (n=3). Cells were not detectable in other organs. This approach demonstrates acute survival and localization of the delivered cells. Peak luminescence values normalized to the day 1 value detected in the hearts of each animal are shown in the graph in FIG. 11B.

Regardless of the apparent decrease in the number of detectable cells by about 1 week, overall morphological and functional improvement in the CDC-treated group persists for at least 6 weeks post-MI (see e.g., FIGS. 12A-12K and FIG. 13). These data suggest that the therapeutic effects of the CDCs are initiated at an early post-administration time point. Thus, these data support the concept of a persistent effect of the administered cells that is not dependent on the continued presence of viable cells and perhaps recruits endogenous signaling cascades and/or endogenous cells to maintain the effect. To that end, in several embodiments, transient engraftment of the cells into recipient cardiac tissue is sufficient to yield anatomical and/or functional benefits.

Histologically, human cells were detected by immunostaining using an antibody against a human nuclear antigen (shown below as green fluorescent nuclei among the blue fluorescence of all nuclei). A representative Masson's Trichrome stained section shows the extent of the infarct at each timepoint examined (FIG. 12A-C). Low magnification images demonstrate the presence of human CDCs in the infarct border zone injection site at 2 days post-MI (FIGS. 12D and 12E are from the boxed area in FIG. 12A) and throughout the border zone and infarct itself at 1 week post-MI (FIGS. 12F and 12G are from the boxed area in FIG. 12B). Over the course of the 6 week study period, CDCs distributed throughout the infarct, border zone, and eventually the remote myocardium (FIGS. 12H-12K are from the boxed areas in FIG. 12C). The majority of CDCs could be found engrafted throughout the infarct region (57±3% of the total engrafted) and the immediate border zone (30±5%), but stable engraftment also existed in the remote myocardium (13±3%). Engraftment of CDCs into murine cardiac tissue was also confirmed by western blot using human-specific antibodies (see FIG. 22). Human CDCs reconstituted large portions of the mouse hearts 6 weeks after delivery.

These data therefore demonstrate that, in several embodiments, CDCs administered to a subject having damaged or diseased cardiac tissue are capable of being retained in damaged or diseased cardiac tissue for both short term and longer time frames. In some embodiments, cells are retained for between about 1-10 days, 2-9 days, 3-8 days, or 4, 5, or 6 days, or overlapping ranges thereof. In some embodiments, there is detectable cell loss (e.g., loss of retention of the cells in the tissue and/or loss of viability of the cells) over the short term. In some embodiments, no or limited cell loss occurs, and administer cells are retained for about 1 week, about 4 weeks, about 6 weeks, or longer. In some embodiments, cells are retained for between about 1-2 weeks, 2-3 weeks, 3-4 weeks, 4-6 weeks, 6-10 weeks, 10-15 weeks, and overlapping ranges thereof. In some embodiments, cells are permanently retained (e.g., for the lifetime of the recipient). As discussed more fully below, in some embodiments, the long-term retention of cells within a target site is not critical to the successful regeneration of cardiac tissue (or improvement in cardiac function).

Efficacy of Human CDCs in Mouse Model

To assess efficacy, CDCs from 21 different randomly-selected preclinical patients were utilized for functional experiments. Twenty-one mice were subject to experimental MI (as described above) were injected with CDCs. Thirty-five mice served as controls (17 injected with normal human neonatal dermal fibroblasts (NHDFs), and 18 with PBS). Echocardiograms performed in normal mice prior to MI revealed a left ventricular ejection fraction (LVEF) of ~80%. Two days after MI, there were no significant differences among the groups in terms of LVEF, although all had a substantial decline in function indicating a successful MI that was uniform in severity in all groups. Data for all animals summarized in FIG. 13. CDC-injected animals showed no significant deterioration of LV function from 2 days post-MI to 3 weeks. Moreover, CDC— injected animals showed no decrease in function at 6 weeks post-MI. Given the relatively long-term time point for a mouse model (>10% of the typical murine lifespan of ~1 year), persistence CDC of the benefit was unexpected. At 3 and 6 weeks, LVEF was significantly higher in the CDC-treated group than in either the NHDF treated or the PBS-treated group. LVEF in the two control groups were indistinguishable from each other.

In several embodiments, administration of CDCs prevents further loss of cardiac function due to MI. In some embodiments, loss of cardiac function is less than about 45% to about 40%, less than about 40% to about 35%, less than about 35% to about 30%, less than about 30% to about 25%, less than about 25% to about 20%, less than about 20% to about 15%, less than about 15% to about 10%, less than about 10% to about 5%, less than about 5% to about 1%, and overlapping ranges thereof. In some embodiments, loss of function is reduced compared to non-CDC treatments. In some embodiments, cardiac function is increased over time, based on the administration of CDCs.

In several embodiments, administration of CDCs induces increases in cardiac function due post-MI. In some embodiments, cardiac function is increased by up to about 5%, up to about 10%, up to about 15%, up to about 20%, up to about 25%, up to about 30%, up to about 35%, up to about 40%, and overlapping ranges thereof. In some embodiments, cardiac function is increased to levels beyond those levels existing pre-MI.

In several embodiments, CDC administration provides an initial short term benefit. In some embodiments, this initial benefit continues for a longer time period. In some embodiments, the time frame ranges from about 3-6 weeks, or longer. In several embodiments, the benefit is realized for about 1-2 weeks, 2-3 weeks, 3-4 weeks, 4-6 weeks, 6-10 weeks, 10-15 weeks, and overlapping ranges thereof. In some embodiments, the CDC-derived benefit is realized for the lifetime of the recipient.

A morphometric analysis was also conducted at the 6 week study endpoint to assess the effects of CDC treatment on infarct remodeling. Mouse hearts were excised, washed in PBS, arrested in diastole with ice-cold KCl, frozen and sectioned transversely in 5-8 μm slices. For a morphometric analysis, tissue sections were selected from the largest extent of the infarct area and stained using Masson's Trichrome (representative results are shown in FIG. 12). Photographs encompassing the entire section were acquired. Infarct wall thicknesses and tissue viability within the infarct zone were calculated from Masson's Trichrome-stained sections by tracing borders manually and then using ImageJ software (NIH) to make measurements. Three to six sections were analyzed per animal and values averaged. In several embodiments, administration of CDCs results in a larger tissue thickness in the infarct area. In turn, in some embodiments, the larger thickness results in an increased percentage of viable myocardium. In several embodiments, percentage of viable myocardium in the infarct area ranges from about 15% to about 20%, from about 20% to about 25%, from about 25% to about 30%, from about 30% to about 35%, from about 35% to about 40%, and overlapping ranges thereof. In some embodiments, viable myocardium in the infarct zone is greater than 40%. In some embodiments, these increases are also associated with increased cardiac function.

In addition, whole hearts and Masson's Trichrome-stained tissue sections were examined for evidence of tumor formation. No tumors were detected in the hearts of any animal. Thus, in several embodiments allogeneic administration of CDCs serves accomplish one or more of increasing cardiac function, increasing cardiac tissue thickness in the infarct zone, increase the percentage of viable myocardium in the infarct zone. In some embodiments, the above are accomplished in the absence of tumor (e.g., teratoma) formation.

Efficacy of CDC Sub populations in Mouse Model

The efficacy of the cardiac mesenchymal cell and the cardiac progenitor cell sub-populations alone were tested in comparison to the total CDC population. A magnetic-activated cell sorting technique was utilized to enrich the sub-populations of interest, CD90$^+$ cardiac mesenchymal cells and c-kit$^+$ cardiac progenitor cells. CDCs were sorted using the CELLection Pan Mouse IgG Kit (Invitrogen) and a Dynal Magnetic Particle Concentrator-15 (Invitrogen). The following monoclonal antibodies were utilized for the first labeling step: CD90-FITC (1:10, Dianova), c-kit-APC (1:10, BD Pharmingen), and CD105-PE (1:10, R&D Systems). After staining and washing, cells were labeled with prewashed CELLection Dynabeads conjugated via a DNA linker to a secondary antimouse IgG antibody. After staining and diluting, the labeled cell solution was placed into the MPC-15 and the unlabeled cell fraction aspirated and discarded. The labeled cell fraction was resuspended in releasing buffer to allow for cleavage of the DNA linker and release of the Dynabeads from the cells. The cell and Dynabead solution was placed into the MPC-15, the cell fraction was collected and the Dynabeads were discarded. After another wash, cells were resuspended in media for culture overnight (prior to in vivo delivery).

Enriched CDC sub-populations were then tested in the same mouse MI model described above. CDCs enriched for CD105, present on 97% of all CDCs, were used as a control. The cardiac function (as measured by LVEF) of mice with a CD-105-enriched population was comparable to CDC-injected mice. See FIG. 14. These data indicate that the sorting protocol did not itself significantly impair the therapeutic potential of CDCs. Thus, in several embodiments, cell sorting for one or more particular markers present on (or absent from) CDCs is used to enrich a population of CDCs for one or more particular markers.

LVEF for c-kit- and CD90-injected mice were indistinguishable from one another. Both of these groups were significantly outperformed by the CD105-injected mice and the CDC-injected mice. All groups were then compared to mice treated with fibroblasts and mice treated with PBS. c-kit-injected mice had significantly greater LVEF than both fibroblast- and PBS-injected mice. The CD90-injected group approached significance when compared with the fibroblast and PBS groups. While the therapeutic mechanisms of action of these two distinct sub-populations may differ, both offer similar global functional benefits to those enriched for CD-105 and unenriched CDCs. Thus, in some embodiments, cell sorting/enrichment is used to prepare a sub-population for use in allogeneic therapies. However, in several embodiments, use of a CDC population that has not been enriched for any one marker (including but not limited to c-kit) is particularly advantageous, as the required manipulation and handling of the cells is reduced. Thus, the generation of a population of CDCs for allogeneic therapies is simpler, more rapid, and less likely to be affected by contamination.

Differentiation of Human CDCs in Infarcted Mice

The extent to which CDCs proliferated and formed new cardiomyocytes over the study time period (e.g., the 6 weeks post-MI) was investigated. Mitotically-active CDCs were identified by expression of a human-reactive Ki67 (FIG. 15A-15C). The percentage of Ki67$^+$ CDCs increased from 2 days to 4 days post-MI from 4% to 6% (7 of 112 counted), after which time it became difficult to detect proliferative CDCs (see FIG. 15D-15F). As many as 25% (28 of 111 counted) of CDCs were cardiac-committed at 2 days post-MI as evidenced by expression of Nkx2.5 (FIG. 15G-15I). Human CDCs did not express cTnI at 2 days post-MI (FIG. 15M-15O), but could be found lodged within regions of dead and dying cardiomyocytes (evidenced by loss of sarcomeric organization and anucleation). By 1 week post-MI, infiltration of mouse progenitors into the infarct was apparent. Clusters of Nkx2.5$^+$ cells of both human (yellow arrows) and mouse (white arrows) origin were prominent. After the early proliferative CDC response had largely resolved, cardiomyocyte differentiation appeared to commence, as newly forming cardiomyocytes of both human and mouse origin could be identified within the infarct. These newly forming cardiomyocytes were identified as such due diffuse cytoplasmic expression of cTnI (see FIG. 15P-15R).

At the end of the 6 week period, CDCs had formed not only cardiomyocytes, but also non-cardiomyocytes throughout the heart, as demonstrated in FIG. 16. FIG. 16 shows fluorescence in situ hybridization using a human-specific centromeric probe and the red fluorescence of cardiac troponin I (FIGS. 16A-16D). Human nuclei of interest are outlined in FIGS. 16E-16H. Example cardiomyocyte nuclei are shown in FIGS. 16M-16P at higher magnification.

These data indicate that, in several embodiments, CDCs not only have the capacity to proliferate, but CDCs also have the capacity to differentiate and repopulate damaged myocardium by forming cardiomyocytes as well as non-cardiomyocytes. Moreover, in several embodiments, administered CDCs, also attract endogenous cardiac progenitor cells. Taken together, in several embodiments, one or more of these characteristics of CDCs are responsible for the resultant increase in cardiac tissue viability, regeneration, and/or overall function.

In Vitro Analysis of Paracrine Factors from Regenerative Cells

In order to characterize the paracrine signals that, in several embodiments provide a beneficial therapeutic effect, the cytokines and growth factors released from regenerative cells were screened. Also assessed was whether the released cytokines and growth factors yield favorable biological effects on neonatal rat ventricular myocytes (NRVMs) and human umbilical vein endothelial cells (HUVECs).

Human cardiospheres and CDCs were obtained from percutaneous septal endomyocardial biopsies from 21 different patients as described above.

Media were conditioned for 48 hours by cardiospheres and IICSps after 4-5 days of culture on poly-D-Lysine, or by CDCs and NHDFs when they were approximately 90% confluent. Media for conditioning comprised 2.5% FBS complete explant medium (CEM), or glucose-free FBS-free basal medium (BM): Medium 199, 10 mmol/L HEPES, 0.1 mmol/L MEM non-essential amino acids, 2 mmol/L L-glutamine, 0.8 μg/mL vitamin B12, 2 unit/mL penicillin. Conditioned media (CM) were stored at −80° C. until used. In some experiments, CMs were pre-incubated on a shaker for 1 hour at room temperature with anti-VEGF and/or anti-HGF neutralizing antibodies. As discussed above, changes to the culturing protocol (e.g., % oxygen, media changes, and the like) are used in some embodiments.

Serum-free CMs from and CDCs were screened for secreted factors using a protein array according to the manufacturer's protocol (Ray Biotech).

Neonatal rat ventricular myocytes (NRVM) were isolated by standard procedures known in the art. Culture plates were incubated in humidified 2% $O_2$ atmosphere for 24 or 72 hours with CM or FBS-free BM (lower portion of FIG. 19). A portion of the cells were then collected by trypsinization, labeled with Annexin V-FITC and 7AAD and analyzed by flow cytometry for indications of apoptosis.

Human umbilical vascular endothelial cells (HUVEC) were plated on pre-cast, matrix-coated 96-well plates. They were plated with either endothelial cell media (ECM), as a positive control, or with CM, or with FBS-free BM, as the negative control (see FIG. 17 for a protocol outline). After 18 hours, total tube length formed was measured microscopically.

Cell cultures were lysed in lysis buffer (20 mmol/L TrisHCl, 5 mmol/L EDTA, 50 mmol/L NaCl, 1% SDS) with proteinase inhibitors cocktail (Sigma), and homogenized by sonication. Tissue samples were lysed in lysis buffer with proteinase inhibitors cocktail (Roche) and homogenized with a rotor-stator homogenizer. Homogenates were spun at 12,000 rcf for 15 minutes at 4° C. Supernatants were then collected and stored at −80° C., after quantification by Lowry assay of the protein content (BioRad). Western blots were performed as described above. Primary antibodies used were as follows: hVEGF and pan-GAPDH (Abcam), hHGF and hIGFI (R&D Systems), hGAPDH (LabFrontier), Akt (Cell Signaling Technology), Caspase 3 (Csp3; Santa Cruz). Human specificity was confirmed. Membranes were washed in TBST, incubated with HRP-conjugated secondary antibodies (Pierce; Santa Cruz), and developed with ECL (Amersham) or West-Femto substrate (pierce). Western blots on media were performed with the Nupage system, loading 30 μl of media per lane. After blocking, membranes were incubated with HRP-conjugated anti-mouse IgG antibody (Santa Cruz). Densitometric analysis was performed with ImageJ software and plotted as ratios to the GAPDH signal.

RNA from cells and tissue samples was extracted with column-based kits (Qiagen). Reverse transcription was performed on 1ug starting RNA (Stratagene) in a 20 μl reaction, and 2 μl of cDNA product were then subjected to PCR (Invitrogen) with human specific or pan-specific primers for 35 thermal cycles.

In preparation for immunofluorescence and histology, cardiospheres and CDCs were fixed for 10 minutes with ethanol-acetone 50:50% at 4° C. Hearts were cut in 5 μm sections. After deparaffinization and rehydration of the tissue sections, slides were washed and permeabilized with 0.1% Triton X-100 in PBS with 1% BSA, then blocked in 10% goat serum and incubated overnight at 4° C. in 1% goat serum with primary antibodies: anti h VEGF and human nuclear antigen (HNA; Chemicon), hHGF, hIGFI and CD 105 (R&D Systems), FN, KDR and c-kit (Abeam), Met and nkx2.5 (Santa Cruz), IGFI-R (Upstate). Slides were then washed and incubated with Alexa Fluor 488 or 568-conjugated secondary antibodies (Invitrogen). Incubation with secondary antibodies alone did not give any detectable background signal.

For capillary staining, tissue sections were incubated for 2 hours with FITC-conjugated Isolectin B4 (Lab Frontier) and Alexa-S68-Phalloidin (Invitrogen); a total of 26700 nuclei were analyzed overall on multiple sections of the border zone, of which 3300 for the assessment of CDC contribution. Co-incubation of isolectin B4 with 500 mM galactose was used as a negative control.

TUNEL staining was performed according to the manufacturer's instructions (In situ Cell Death Detection Kit, TMR red, Roche) and quantified on a total of 20500 nuclei in the border zone.

Confocal fluorescence imaging was performed on an Eclipse TE2000-U equipped with a krypton/argon laser using UltraVIEW software (Perkin Elmer). For image analysis of capillary and TUNEL slides, the ImageJ software was used for binary threshold of fluorescent images for each channel and consequent particle count. Masson's Trichrome staining was performed by standard methods. Briefly, staining was performed according to the kit manufacturer instructions (Sigma). High resolution images were acquired and processed with ImageJ software: color channels were split and the infarct area was manually traced on the blue channel. Threshold adjustment and area measurement functions allowed automatic calculation of the collagen-stained fraction within the defined infarct region.

Protein Array Screening of Conditioned Media

Analysis of serum free conditioned media by protein array analysis yielded 79 spots corresponding to various cytokines and growth factors. FIG. 18 shows two representative blots (18A) from cardiospheres and CDCs derived from the same patient sample, together with the corresponding densitogram (18B and 18C), showing the cardiosphere/CDC optical density ratios for each factor. Three candidates were selected for further analysis, VEGF, HGF and IGFI. This was based on their identity as non immune-modulatory factors, the high CSp/CDC ratio (suggesting enhanced secretion in three-dimensional culture) and established roles in cardiac pathophysiology, particularly in myocardial infarction and heart failure.

Regenerative Cells Release Growth Factors In Vitro

The various types of regenerative cells were analyzed to compare their relative paracrine potencies. Quantification of VEGF, HGF and IGF-1 protein levels (by standard ELISA techniques) in the conditioned media from cardiospheres, CDCs, and IICSps indicate that all three regenerative cell types secrete significant amounts of these growth factors. See FIG. 19A. During 48 hours of conditioning in low serum, cardiospheres released VEGF, HGF and IGFI. By contrast, CDCs and IICSps released only VEGF in measurable amounts, although secretion by IICSps was at the level measured in cardiospheres. In several embodiments, VEGF, HGF, and IGFI are all released, while in some embodiments, one or more are released. In some embodiments, release of growth factors is time-dependent (e.g., one or more are released at an early time-point, while one or more are released at a later time-point).

Although different culture serum concentrations and different cell densities were also analyzed, IGFI secretion was not detected in CDCs or IICSps. CDCs are capable of releasing HGF, under certain culture conditions. CDCs cultured in basal media release detectable amounts of HGF as detected by ELISA (see FIG. 19B).

Immunofluorescent analysis of cardiospheres revealed ample VEGF, HGF and IGFI (FIG. 19C-19D). Reverse transcription PCR on RNA isolated from cardiospheres, CDCs and IICSps also confirmed the expression of VEGF, HGF and IGFI mRNAs (FIG. 19E). No growth factors were detected by ELISA in normal human dermal fibroblast (NHDF)-CM in any of the conditions tested, although the corresponding mRNA was detected by PCR. NHDFs were also grown as spheres on poly-D-lysine, but cell-associated growth factors were not detected by immunofluorescence (data not shown) nor were secreted growth factors detected in CM by ELISA (FIG. 19A).

Cardiospheres and CDCs also express the receptors for VEGF, HGF and IGFI (respectively KDR, Met, IGFI-R), as assessed by immunofluorescence and RT-PCR (see FIG. 20).

Effects of Regenerative Cells Conditioned Media on Cardiac Cell Viability

Figure 21A:
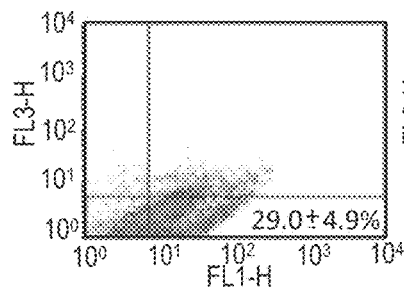
Figure 21B:
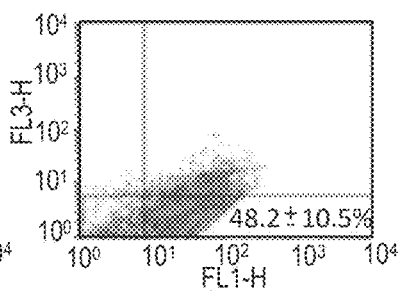
Figure 21C:
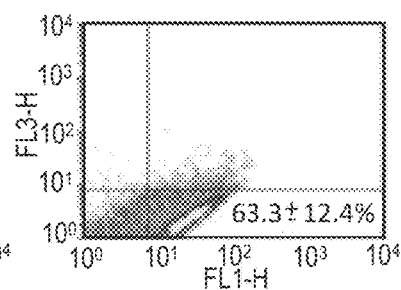
Figure 21D:
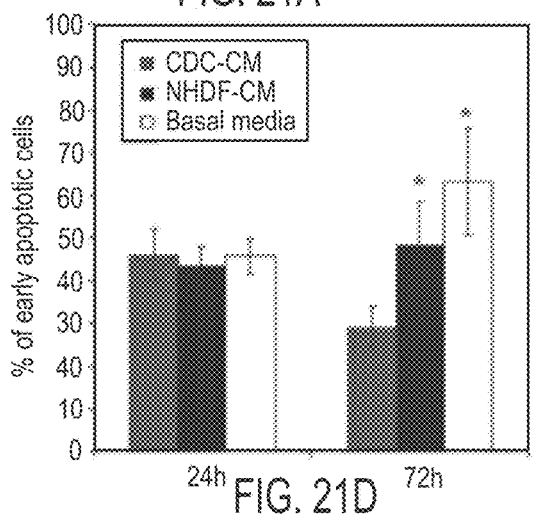
Figure 21E:
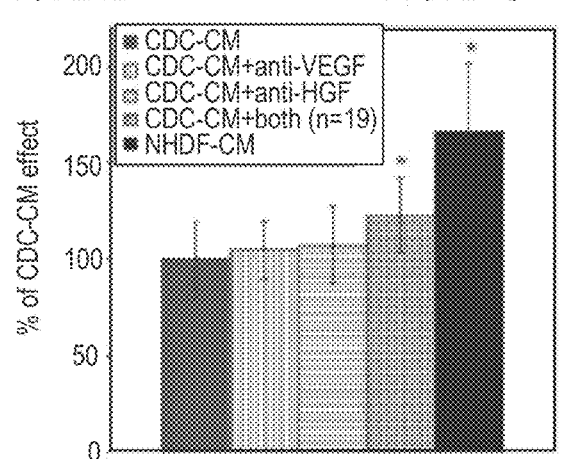

Conditioned media from CDCs and NHDF cells were collected in fetal bovine serum-free basal media and used in place of NRVM media. After 24 or 72 hours in 2% hypoxia, the percentage of early apoptotic NRVMs was assessed by Annexin V/7-AAD labeling. No differences were detected after 24 hours, however after 72 hours the percentage of early apoptotic NRVMs was dramatically lower in the CDC-CM (FIG. 21A) compared to the NHDF-CM (FIG. 21B) and the control FBS-free BM (FIG. 21C). The summary FACS data is represented in FIG. 21D. When CDC-CM was pre-incubated with neutralizing anti-VEGF and HGF antibodies and used for culturing NRVMs for 72 hours, the apoptosis-reducing effect was significantly reduced (FIG. 21E). The neutralization of both secreted growth factors resulted in an excess 23% early apoptotic NRVMs compared to plain CDC-CM. Significance, in all examples, was evaluated using standard statistical techniques and significant differences are represented by p values<0.05, unless otherwise specified.

Effects of Regenerative Cells Conditioned Media on Angiogenesis

Figure 21F:
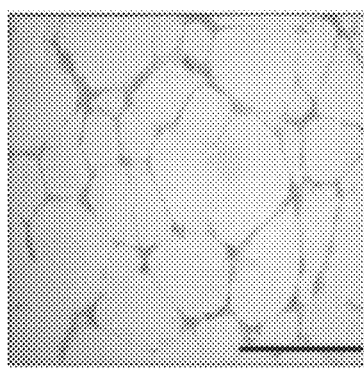
Figure 21G:
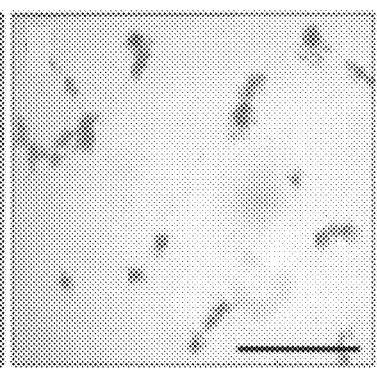
Figure 21H:
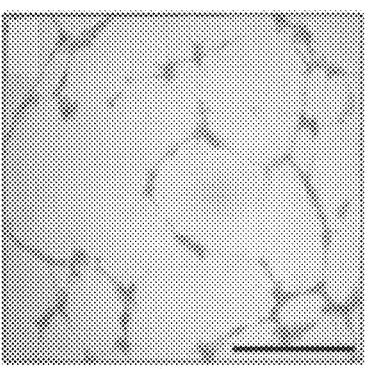
Figure 21I:
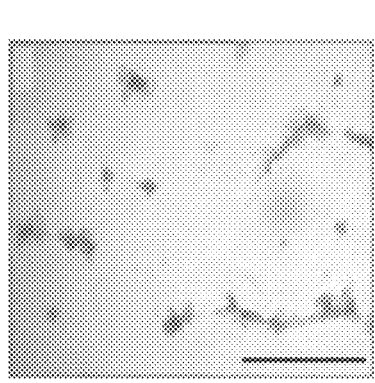
Figure 21J:
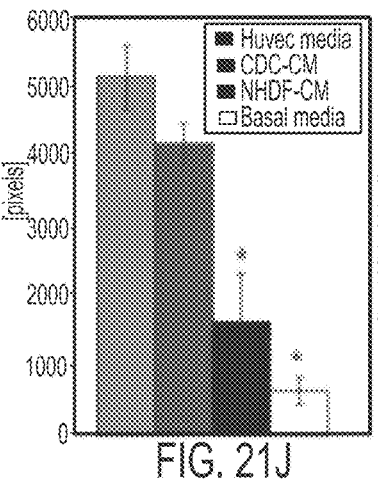
Figure 21K:
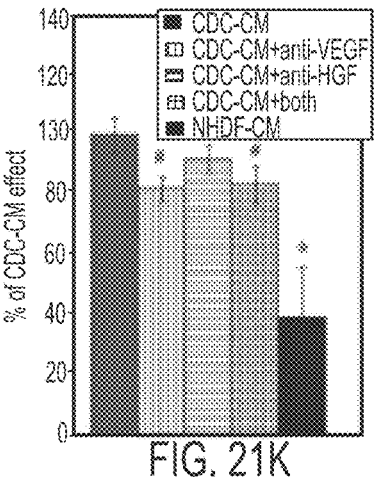

To determine if paracrine signals from the CDCs may be mechanistically involved in the blood vessel formation, HUVECs were cultured in either endothelial cell media (ECM; the normal media used to culture HUVECs), fetal bovine serum-free basal media, or CDC-CM (see FIGS. 21F, 21G, and 21H, respectively). The ability of HUVECs to form complex tube networks was lost in BM, but when cultured in CDC-CM this ability was almost completely recovered (compare 21G with 21H). The tube-forming ability of HUVECs cultured in CDC-CM was significantly greater than that of HUVECs cultured in NHDF-CM (FIG. 21J). Pre-incubation with anti-VEGF or both anti-VEGF and anti-HGF neutralizing antibodies caused a slight but significant reduction of the total tube length per well (FIG. 21K).

In summary, the preliminary screening of human regenerative cells and their conditioned media revealed that these cell populations are capable of releasing many different cytokines and growth factors. Cardiospheres were found to spontaneously release significant and higher amounts of VEGF, HGF and IGFI in vitro as compared to CDCs. CDCs secrete only VEGF and HGF, although they maintain the transcription of all their mRNAs. However, IICSps were able to secrete VEGF at levels comparable to cardiospheres, suggesting the 3D structure of cardiospheres may influence release of VEGF. This may be due to hypoxic stimulation of the cells residing in the interior layers of the cardiospheres. These results suggest that: a) the primary CSp is the stage at which paracrine abilities are maximal in vitro; b) VEGF release is affected by the 3D structure; c) HGF and IGFI release fades with progressive time in culture. Furthermore, the expression of receptors for these growth factors on regenerative cells suggests a possible autocrine feedback effect.

Although these results suggest that cardiospheres are more potent in terms of paracrine signal release in vitro, other cell types may be equally, or more potent in a the more complex physiological environment in vivo. To this end, functional in vitro analysis was performed to test the effects of CDC-CM on cell viability and angiogenesis. The present experiments demonstrated that CDC-CM reduces the frequency of apoptosis initiation in ventricular myocytes. This pro-survival effect is partially due to synergy between secreted VEGF and HGF, as NRVM viability was reduced after pre-incubation of the CDC-CM with both anti-VEGF and HGF neutralizing antibodies. CDC-CM has also potent pro-angiogenic effects, as demonstrated by promoting formation of complex tube networks by HUVECs.

These data indicate that regenerative cells secrete growth factors that positively impact the survival of ventricular myocyte cells and the angiogenic capacity of endothelial cells. Thus, in several embodiments, these secreted growth factors play a role in the in vivo repair of damaged myocardial tissue by enhancing the survival of endogenous cells and/or increasing angiogenesis in the myocardial tissue, among other possible mechanisms.

Detection of Human Growth Factors in Mouse Model

Western blot analysis using human-specific antibodies was used to detected engraftment of CDCs that were injected into murine cardiac tissue as described above. Additionally, western blot was used to demonstrate the presence of human growth factors within the infarcted mouse heart. In several embodiments, growth factors from the administered CDCs, such as VEGF, HGF, IGF-1 contribute to the functional benefits observed. Animals were sacrificed 1 day, 1 week or 3 weeks after cell delivery. Regional tissue samples, ranging from 15 to 20 mg on average, were taken from infarct (INF), border zone (BZ), right ventricle (RV) and septum (SEP) areas for WB. Tissue samples were lysed in lysis buffer with proteinase inhibitors cocktail, homogenized, and spun. Supernatants were then collected and stored, after quantification by Lowry assay of the protein content. Lysates were loaded on 4-12% Bis-Tris gels (Invitrogen), and blots 50 µg of protein per lane was performed with the Nupage mini-gels system (Invitrogen). Primary antibodies against human VEGF and pan-GAPDH (Abcam), human HGF and human IGF1 (R&D Systems), and human GAPDH (LabFrontier) were used. Membranes were washed and incubated with HRP-conjugated secondary antibodies. Human growth factors were detectable with human specific antibodies only in lysates from CDC-injected animals, although hGAPDH was evident in the INF and BZ of both CDC- and NHDF-injected animals. These data indicate the cells survive for at least three weeks in CDC-injected and for at least 1 week in NHDF-injected hearts (see FIG. 22) Growth factors were also detectable in remote areas, like the RV and SEP, 1 day after cell delivery. After 3 weeks, bands for hHGF and hIGF-1 were faint, but detectable, although hVEGF could no longer be found detected. The absence of a hGAPDH band in the BZ after 24 hours can be attributed, at least in part, to the difficulty in distinguishing the infarct from the peri-infarct zone at such an early time point.

Despite the apparent reduction in expression of human growth factors over time, CDCs had clearly engrafted and survived, as evidenced by the detection of hGAPDH in tissue lysates. These data suggest that, in several embodiments, CDCs exert an effect on the recipient tissue early after transplantation, which has long lasting effects. In some embodiments, the engraftment of the CDCs itself triggers this effect. However, in several embodiments, paracrine effects are responsible for initiating a cascade of events that lead to functional improvements at later time point. In some embodiments, the initially administered CDCs are no longer present, yet the paracrine effects and the ensuing cascade are still active in repairing and/or regenerating cardiac tissue. In several embodiments, CDCs benefit the injured heart by direct myocardial regeneration with a large portion of their effect being due to the secretion of paracrine factors that stimulate endogenous repair pathways. Based on a quantitative analysis of the contribution of engrafted human cells (discussed in more detail below), it can be estimated that the paracrine effect accounts for at least 50% of the total effect, in one embodiment. In several embodiments, the paracrine effect is responsible for about 50% to about 60% of the total effect, for about 60% to about 70% of the total effect, for about 70% to about 80% of the total effect, or greater that 80% of the total effect. In some embodiments, the paracrine effect is entirely responsible for the myocardial regeneration and/or increased cardiac function.

CDC-Injected Tissue Displays Higher Tissue Viability and Capillary Density

Figure 23A:
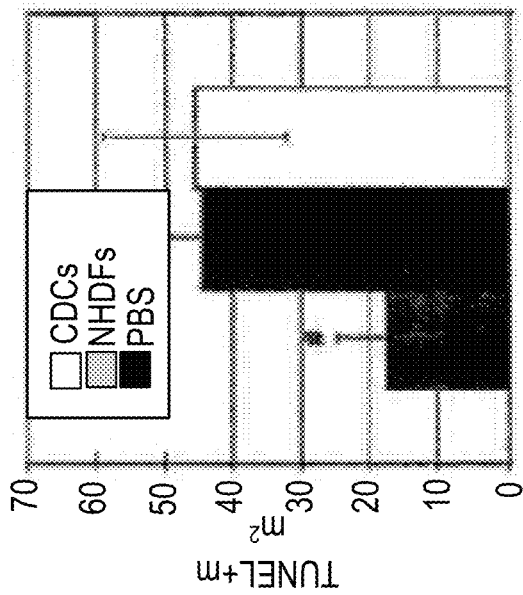

As discussed above, one week after cell delivery, human growth factor levels remained high in the heart of mice injected with CDCs (see FIG. 22). Lysates from CDC-injected mice contained higher levels of Akt protein compared to NHDF-injected animals, as shown by WB and relative densitometric analysis (FIG. 23A). Moreover, active Csp3 expression was reduced in CDC-injected hearts relative to controls (FIG. 23B). These results correlate with a reduced apoptotic rate (FIG. 23C) and higher capillary density in the border zone of CDC-injected mice (FIG. 23D), compared to controls, as assessed by TUNEL and isolectin B4 staining, respectively. Taken together, these data indicate that CDCs suppress post-ischemic apoptosis and improve blood supply. Thus, in several embodiments, reduction in apoptosis accounts for at least a portion of the higher tissue viability. In several embodiments, increased angiogenesis, alone or in combination, with reduced apoptosis, accounts for the increased tissue viability.

Direct Versus Indirect Regenerative Contribution

Figure 24A:
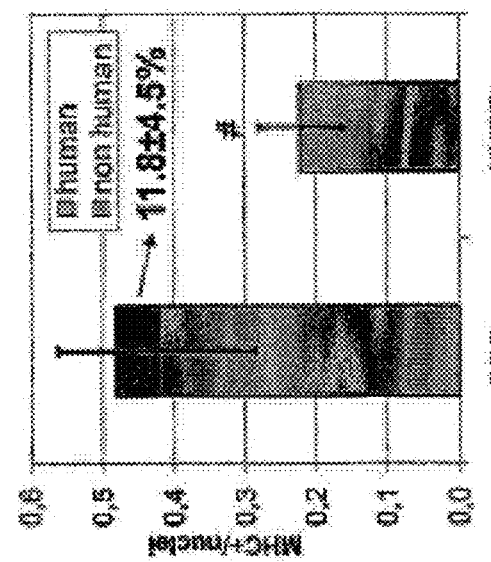
Figure 24B:

As a means of quantifying how much of the functional improvement due to CDC administration is related to direct regeneration versus indirect paracrine effects, the relative contribution of human CDCs to the capillary density in the tissue areas where CDCs were detectable after 1 week was calculated. Despite an overall doubling of capillary density in CDC-injected mice, only 9.6±2.7% of the total capillaries were found to be of human origin (FIGS. 24A and 24B). This amounts to ~20% of the enhanced angiogenesis; thus, the angiogenic effect reflects both direct regeneration and paracrine effects, with latter predominating.

Figure 24C:
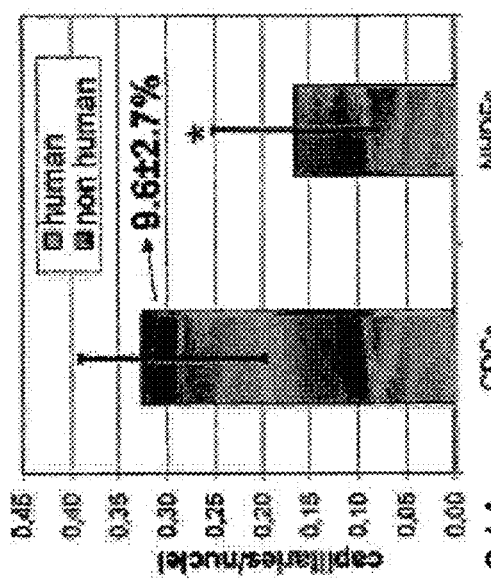
Figure 24D:
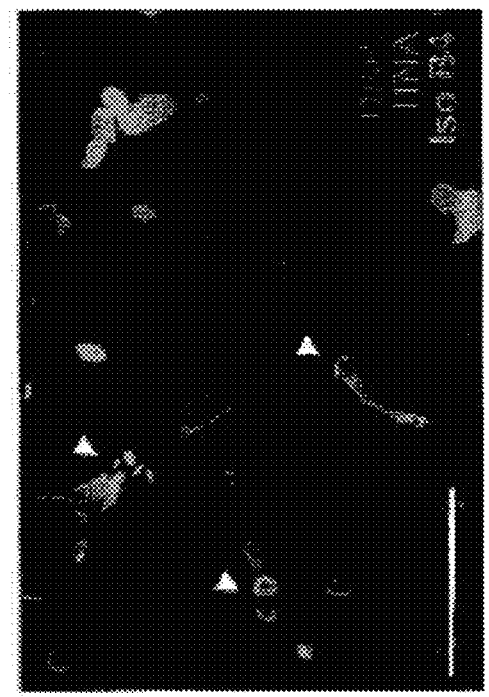

With respect to the cardiomyogenic effect of CDC transplantation, after 1 week the infarct area of CDC-injected mice contained a higher percentage of viable myocardium (FIG. 25A), as assessed by Masson's trichrome staining Within those viable areas, 11.8±4.5% of the MHC-expressing cells were of human origin (FIGS. 24C and 24D). While significant, this explains only half of the ~20% increase in relative tissue viability revealed by Masson's trichrome staining, and only ~25% of the overall doubling in MHC nuclei (FIG. 24C). Thus, both direct regeneration and paracrine effects underlie the cardiomyogenic effects of CDC transplantation. No human capillaries or MHC-positive cells were detectable in the NHDF-injected hearts.

This Example has therefore demonstrated that when injected intramyocardially in infarcted SCID mice, CDCs release, among other growth factors, VEGF, HGF and IGFI. These growth factors are detectable for at least 1 week after cell. Growth factor release is not simply a result of cell administration or engraftment, as both CDCs and NHDF cells engrafted into cardiac tissue, rather growth factors secreted by transplanted cells were detectable only in CDC-injected animals. Additionally, only CDC-injected animals demonstrated a significant functional improvement.

Growth factors were detected in remote areas of the heart 24 hours after cell injection. Remote areas did not appear to contain growth factors after 1 week, suggesting that diffusion of growth factors occurs at the earlier time point. This may be due to the relatively intact vascular system at the earlier time, which loses functionality in the more mature infarct scar 1 week after surgery, thus restraining human growth factors to tissue more local to the CDC engraftment zone. Alternatively, the early spread into neighboring areas may simply reflect a greater intensity of growth factor production soon after injection. This may be due to a higher production rate by newly-injected cells, or may be due to the presence of more cells at early post-injection time points.

Figure 23C:
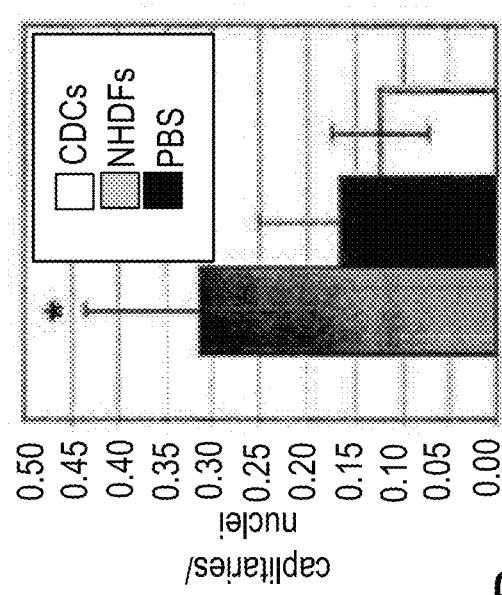
Figure 23N:
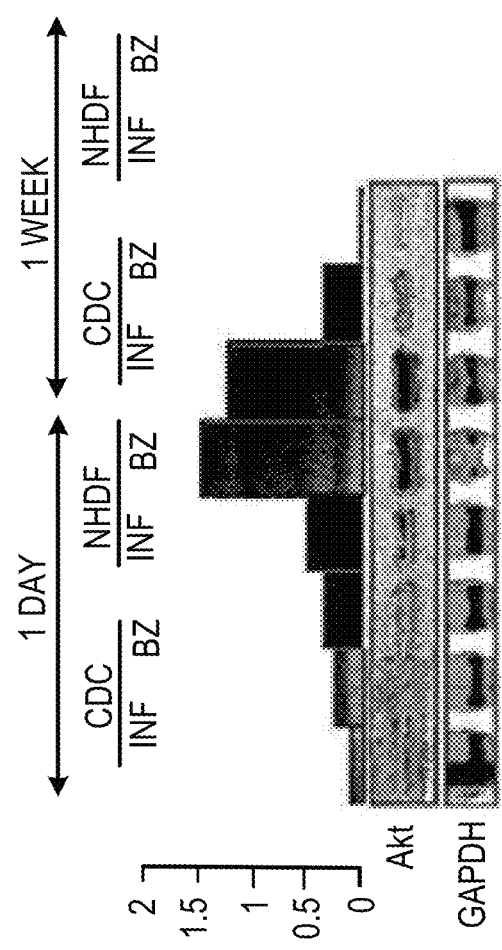
Figure 23D:
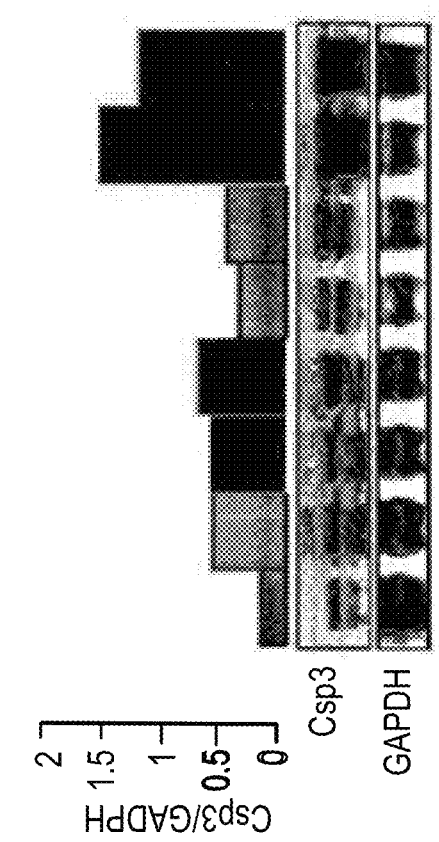

Cell survival, particularly in an unfavorable environment (such as ischemic cardiac tissue), mostly depends on the cells' ability to overcome death triggers and secondarily to promote angiogenesis. In this respect, the in vitro anti-apoptotic and pro-angiogenic effects demonstrated in the prior example correlate with the in vivo observation that, 1 week after cell delivery, Akt was up-regulated in tissue samples from CDC-injected animals. Contemporaneously, the active form of the apoptotic effector Csp3 was less expressed in CDC— compared to NHDF-injected hearts (FIG. 23B). Furthermore, the rate of TUNEL-positive cells was significantly reduced in the border zone of CDC-injected mice, which also displayed higher capillary density compared to controls (FIG. 23C-23D). Overall, these results imply that the injection of CDCs in infarcted SCID mouse hearts favors higher tissue viability in the infarct and peri-infarct areas, and consistently correlates with reduced apoptosis and improved blood supply. This conclusion is consistent with previous histological data showing a higher percentage of viable myocardium in the infarct area of CDC-injected, as compared to NHDF-injected mice (which was also confirmed at the 1 week time point in the present study).

While injected CDCs and/or their progeny persist for at least three weeks post-administration, in several embodiments the persistence of CDCs reflects their multilineage differentiation. In several embodiments, the persistence of CDCs reflects a survival advantage conferred by paracrine effects such as those described here. In several embodiments a combination of both mechanisms is at play. The present study demonstrates that CDCs directly contribute to approximately 10% of the overall capillary density in the areas of CDC engraftment. However, there remains a statistically significant difference between the capillary density of the CDC and the NHDF groups, confirming the major role of indirect paracrine induction by CDCs.

With respect to their contribution to cardiomyogenesis, direct regeneration and paracrine mechanisms supporting regeneration appeared to be more equivalent in their effects. Given that long-term engraftment of transplanted cells is low, it seems reasonable to focus on enhanced engraftment as a prime strategy to boost the overall efficacy of cell therapy, even if the final benefit reflects both direct and indirect regeneration.

While the use of cytokines and growth factors as cardiac therapeutic tools has been carefully investigated in the past few years, especially by means of gene therapy, many such protocols involve risks such as pathologic angiogenesis, severe inflammatory reactions and arrhythmias. The possibility of growth factor release under biological and physiological control through regenerative cell therapy might offer an ideal combination of strategies in that regenerative cells are able to differentiate directly and to concurrently secrete beneficial molecules and harness endogenous repair.

Direct injection of HGF and IGF-1 into the myocardium has been shown to successfully mobilize endogenous cardiac stem cells. Given that CDC transplantation produces these same growth factors, as shown herein, this study suggests that recruitment of endogenous stem cells is a likely contributor to the functional improvement demonstrated in this study.

These data, taken together, demonstrate that regenerative cells secrete significant amounts of pro-survival and pro-angiogenic growth factors in vitro, and in an in vivo cardiac cell therapy model. This Role Model Effect appears to be a key mechanism, together with the natural propensity of regenerative cells for cardiac differentiation, contributing to the regenerative potential and therapeutic effects of regenerative cells in the post-infarction period.

Efficacy of CDC Cell Banks in Mouse Model

Based on the discussion above regarding the generation of cell banks, which are used in some embodiments, the following sets forth an example of a contemplated experiment using allogeneic cells generated and banked prior to use. The same mouse MI model will be employed. CDCs having gone through the manufacturing process described above, including intermediate banking, will be suspended and delivered in a cryopreservation solution (CRYOSTOR® CS5). Also as discussed above, CRYOSTOR® CS5 used, in some embodiments as an excipient that is combined with the CDCs. Control groups will consist of mice injected with CRYOSTOR® CS5 alone, mice injected with CDCs suspended in PBS, and mice injected with PBS alone. In addition to measuring function 3 weeks post-MI, histology will be performed to assess the degree of local tissue damage that may occur due to the 5% dimethylsulfoxide (DMSO) contained in the cryopreservation solution.

Example 11—Immunologic Properties of Regenerative Cells

In order to understand the potential for cardiac tissue repair via allogeneic transplant of regenerative cells, the immune responses initiated against allogeneic regenerative cells was characterized. Both in vitro and in vivo analyses were performed using an established rat model. CDCs were isolated from two rat strains with different MHC haplotypes (Wistar Kyoto and Brown Norway). Cross-transplantation of organs from these mismatched strains has been used as a model for allograft rejection. CDCs were isolated from Wistar Kyoto rats and ex vivo expanded, as described above. These CDCs were intramyocardially injected into either Wistar Kyoto rats (syngeneic/autologous model) or Brown Norway rats (allogeneic model). In some rats, human CDCs were injected (xenogeneic model). Expanded CDCs (or PBS for control groups) were injected immediately after MI was simulated via LAD ligation, as described above. Injections comprised $2 \times 10^6$ CDCs in 100 μL total injection volume (50 μL at each of two peri-infarct sites). In all transplants, male Wistar-Kyoto rats were the donors and female rats were the recipients, thus enabling mRNA isolated from rats post-injection to be used in quantitative y-chromosome real time PCR reactions to determine engraftment of cells into the target tissue.

Rats underwent echocardiography to assess efficacy, were subjected to blood draws to assess the level of pro- and anti-inflammatory cytokines present in the serum, and were euthanized at the end of the study for histology to examine the degree of immune rejection evident or PCR to quantify the percentage of CDCs engrafted.

In Vitro Immunologic Properties of Allogeneic Cdcs

The immunologic properties of rat and human CDCs (rCDCs and hCDCs, respectively) were first examined in vitro. Established flow cytometry methods were used to assess the expression of MHC Class I and Class II antigens and before and after stimulation with interferon-γ, a known immunostimulatory molecule, for 1 day or for 5 days. With regard to immune antigens, both rCDCs and hCDCs express MHC I but not MHC class II surface antigens (FIGS. 26B and 26F). Incubation with interferon-γ upregulated both MHC I and MHC II expression in a time-dependent manner (FIGS. 26C/D and 26G/H). CD80/CD86 are expressed on antigen presenting cells and provide co-stimulatory signals needed for T cell activation and survival. Expression of both CD80 and CD86 was relatively low in both rCDCs and hCDCs at baseline. Stimulation with interferon-γ did not significantly induce expression of these co-stimulatory molecules (see e.g., FIG. 26I). Several other markers did not differ in expression levels between rCDCs and hCDCs (see e.g., FIG. 26J).

The observed baseline immunophenotype of CDCs is beneficial for allogeneic applications. In several embodiments, the higher baseline levels of MHC class I antigen expression are beneficial, as this antigen, at least in part, protects the cells from natural-killer cell-mediated destruction. Similarly, the low level expression of MHC class II antigens (potent activators of the immune system) allows, in several embodiments, allogeneic CDCs to escape direct recognition from CD4+ T helper cells. While MHC class I antigens may activate effector T cells in certain cases, the low quantities of costimulatory molecules (CD80/CD86) would induce an interruption in the signaling pathway, thereby likely leaving T cells inactive.

Lymphocyte proliferation was measured by BrdU incorporation. Well-known methods were used to evaluate immunogenicity, which are described in brief. Spleens were harvested aseptically from euthanized WKY and BN rats, mechanically dissociated and filtered through a 100 μm nylon mesh. Erythrocytes were lysed with 0.83% ammonium chloride, cells were washed in RPMI 1640, dead cells were removed by density centrifugation and cell viability was assessed by trypan blue dye exclusion. Stimulating rCDCs and hCDCs were mitotically inactivated with 50 μg/ml mitomycin C (Sigma-Aldrich) in the dark at 37° C. for 30 minutes and washed three times with RPMI 1640. $10^4$ stimulating CDCs were cocultured with $10^5$ responderlymphocytes in 200 μl of culture medium (RPMI 1640 supplemented with 10% FBS) in 96-well flat-bottom plates for 5 days. The following experimental conditions were tested in quadruplicates: a) rCDCs cocultured with WKY lymphocytes (syngeneic coculture); b) rCDCs cocultured with BN lymphocytes (allogeneic coculture); c) hCDCs cocultured with BN lymphocytes (xenogeneic coculture). All appropriate controls were also tested. BrdU was added to the cocultures for the last 24 hours and responder cell proliferation was assessed by the Cell Proliferation Biotrak ELISA System (GE Healthcare) according to the manufacturer's instructions. Absorbance was measured with a microplate reader (Bio-Rad) at 450 nm. Alloreactive and xenoreactive lymphocyte proliferation is presented as relative proliferative response, normalized to syngeneic coculture proliferation (stimulation index). The cell-free supernatant of the cocultures was collected and the levels of secreted IFN-g, IL-1b, IL-13, IL-4, IL-5, KC/GRO and TNF-α were measured by electrochemiluminescence. The levels of secreted IL-2 were measured using enzyme-linked immunosorbent assay (ELISA) kits, according to the manufacturer's protocols (R&D Systems).

Co-culture of rat CDCs with allogeneic lymphocytes induced negligible lymphocyte proliferation, which was comparable to that induced by syngeneic CDCs and less than that of xenogeneic human CDCs (FIG. 26K-26M). The lymphocyte proliferation induced by allogeneic CDCs was not significantly different than that induced by syngeneic CDCs (syngeneic stimulation index: 1.4±0.2; p=ns versus allogeneic). In contrast, xenogeneic hCDCs induce a strong proliferative response (stimulation index: 2.6±0.6; p<0.01 vs. syngeneic or allogeneic cocultures; FIG. 26N). Quantification of inflammatory cytokines in the coculture supernatants by electrochemiluminescence and ELISA demonstrated comparable levels of pro-inflammatory (IFN-γ, TNF-α, IL1b, IL2, KC/GRO) and anti-inflammatory (IL5, IL13, IL4) cytokines in syngeneic and allogeneic cocultures. Again in contrast, in the xenogeneic cultures, secretion of all inflammatory cytokines was markedly increased, indicating significant activation of responder lymphocytes (FIG. 26O). Consistent with these in vitro results, the in vivo immune response (discussed in more detail below), was not significantly different between allogeneic and syngeneic cell transplants.

Engraftment of Allogeneic CDCs in Rat Model

To enable measurements of cell engraftment in vivo, CDCs were transduced with a lentiviral construct expressing GFP. Quantitative PCR was performed 1 week and 3 weeks post cell injection in order to monitor transplanted cell engraftment after syngeneic, allogeneic and xenogeneic cell transplantation. Cells isolated from male donor WKY rats and male human biopsies were injected into the myocardium of female recipients and quantified absolute cell engraftment by real-time PCR using the (rat and human respectively) SRY gene located on the Y chromosome as target. In brief, the recipient heart was explanted, weighted, homogenized and genomic DNA was isolated using the DNA Easy minikit (Qiagen), according to the manufacturer's protocol. The TaqMan® assay (Applied Biosystems) was used to quantify the number of transplanted cells with the rat (for syngeneic and allogeneic transplantation) and human (for xenogeneic transplantation) SRY gene as template. A standard curve was constructed with samples derived from multiple log dilutions of genomic DNA, isolated from male rat hearts and samples of male human myocardium, spiked with 50 ng of female rat genomic DNA as control. The copy number of the SRY gene at each point of the standard curve was calculated based on the amount of DNA in each sample and the total mass of the rat genome per diploid cell. All samples were tested in triplicates. For each reaction, 50 ng of template DNA was used. The result from each reaction, copies of the SRY gene in 50 ng of genomic DNA, was expressed as the number of engrafted cells/heart by extrapolation to the total DNA content of each heart, taking into account that there is one copy of the SRY gene per transplanted cell. FIG. 27A depicts the experimental scheme employed to study engraftment and function. FIG. 27B describes the experimental and control groups used to evaluate engraftment and function.

Two million male syngeneic, allogeneic or xenogeneic CDCs were implanted into the ischemic myocardium of female rats, immediately after LAD ligation. Similar to the immunogenicity results discussed above (e.g., the limited differences in immune induction between syngeneic and allogeneic cultures) engraftment of allogeneic and syngeneic CDCs was not significantly different between allogeneic and syngeneic transplants at 1 week post MI (absolute cell number: 117,587±94181 vs. 122,662±68,637; p=ns). In contrast, the majority of xenogeneic CDCs fail to engraft within 1 week of transplantation (absolute cell number: 10,535±4012; p<0.05 compared to syn, allo groups). Data related to 1-week engraftment are shown in FIG. 27C.

Three weeks after experimental infarction and CDC delivery, cell engraftment decreased markedly (to <1% of cells transplanted) in both syngeneic and allogeneic groups. However, the residual number of engrafted cells is higher after syngeneic transplantation (absolute cell number: 13,343±6427 vs. 3169±4012; p<0.05). This likely reflects gradual destruction and clearance of the allogeneic cells by the host immune system. No engrafted xenogeneic cells were detected after 3 weeks. Data are presented in FIG. 27D.

These results indicate, that, in some embodiments, allogeneic CDCs are cleared more rapidly than syngeneic CDCs between days 8 and 21 post-delivery. In some such embodiments, the beneficial effects of allogeneic CDCs have already been realized (or put in motion), such that the survival and residency of the delivered cells is no longer necessary. Moreover, based on the immunogenicity data discussed above, these data indicate that the immune response is not solely responsible for the decreased number of engrafted cells. Endogenous mechanisms to remove transplanted cells, and/or the natural lifespan of the administered cells may account for the decrease.

Immune Response to Allogeneic CDCs in Rat Model

Consistent with the limited in vitro induction of pro-inflammatory cytokines by allogeneic CDCs, administration of allogeneic CDCs induced only a mild local immune reaction in the heart. In fact, the immune reaction is barely visible using a standard H&E stain (example figures shown at 3 weeks post-MI, FIG. 28B-28C). Significant infiltration is seen in the xenogeneic transplant (FIG. 28A). Further, using an established pathological assessment scale, the ISHLT grading system, which is used in clinical practice to diagnose rejection, the level of rejection seen in H&E sections were scored at 1 week, 3 weeks, and 6 months post-MI. Four to five animals and 48-60 sections were scored in each group (Grade 0=No rejection, Grade 1R=Interstitial and/or perivascular infiltrate with up to one focus of myocyte damage, Grade 2R=Two or more foci of infiltrate with associated myocyte damage, Grade 3R=Diffuse infiltrate with multifocal myocyte damage). The analysis was conducted by a blinded cardiac pathologist. No significant immune rejection could be detected in the allogeneic setting at any time point (see 28B and 28D, data for 6 weeks not shown). In contrast, xenogeneic cell transplantation resulted in significant mononuclear infiltration that could be detected in the infarct scar and border zone 1 week (FIG. 28D) and 3 weeks (FIG. 28F) post treatment. As shown in FIG. 28A, the infiltrating cells were located at interstitial and perivascular spaces, but notably, no foci of myocyte damage could be detected. The lack of foci suggests that immune rejection of xenogeneic CDCs did not inflict additional damage to the myocardium. The immune response was resolved in all groups at 6 months post-MI.

Despite its utility in the clinical assessment of transplant rejection, detection of small foci of rejection by H&E staining is complicated in a post-MI setting due to the natural inflammatory response to the ischemic insult. In order to corroborate the histochemical data, immunostaining against a variety of immune cell markers was performed for each time point. This approach allows a characterization/identification of the infiltrating inflammatory cells. After allogeneic transplants, immunohistochemistry revealed rare events of rejection. A few small and sparse infiltrates around some transplanted cells were detected 3 weeks post-treatment. See for example FIGS. 28H, 28I, and 28J. These infiltrates comprised mainly CD3+ T lymphocytes (with equal contributions of CD8+ T cytotoxic and CD4+ T helper subpopulations) and to a lesser extent CD45R+B lymphocytes and CD11c+ dendritic cells (see FIG. $28K_1$-$28K_{15}$ and also 29A-29C, which depict syngeneic, allogeneic, and xenogeneic transplants, respectively). Based on the similar quantities of CD4+ and CD8+ T lymphocytes in the graft area, as well as the presence of dendritic cells, it is possible that an indirect pathway of allorecognition plays a greater role in the immune rejection of transplanted cells. For example, antigens shed by apoptotic donor CDCs may be phagocytosed by host antigen presenting cells (like dendritic cells) and subsequently presented to CD4+ cells, thus activating the immune cascade. However, in some cases, participation of the direct pathway of allorecognition also likely plays a role. Notably, the increased lymphohistiocytic infiltration was significantly lower than that seen with xenogeneic transplantation (FIGS. 28L and 28M; and also FIGS. 29D and 29E), and had completely resided by 6 months (data not shown). The higher infiltration of CD68+ macrophages (which in general did not localize within the infiltrates but were evenly dispersed along the infarct) detected at 1 and 3 weeks post MI in the xenogeneic and control groups was consistent with the larger infarct size observed in those groups.

Furthermore, there were no significant signs of systemic immunogenicity (FIGS. 30A-30G) in the animals who received allogeneic CDCs as evidenced by serum concentrations of pro-inflammatory cytokines IFN-γ, IL-10, KC/GRO, TNF-α, (FIGS. 30A, 30B, 30F, and 30G, respectively), or the anti-inflammatory cytokines IL-13, IL-4, and IL-5 (FIGS. 30C, 30D, and 30E, respectively). In contrast, in the xenogeneic transplants, the circulating levels of IFN-γ, IL1β, IL13 and IL4 were markedly increased. Taken together, these data indicate that the systemic inflammatory response observed after xenogeneic transplantation did not occur in the allogeneic setting. Thus, in some embodiments, allogeneic transplants provide the unexpectedly beneficial combination of functional and morphological improvements in damaged cardiac tissue, without the expected immune response. For these reasons, among others disclosed herein, allogeneic cells are particularly advantageous in some embodiments.

Allogeneic CDCs Elicit a Cellular but not a Humoral Response Memory

In order to assess the development of cellular memory immune response after allogeneic CDC transplantation, the alloreactivity of lymphocytes isolated from spleens of allogeneic recipients 3 weeks post-transplantation was assessed by one-way mixed lymphocyte reactions. Lymphocytes from sensitized animals exhibited higher proliferation after coculture with allogeneic CDCs (stimulator index 2.32±0.52), compared to naïve lymphocytes (p<0.05) or syngeneic cocultures (p<0.01). In addition, markedly increased levels of inflammatory cytokines in the supernatants of sensitized lymphocyte cocultures were detected by electrochemiluminescence and ELISA. These results are indicative of a T cell memory response and are in accordance with the immunohistochemistry data discussed below, which shows a predominant role of T cells in the sparse mononuclear infiltrates observed 3 weeks post allogeneic transplantation (FIG. 28C).

In order to assess the development of a humoral memory response, recipient rat sera obtained 1 and 3 weeks post-transplantation were screened for circulating anti-donor antibodies. No alloreactive antibodies were detected in any recipients of allogeneic CDCs at any timepoint. This finding is in contrast to the xenogeneic transplants in which high titers of xenoreactive IgM antibodies were detected 1 and 3 weeks post transplantation. Additionally, a progressive increase of xenoreactive IgG antibodies was observed from week 1 to week 3. The development of anti-donor antibodies in xenogeneic recipients, but not in allogeneic recipients, is consistent with the significantly higher (~8 fold) B cell myocardial infiltration observed in the xenogeneic setting (FIGS. 28L-28M).

Efficacy of Allogeneic CDCs in Rat Model

Morphometric analysis of explanted hearts 3 weeks post infarction showed severe LV chamber dilatation and infarct wall thinning in animals in the xenogeneic and control groups (FIG. 31A, bottom row). In contrast, the syngeneic and allogeneic groups exhibited smaller scar size, increased infarcted wall thickness and attenuation of LV remodeling (FIG. 31A). Scar size and infarcted wall thickness did not differ among animals treated with syngeneic or allogeneic CDCs, which indicates, in some embodiments, that similar physical (e.g., treatment effects are obtained whether autologous or allogeneic cells are used. (FIGS. 31B-31C).

To assess functional benefit of CDC transplantation, global cardiac function was assessed by echocardiography, quantifying fractional area change (FAC), left ventricular ejection fraction (LVEF), and fractional shortening (FS). At baseline (DO), FAC, LVEF and FS did not differ among treatment groups, indicating a similar degree of initial injury. Over the first 3 weeks after infarction, indices of function failed to improve in the xenogeneic and control groups, whereas FAC, LVEF and FS all rose significantly in both the allogeneic and syngeneic groups (FIGS. 31D-31F). Notably, the functional benefit observed at 3 weeks persisted out to 6 months post infarction in the allogeneic and autologous groups, but not in xenogeneic or control group. A treatment effect summary is shown in FIG. 31G, which show that, despite their lower engraftment at 3 weeks, allogeneic cells are equivalent to syngeneic (which are modeling autologous cells in this experiment) in terms of providing functional repair to damaged cardiac tissue Both syngeneic and allogeneic CDCs led to similar improvements in cardiac function in the rat model 3 weeks, 12 weeks, and 6 months post-MI (FIG. 31). Both syngeneic and allogeneic groups differed significantly from control animals at each timepoint. The xenogeneic group showed a decline in function at 3 weeks post-MI that is significantly different from the result seen in the syngeneic and allogeneic groups. This study indicates that allogeneic CDC transplantation without immunosuppression is safe and improves heart function in a rat model without the need for persistent cell engraftment.

To further investigate possible mechanisms of the benefits provided by allogeneic transplants, the fate of the transplanted cells themselves as well as indirect mechanisms of benefit were evaluated. Immunohistochemistry revealed that syngeneic and allogeneic CDCs primarily resided in the border zone and infarct scar. A subset of administered cells were found have reentered the cell cycle at 1 and 3 weeks post-MI, as indicated by Ki-67 positivity and BrdU incorporation. Rare events of cardiomyogenic (GFP+/αSA+ cells) and angiogenic (GFP+/vWf+ cells) differentiation of surviving CDCs could be detected in both the syngeneic and the allogeneic setting. While the majority of GFP+/αSA+ cells were small and exhibited an immature cardiomyocyte phenotype (FIG. 31H), mature GFP/αSA+ cells structurally integrated into the host myocardium could also be detected (FIG. 31I, white arrow). In addition, GFP+/vWf+ cells were found to be incorporated in microvessels in the risk region (FIG. 31J, white arrows). These results demonstrate the multilineage potential of CDCs, e.g., that CDCs can generate the various cell types needed for complete cardiac repair. However, direct differentiation of administered cells was low, and thus, in some embodiments, unlikely to fully account for the observed robust functional benefit of allogeneic cell transplant. Thus, in some embodiments, the direct effect of administered cells is only partially responsible for the observed benefits (e.g., physical and functional cardiac repair).

Endogenous cardiac regeneration is another possible mechanism and was therefore evaluated. Endogenous regeneration may involve one or more of endogenous cardiomyocyte cell cycle re-entry, recruitment of endogenous progenitor cells to the site of cell transplantation, and/or enhanced angiogenesis. Both syngeneic and allogeneic CDC therapy stimulated resident cardiomyocyte cell-cycle re-entry. The number of cycling host cardiomyocytes (GFP−/αSA+/Ki67+ and GFP−/αSA+/BrdU+ cells) was markedly increased in CDC-treated hearts compared to controls (FIGS. 31K-31M, 31N-31P, 31W, and 31X) at 1 and 3 weeks post MI. However, the number of GFP−/αSA+/Ki67+ and GFP−/αSA+/BrdU+ cells significantly decreased from 1 week to 3 weeks, dropping to nearly undetectable levels at 6 months, suggesting that, in some embodiments, the re-entry of endogenous cardiac cells into the cell cycle is perhaps an acute effect. In other embodiments, however, this effect may be longer-lasting. Syngeneic and allogeneic CDC transplantation also recruited endogenous stem cells (FIGS. 31Q-31S and 31Y) as evidenced by the increased number of GFP−/c-Kit$^+$ in CDC-treated hearts compared to controls at 1 week and 3 weeks post MI. As with resident cycling myocytes, the number of endogenous progenitors significantly decreased as a function of time.

Finally, it was determined that both syngeneic and allogeneic CDC transplantation enhanced angiogenesis in the infarct border zone. Vessel density, identified by immunostaining for vWf, was markedly increased 3 weeks after cell therapy compared to controls (FIGS. 31T-31V and 31Z). While control hearts did display some activity in these endogenous reparative mechanisms, both syngeneic and allogeneic showed a greater magnitude than that of control cells.

These data thus indicate that either syngeneic or allogeneic transplants yield functional improvements, while control groups lose cardiac function over time. Additionally, in vivo data evaluating infarct size indicate that infarct size is significantly smaller in both cell therapy groups compared to controls. See, e.g., FIG. 25. Additionally, the data presented herein suggests that exogenous CDC administration stimulates activation of endogenous repair and/or regeneration pathways. Thus, indirect mechanisms may be, in some embodiments, largely responsible for the observed benefit following CDC therapy.

To further investigate the indirect effects, myocardial levels of beneficial paracrine factors in the infarct border zone were analyzed. Western Blot analysis revealed increased secretion of VEGF, IGF-1 and HGF in hearts treated with syngeneic and allogeneic CDCs, compared to controls, at day 1, day 4 and day 7 post MI (FIG. 31AA-DD). 3 weeks post MI, no difference in secretion of these factors could be observed among groups. This indicates that syngeneic and allogeneic CDCs are equivalent in terms of their generated paracrine effects, both in magnitude and in time course. In some embodiments, the factors evaluated above are primary players in the indirect repair effect, however, in some embodiments, other factors (described elsewhere herein) may also play a role.

Both rat and human CDCs show similar patterns of MHC expression at baseline and after IFN stimulation. As with the human CDCs, IFN stimulation induces upregulation of rat CDC MHC I, II molecules. Co-culture of rat CDCs with allogeneic lymphocytes induces lymphocyte proliferation and secretion of pro-inflammatory cytokines However, the level of immune response is significantly lower when compared to xenogeneic co-culture.

In vivo, rat syngeneic and allogeneic CDCs demonstrate similar survival rates at Day 8 after experimentally induced MI. At Day 21, cell survival after syngeneic transplantation is significantly higher. This suggests that the pro-immunogenic characteristics that CDCs display in vitro, induce an in vivo immune response between day 9 and day 21. Regardless, overall cell survival is poor in both syngeneic and allogeneic groups. It is possible, that more than one mechanism of cell death is involved, depending on the group. For example, higher levels of apoptosis may be involved in reducing the overall survival of the allogeneic cells while a lesser amount of apoptosis couples with increased necrosis may account for cell loss in the syngeneic group.

Despite the significantly reduced number of cells present after 21 days, both syngeneic and allogeneic CDC transplantation led to significant improvement of LV function after MI, as compared to controls. The treatment effect is similar between the two types of transplants at day 21. Moreover, infarct size is reduced in the two groups as compared to controls. This suggests that, as discussed above, an early, but long-lasting effect is induced by the transplant of cells into damaged myocardium. It is possible that the paracrine effects described in the prior Examples are responsible for inducing a cascade of events that serve to improve cardiac function by repairing damaged tissue or generating new, functional tissue. It is also possible that these early signals recruit endogenous cardiac stem cells that augment cardiac function and induce tissue repair. In either case, the data presented here indicate that the presence of viable transplanted cells is not a necessary precursor to improved cardiac function and/or tissue repair. It appears that the transplanted cells function as a trigger, and thus, in some embodiments, induce and/or recruit repair mechanisms, then are removed by various cell death pathways, including, but not limited to phagocytosis, autophagy, apoptosis, enzymatic degradation, among others. In this light, the allogeneic cell transplant becomes even more attractive, not only because of the practical advantages discussed above, but because the life span of the transplanted cells appears to be short enough that the induced immune responses are not significant enough to interfere with functional repair of the damaged tissue.

Example 12—Pre-Clinical Trials Using Autologous Cells

Cardiosphere-derived cells (CDCs) and their 3-dimensional precursors, cardiospheres were tested, according to several embodiments of the invention, for cellular cardiomyoplasty in a mini-pig model of heart failure post-myocardial infarction (MI). Although porcine studies were conducted, data can be extrapolated to human patients according to several embodiments of the invention.

According to one embodiment, autologous cardiospheres or CDCs grown from endomyocardial biopsies were injected via thoracotomy four weeks post-anteroseptal MI. Engraftment optimization with luciferase-labeled CDCs guided the choice of cell dose (0.5M cells/site) and target tissue (20 periinfarct sites). Pigs were randomized to placebo (n=11), cardiospheres (n=8) or CDCs (n=10). Functional data were acquired before injection and again 8 weeks later, after which organs were harvested for histopathology. Beyond the immediate perioperative period, all animals survived to protocol completion. Ejection fraction was equivalent at baseline but, at 8 weeks, was higher than placebo in both of the cell-treated groups (placebo vs. CDC p=0.01; placebo vs. cardiospheres p=0.01). Echocardiographic and hemodynamic indices of efficacy improved disproportionately with cardiospheres. Likewise, adverse remodeling was more attenuated with cardiospheres than with CDCs. Provocative electrophysiologic testing showed no differences among groups, and no tumors were found.

Thus, according to several embodiments, dosage-optimized direct injection of cardiospheres or CDCs is safe and effective in preserving ventricular function in ischemic cardiomyopathy. In one embodiment, CDCs and cardiospheres have equivalent effects on LVEF. In some embodiments, cardiospheres are superior in improving hemodynamics and regional function, and in attenuating ventricular remodeling.

In several embodiments of the invention, the regenerative cells delivered to patients are cardiospheres. In other embodiments, the regenerative cells are CDCs. In yet other embodiments, the regenerative cells are a combination of cardiospheres and CDCs. In some embodiments, regenerative cells are useful for treating dysfunction (e.g., left ventricular dysfunction) post-MI.

In some embodiments, CDCs delivered to subjects (e.g., non-human mammals, human patients) are a heterogeneous mix of cells expanded from cardiac tissue, with formation of self-assembling spherical clusters of heart-derived cells (cardiospheres) as an intermediate processing step. In several embodiments, CDCs are clonogenic and exhibit multi-lineage potential, thus fulfilling key criteria for cardiac stem cells, and they can be readily and reliably expanded from tiny specimens of heart muscle. According to one embodiment, approximately 20 mg samples yield about 1.5 million CDCs on average within 45 days.

In one embodiment, cardiospheres having a size of about 50-200 μm in diameter are used. In one embodiment, delivery mechanisms other than intracoronary administration are used to reduce the risk of embolization at the arteriolar level. For example, in one embodiment, cardiospheres are delivered by intramyocardial injection. In one embodiment, cardiospheres having a size of about 50-150 μm in diameter are used. In several embodiments, CDCs are particularly advantageous due to their size being less than that of cardiospheres. In some embodiments, CDCs are of a size that is associated with little to no risk of embolization of at the arteriolar level. For example, in several embodiments, CDCs are less than about 50 μm in diameter. In some embodiments, CDCs are less than about 40 μm in diameter, less than about 30 μm in diameter, less than about 20 μm in diameter, and less than about 10 μm in diameter. In some embodiments, CDCs range from about 5-10 μm in diameter, about 6-11 μm in diameter, about 7-12 μm in diameter, about 8-13 μm in diameter, about 9-14 μm in diameter, about 10-15 μm in diameter, about 11-16 μm in diameter, about 12-17 μm in diameter, about 13-18 μm in diameter, about 14-19 μm in diameter, about 15-20 μm in diameter, and overlapping ranges thereof. In some embodiments, CDCs are less than about 75% of the size of a cardiosphere. In some embodiments, CDCs are less than about 50% of the size of a cardiosphere. In some embodiments, CDCs are less than about 25% of the size of a cardiosphere. In some embodiments, CDCs range from about 75% to about 70% of the size of a cardiosphere, from about 70% to about 65% of the size of a cardiosphere, from about 65% to about 60% of the size of a cardiosphere, from about 60% to about 55% of the size of a cardiosphere, from about 55% to about 50% of the size of a cardiosphere, from about 50% to about 45% of the size of a cardiosphere, from about 45% to about 40% of the size of a cardiosphere, from about 40% to about 35% of the size of a cardiosphere, from about 35% to about 30% of the size of a cardiosphere, from about 30% to about 25% of the size of a cardiosphere, from about 25% to about 20% of the size of a cardiosphere, from about 20% to about 15% of the size of a cardiosphere, from about 15% to about 10% of the size of a cardiosphere, from about 10% to about 5% of the size of a cardiosphere, from about 5% to about 1% of the size of a cardiosphere, and overlapping ranges thereof. In several embodiments, CDCs are particularly advantageous because of their size, which, being less than that of cardiospheres, enables a greater degree of engraftment, which, in some embodiments, increases the beneficial effects of CDC administration, whether due to the engraftment itself or an increased paracrine effect related thereto. It shall be appreciated, that the source of the CDCs, be it an autologous, xenogeneic, or allogeneic source, does not substantially impact the advantages realized in certain embodiments due to the smaller size of CDCs.

Two studies were performed to examine regenerative cells according to several embodiments of the invention. Study 1 (FIG. 32A) consisted of open-label experiments to quantify engraftment 24 hours after intramyocardial CDC injection in the porcine MI model. The engraftment data were used to inform the dosage and target tissue of injection of CDCs for Study 2 which was a pivotal placebo-controlled, blinded randomized study of safety and efficacy of either cardiosphere or CDC direct intramyocardial injection. (FIG. 32B).

Animals were randomized to receive either placebo or about 10 million cells in cardiosphere or CDC form, administered as 20 injections of 0.5 million per site. Other cell and/or injection numbers are used in other embodiments. The dose of 10 million cells was selected on the basis of the engraftment data from study 1, which had demonstrated, according to one embodiment, that the highest percentage engraftment of cells occurred when a smaller number was injected at each site in the periinfarct border zone. (FIG. 33). Cells or placebo were injected under direct visualization by open chest surgery performed 4 weeks after MI. The pigs were then followed for eight more weeks, to assess safety and efficacy. Thus, in one embodiment, injections are made in the periinfarct border zone. In other embodiments, injections are made outside of said zone.

General anesthesia was induced in adult female Yucatan mini-pigs. Endotracheal intubation was then performed and anesthesia maintained. The mini-pigs were subjected to an anteroseptal MI by inflation of an angioplasty balloon in the mid-LAD to cause coronary occlusion for 2.5 hours. Catheters were inserted via the left carotid artery. After reperfusion, during the same episode of general anesthesia, 4-6 right ventricular biopsies were obtained using a standard clinical cardiac bioptome introduced via the right internal jugular vein. The biopsies were immediately placed into ice-cold cardioplegia solution (e.g., $Ca^{++}$ and $Mg^{++}$ free PBS with 5% dextrose, mannitol 68.6 mmol/L, KCl 1.6 mmol/L, $NaHCO_3$ 3.1 mmol/L and heparin) and cardiospheres or CDCs were grown from these biopsy samples.

According to several embodiments of the invention, cardiac biopsy specimens (10-40 mg) were minced, and subjected to collagenase IV digestion. These explants were plated onto fibronectin-coated plastic plates with cardiac explant medium (IMDM (Invitrogen), 20% FBS, 1% penicillin-streptomycin, 1% L-glutamine, 0.1 mM 2-mercaptoethanol). A monolayer of adherent cells grew out from the biopsy, which was harvested after 1-2 weeks. The harvested outgrowth was re-plated onto poly-D-lysine coated wells. Under these conditions, within 3-5 days the majority of the cells gave rise to free-floating clusters of cells (e.g., cardiospheres). In a third phase, the adherent cells were discarded, while the floating cardiospheres were collected and plated once again onto fibronectin-coated cellware. The cardiospheres adhered and flattened to form a monolayer of cells referred to as CDCs, which were passaged as they became confluent. So called "secondary cardiospheres" were used in the in vivo experiments, meaning that an equivalent number of CDCs (e.g., about 10 million) were harvested and counted, then plated back into poly-D-lysine coated wells where they formed cardiospheres for a second time, which were injected into the animals.

Cultured cells were transduced at the outgrowth stage with a lentiviral vector encoding the firefly luciferase gene, and further processed to create CDCs. Seven animals that had been subjected to the MI and RV biopsy protocols, received intramyocardial injection of 0.5, 2.0 or 10 million CDCs per injection site in intrainfarct, periinfarct (borderzone) or remote normal ventricular locations. (See FIG. 33) Other dosages may be used according to other embodiments of the invention. The animals were sacrificed 24 hours later for assessment of cell engraftment.

Thirty-three pigs had general anesthesia induced a second time, 4 weeks after MI, with the same drugs. Intramyocardial direct injection was performed by open chest surgery under sterile conditions. Sternotomy was performed and the pericardium opened to expose the heart. Twenty intramyocardial injection of either cardiospheres (0.5 million cells suspended in 00.1 mL per injection), CDCs (0.5 million cells suspended in 00.1 mL per injection) or placebo (00.1 mL of medium alone) were performed into the beating heart, using a 1 mL tuberculin syringe and 26 gauge needle. The injections were spaced around the perimeter of the macroscopically visible infarct scar, approximately 1 cm from the gross border. Other injection sites are used in according with other embodiments of the invention. 11 pigs were allocated to receive placebo (vehicle alone), 8 allocated to receive cardiosphere injections, and 10 allocated to receive CDC injections.

About 0.5M cells/site was administered per site in the periinfarct zone for the study 2. Quantification of off-target expression at 24 hrs revealed no measurable cells in liver, spleen or kidney, but 0.9% of injected CDCs could be detected in the lungs (see Table 4.) In several embodiments, the percentage retained in the heart can be increased by iron-loading cells and applying an apical magnet, as described in PCT Application No. PCT/US2010/054358, the disclosure of which is herein incorporated by reference.

TABLE 4

| Cell distribution in non-target tissues. | | | | | | | |
|---|---|---|---|---|---|---|---|
| | Pig 1 | Pig 2 | Pig 3 | Pig 4 | Pig 5 | Pig 6 | Pig 7 |
| Lung | 1.8% | 0.3% | 2.4% | 0.6% | 0.6% | 0.3% | 0.4% |
| Liver | — | — | — | — | — | — | — |
| Spleen | — | — | — | — | — | — | — |
| Kidney | — | — | — | — | — | — | — |

On the basis of the 24 hour engraftment data, a dosage of 0.5M CDCs (or an equivalent cell number of cardiospheres) per site was selected, and direct intramyocardial injections performed in 20 periinfarct sites, giving a total cell dosage of 10 million CDCs. FIG. 34A shows the LVEF data derived from contrast ventriculography. LVEF at baseline was equivalent in the three groups. FIG. 34B also demonstrates that, eight weeks post-injection, LVEF was significantly higher than placebo in both of the cell treated groups, while there was no significant difference in final LVEF between the CDC and the cardiosphere-treated groups. FIG. 34C shows that the treatment effect (final minus baseline LVEF) was significantly higher than placebo in both of the cell treated groups. Thus, according to some embodiments of the invention, cardiac function is improved when CDCs are administered. In some embodiments, cardiospheres improve cardiac function.

Echocardiographic measurement of LVEF yielded qualitatively similar differences in final LVEF and delta LVEF measurements, though the differences between the groups were not statistically significant by this modality (Table 5). Echocardiographic measurement did, however, demonstrate progressive ventricular dilatation in placebo and CDC groups, which was attenuated in the cardiosphere-treated animals (FIG. 35B and Table 5). Baseline systolic and diastolic LV volume measurements were randomly lower in the CDC-treated animals (Table 5).

embodiments, the invention provides improve morphology and function in the infarct region with allogeneic CDC or cardiosphere injections.

Table 6 and FIG. 35A outline the results of LV pressure-volume loop analysis. Most measurements were made at steady state. However one important measurement, end-systolic elastance (Emax) was derived, by definition, as the slope of the end-systolic pressure-volume relationship from the family of loops produced during balloon occlusion of the inferior vena cava. (FIG. 35A). Emax is a rigorous load-independent measure of contractility. Final Emax in the

TABLE 5

Echocardiographic Indices

| | | Placebo (n = 9) | CDC (n = 9) | CSph (n = 5) | p values: ANOVA | Placebo vs. CDC | Placebo vs. CSph | CDC vs. CSph |
|---|---|---|---|---|---|---|---|---|
| Ejection fraction | Baseline | 43 ± 7 | 44 ± 12 | 43 ± 5 | 0.98* | — | — | — |
| | Final | 40 ± 7 | 47 ± 5 | 44 ± 5 | 0.07 | — | — | — |
| | Treatment effect (delta) | −3 ± 11 | +3 ± 10 | +1 ± 5 | 0.39 | — | — | — |
| systolic volume, mL | Baseline | 29.5 ± 4.8 | 24.7 ± 5.0 | 31.4 ± 3.9 | 0.04 | 0.04 | 0.49 | 0.02 |
| | Final | 40.5 ± 11.8 | 34.7 ± 7.2 | 31.8 ± 5.6 | 0.21 | — | — | — |
| | Treatment effect (delta) | +10.9 ± 13.2 | +10.0 ± 6.2 | +0.4 ± 5.4 | 0.13 | — | — | — |
| Diastolic volume, mL | Baseline | 52.0 ± 9.4 | 44.2 ± 5.3 | 55.6 ± 9.8 | 0.04 | 0.054 | 0.44 | 0.02 |
| | Final | 66.1 ± 12.9 | 65.0 ± 10.7 | 56.2 ± 7.8 | 0.27 | — | — | — |
| | Treatment effect (delta) | +14.0 ± 15.0 | +20.8 ± 10.1 | +0.7 ± 8.5 | 0.02 | 0.25 | 0.06 | <0.01 |

Abbreviation: CSph, cardiospheres
*Baseline Ejection fraction did not exhibit homogeneity of variance between groups, so the Kruskal-Wallis test was performed instead of ANOVA In addition, echocardiography revealed that final measurements of LV septal wall thickness were increased in both of the cell-injected groups relative to placebo (FIG. 36B). The thickening fraction of the apical septum was also increased in cardiosphere-injected pigs. (FIG. 36C). Thus, in one embodiment cardiospheres are particularly efficacious. According to some embodiments, the invention provides improve morphology and function in the infarct region with autologous CDC or cardiosphere injections. In other cardiosphere group was higher than in placebo-treated pigs, indicating improved left ventricular contractility in these animals (placebo 1.03±0.29, CDC 1.66±0.45, cardiosphere 3.16±1.32 mmHg/mL. Kruskal-Wallis p=0.003. Placebo vs. CDC, p=NS; Placebo vs. cardiosphere, p=0.03; Cardiosphere vs. CDC, p=NS). Emax in the CDC group tended to increase but was not significantly higher than in placebo-treated animals.

TABLE 6

Pressure-Volume Loop derived Indices

| | | Placebo (n = 11) | CDC (n = 10) | Cardiosphere (n = 7) | ANOVAp |
|---|---|---|---|---|---|
| Heart rate, bpm | Baseline | 121 ± 12 | 119 ± 12 | 117 ± 17 | 0.72 |
| | Final | 112 ± 17 | 109 ± 13 | 117 ± 19 | 0.65 |
| | Treatment effect (delta) | −9 ± 16 | −9 ± 12 | −1 ± 36 | 0.72** |
| $P_{max}$ mmHg | Baseline | 97.0 ± 11.5 | 86.9 ± 6.9 | 93.8 ± 14.6 | 0.13 |
| | Final | 87.1 ± 11.4 | 88.4 ± 10.4 | 86.2 ± 8.1 | 0.90 |
| | Treatment effect (delta) | −9.9 ± 12.9 | +1.5 ± 11.2 | =7.9 ± 16.0 | 0.14 |
| LVEDP, mmHg | Baseline | 14.6 ± 3.1 | 14.5 ± 5.1 | 18.0 ± 5.3 | 0.20 |
| | Final | 12.6 ± 3.7 | 16.0 ± 6.2 | 12.1 ± 4.1 | 0.19 |
| | Treatment effect (delta) | −1.9 ± 3.4 | +1.5 ± 4.4 | −5.8 ± 1.7 | 0.01* |
| dP/mt max | Baseline | 1967 ± 370 | 17709 ± 278 | 1784 ± 693 | 0.56 |
| | Final | 1589 ± 446 | 1430 ± 370 | 1422 ± 333 | 0.58 |
| | Treatment effect (delta) | −378 ± 462 | −340 ± 280 | −382 ± 876 | 0.93 |
| dP/dt min | Baseline | −1984 ± 480 | −1584 ± 346 | −1784 ± 394 | 0.11 |
| | Final | −1516 ± 291 | −1527 ± 357 | −1546 ± 444 | 0.99 |
| | Treatment effect (delta) | 468 ± 600 | 56 ± 501 | 247 ± 520 | 0.25 |

TABLE 6-continued

Pressure-Volume Loop derived Indices

|  |  | Placebo (n = 11) | CDC (n = 10) | Cardiosphere (n = 7) | ANOVAp |
|---|---|---|---|---|---|
| tau, seconds | Baseline | 39.84 ± 4.87 | 38.93 ± 5.51 | 41.28 ± 7.21 | 0.70 |
|  | Final | 41.25 ± 7.21 | 40.92 ± 4.57 | 41.88 ± 3.82 | 0.94 |
|  | Treatment effect (delta) | +1.41 ± 8.39 | +1.98 ± 6.12 | −0.03 ± 5.42 | 0.84 |

Abbreviations: $P_{max}$, the maximum pressure generated by the left ventricle during the cardiac cycle; LVEDP, left ventricular end-diastolic pressure; dP/dt max, the maximum rate of rise of left ventricular pressure; tau, a measure of left ventricular relaxation.
*For further details about post-hoc comparisons of delta LVDDP between the three groups, please refer to FIG. 35C.
**The delta heart rate variable did not exhibit homogeneity of variance between groups, so the Kruskal-Wallis test was performed instead of ANOVA.

Steady state hemodynamics showed few differences (Table 6) except for a greater fall in LV end-diastolic pressure in the cardiosphere-treated group (FIG. 34C). Taken together with the lesser increase of end-diastolic volume in this group, cardiosphere injected animals experience disproportionate benefit with regard to attenuation of adverse ventricular remodeling relative to the other two groups (CDCs or placebo).

Ventricular tachycardia was readily inducible by application of programmed extra-stimuli in all animals prior to sacrifice, consistent with previous reports. However, there were no deaths (sudden or otherwise) in either group after the immediate periprocedural period. Necropsy, with gross analysis as well as histology of heart, brain, kidney, lung, liver and spleen (Table 3) detected no tumors eight weeks after intramyocardial injection of CDCs or cardiospheres.

Fluorescence immuno-histochemistry in the two animals with lacZ$^+$ CDCs, revealed the presence of labeled cells 8 weeks after injection. FIGS. 37A-37B shows two examples of islands of cardiomyocytes with lacZ-positive nuclei in the periinfarct zone, one from each animal that received intramyocardial genetically-labeled CDCs. Thus, in one embodiment, a proportion of injected autologous CDCs, or their progeny which will also be labeled by this integrating vector, persist for 8 weeks within the border zone of infarcted myocardium. In some embodiments, human cardiospheres have improved engraftment as compared to human CDCs when injected into SCID mouse hearts under certain conditions and delivery mechanisms.

In several embodiments, direct surgical injection of autologous cardiospheres or CDCs effectively halts the deterioration in LVEF after a large myocardial infarction, compared to a 7% absolute reduction in LVEF over eight weeks of observation in placebo-treated animals. Cardiospheres increased end-systolic elastance and attenuated the ventricular dilatation associated with myocardial infarction. Although not demonstrated in the study, CDC's may also exhibit similar effects under certain conditions.

According to several embodiments, short-term engraftment of about 8% regardless of injected cell dose in remote normal myocardium is feasible. In some embodiments, in the infarct border zone, the percent survival at 24 hrs decreases progressively from ~8% to <1% as dosage escalates. Thus, in one embodiment, the proportional engraftment of injected cells is improved by injection of lower cell doses at each injection site. In one embodiment, survival in the border zone may be limited by the tenuously-perfused, substrate limited, peri-infarct environment. In this scenario, while the absolute number of injected cells able to survive remains about the same, percentage survival of injected cells is greater with injection of lower numbers of cells per site.

In some embodiments, engraftment rates are from 5%-10%, 10%-20%, 20-50%, 50-75% and higher. In several embodiments, the following dosages of CDCs or cardiospheres per site are used: 0.1-0.2M, 0.2-0.3M, 0.3-0.4M, 0.4-0.5M, 0.5-0.6M, 0.6-0.7M, 0.7-0.8M, 0.8-0.9M, 0.9-1.0M, 1.0-1.5M, 1.5-2.0M, and higher, or overlapping ranges thereof. The following number of injection sites are used in some embodiments: 1, 1-5, 5-10, 10-15, 15-20, 20-25, 25-50, and more sites, and overlapping rages thereof.

In some embodiments, the preservation of global LVEF in cell-treated animals, compared to the deterioration in the placebo group is provided with intramyocardial injection. In several embodiments, cardiospheres are used to provide hemodynamic benefit and/or attenuation of adverse remodeling.

In some embodiments, CDCs comprise a natural mixture of progenitor and support cells expanded from myocardial biopsy specimens, with clonogenicity and multi-lineage potential. In one embodiment, CDCs provide significant functional improvements even when engraftments rates are low. In one embodiment, functional benefit involves indirect effects to boost angiogenesis and cardiomyogenesis.

In some embodiments. regenerative cells described herein (e.g., allogeneic or autologous cardiospheres and CDCs,) can be administered in procedures where open chest surgery is performed (e.g., for other therapy, such as implantation of cardiac devices). In some embodiments, less invasive methods of intramyocardial administration, such as trans-endocardial catheter-mediated delivery are used. In one embodiment, regenerative cells are administered via an intracoronary route.

Example 13—Clinical Trials Using Autologous Cells

The preliminary safety and efficacy of autologous CDCs in patients with ischemic left ventricular dysfunction and a recent myocardial infarction have been evaluated in a Phase I clinical trial (CADUCEUS, NCT00893360, which is incorporated by reference herein). Twenty-four patients (at least 18 years of age with recent myocardial infarction and ischemic left ventricular dysfunction) have or are scheduled to undergo a cardiac biopsy to obtain tissue for generating the cell product. Autologous cardiosphere-derived stem cells, with a low dose of 12.5 million and a high dose of 25 million, are generated. Within 8 weeks of biopsy, and on average within 4 weeks, patients receive CDCs by intracoronary infusion in the infarct-related artery.

A total of 14 subjects have completed the 6 month follow up. In the 12.5 million cell group, 4 subjects who received cells, 4 control subjects and 1 intention to treat subject have completed their 6 month visit. In the 25 million cell group, 3 subjects who received cells, 1 control subject, and 1 intention-to-treat subject have completed their 6 month visit.

Magnetic resonance imaging (MRI) is being used to assess secondary efficacy endpoints, including: changes in MRI-assessment of function in the region which received CDC therapy; changes in MRI assessment of infarct size expressed in absolute value (grams) and as a percent of LV mass; changes in MRI assessment of perfusion in the region which received CDC therapy; changes in MRI assessment of global LV function; and changes in MRI assessment of LV end-diastolic and end-systolic volumes.

In terms of efficacy, the data sets are incomplete. Results to date have been summarized in tabular format below. Six-month follow-up MRIs have been completed for a subset of the study subjects: all 4 patients randomized to receive 12.5 M CDCs and 5 controls.

Although preliminary, the results to date are encouraging, in that the relative changes in infarct size by % LV infarcted are already showing differences between CDCs and controls. At baseline, i.e. before cell infusion, infarct size was equivalent in the two groups (CDC 23.22% vs. Control 24.78%, p=0.84). By six months, those values trended in opposite directions, CDCs getting smaller, as expected from the preclinical data (please refer to IND #13930 for details), and controls creeping upwards (CDC 17.14% vs. Control 28.97%, p=0.12). Comparison of the deltas (baseline minus 6 months) reveals a significant difference (CDC −6.08% vs. Control+4.2%, p=0.021).

The p values for absolute infarct mass are now nearly significant when comparing infarct mass between the groups at 6 months, and for the comparison of the change in infarct mass: Infarct Mass (g) Baseline: CDC 26.24 g vs. Control 28.95 g, p=0.78 6 months: CDC 19.34 g vs. Control 32.07 g, p=0.0684 Delta: CDC −6.9 g vs. Control+3.12 g, p=0.0676

Example 14—Protocols for Manufacturing of CDCs

Cell Processing

A schematic showing one embodiment of cell processing is shown in FIG. 38A-38F. In one embodiment, hearts will be collected from donors and transported to the manufacturing facility. As described above the tissue will go through three stages: 1) explants (EXP) stage: cell outgrowth from the tissue; 2) cardiospheres (CSP) stage: enrichment of cardiac stem cells by culturing; and 3) cardiosphere-derived cells (CDCs) stage: expansion of cells. A master cell bank (MCB) and working cell bank (WCB) of CDCs will be created as described below. In several embodiments, aliquots of the WCB equivalent to a single drug dosage will be formulated as the final composition to be administered.

Cell Banking System

In several embodiments, a cell banking system is provided comprising a plurality of cryogenically preserved, single use, populations of CDCs for administration. In some embodiments, a master cell bank is provided. In some embodiments, a working cell bank is additionally provided (with CDCs that have undergone a greater number of passages). The disclosure herein details an example of a contemplated cell banking system.

In several embodiments, endomyocardial biopsies will be used to generate the cell population for banking. In other embodiments, donor-quality hearts will be dissected and biopsy-sized pieces are collected from the right ventricular septal wall, the atria, the apex, the right ventricular epicardium, or the left ventricular epicardium. Data demonstrate that CDCs can be produced using tissue from all regions reliably (discussed above). In some embodiments, specimens will be processed immediately after collection, while in other embodiments, they will be processed after up to about 6 days of storage in cold cardioplegia solution, and in still other embodiments after cryopreservation and subsequent thawing. In some embodiments, a delay (from collection to processing) of about 3 days is the preferred maximal delay. As discussed above, data demonstrate that the above mentioned tissue storage delays affect resultant CDC yield in an acceptable manner.

In several embodiments, a master cell bank (MCB) will be created from the source material and a working cell bank (WCB) will be created from the MCB. The WCB will be aliquoted into single drug dosages which are the final product. In some embodiments, the MCB will comprise cells that have gone through the three stages of the culture process detailed above: 1) the explants (EXP) stage: cell outgrowth from the tissue; 2) cardiospheres (CSP) stage: enrichment of cardiac stem cells; 3) cardiosphere-derived cells (CDCs) stage: expansion of cells. In several embodiments, CDCs will be cryopreserved at 5 million cells per milliliter and stored in a liquid nitrogen tank located adjacent to the manufacturing facility. Other concentrations of CDCs may also be used, for example, a range of about 2-3 million cells per milliliter, about 3-4 million cells per milliliter, about 4-5 million cells per milliliter, and overlapping ranges thereof. In some embodiments, concentrations above 5 million cells per milliliter will be used, as the higher concentration help to ensure that, even if a portion of the cells die after cryopreservation, sufficient numbers are available in the dose for use in therapy.

Genetic and phenotypic stability of the MCB will be assessed after cryopreservation. Viability of the MCB will be assessed prior to cryopreservation and post-thaw.

The WCB will consist of CDCs from the MCB that undergo additional passages. Genetic and phenotypic stability of the WCB will be assessed prior to cryopreservation. Viability of the WCB will be assessed prior to cryopreservation and post-thaw. The final product consists of those cells cryopreserved from the WCB. In several embodiments, a single WCB aliquot will be removed from the freezer for administration to the patient. The post-thaw WCB aliquot represents the final product to be delivered as the therapeutic. Stability of a cryopreserved product is demonstrated above and will be confirmed for each lot of final product produced. Efficacy of the final product will be verified in a mouse model of myocardial infarction (see Examples for study plan).

As detailed above, a proof of concept banking system was generated. CDCs were passaged to P1 to create the MCB and subjected to testing as summarized below. A fraction of CDCs underwent further passaging to P6 in order to generate a WCB. The yield presented for the WCB is the potential yield extrapolated from the growth seen with the fraction of cells expanded. CDCs will be taken up to P6 to generate the MCB and up to P12 for the WCB used in one embodiment. Testing to be employed on the MCB, WCB, and final product is described in detail above.

Reagents and Excipients

In several embodiments, several reagents used in the processing, culturing, cryopreservation, and administration of CDCs are animal origin free (except for reagents such as serum and/or fibronectin, which are of inherently animal origin). In some embodiments, the cultured cells are treated to remove any products of animal origin. In one embodiment, fetal bovine serum is removed by washing the cells. In one embodiment, the cells are washed with phosphate buffered saline. In several embodiments, washing of cells removes fetal bovine serum such that the concentration remaining is less than about 0.05%. In one embodiment, less than 0.0005 percent fetal bovine serum remains.

In several embodiments, dedicated protocols for collecting, manufacturing, and storing CDCs dedicated to allogeneic therapies are used, which are detailed above. While in some embodiments, endomyocardial biopsies may be used as a tissue source, in several embodiments, transplant-quality hearts to generate allogeneic CDCs. In some embodiments, a master cell bank is generated and in some embodiments, a working cell bank is generated. Thus, in some embodiments, allogeneic CDCs are cryopreserved prior to administration to the patients. Depending on whether CDCs are cryopreserved (certain allogeneic embodiments) or administered to a patient without cryopreservation (certain autologous and certain allogeneic embodiments) the final excipients in the administered composition will vary. The single excipient in cryopreserved products is CRYOSTOR® CS5, a cryoprotectant solution. CRYOSTOR®CS5 is GMP manufactured, made with USP grade components, serum-free, protein-free, and animal-origin free.

Example 15—Clinical Trials Using Allogeneic Cells

Cardiosphere-derived cells were used in patients with left ventricular dysfunction and a recent myocardial infarction with product delivery occurring by intracoronary infusion via an over-the-wire balloon catheter. The following sets forth an example of a contemplated trial using allogeneic cells.

In several embodiments, allogeneic cells would be used in patients with damaged heart tissue. Damaged heart tissue includes heart tissue with sub-optimal function. In one embodiment, the patients have one or more of the following: left ventricular dysfunction, prior myocardial infarction and LVAD placement. Patient may be receiving LVAD placement either as a bridge to transplantation or as destination therapy. In one embodiment, the patients will be undergoing LVAD placement simultaneously with the administration of allogeneic cells. In some embodiments, the use of allogeneic cells as an adjunct to another therapy (e.g., LVAD) will work synergistically with said therapy. In one embodiment, the delivery of regenerative cells (autologous or allogeneic) according to several embodiments herein is used prior, during and/or after heart transplant surgery.

Several delivery approaches may be used. For example, intramyocardial injection using a standard needle and syringe and an epicardial approach during LVAD placement is used in some embodiments. In one embodiment, intramyocardial injection using a dosage of about 5-15 million (e.g., 10 million) CDCs is used. Other agents, such as preservatives, carriers and recipients may be delivered with the cells, including but not limited to DMSO. In one embodiment, 2 mLs of solution containing 5% DMSO (100 μLs of DMSO) will be administered by intramyocardial injection. In one embodiment, patients will receive a single dose of 10 million CDCs delivered with a standard needle and syringe. Each injection will consist of 100 microliters containing 0.5 million CDCs. A total of 20 epicardial injections will be made during LVAD placement. Dosages, number of injections an injection sites will vary in other embodiments.

In one embodiment, patients treated with allogeneic cells (or autologous cells) according to several embodiments described herein, will show one or more of the following improvements: (i) weaning success during the study period such that LVAD removal is feasible, (ii) improved LVAD RPM at which aortic valve opening in every cardiac cycle is seen by transthoracic echo, the corresponding LV ejection fraction, wall thickness, and mass, (iii) improved perfusion and coronary blood flow reserve, and (iv) improved walk distance/times and other exercise test parameters.

In some embodiments, patients will be weaned of LVAD (or other therapy) through the use of regenerative cell therapy. In one embodiment, weaning will take place over the course of 1-3 months. In one embodiment, on a weekly basis, patients will undergo transthoracic echo to assess LV function and aortic valve opening and to assure aortic valve closure and adequate volumetric pump flow rate during RPM adjustment. LVAD flow will be adjusted downward 100-500 RPM per week until the target level of 9000 RPM is reached (baseline settings are typically 9500-10000 RPM). Pump flow rate and RPM will be recorded before and after pump adjustment. During this time, INR will be maintained between 1.5 and 2.5 to minimize the risk of thrombus formation. During these weekly visits, the 6-minute walk test and cardiopulmonary exercise test (as patients are able) will be performed. LVAD explantation will be considered if patients are able to perform cardiopulmonary exercise tests.

In one embodiment, once the LVAD flow has been adjusted to 9000 RPM, patients will be admitted to the hospital to undergo a rapid wean. An echocardiogram will be performed at 9000 RPM to measure baseline EF, LV dimensions and Systolic velocity (Sm) of the basal segments (septal and lateral wall) by Tissue Doppler. The device will then be gradually adjusted to 6000 RPM with reductions of 1000 RPM occurring every 4-6 hours. A BNP value will also be obtained every 4-6 hours. If the patient reports symptoms or there is an increase in BNP to a value >1000 pg/mL, the rapid weaning attempt will be terminated, and the LVAD speed will be adjusted back to 9000 RPM. 6000 RPM has been determined to be a safe speed for device function, without increased risk for thrombosis or backflow from the aorta to the LV. The device will remain at this speed for 16-24 hours. If the patient successfully completes the 16-24 hour period at 6000 RPM (asymptomatic, BNP <1000 pg/mL), an echocardiogram to measure changes in EF, LV dimensions and Sm will follow. If EF>45%, right heart catheterization will follow, with the device at 6000 RPM, in order to measure PCWP. Finally, a symptom limited CPX will follow, with the device set at 6000 RPM. If the patient satisfies the explantation criteria (see below) the device will be set back to the optimal RPM level specified before the initiation of the weaning protocol, until explantation occurs. In some embodiments, LVAD explantation will be performed if the following criteria are met: (i) a LVEF >45%, (ii) LVEDD <55 mm, (iii) Sm >8 cm/sec, (iv) a change in these three parameters of <10% at 6000 RPM compared to 9000 RPM, (v) LVEDP <12 mm (vi) Hg or PCWP <12 mm Hg, (vii) resting cardiac index >2.8 L/min/m$^2$, (viii) exercise VO2 max >16 mL/kg/min at 6000 RPM, and (ix) adequate right ventricular function (under minimal LVAD support at 6000 rpm), assessed by echocardiography and right heart catheterization. In one embodiment, at least one of the criteria is met before explanation. Thus, according to several embodiments of the invention, administration of regenerative cells advantageously permits LVAD explantation.

Example 16—Efficacy of CDCs for Myocardial Repair Versus Alternative Stem Cell Types As discussed above, several embodiments of the present invention comprise use of CDCs for regeneration and/or repair of damaged cardiac tissue. Use of heart-derived cells e.g., cardiospheres, CDCs) for regenerative cardiology is but one of several approaches presently being employed in the pursuit of cardiac cell therapy. Multiple extra-cardiac cell types, including bone marrow mononuclear cells (BM-MNCs), bone marrow-derived mesenchymal stem cells (BM-MSCs), adipose tissue-derived mesenchymal stem cells (AD-MSCs), endothelial progenitor cells, and myoblasts are under investigation for use in regeneration of the damaged heart. Moreover, even within heart-derived cells, there are multiple approaches being investigated. For example, the CDCs disclosed herein (mixture of stromal, mesenchymal and progenitor cells) are used in several embodiments to effect cardiac repair and/or regeneration. While in some embodiments, selection is performed, in several embodiments, the CDCs are not selected for, or enriched based on expression of any particular markers. One alternative approach is to purify the c-kit$^+$ subpopulation from mixed heart-derived cells. Thus, the present study was performed to compare the efficacies of several of these various cell types in repairing and/or regenerating cardiac tissue by direct and/or indirect mechanisms.

Methods

Cell Sources

Human CDCs were obtained and expanded as described above. Human BM-MSCs and BM-MNCs were purchased from Lonza (Walkersville, Md.). Human AD-MSCs were purchased from Invitrogen (Carlsbad, Calif.). These cells were freshly-isolated from healthy donors. The c-kit$^+$ stem cell subpopulation was purified from the expanded CDC population using a CELLection Pan Mouse IgG Kit and a Dynal Magnetic Particle Concentrator-15 (Invitrogen).

For confirmatory rat studies, four-month-old Wistar Kyoto rats were used to expand CDCs, BM-MSCs, and AD-MSCs. BM-MNCs were also collected from the same rats by gradient centrifugation. Freshly-collected BM-MNCs and twice-passaged CDCs, BM-MSCs, and AD-MSCs were used for the rat experiments discussed below.

Unless otherwise noted, IMDM basic medium (Gibco) supplemented with 10% FBS (Hyclone) and 20 mg/ml gentamycin was used to culture all cell lines.

Flow Cytometry

Characterization of CDCs, BM-MSCs, AD-MSCs, and BM-MNCs was evaluated by flow cytometry using established methods. Briefly, cells were incubated with FITC or PE-conjugated antibodies against CD29, CD31, CD34, CD45, CD90, CD105, c-kit, and CD133 (eBioscience) for 30 minutes. Isotype-identical antibodies served as negative control. Quantitative analysis was performed using a FACSCalibur flow cytometer with CellQuest software (BD Biosciences).

ELISA

For evaluation of growth factor production, cells were seeded in 24-well culture plates at densities of $1 \times 10^6$/ml (BM-MNCs) or $1 \times 10^5$/ml (all other cell types) in FBS-free IMDM media (all cell types) for 3 days. Supernatants were collected and the concentrations of angiopoietin-2, bFGF, HGF, IGF-1, PDGF, SDF-1, and VEGF were measured with human ELISA kits (R&D Systems Inc.), according to the manufacturer's instructions. For evaluation of cytokine production by cultured rat cells, concentrations of HGF (B-Bridge International, Inc.), IGF-1, and VEGF (R&D Systems Inc.) were measured in the supernatants after 3 days of culture.

To compare the production of growth factors from the purified c-kit$^+$ subpopulation and unsorted CDCs, cells ($5 \times 10^4$/ml) were seeded in 24-well culture plates and cultured for 2 days under 20% $O_2$. Growth factors in conditioned media were measured by ELISA as described above.

Immunostaining

To determine myogenic differentiation in vitro, cells were seeded on fibronectin-coated 4-chamber culture slides. After 7 days of culture, cells were fixed, blocked with goat serum for 30 minutes, and then incubated with mouse anti-human troponin T antibody (R&D Systems Inc.) for human cells or with goat anti-rat troponin T antibody for rat cells. After 1 hour incubation at room temperature, culture slides were washed and then incubated with a PE-conjugated secondary antibody. Cell nuclei were stained with DAPI. Cardiomyogenic differentiation was quantified by counting positively-stained cells.

In Vitro Angiogenesis Assay

Angiogenic potency was assayed by tube formation using a kit (Chemicon Int.), according to the manufacturer's instructions. Briefly, cells were seeded on ECMatrix™-coated 96-well plates at a density of $2 \times 10^5$ cells (BM-MNCs) or $2 \times 10^4$ cells (all other cell types) per well. HUVEC cells were included as positive controls. After 6 hours, tube formation was imaged. The total tube length was then measured with Image-Pro Plus software (version 5.1.2, Media Cybernetics Inc., Carlsbad, Calif.).

TUNEL Assay

To quantify the resistance to oxidative stress in vitro, cells were seeded on fibronectin-coated 4-chamber culture slides. After 24 hours of culture, cells were cultured with or without the addition of 100 μM $H_2O_2$ to the medium for another 24 hours. Cells were fixed, and apoptotic cells were detected by TUNEL assay using the In Situ Cell Death Detection Kit (Roche Diagnostics, Mannheim, Germany), according to the manufacturer's instructions. Cell nuclei were stained with DAPI; apoptotic cells were counted by TUNEL-positive nuclei.

Myocardial Infarction Model and Cell Implantation

Acute myocardial infarction was created in male SCID-beige mice (10-12 weeks old), as described above. Cells were injected at four points in the infarct border zone with a total of 40 μA of one of the following: phosphate-buffered saline (Control, n=8), $1 \times 10^5$ CDCs (CDCs, n=20), $1 \times 10^5$ BM-MSCs (n=20), $1 \times 10^5$ AD-MSCs (n=20), $1 \times 10^6$ BM-MNCs (high BM-MNCs, n=11), or $1 \times 10^5$ BM-MNCs (low BM-MNCs, n=9). Two dosages were studied with the BM-MNCs, including one with 10-fold more cells than in the comparator groups, because MNCs are smaller than the other cell types, thus the higher dose avoids experimental bias against this cell type in terms of total transplanted cell mass.

C-kit-selected and non-selected CDCs were compared in a separate study by injecting $1 \times 10^5$ purified c-kit$^+$ cells (c-kit$^+$, n=16) and $1 \times 10^5$ unsorted CDCs (unsorted, n=11) into the infarcted hearts of SCID mice, using the methods described above.

Echocardiography

Mice underwent echocardiography 3 hours (baseline) and 3 weeks after surgery using Vevo 770™ Imaging System (VISUALSONICS™, Toronto, Canada). After the induction of light general anesthesia, the hearts were imaged twodimensionally in long-axis views at the level of the greatest left ventricular (LV) diameter. LV end diastolic volume, LV end systolic volume, and LV ejection fraction (LVEF) were measured with VisualSonics V1.3.8 software from 2D long-axis views taken through the infarcted area. Blinded reading of echos was conducted independently by two experienced echocardiographers (K. M. and J. T.). The results correlated well (FIGS. 39A-39B), so the averages of the two readings for LVEF in each mouse were used for statistical analysis.

Histology

Mice were sacrificed 3 weeks after treatment. Hearts were sectioned in 5 µm sections and fixed with 4% paraformaldehyde. The engraftment of implanted human cells was identified by immunostaining for human nuclear antigen (HNA; Chemicon Int.). To measure cell engraftment, 10 images of the infarct and border zones were selected randomly from each animal. To quantify the apoptotic cells in the heart, slides were fixed and apoptotic cells were detected by TUNEL assay as described above. The differentiation of implanted human cells into cardiomyocytes in the infarcted hearts of SCID mice was identified by immunostaining with monoclonal antibodies against human specific α-sarcomeric actin (Sigma), as described above. For morphometric analysis, animals in each group were euthanized at 3 weeks (after cardiac function assessment) and the hearts were harvested and frozen in OCT compound. Sections every 100 µm (5 µm thick) were prepared. Masson's trichrome staining was performed as per manufacturer's instructions (HT15 Trichrome Staining (Masson) Kit; Sigma). Images were acquired with a PathScan Enabler IV slide scanner (Advanced Imaging Concepts, Princeton, N.J.). From the Masson's trichrome-stained images, morphometric parameters including infarct wall thickness and infarct perimeter were measured in each section with NIH ImageJ software.

Statistical Analysis

All results are presented as mean±standard deviation (SD) except as noted. Statistical significance was determined by one-way ANOVA followed by LSD post hoc test (Dr. SPSS II, Chicago, Ill.). Three outliers (2 from CDC group and 1 from AD-MSC group), which differed from the means of each group by >2 SDs, were omitted, and differences were considered statistically significant when p<0.05.

Results

Characterization of Cell Phenotypes

Unlike BM-MNCs, which grow in suspension as small round cells, all other cell types studied (CDCs, BM-MSCs, and AD-MSCs) typically grow as adherent monolayers (compare FIGS. 40A-40C to 40D). Flow cytometry distinguished BM-MNCs from other cell types by the predominant expression of pan-hematopoietic marker CD45 (74.7%), as compared to <1% in CDCs, BM-MSCs, and AD-MSCs (FIG. 40E).

Conversely, >99% of CDCs, BM-MSCs, and AD-MSCs expressed CD105, a TGF-β receptor subunit commonly associated with MSCs. However, these three cell types can be distinguished by CD90: >99% of BM-MSCs and 85% of AD-MSCs expressed CD90, but only 18% of CDCs expressed this marker. CD90 (well-known as Thy-1) was originally discovered as a thymocyte antigen. In humans, Thy-1 is also expressed by endothelial cells, smooth muscle cells, a subset of CD34$^+$ bone marrow cells, and umbilical cord blood, fibroblasts, and fetal liver-derived hematopoietic cells. CD90 is widely used as a marker of a variety of stem cells, e.g. MSCs, hepatic stem cells, keratinocyte stem cells, putative endometrial progenitor/stem cells, and hematopoietic stem cells. Thus, in some embodiments, CDCs contain a minority of fibroblast and/or weakly-committed hematopoietic cells, which is in contrast to the dominance of such populations in the cells of bone marrow and adipose origins. In some embodiments, CD90 expression in CDCs marks the cardiac mesenchymal subpopulation. In still additional embodiments, at least a portion of CDCs do not express CD90.

In Vitro Secretion of Growth Factors

As discussed above, paracrine mechanisms are at least partially responsible, in some embodiments, for the repair and or regeneration of cardiac tissue. Production of six growth factors (angiopoietin-2, bFGF, HGF, IGF-1, SDF-1, and VEGF) by the various cell types was compared. Compared to the other cell types, CDCs were unique in their ability to secrete large amounts of all growth factors studied (see FIGS. 41A-41F). In contrast to CDCs, the other cell types failed to express comparable levels of one or more growth factors:

BM-MNCs produced little VEGF and SDF-1; BM-MSCs secreted little IGF-1 and bFGF; and AD-MSCs were not rich sources of HGF and SDF-1. FIGS. 41G-41J depicts schematically the secretion of each of the six studied cytokines in each given cell type, as wheel-and-spoke diagrams in which the length of each spoke is proportional to the growth factor concentration in conditioned media. The symmetrical starburst pattern highlights the uniquely well-balanced paracrine profile of CDCs.

In order to ensure that these findings did not reflect donor-specific idiosyncrasies (commercially purchased cell types were from different donors), growth factor secretion by the various cell types derived from individual rats were also compared. Correlating with the results above, higher levels of VEGF, IGF-1, and HGF (FIGS. 42A, 42B, and 42C, respectively) were detected in media conditioned by rat CDCs as compared to rat BM-MSCs, AD-MSCs, and BM-MNCs, all collected from the same animals. In several embodiments, it is this unexpectedly balanced secretion of various paracrine factors that provides, at least in part, the therapeutic benefits of the CDCs. In some embodiments, the well-balanced release of growth factors by CDCs, which are acting as localized production factories post-administration, favors enhanced myocardial repair through paracrine mechanisms after implantation into the heart. However, in some embodiments, the generation of one or more of these factors that is greater than the amount generated by the other cell types is responsible, at least in part, for the enhanced efficacy of CDCs. For example, in some embodiments, the amount of VEGF secreted by CDCs is greater than that of the other cell types, and lead (at least in part) to the enhanced therapeutic effect seen post-CDC administration. In still additional embodiments, generation of one or more of these factors (or other factors disclosed herein) functions in concert with direct mechanisms (e.g., engraftment of the CDCs themselves) to effect cardiac repair and or regeneration.

Tube Formation

The angiogenic ability of the various cell types was quantified using an in vitro tube-forming assay. All cell types showed the ability to form capillary-like networks on matrigel within 6 hours (FIG. 43C, upper left, upper right, and lower left panels), with the exception of BM-MNCs (FIG. 43C, lower right panel). Quantitative analysis showed that the mean tube length of the capillary-like networks was greater in CDCs than in the other cell types (p<0.05, FIG. 43D). Thus, in several embodiments, administration of CDCs yields a greater angiogenic effect in the target tissue. In some embodiments, this effect yields formation of longer vessels, thereby maintaining or improving blood supply to cardiac tissue. In some embodiments, the longer vessels formed allow blood supply to bypass a damaged region. In some embodiments, the increased angiogenic effect yields a more dense or more branched network of vessels (e.g., capillaries), which thereby maintains or improves regionalized blood supply to cardiac tissue (e.g., a certain region of cardiac tissue is more thoroughly perfused). Combinations of increased length and increased density result in some embodiments. This increase in the vascular infrastructure results in greater capacity for distribution of blood to the cardiac tissue. As a result, in several embodiments, the increased angiogenic effect of CDCs mediates the functional recovery and or anatomical repair and/or regeneration of cardiac tissue through one or more of increased blood flow, increased ability to distribute paracine factors, increased oxygen delivery to the myocardium, and combinations thereof.

Resistance to oxidative stress

According to several embodiments disclosed herein, the short-term survival and/or engraftment of administered cells plays a role in the repair or regeneration of damaged cardiac tissue. Survival of the administered cells despite the rigors of transplantation procedures enables CDCs, in some embodiments, to provide greater therapeutic benefits. For example, enhanced cell resilience to oxidative stress favors both transplanted cell engraftment and resultant functional benefit. Sensitivity to oxidative stress was assessed by exposing cells to $H_2O_2$, a powerful oxidant. After 24 hours of exposure to 100 μM $H_2O_2$, the number of apoptotic cells tended to be lower in human CDCs as compared to human BM-MNCs (p=0.067, FIG. 44B), but there was no significant difference among CDCs, BM-MSCs, and AD-MSCs. In rat cells, higher apoptosis was observed in BM-MNCs compared to any of the other three cell types after $H_2O_2$ (p<0.05, FIG. 45B). Taken together, these data highlight a relative deficiency of BM-MNCs in terms of resistance to oxidative stress. These data also suggest, that, in some embodiments, CDCs show resistance to oxidative stressors. As a result, the increased resistance may enable CDCs (or cardiospheres) to survive longer, function more robustly, and/or engraft to a greater degree than other stem cell types. In combination with other characteristics (e.g., paracrine profile) of the CDCs generated according the methods disclosed herein, a greater therapeutic efficacy is realized, in several embodiments.

Cardiomyogenic differentiation

As discussed above, in several embodiments CDCs are suitable for differentiation into cardiomyocytes. In some embodiments, this accounts for (at least a portion of) the repair or regeneration of damaged or diseased cardiac tissue via a direct mechanism. The ability of the various cell types to undergo spontaneous cardiomyogenic differentiation in vitro was assessed by immunostaining for cardiac-specific troponin T. Many human CDCs expressed troponin T (see, e.g., FIGS. 43A and 43B), in contrast to human BM-MSCs, AD-MSCs, or BM-MNCs, few of which were positive for troponin T. Quantitative analysis showed that ~9% of CDCs expressed troponin T, while <1% did so in the other cell types (FIG. 43B). Similar findings were observed using rat CDCs, BM-MSCs, AD-MSCs, and BM-MNCs, all collected from the same animals (FIGS. 46A-46B). Thus, in some embodiments, the direct differentiation of CDCs (or other cardiac stem cells such as cardiospheres) into cardiac cells serves as a primary mechanism for the repair and/or regeneration of functional cardiac tissue. In some embodiments, the direct differentiation is a as a complementary mechanism, working in concert with the paracrine effects discussed herein.

Cell engraftment and in vivo differentiation

As disclosed above, the methods and compositions disclosed herein yield a positive correlation between long-term cell engraftment and functional benefit (e.g., functional and/or anatomical cardiac repair and/or recovery). Engraftment and differentiation of human cells 3 weeks after direct intramyocardial injection into the infarcted hearts of SCID mice was evaluated. Histology revealed expression of α-sarcomeric actin (αSA) in some of the surviving progeny of human CDCs (positive for human nuclear antigen [HNA]; FIG. 47A), confirming the cardiomyogenic differentiation in vivo. In contrast, human cells positive for α-sarcomeric actin were observed rarely and inconsistently in mice injected with BM-MSCs, AD-MSCs, and BM-MNCs (data not shown). Quantitative image analysis confirmed that the engraftment (e.g., the numbers of $HNA^+$ cells) was greater in mice implanted with human CDCs than with comparator cells (p<0.05, FIG. 47B). In addition, the numbers of cardiomyocytes derived from the transplanted cells ($HNA_+$/$αSA^+$) were greater in mice implanted with human CDCs than with any of the other cell types (p<0.01, FIG. 47C). In several embodiments, the increased cardiomyogenic differentiation attributable to CDCs is responsible for the greater therapeutic efficacy of CDCs. In some embodiments, the increased engraftment alone is responsible for improved efficacy, not only because a greater number of administered CDCs are retained in the target cardiac tissue, but because there is an associated greater increase of paracrine factor production. In some embodiments, the greater degreed of cardiomyogenic differentiation is responsible for the greater efficacy (e.g., direct mechanisms of repair are dominant). In several embodiments, these effects of CDCs (increased engraftment, increased cardiac differentiation, paracrine effects) function in concert to for a multi-pronged mechanism of cardiac tissue repair and/or regeneration.

Cell apoptosis

In addition to tissue regeneration, tissue preservation may be a salutary component of cell therapy for acute myocardial infarction. To evaluate this possibility, apoptotic nuclei in the infarcted region of control mice and mice injected with each of the comparator cell types were evaluated. TUNEL staining revealed apoptotic nuclei in the infarcted hearts 3 weeks after treatment (FIGS. 48A-48B). Given the timepoint, it is likely that the acute phase of cell death due to ischemia may have already resolved. Thus, the apoptotic nuclei may be a reflection of long-term remodeling and heart failure. The total number of apoptotic cells in the infarct and peri-infarct area was counted. The hearts of mice implanted with CDCs exhibited fewer TUNEL-positive cells, compared to all other cell-treated groups (p<0.05, FIG. 48C). As discussed above, the greater production of pro-angiogenic and anti-apoptotic factors by CDCs may be responsible, at least in part, for the reduced apoptosis of CDCs. Moreover, in some embodiments, the reduced apoptosis may be responsible for the increased engraftment/survival of CDCs. In some embodiments, however, the increased engraftment may be responsible for the reduced apoptosis (e.g., the engrafted cells are in a preferred environment for survival as compared to loosely attached or non-engrafted cells). Regardless of the temporal order of these mechanisms, the reduced amount of apoptosis allows for one or more of increased CDC survival, increased cardiomyogenic differentiation, and increased paracrine factor production, which in turn result in one or more of improved cardiac anatomy (e.g., reduced infarct size) or improved cardiac function (e.g., increased LVEF). Moreover, in several embodiments the reduction in apoptosis is realized not only in the acute phase of cell death (e.g., at short time periods after an ischemic event), but also in the long-term (e.g., ameliorating long-term remodeling and/or heart failure).

Cardiac function

Clinically, one of the most meaningful endpoints of cardiac cell therapy is the ability to produce functional benefit after transplantation into the injured heart. Echocardiography was used to measure cardiac function, and all images were interpreted blindly and independently by two experienced sonographers (see FIGS. 39A-39B). FIG. 49 summarizes the results. The LVEF at baseline (i.e., two hours post-infarction) was comparable among all groups. This indicates similar ischemic injury among the groups. Among the various treatments, the implantation of CDCs resulted in the greatest LEVF at 3 weeks ($p=0.038$ vs. BM-MSC; $p=0.002$ vs. AD-MSC; $p=0.002$ vs. high BM-MNC; $p=0.001$ vs. low BM-MNC group; and $p<0.001$ vs. Control). BM-MSCs also improved cardiac function ($p=0.009$ vs. Control) and AD-MSCs tended to improve function ($p=0.073$ vs. Control), while the other cell types, although higher on average than controls, had no statistically significant functional benefit. Thus, in some embodiments, administration of stem cells prevents the decline in cardiac function that results from cardiac injury absent any therapeutic intervention. Advantageously, the administration of cardiac stem cells (e.g., CDCs) not only prevents this decline in function, but yields improved function over time. In several embodiments function is improved at least about 5% over a baseline function (e.g., function after injury). In several embodiments function is improved at least about 10% over a baseline function. In still additional embodiments, greater improvements in function are realized.

Ventricular remodeling

Potentiating the functional benefits of cell therapy is attenuation of adverse ventricular remodeling. To evaluate this effect, the morphological consequences of transplantation of the various cell types on myocardial infarct size and wall thinning were evaluated. Heart morphometry at 3 weeks showed severe LV chamber dilatation and infarct wall thinning in the control hearts (FIGS. 50A-50F). In contrast, all the cell-treated groups exhibited attenuated LV remodeling. Compared to control, the implantation of any type of human cells decreases fractional infarct perimeter and, conversely, increases the minimal infarct wall thickness, 3 weeks after treatment ($p<0.05$ vs. Control group, FIGS. 50G-50H). Despite the positive benefits due to administration of any cell type, the protective effect was greatest in the CDC-treated hearts. CDC-treated hearts had thicker infarcted walls (FIG. 50G; $p<0.01$), but a smaller fractional infarct perimeter (FIG. 50H; $p<0.05$) as compared to any of the other cell-treated groups. Thus, in addition to the above-discussed improved function, the administration of CDCs, in several embodiments, also improves or mitigates the remodeling that occurs after an injury to the heart (e.g., an ischemic event). In some embodiments, infarct size is reduced by 10% to about 50% as compared to infarct size in an untreated subject. In some embodiments, infarct size is reduced 2-fold, 3-fold, 5-fold or greater. In some embodiments, functional cardiac tissue mass is increased (e.g., increased wall thickness). In several embodiments, the increases are about 2-fold, 3-fold, 5-fold or greater than an untreated control. In some embodiments, the combination of reduced infarct (or other damage) size and increased functional mass provide a synergistic increase in cardiac function.

Unsorted CDCs versus the c-kit$^+$-purified cell subpopulation

Having established that CDC populations that are unselected for any particular marker were the most efficacious cell type among those studied, a comparison of such CDCs was made against purified c-kit$^+$ cells. Unsorted CDCs were compared to equal numbers of c-kit$^+$ stem cells purified from CDCs by magnetic cell sorting. Purified c-kit$^+$ cells were determined to be inferior to unsorted CDCs in terms of functional benefit after transplantation into the infarcted heart, although they did outperform vehicle-injected controls (FIG. 51A). The sorting procedure did not itself compromise cell functional efficacy, as CDCs sorted for CD105 (expressed by >99% of CDCs) exhibited an LVEF comparable to that of unsorted CDCs (data not shown). The c-kit antibody used for purification is known to interfere only minimally with ligand binding, receptor phosphorylation, and internalization in c-kit-expressing cell lines. Also, magnetic-activated cell sorting for mast cells using this c-kit antibody neither induced histamine release nor did it impair the ability of cells to release histamine when stimulated. The therapeutic superiority of the CDCs versus the purified c-kit$^+$ subpopulation suggests that, in some embodiments, the mixed CDC population (e.g., stromal, mesenchymal, and c-kit$^+$ cells) function in concert to enhance overall paracrine potency, direct repair mechanisms, and in turn functional and anatomical benefits.

To investigate one potential mechanism for the functional superiority of CDCs, production of a variety of paracrine factors in conditioned media from sorted and unsorted cells was evaluated. Indeed, unsorted CDCs produced higher amounts of paracrine factors in vitro as compared to purified c-kit$^+$ cells (FIGS. 51B-51E). As discussed above, in some embodiments, the well-balanced release of growth factors by CDCs promotes enhanced myocardial repair through paracrine mechanisms after implantation into the heart. In some embodiments, the combination of the balanced profile and the overall greater amount of production is responsible for the increased efficacy of cell therapy with unsorted CDCs. In some embodiments, it is the overall greater amount of production which is responsible for the increased efficacy of cell therapy with unsorted CDCs. In still additional embodiments, generation of one or more of these factors (or other factors disclosed herein) functions in concert with direct mechanisms (e.g., engraftment of the CDCs themselves) to effect cardiac repair and or regeneration.

What is claimed is:

1. A method of treating a subject having diseased or damaged cardiac tissue, the method comprising administering to the subject a therapeutically effective amount of cardiosphere-derived cells (CDCs),
   wherein said CDCs are a population of cells obtained by plating and expanding cardiospheres (CSps) as an adherent monolayer culture on a solid surface of a culture vessel in a culture medium supplemented with serum;
   wherein said CDCs are not further manipulated to form secondary cardiospheres (IICSps);
   wherein CD105 is present on about 90.0±4.7% of said CDCs; and
   wherein said culture vessel is coated with fibronectin, a hydrogel, a polymer, laminin, serum, collagen, gelatin, or poly-L-lysine.

2. The method of claim 1, wherein said CDCs are allogeneic to the subject.

3. The method of claim 1, wherein said CDCs are autologous to the subject.

4. The method of claim 1, wherein CSps are disaggregated before they are plated and expanded as an adherent monolayer culture on a solid surface of a culture vessel.

5. The method of claim 4, wherein the disaggregated CSps are plated and expanded in a culture medium supplemented with about 20% serum v/v.

6. The method of claim 4, wherein said serum is fetal calf serum or fetal bovine serum.

7. The method of claim 6, wherein said culture medium is not supplemented with thrombin.

8. The method of claim 7, wherein said administration is local administration or intravenous administration.

9. The method of claim 8, wherein said administration is local administration.

10. The method of claim 1, wherein said culture vessel is coated with fibronectin.

11. A method of treating a subject having diseased or damaged cardiac tissue, the method comprising administering to the subject a. therapeutically effective amount of cardiosphere-derived cells (CDCs), wherein said CDCs are a population of cells obtained by:
 collecting cardiospheres (CSps);
 plating said CSps onto a culture vessel; and
 expanding said CSps as an adherent monolayer culture on a solid surface of said culture vessel in a culture medium supplemented with serum to form said therapeutically effective amount of said CDCs,
 wherein CD105 is present on 90.0±4.7% of said CDCs; and
 wherein said culture vessel is coated with fibronectin, a hydrogel, a polymer, laminin, serum, collagen, gelatin, or poly-L-lysine.

12. A method of treating a subject having diseased or damaged cardiac tissue, the method comprising administering to the subject a therapeutically effective amount of cardiosphere-derived cells (CDCs),
 wherein said CDCs are a population of cells obtained by plating and expanding cardiospheres (CSps) as an adherent monolayer culture on a solid surface of a culture vessel in a culture medium supplemented with serum;
 wherein CD105 is present on about 90.0±4.7% of said CDCs; and
 wherein said culture vessel is coated with fibronectin, a hydrogel, a polymer, laminin, serum, collagen, gelatin, or poly-L-lysine.

13. A method of treating a subject having diseased or damaged cardiac tissue, the method comprising administering to the subject a therapeutically effective amount of cardiosphere-derived cells (CDCs), wherein said CDCs are a population of cells obtained by plating and expanding cardiospheres (CSps) as an adherent monolayer culture on a solid surface of a culture vessel in a culture medium supplemented with serum;
 wherein CD105 is present on about 90.0±4.7% of said CDCs; and
 wherein said culture vessel is coated with fibronectin, a hydrogel, a polymer, laminin, serum, collagen, gelatin, or poly-L-lysine.

* * * * *